(12) United States Patent
Guillemont et al.

(10) Patent No.: US 11,180,472 B2
(45) Date of Patent: Nov. 23, 2021

(54) ANTIBACTERIAL COMPOUNDS

(71) Applicant: Janssen Sciences Ireland UC, Little Island (IE)

(72) Inventors: Jérôme Émile Georges Guillemont, Andé (FR); Magali Madeleine Simone Motte, Louviers (FR); Pierre Jean-Marie Bernard Rabiosson, Rosieres (BE); Abdellah Tahri, Anderlecht (BE)

(73) Assignee: Janssen Sciences Ireland UC, Little Island (IE)

( * ) Notice: Subject to any disclaimer, the term of this patent is extended or adjusted under 35 U.S.C. 154(b) by 0 days.

(21) Appl. No.: 16/848,337

(22) Filed: Apr. 14, 2020

(65) Prior Publication Data

US 2020/0239434 A1 Jul. 30, 2020

Related U.S. Application Data

(60) Continuation of application No. 16/460,334, filed on Jul. 2, 2019, now abandoned, which is a division of application No. 15/736,375, filed as application No. PCT/EP2016/065499 on Jul. 1, 2016, now Pat. No. 10,364,232.

(30) Foreign Application Priority Data

Jul. 2, 2015  (EP) .................................... 15174936
Jun. 16, 2016 (EP) .................................... 16174713
Jun. 16, 2016 (EP) .................................... 16174718

(51) Int. Cl.
| | | |
|---|---|---|
| C07D 401/12 | (2006.01) |
| C07D 487/10 | (2006.01) |
| C07D 401/14 | (2006.01) |
| A61K 31/519 | (2006.01) |
| A61K 31/429 | (2006.01) |
| C07D 403/12 | (2006.01) |
| C07D 487/04 | (2006.01) |
| C07D 513/04 | (2006.01) |
| C07D 519/00 | (2006.01) |
| A61K 45/06 | (2006.01) |
| A61K 31/404 | (2006.01) |
| A61K 31/437 | (2006.01) |
| A61K 31/438 | (2006.01) |
| A61K 31/444 | (2006.01) |
| A61K 31/4745 | (2006.01) |
| A61K 31/496 | (2006.01) |
| A61K 31/4985 | (2006.01) |
| C07D 471/04 | (2006.01) |
| A61P 31/04 | (2006.01) |
| A61K 31/4709 | (2006.01) |

(Continued)

(52) U.S. Cl.
CPC .......... *C07D 401/12* (2013.01); *A61K 31/404* (2013.01); *A61K 31/429* (2013.01); *A61K 31/437* (2013.01); *A61K 31/438* (2013.01); *A61K 31/444* (2013.01); *A61K 31/4709* (2013.01); *A61K 31/4745* (2013.01); *A61K 31/496* (2013.01); *A61K 31/498* (2013.01); *A61K 31/4985* (2013.01); *A61K 31/519* (2013.01); *A61K 45/06* (2013.01); *A61P 31/04* (2018.01); *A61P 31/06* (2018.01); *C07D 401/14* (2013.01); *C07D 403/12* (2013.01); *C07D 471/04* (2013.01); *C07D 487/04* (2013.01); *C07D 487/10* (2013.01); *C07D 513/04* (2013.01); *C07D 519/00* (2013.01)

(58) Field of Classification Search
CPC .. C07D 401/12; C07D 487/10; C07D 401/14; C07D 519/00; A61K 31/519; A61K 31/4709; A61K 31/429
USPC ......................................................... 514/279
See application file for complete search history.

(56) References Cited

U.S. PATENT DOCUMENTS

| | | | |
|---|---|---|---|
| 6,090,820 A | 7/2000 | Barbachyn et al. | |
| 8,304,419 B2 * | 11/2012 | Chong .................. | C07C 311/29 514/263.1 |

(Continued)

FOREIGN PATENT DOCUMENTS

| | | |
|---|---|---|
| JP | 2011046745 | 3/2011 |
| KR | 1999/008399 | 1/1999 |

(Continued)

OTHER PUBLICATIONS

International Search Report for PCT/EP2016/065503 dated Aug. 12, 2016.

(Continued)

*Primary Examiner* — Niloofar Rahmani
(74) *Attorney, Agent, or Firm* — Sofia Kopelevich

(57) ABSTRACT

The present invention relates to the following compounds

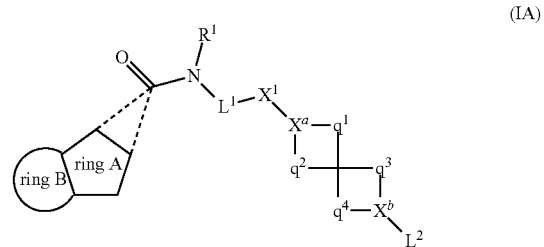

(IA)

wherein the integers are as defined in the description, and where the compounds may be useful as medicaments, for instance for use in the treatment of tuberculosis.

14 Claims, No Drawings

(51) Int. Cl.
A61K 31/498 (2006.01)
A61P 31/06 (2006.01)

(56) References Cited

U.S. PATENT DOCUMENTS

| | | | |
|---|---|---|---|
| 9,029,389 | B2 | 5/2015 | No et al. |
| 10,155,756 | B2 | 12/2018 | Lu et al. |
| 2011/0183342 | A1 | 7/2011 | Lewinsohn et al. |
| 2014/0073622 | A1 | 3/2014 | Soneda et al. |
| 2016/0318925 | A1 | 11/2016 | Miller et al. |
| 2017/0313697 | A1 | 11/2017 | Lu et al. |

FOREIGN PATENT DOCUMENTS

| | | |
|---|---|---|
| KR | 2014/0011017 | 1/2014 |
| KR | 2014/0065902 | 5/2014 |
| KR | 2015/0060224 | 6/2015 |
| MA | 27360 | 6/2005 |
| WO | WO 1996/15130 | 5/1996 |
| WO | WO 2004/011436 | 2/2004 |
| WO | WO 2005/012292 | 2/2005 |
| WO | WO 2008/082490 | 7/2008 |
| WO | WO 2009/120789 | 10/2009 |
| WO | WO 2010/078408 | 8/2010 |
| WO | WO 2011/057145 | 5/2011 |
| WO | WO 2011/113606 | 9/2011 |
| WO | WO 2013/033070 | 3/2013 |
| WO | WO 2013/033167 | 3/2013 |
| WO | WO 2013/127269 | 9/2013 |
| WO | WO 2014/015167 | 1/2014 |
| WO | WO 2015/014993 | 2/2015 |
| WO | WO 2016/062151 | 4/2016 |
| WO | WO 2016/073524 | 5/2016 |
| WO | WO 2017/001660 | 1/2017 |
| WO | WO 2017/001661 | 1/2017 |
| WO | WO 2017/216281 | 12/2017 |
| WO | WO 2017/216283 | 12/2017 |
| WO | WO 2018/158280 | 9/2018 |

OTHER PUBLICATIONS

International Search Report for PCT/EP2017/064652 dated Jul. 21, 2017.
International Search Report for PCT/EP2017/064654 dated Jul. 21, 2017.
International Search Report for PCT/EP2016/065499 dated Sep. 9, 2016.
International Search Report for PCT/EP2018/054860 dated May 28, 2018.
Bundegaard, H. "Design of Prodrugs" p. 1-92, Elesevier, New York-Oxford (1985).
Cihan-Üstündag et al, Molecular Diversity, 2012, vol. 16 (3), pp. 525-539
Database Registry Chemical Abstract Service, RN 1783117-90-7; Jun. 18, 2015, XP 055221200.
Database Registry Chemical Abstract Service, RN 1156922-31-4; Jun. 14, 2009, XP055221197.
Database Registry Chemical Abstract Service, RN 1409441-72-0; Dec. 2, 2012, XP 055221191.
Database Registry Chemical Abstract Service, RN 1638404-01-9; Dec. 10, 2014, XP055221179.
Database Registry Chemical Abstract Service, RN 1394533-85-7; Sep. 18, 2012, XP 055221174.
Database Registry Chemical Abstract Service, RN 1638474-30-2; Dec. 11, 2014, XP055221208.
Güzel et al, General Papers Arkivoc 2006, xii, pp. 98-110.
Kang et al., J. Medicinal Chemistry, 2014, 57 (12), pp. 5293-5305.
Moraski et al, ACS Medicinal, Chemistry Letters, vol. 4, No. 7, pp. 675-679, 2013.
Moraski et al. ACS Infectious, Diseases, vol. 1, No. 2, pp. 85-90, 2015.
Ollinger et al, Plos One, vol. 8, No. 4, pp. e60531, 2013.
Pethe et al "Discovery of Q203, a potent clinical candidate for the treatment of tuberculosis", Nature Medicine, 19, 1157-1160 (2013).
Tang et al, ACS Medicinal Chemistry, Letters, vol. 6, No. 7, pp. 814-818, 2015.
Tester, R. et al., Bioorganic and Medicinal Chemistry Letters 20 (2010) 2560-2563.
Tiwari et al., ACS Med Chem Lett, 2014, vol. 5, pp. 587-591.
CAS Registry No. 1831341-34-4; STN entry date: Dec. 17, 2015; 2H-Pyrazolo[4,3-c]pyridine-3-carboxamide, N-[[4-(cyclohexylmethylamino)phenyl]methyl]-4,5,6,7-tetrahxdro-, hydrochloride (1:1), (CA Index Name).
CAS Registry No. 1831341-33-3; STN entry date: Dec. 17, 2015; 2H-Pyrazolo[4,3-c]pyridine-3-carboxamide, N-[[4-(cyclohexylmethylamino)phenyl]methyl]-4,5,6,7-tetrahydro-, (CA Index Name).
CAS Registry No. 1625238-97-2; STN entry date: Sep. 24, 2014; Pyrazolo[1,5-a]pyrimidine-3-carboxamide, N-[[4-(cyclohexylmethylamino)phenyl]methyl]-2-methyl-, (CA INDEX NAME).
CAS Registry No. 1320875-52-2; STN entry date: Aug. 21, 2011; Pyrazolo[1,5-a]pyrimidine-3-carboxamide, N-[[4-(cyclohexylmethylamino)phenyl]methyl]-5,7-dimethyl-, (CA Index Name).
CAS Registry No. 1278717-74-0; STN entry date: Apr. 13, 2011; Pyrazolo[1,5-a]pyrimidine-3-carboxamide, N-[[4-(cyclohexylmethylamino)phenyl]methyl]-2,5,7-trimethyl-, (CA Index Name).
Chetty et al., "Recent advancements in the development of antituberculosis drugs", Bioorganic & Medicinal Chemistry Letters, Pergamon, Amsterdam, NL, vol. 27, No. 3, Nov. 29, 2016 (Nov. 29, 2016), pp. 370-386.
CAS Registry No. 1299681-23-4; STN entry date: May 24, 2011; Furo [2, 3-d) pyrimidine-5-carboxamide, N-[[4-(cyclohexylmethylamino)phenyl]methyl}-3,4-dihydro-6-methyl-4-oxo-furo [2, 3-d] pyrimidine-5-carboxamide.
CAS Registry No. 1289433-56-2; STN entry date: May 3, 2011; Furo [2, 3-d] pyrimidine-5-carboxamide, N-[[4-(cyclohexylmethylamino)phenyl]methyl]-3,4-dihydro-3,6-dimethyl-4-oxo-furo [2, 3-d] pyrimidine-5-carboxamide.
Gualano G et al., Infectious Disease Reports, 2016, vol. 8 (2), pp. 43-49.
Lamprecht D et al., Nature Communications, vol. 7 (1), pp. 1-14.
Zhang et al., Microbiological Spectrum, Mechanisms of Pyrazinamide Action and Resistance, vol. 2 issue 4, pp. 1-12.
Zumla A et al., The Lancet Respiratory Medicine, 2015, vol. 3(3), pp. 220-234.

* cited by examiner

ANTIBACTERIAL COMPOUNDS

CROSS REFERENCE TO RELATED APPLICATIONS

This application is a Continuation of application Ser. No. 16/460,334 filed on Jul. 2, 2019, which is a Division of application Ser. No. 15/736,375, filed on Dec. 14, 2017, now U.S. Pat. No. 10,364,232, filed as Application No. PCT/EP2016/065499 on Jul. 1, 2016, the entire disclosures of which are hereby incorporated in their entirety.

The present invention relates to novel compounds. The invention also relates to such compounds for use as a pharmaceutical and further for the use in the treatment of bacterial diseases, including diseases caused by pathogenic mycobacteria such as *Mycobacterium tuberculosis*. Such compounds may work by interfering with ATP synthase in *M. tuberculosis*, with the inhibition of cytochrome $bc_1$ activity as the primary mode of action.

Hence, primarily, such compounds are antitubercular agents.

BACKGROUND OF THE INVENTION

*Mycobacterium tuberculosis* is the causative agent of tuberculosis (TB), a serious and potentially fatal infection with a world-wide distribution. Estimates from the World Health Organization indicate that more than 8 million people contract TB each year, and 2 million people die from tuberculosis yearly. In the last decade, TB cases have grown 20% worldwide with the highest burden in the most impoverished communities. If these trends continue, TB incidence will increase by 41% in the next twenty years. Fifty years since the introduction of an effective chemotherapy, TB remains after AIDS, the leading infectious cause of adult mortality in the world. Complicating the TB epidemic is the rising tide of multi-drug-resistant strains, and the deadly symbiosis with HIV. People who are HIV-positive and infected with TB are 30 times more likely to develop active TB than people who are HIV-negative and TB is responsible for the death of one out of every three people with HIV/AIDS worldwide.

Existing approaches to treatment of tuberculosis all involve the combination of multiple agents. For example, the regimen recommended by the U.S. Public Health Service is a combination of isoniazid, rifampicin and pyrazinamide for two months, followed by isoniazid and rifampicin alone for a further four months. These drugs are continued for a further seven months in patients infected with HIV. For patients infected with multi-drug resistant strains of *M. tuberculosis*, agents such as ethambutol, streptomycin, kanamycin, amikacin, capreomycin, ethionamide, cycloserine, ciprofoxacin and ofloxacin are added to the combination therapies. There exists no single agent that is effective in the clinical treatment of tuberculosis, nor any combination of agents that offers the possibility of therapy of less than six months' duration.

There is a high medical need for new drugs that improve current treatment by enabling regimens that facilitate patient and provider compliance. Shorter regimens and those that require less supervision are the best way to achieve this. Most of the benefit from treatment comes in the first 2 months, during the intensive, or bactericidal, phase when four drugs are given together; the bacterial burden is greatly reduced, and patients become noninfectious. The 4- to 6-month continuation, or sterilizing, phase is required to eliminate persisting bacilli and to minimize the risk of relapse. A potent sterilizing drug that shortens treatment to 2 months or less would be extremely beneficial. Drugs that facilitate compliance by requiring less intensive supervision also are needed. Obviously, a compound that reduces both the total length of treatment and the frequency of drug administration would provide the greatest benefit.

Complicating the TB epidemic is the increasing incidence of multi-drug-resistant strains or MDR-TB. Up to four percent of all cases worldwide are considered MDR-TB—those resistant to the most effective drugs of the four-drug standard, isoniazid and rifampin. MDR-TB is lethal when untreated and cannot be adequately treated through the standard therapy, so treatment requires up to 2 years of "second-line" drugs. These drugs are often toxic, expensive and marginally effective. In the absence of an effective therapy, infectious MDR-TB patients continue to spread the disease, producing new infections with MDR-TB strains. There is a high medical need for a new drug with a new mechanism of action, which is likely to demonstrate activity against drug resistant, in particular MDR strains.

The term "drug resistant" as used hereinbefore or hereinafter is a term well understood by the person skilled in microbiology. A drug resistant *Mycobacterium* is a *Mycobacterium* which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs. MDR tuberculosis is a specific form of drug resistant tuberculosis due to a bacterium resistant to at least isoniazid and rifampicin (with or without resistance to other drugs), which are at present the two most powerful anti-TB drugs. Thus, whenever used hereinbefore or hereinafter "drug resistant" includes multi drug resistant.

Another factor in the control of the TB epidemic is the problem of latent TB. In spite of decades of tuberculosis (TB) control programs, about 2 billion people are infected by *M. tuberculosis*, though asymptomatically. About 10% of these individuals are at risk of developing active TB during their lifespan. The global epidemic of TB is fuelled by infection of HIV patients with TB and rise of multi-drug resistant TB strains (MDR-TB). The reactivation of latent TB is a high risk factor for disease development and accounts for 32% deaths in HIV infected individuals. To control TB epidemic, the need is to discover new drugs that can kill dormant or latent bacilli. The dormant TB can get reactivated to cause disease by several factors like suppression of host immunity by use of immunosuppressive agents like antibodies against tumor necrosis factor α or interferon-γ. In case of HIV positive patients the only prophylactic treatment available for latent TB is two-three months regimens of rifampicin, pyrazinamide. The efficacy of the treatment regime is still not clear and furthermore the length of the treatments is an important constrain in resource-limited environments. Hence there is a drastic need to identify new drugs, which can act as chemoprophylatic agents for individuals harboring latent TB bacilli.

The tubercle bacilli enter healthy individuals by inhalation; they are phagocytosed by the alveolar macrophages of the lungs. This leads to potent immune response and formation of granulomas, which consist of macrophages infected with *M. tuberculosis* surrounded by T cells. After a period of 6-8 weeks the host immune response cause death of infected cells by necrosis and accumulation of caseous material with certain extracellular bacilli, surrounded by macrophages, epitheloid cells and layers of lymphoid tissue at the periphery. In case of healthy individuals, most of the mycobacteria are killed in these environments but a small proportion of bacilli still survive and are thought to exist in a non-replicating, hypometabolic state and are tolerant to killing by anti-TB drugs like isoniazid. These bacilli can remain in the altered physiological environments even for individual's lifetime without showing any clinical symptoms of disease. However, in 10% of the cases these latent bacilli may reactivate to cause disease. One of the hypothesis about development of these persistent bacteria is pathophysiological environment in human lesions namely, reduced oxygen tension, nutrient limitation, and acidic pH. These factors have been postulated to render these bacteria phenotypically tolerant to major anti-mycobacterial drugs.

In addition to the management of the TB epidemic, there is the emerging problem of resistance to first-line antibiotic agents. Some important examples include penicillin-resistant *Streptococcus pneumoniae*, vancomycin-resistant enterococci, methicillin-resistant *Staphylococcus aureus*, multi-resistant salmonellae.

The consequences of resistance to antibiotic agents are severe. Infections caused by resistant microbes fail to respond to treatment, resulting in prolonged illness and greater risk of death. Treatment failures also lead to longer periods of infectivity, which increase the numbers of infected people moving in the community and thus exposing the general population to the risk of contracting a resistant strain infection.

Hospitals are a critical component of the antimicrobial resistance problem worldwide. The combination of highly susceptible patients, intensive and prolonged antimicrobial use, and cross-infection has resulted in infections with highly resistant bacterial pathogens.

Self-medication with antimicrobials is another major factor contributing to resistance. Self-medicated antimicrobials may be unnecessary, are often inadequately dosed, or may not contain adequate amounts of active drug.

Patient compliance with recommended treatment is another major problem. Patients forget to take medication, interrupt their treatment when they begin to feel better, or may be unable to afford a full course, thereby creating an ideal environment for microbes to adapt rather than be killed.

Because of the emerging resistance to multiple antibiotics, physicians are confronted with infections for which there is no effective therapy. The morbidity, mortality, and financial costs of such infections impose an increasing burden for health care systems worldwide.

Therefore, there is a high need for new compounds to treat bacterial infections, especially mycobacterial infections including drug resistant and latent mycobacterial infections, and also other bacterial infections especially those caused by resistant bacterial strains.

Anti-infective compounds for treating tuberculosis have been disclosed in e.g. international patent application WO 2011/113606. Such a document is concerned with compounds that would prevent *M. tuberculosis* multiplication inside the host macrophage and relates to compounds with a bicyclic core, imidazopyridines, which are linked (e.g. via an amido moiety) to e.g. an optionally substituted benzyl group.

International patent application WO 2014/015167 also discloses compounds that are disclosed as being of potential use in the treatment of tuberculosis. Such compounds disclosed herein have a bicycle (a 5,5-fused bicycle) as an essential element, which is substituted by a linker group (e.g. an amido group), which itself may be attached to another bicycle or aromatic group. Such compounds in this document do not contain a series of more than three rings.

Journal article *Nature Medicine*, 19, 1157-1160 (2013) by Pethe et al "Discovery of Q203, a potent clinical candidate for the treatment of tuberculosis" identifies a specific compound that was tested against *M. tuberculosis*. This compound Q203 is depicted below.

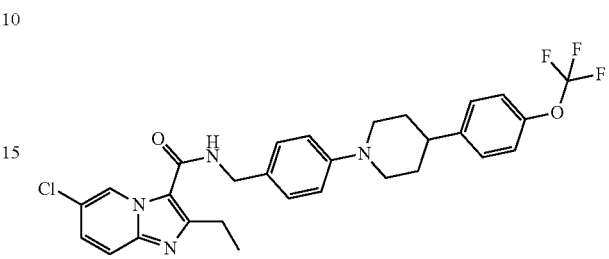

This clinical candidates is also discussed in journal article, *J. Medicinal Chemistry*, 2014, 57 (12), pp 5293-5305. It is stated to have activity against MDR tuberculosis, and have activity against the strain *M. tuberculosis* H37Rv at a $MIC_{50}$ of 0.28 nM inside macrophages. Positive control data (using known anti-TB compounds bedaquiline, isoniazid and moxifloxacin) are also reported. This document also suggests a mode of action, based on studies with mutants. It postulates that it acts by interfering with ATP synthase in *M. tuberculosis*, and that the inhibition of cytochrome $bc_1$ activity is the primary mode of action. Cytochrome $bc_1$ is an essential component of the electron transport chain required for ATP synthesis. It appeared that Q203 was highly active against both replicating and non-replicating bacteria.

International patent application WO 2015/014993 also discloses compounds as having activity against *M. tuberculosis*. International patent applications WO 2013/033070 and WO 2013/033167 disclose various compounds as kinase modulators.

The purpose of the present invention is to provide compounds for use in the treatment of bacterial diseases, particularly those diseases caused by pathogenic bacteria such as *Mycobacterium tuberculosis* (including the latent disease and including drug resistant *M. tuberculosis* strains). Such compounds may also be novel and may act by interfering with ATP synthase in *M. tuberculosis*, with the inhibition of cytochrome $bc_1$ activity being considered the primary mode of action.

SUMMARY OF THE INVENTION

There is now provided a compound of formula (I)

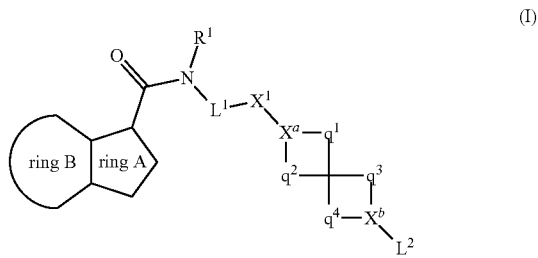

wherein
R$^1$ represents C$_{1-6}$ alkyl or hydrogen;
L$^1$ represents a linker group —C(R$^a$)(R$^b$)— (or is not present);
X$^1$ represents an optional aromatic linker group;
R$^a$ and R$^b$ independently represent hydrogen or C$_{1-6}$ alkyl (optionally substituted by one or more fluoro atoms);
X$^a$ represents C(R$^c$) or N;
X$^b$ represents C(R$^d$), N, O (in which case L$^2$ is not present) or C=O (in which case L$^2$ is also not present);
R$^c$ and R$^d$ independently represent H or —OR$^e$ (wherein R$^e$ represents H or C$_{1-6}$ alkyl optionally substituted by one or more fluoro atoms);
q$^1$ represents —X$^c$—(CH$_2$)$_{n1}$—X$^d$—;
n1 represents 0, 1 or 2;
q$^2$ represents —X$^e$—(CH$_2$)$_{n2}$—X$^f$—;
n2 represents 0, 1 or 2, but wherein n1 and n2 do not both represent 0;
X$^c$ (which is attached to X$^a$) is either not present, or, when X$^a$ represents CH, then X$^c$ may represent —O—, —NH— or —S—;
X$^d$ is either not present, or, when n1 represents 2 or when X$^c$ is not present, X$^e$ represents C(R$^c$) and n1 represents 1, then X$^d$ may also represent —O—, —NH— or —S—;
X$^e$ and X$^f$ independently are either not present, or may independently represent —O—, —NH— or —S—, provided that the aforementioned heteroatoms are not directly attached to or α to another heteroatom;
q$^3$ represents —X$^g$—(CH$_2$)$_{n3}$—X$^h$—;
q$^4$ represents —X$^i$—(CH$_2$)$_{n4}$—X$^j$—;
n3 represents 0, 1 or 2;
n4 represents 0, 1 or 2, but wherein n3 and n4 do not both represent 0;
X$^g$, X$^h$, X$^i$ and X$^j$ independently are either not present, or may represent —O—, —NH— or —S—, provided that the aforementioned heteroatoms are not directly attached to or α to another heteroatom;
when X$^b$ represents O or C=O, then L$^2$ is not present;
when X$^b$ represents C(R$^d$) (e.g. CH) or N, then L$^2$ may represent hydrogen, halo, —OR$^f$, C$_{1-6}$ alkyl (optionally substituted by one or more halo, e.g. fluoro atoms) or an aromatic group (optionally substituted by one or more substituents selected from halo, C$_{1-6}$ alkyl (itself optionally substituted by one or more substituents selected from fluoro, —CF$_3$ and/or —SF$_5$), —OC$_{1-6}$alkyl (itself optionally substituted by one or more fluoro atoms), —O-phenyl (itself optionally substituted by halo, C$_{1-6}$alkyl, C$_{1-6}$fluoroalkyl and/or —OC$_{1-6}$alkyl) or —SF$_5$);
R$^f$ represents hydrogen or C$_{1-6}$ alkyl (optionally substituted by one or more fluoro); ring A is a 5-membered aromatic ring containing at least one heteroatom (preferably containing at least one nitrogen atom);
ring B is a 5- or 6-membered ring, which may be aromatic or non-aromatic, optionally containing one to four heteroatoms (preferably selected from nitrogen, oxygen and sulfur);
either ring A and/or ring B may be optionally substituted by one or more substituents selected from: halo, C$_{1-6}$ alkyl (optionally substituted by one or more halo, e.g. fluoro atoms) and/or —OC$_{1-6}$alkyl (itself optionally substituted by one or more fluoro atoms), or a pharmaceutically-acceptable salt thereof;
which compounds may be referred to herein as "compounds of the invention".

In particular, in a major embodiment of the invention, the following compounds of formula (IA) are provided for use in the treatment of tuberculosis:

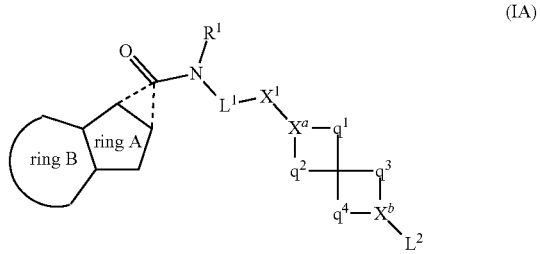

(IA)

wherein
R$^1$ represents C$_{1-6}$ alkyl or hydrogen;
L$^1$ represents a linker group —C(R$^a$)(R$^b$)—;
X$^1$ represents an optional carbocyclic aromatic linker group (which linker group may itself be optionally substituted by one or more substituents selected from fluoro, —OH, —OC$_{1-6}$ alkyl and C$_{1-6}$ alkyl, wherein the latter two alkyl moieties are themseleves optionally substituted by one or more fluoro atoms);
R$^a$ and R$^b$ independently represent hydrogen or C$_{1-6}$ alkyl (optionally substituted by one or more fluoro atoms);
X represents C(R$^c$) or N;
X$^b$ represents C(R$^d$), N, O (in which case L$^2$ is not present) or C=O (in which case L$^2$ is also not present);
R$^c$ and R$^d$ independently represent H, F or —OR$^e$ (wherein R$^e$ represents H or C$_{1-6}$ alkyl optionally substituted by one or more fluoro atoms), or, R$^d$ and L$^2$ may be linked together to form a 4- to 6-membered cyclic group (i.e. a spiro-cycle), optionally containing one to three heteroatoms;
q$^1$ represents —X$^c$—(CH$_2$)$_{n1}$—X$^d$—;
n1 represents 0, 1 or 2;
q$^2$ represents —X$^e$—(CH$_2$)$_{n2}$—X$^f$—;
n2 represents 0, 1 or 2, but wherein n1 and n2 do not both represent 0;
X$^c$ (which is attached to X$^a$) is either not present, or, when X$^a$ represents CH, then X$^c$ may represent —O—, —NH— or —S—;
X$^d$ is either not present, or, when n1 represents 2 or when X$^c$ is not present, X$^a$ represents C(R$^c$) and n1 represents 1, then X$^d$ may also represent —O—, —NH— or —S—;
X$^e$ and X$^f$ independently are either not present, or may independently represent —O—, —NH— or —S—, provided that the aforementioned heteroatoms are not directly attached to or α to another heteroatom;
q$^3$ represents —X$^g$—(CH$_2$)$_{n3}$—X$^h$—;
q$^4$ represents —X$^i$—(CH$_2$)$_{n4}$—X$^j$—;
n3 represents 0, 1 or 2;
n4 represents 0, 1 or 2, but wherein n3 and n4 do not both represent 0;
X$^g$, X$^h$, X$^i$ and X$^j$ independently are either not present, or may represent —O—, —NH— or —S—, provided that the aforementioned heteroatoms are not directly attached to or α to another heteroatom;
when X$^b$ represents O or C=O, then L$^2$ is not present;
when X$^b$ represents C(R$^d$) (e.g. CH) or N, then L$^2$ may represent hydrogen, halo, —OR$^f$, —C(O)—R$^g$, C$_{1-6}$ alkyl (optionally substituted by one or more halo, e.g. fluoro atoms) or an aromatic group (optionally substituted by one or more substituents selected from halo, C$_{1-6}$ alkyl (itself optionally substituted by one or more substituents selected from fluoro, —CF$_3$ and/or —SF$_5$), —OC$_{1-6}$alkyl (itself optionally substituted by one or more fluoro atoms), —O— phenyl (itself optionally substituted by halo, C$_{1-6}$alkyl, C$_{1-6}$fluoroalkyl and/or —OC$_{1-6}$alkyl) or —SF$_5$);

R$^f$ represents hydrogen, C$_{1-6}$ alkyl (optionally substituted by one or more fluoro) or an aromatic group (itself optionally substituted by one or more substituents selected from halo, C$_{1-6}$alkyl and —OC$_{1-6}$alkyl, where the latter two alkyl moieties may themseleves be optionally substituted by one or more fluoro atoms);

R$^g$ represents hydrogen or C$_{1-6}$alkyl (optionally substituted by one or more substituents selected from fluoro, or —OC$_{1-3}$ alkyl, which latter moiety is also optionally substituted by one or more fluoro atoms) or an aromatic group (optionally substituted by one or more substituents selected from halo, C$_{1-6}$ alkyl or —OC$_{1-6}$alkyl);

ring A may be attached to the requisite amide moiety (i.e. the —C(O)—N(R$^1$)— moiety) via either one of two possible bonds represented by the dotted lines, which bonds are linked to ring A at two different atoms (of that ring);

ring A is a 5-membered aromatic ring containing at least one heteroatom (preferably containing at least one nitrogen atom);

ring B is a 5- or 6-membered ring, which may be aromatic or non-aromatic, optionally containing one to four heteroatoms (preferably selected from nitrogen, oxygen and sulfur); either ring A and/or ring B may be optionally substituted by one or more substituents selected from: halo, C$_{1-6}$ alkyl (optionally substituted by one or more halo, e.g. fluoro atoms) and/or —OC$_{1-6}$alkyl (itself optionally substituted by one or more fluoro atoms), or a pharmaceutically-acceptable salt thereof, which compounds may also be referred to herein as "compounds of the invention".

For instance, compounds of formula (IA) may as described above, may be such that the ring A is linked to the amide moiety via a specific ring atom, as depicted by compounds of formula (I) below:

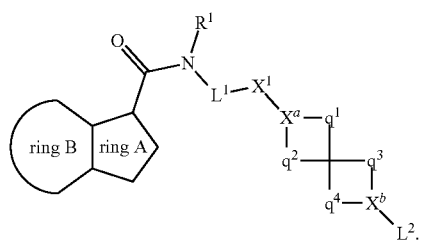

(I)

This embodiment is essentially a graphical depiction of ring A being linked to the requisite amido moiety via a bond represented by one of the dotted lines in formula (IA).

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable acid addition salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

For the purposes of this invention solvates, prodrugs, N-oxides and stereoisomers of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elsevier, New York-Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imineenamine isomerisations. Valence tautomers include interconversions by reorganisation of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^{2}F$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{123}I$, and $^{125}I$. Certain isotopically-labeled compounds of the present invention (e.g., those labeled with $^{3}H$ and $^{14}C$) are useful in compound and for substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the description/Examples hereinbelow, by substituting an isotopically labeled reagent for a non-isotopically labeled reagent.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). Such cycloalkyl groups may be monocyclic or bicyclic and may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group). $C_{3-q}$ cycloalkyl groups (where q is the upper limit of the range) that may be specifically mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double bonds (forming for example a cycloalkenyl group). Substituents may be attached at any point on the cycloalkyl group. Further, where there is a sufficient number (i.e. a minimum of four) such cycloalkyl groups may also be part cyclic.

The term "halo", when used herein, preferably includes fluoro, chloro, bromo and iodo.

Heterocyclic groups when referred to herein may include aromatic or non-aromatic heterocyclic groups, and hence encompass heterocycloalkyl and hetereoaryl. Equally, "aromatic or non-aromatic 5- or 6-membered rings" may be heterocyclic groups (as well as carbocyclic groups) that have 5- or 6-members in the ring.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is between 3 and 20 (e.g. between three and ten, e.g between 3 and 8, such as 5- to 8-). Such heterocycloalkyl groups may also be bridged. Further, such heterocycloalkyl groups may be saturated or unsaturated containing one or more double and/or triple bonds, forming for example a $C_{2-q}$ heterocycloalkenyl (where q is the upper limit of the range) group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, non-aromatic pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N- or S-oxidised form. Heterocycloalkyl mentioned herein may be stated to be specifically monocyclic or bicyclic.

Aromatic groups may be aryl or heteroaryl. Aryl groups that may be mentioned include $C_{6-20}$, such as $C_{6-12}$ (e.g. $C_{6-10}$) aryl groups. Such groups may be monocyclic, bicyclic or tricyclic and have between 6 and 12 (e.g. 6 and 10) ring carbon atoms, in which at least one ring is aromatic. $C_{6-10}$ aryl groups include phenyl, naphthyl and the like, such as 1,2,3,4-tetrahydronaphthyl. The point of attachment of aryl groups may be via any atom of the ring system. For example, when the aryl group is polycyclic the point of attachment may be via atom including an atom of a non-aromatic ring. However, when aryl groups are polycyclic (e.g. bicyclic or tricyclic), they are preferably linked to the rest of the molecule via an aromatic ring. Most preferred aryl groups that may be mentioned herein are "phenyl".

Unless otherwise specified, the term "heteroaryl" when used herein refers to an aromatic group containing one or more heteroatom(s) (e.g. one to four heteroatoms) preferably selected from N, O and S. Heteroaryl groups include those which have between 5 and 20 members (e.g. between 5 and 10) and may be monocyclic, bicyclic or tricyclic, provided that at least one of the rings is aromatic (so forming, for example, a mono-, bi-, or tricyclic heteroaromatic group). When the heteroaryl group is polycyclic the point of attachment may be via any atom including an atom of a non-aromatic ring. However, when heteroaryl groups are polycyclic (e.g. bicyclic or tricyclic), they are preferably linked to the rest of the molecule via an aromatic ring. Heteroaryl groups that may be mentioned include 3,4-dihydro-1H-isoquinolinyl, 1,3-dihydroisoindolyl, 1,3-dihydroisoindolyl (e.g. 3,4-dihydro-1H-isoquinolin-2-yl, 1,3-dihydroisoindol-2-yl, 1,3-dihydroisoindol-2-yl; i.e. heteroaryl groups that are linked via a non-aromatic ring), or, preferably, acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N- or S-oxidised form. Heteroaryl groups mentioned herein may be stated to be specifically monocyclic or bicyclic. When heteroaryl groups are polycyclic in which there is a non-aromatic ring present, then that non-aromatic ring may be substituted by one or more =O group. Most preferred heteroaryl groups that may be mentioned herein are 5- or 6-membered aromatic groups containing 1, 2 or 3 heteroatoms (e.g. preferably selected from nitrogen, oxygen and sulfur).

It may be specifically stated that the heteroaryl group is monocyclic or bicyclic. In the case where it is specified that the heteroaryl is bicyclic, then it may consist of a five-, six- or seven-membered monocyclic ring (e.g. a monocyclic heteroaryl ring) fused with another five-, six- or seven-membered ring (e.g. a monocyclic aryl or heteroaryl ring).

Heteroatoms that may be mentioned include phosphorus, silicon, boron and, preferably, oxygen, nitrogen and sulfur.

When "aromatic" groups are referred to herein, they may be aryl or heteroaryl. When "aromatic linker groups" are referred to herein, they may be aryl or heteroaryl, as defined herein, are preferably monocyclic (but may be polycyclic) and attached to the remainder of the molecule via any possible atoms of that linker group. However, when, specifically carbocylic aromatic linker groups are referred to, then such aromatic groups may not contain a heteroatom, i.e. they may be aryl (but not heteroaryl).

For the avoidance of doubt, where it is stated herein that a group may be substituted by one or more substituents (e.g. selected from $C_{1-6}$ alkyl), then those substituents (e.g. alkyl groups) are independent of one another. That is, such groups may be substituted with the same substituent (e.g. same alkyl substituent) or different (e.g. alkyl) substituents.

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

As mentioned hereinbefore, in a major embodiment of the invention the compounds of the invention are those in which:

L represents a linker group —C($R^a$)($R^b$)—; and $X^1$ represents an optional carbocyclic aromatic linker group; and the compound of formula (IA) represents a compound of formula (I).

Preferred compounds, or other aspects or embodiments, described hereinbelow may relate to such a major embodiment of the invention (in which case inconsistent definitions of $L^1$ or $X^1$ are redundant), where such definitions of $L^1$ and/or $X^1$ may be taken in combination with one or more other features or aspects (e.g. those described hereinbelow, such as some preferred aspects described).

Preferred compounds of the invention include those in which:

when $X^a$ represents C($R^c$), then it is preferably CH;

$X^a$ represents CH or N;

$R^e$ preferably represents hydrogen;

$R^c$ and $R^d$ independently (and preferably) represent H;

$L^1$ preferably represents a linker group as defined by —C($R^a$)($R^b$)— (for the major embodiment of the invention, this linker group is essential);

$X^1$ may not be present, but preferably represents an aromatic linker group (for the major embodiment of the invention, this linker group, when present, has to be a carbocyclic aromatic linker group);

$X^c$ (which is attached to $X^a$) is either not present, or, when $X^a$ represents CH, then $X^c$ may also represent —O—;

$X^d$ is either not present, or, when n1 represents 2 or when $X^c$ is not present, $X^a$ represents $C(R^c)$ and n1 represents 1, then $X^d$ may also represent —O—;

$X^e$ and $X^f$ independently are either not present, or may independently represent —O—, provided that the aforementioned oxygen atom is not directly attached to or α to another heteroatom;

when $X^c$ and/or $X^d$ represent —O—, —NH— or —S—, it is understood that such heteroatoms may not be attached directly (or α to) to another heteroatom.

More preferred compounds of the invention include those in which:

$R^1$ represents hydrogen;

$R^a$ and $R^b$ independently represent hydrogen;

$L^1$ represents —CH$_2$—;

when $X^1$ represents an aromatic linker group (where the point of attachment may be via any atom of the ring system), that aromatic group may be carbocyclic or heterocyclic, so forming, for example, a phenyl, a 5- or 6-membered monocyclic heteroaryl group or a bicyclic aromatic group (such as a 8- or 10-membered aromatic group, which consists of two separate rings fused with each other, in which each ring is 5- or 6-membered so forming a 6,6-, 5,6- or 5,5-fused bicyclic ring), hence including groups such as phenyl, naphthyl (including fully aromatic naphthyl and 1,2,3,4-tetrahydronaphthyl) and the like, so forming e.g. in particular:

-phenylene- (especially a 1,4-phenylene), e.g.:

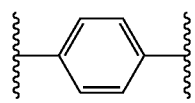

-naphthylene, e.g.:

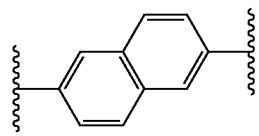

-quinolylene (such as 2-quinolylene), e.g.:

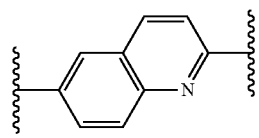 [SMILES: *c1ccc2cc(*)ccc2c1]

Such linker groups that $X^1$ may represent (e.g. phenylene) may be optionally substituted (e.g. by one or more substituents selected from fluoro, CH$_3$, CF$_3$, —OCH$_3$ and —OCF$_3$). In an embodiment such linker groups that $X^1$ may represent are unsubstituted.

In an embodiment (for instance, the major embodiment referred to above) of the invention, the following applies:

$X^1$ represents an optional carbocyclic aromatic linker group, i.e. it may or may not be present;

when $X^1$ is present, then it represents a carbocyclic aromatic linker group, for example a phenyl group or a bicyclic (carbocyclic) aromatic linker group (in which at least one of the rings of the bicycle is aromatic), for instance such that the bicycle consists of two separate rings fused with each other, in which each ring is 5- or 6-membered so forming a 6,6-, 5,6- or 5,5-fused bicyclic ring), hence including groups such as phenyl, naphthyl (including fully aromatic naphthyl and 1,2,3,4-tetrahydronaphthyl) and the like, so forming e.g. in particular:

-phenylene- (especially a 1,4-phenylene), e.g.:

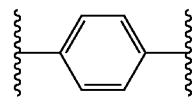 [SMILES: *c1ccc(*)cc1]

-naphthylene e.g.:

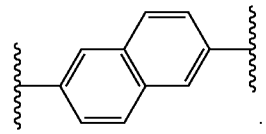 [SMILES: *c1ccc2cc(*)ccc2c1]

In an aspect of the invention, $X^1$, i.e. an aromatic linker group (in an embodiment, a carbocylic aromatic linker group, such as one defined above) is present.

The spiro-cyclic moiety, i.e. the combined $X^a$ and $X^b$- containing ring may be represented as follows:

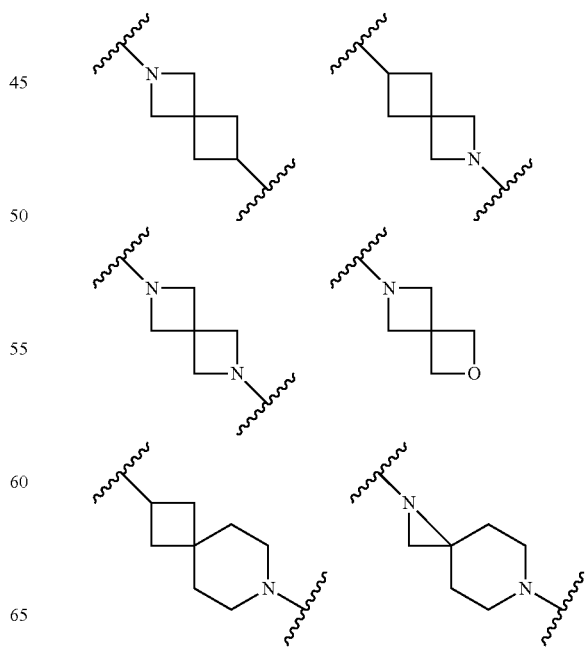

-continued

Other spiro-cyclic moieties that may be mentioned include the following:

Hence, it may be preferred that:
$X^a$ represents N or C(R$^c$) (e.g. CH);
$X^b$ represents N, O, C(R$^c$) (e.g. CH) or C=O;
at least one of $X^a$ and $X^b$ represents N and the other represents C(R$^c$), N or (in the case of $X^b$) O;
it is preferred that both $X^a$ and $X^b$ do not represent C(R$^c$);
$X^c$ is not present or represents —O—;
$X^d$ is not present;
$X^e$ is not present;
$X^f$ is not present;
$X^g$, $X^h$, $X^i$ and $X^j$ independently are not present;
$n^1$ represents 0, 1 or 2;
n2 represents 1 or 2;
n3 represents 1 or 2;
n4 represents 1 or 2;
$L^2$ may represent hydrogen, halo (e.g. fluoro), —OR$^f$, or an aromatic group (optionally substituted by one or two (e.g. one) substituent(s) selected from —OC$_{1-6}$alkyl (itself optionally substituted by one or more fluoro atoms) or —SF$_5$, or, alternatively by halo, e.g. fluoro);
more specifically, $L^2$ may represent hydrogen, halo (e.g. fluoro), —OH, phenyl (optionally substituted by —OCF$_3$, —SF$_5$ and/or alternatively by —OCH$_3$ or fluoro; in a further embodiment, other substituents that may be mentioned include —SCF$_3$), pyridyl (e.g. 3-pyridyl, which is preferably unsubstituted or, alternatively, 2- or 4-pyridyl, which is also preferably unsubstituted), triazolyl or thiazolyl;

alternatively, other $L^2$ groups that may be mentioned include —OR$^f$, for instance in which R$^f$ represents C$_{1-6}$alkyl (e.g. methyl, —CH$_3$) or an aryl group (e.g. phenyl) optionally substituted by C$_{1-3}$alkyl (itself optionally substituted by one or more fluoro atoms, so forming e.g. a —CF$_3$ group) or $L^2$ may represent —C(O)—R$^g$, in which R$^g$ represents hydrogen or C$_{1-3}$alkyl (e.g. methyl; optionally substituted by fluoro so forming e.g. a —CF$_3$ group) or phenyl (preferably unsubstituted); hence $L^2$ may also represent —C(O)H, —C(O)CH$_3$, —C(O)CF$_3$, —C(O)-phenyl, —OCH$_3$ or —O-phenyl, i.e. phenoxy, which latter group may be substituted by a —CF$_3$ moiety (or $L^2$ and R$^d$ may be linked together to form a cyclic group).

In a further embodiment, yet other $L^2$ groups that may additionally be mentioned (e.g. when attached to nitrogen, when $X^b$ is N) include —S(O)$_2$—C$_{1-6}$alkyl groups optionally substituted by one or more fluoro atoms (e.g. forming —S(O)$_2$CF$_3$).

In a further embodiment, $X^b$ may also represent S, S(O) or, in a preferred embodiment, S(O)$_2$.

It is further preferred that:
$q^1$ represents —CH$_2$—, —CH$_2$—CH$_2$—, —O—CH$_2$— or "-" (i.e. in the latter case, n1=0, $X^c$ is not present and $X^d$ is not present);
$q^2$ represents —CH$_2$— or —CH$_2$—CH$_2$—;
$q^3$ represents —CH$_2$— or —CH$_2$—CH$_2$—;
$q^4$ represents —CH$_2$— or —CH$_2$—CH$_2$—.

It is preferred that compounds of the invention comprise:
ring A, which is an aromatic ring containing at least one to three (e.g. one or two) heteroatoms, preferably contains at least one nitrogen atom;
ring B is more preferably also an aromatic ring (e.g. a 5- or especially a 6-membered aromatic ring), preferably containing at least one nitrogen atom.

It is preferred that Ring A of the compounds of the invention are represented as follows:

Other preferred ring A moieties include:

Monocyclic heteroaryl groups that may be mentioned include 5- or 6-membered rings containing one to four heteroatoms (preferably selected from nitrogen, oxygen and sulfur). It is preferred that Ring B of the compounds of the invention are represented as follows:

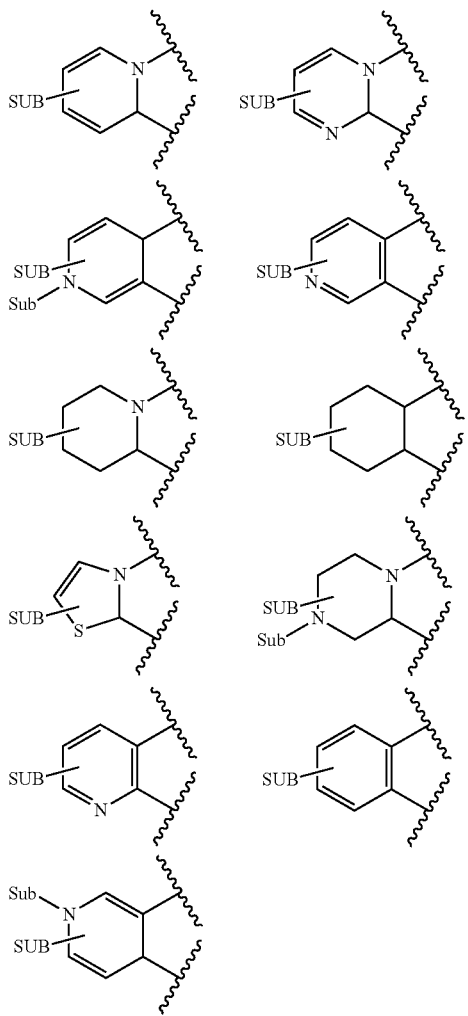

where "SUB" may be a relevant optional substituent (or more than when relevant substituent, where possible) on a carbon atom or, where possible, on a heteroatom e.g. on a NH, thus replacing the H.

Other preferred "Ring B" moieties include:

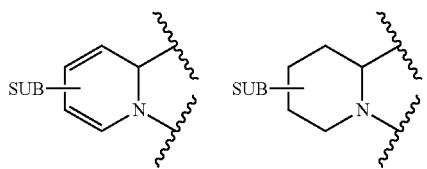

Preferred substituents (when present; e.g such optional substituents may be absent or there may be one) on ring B include $C_{1-3}$ alkyl (e.g. methyl) or halo (e.g. bromo or, more preferably, chloro). Other preferred substituents on ring B include —$OC_{1-6}$alkyl (e.g. —$OC_{1-3}$alkyl, such as —$OCH_3$).

Preferred substituents (when present; preferably, there may be one or two substituents) on ring A include $C_{1-3}$ alkyl (e.g. methyl or ethyl). When $L^2$ represents an aromatic group (e.g. phenyl or pyridyl) and such groups are substituted, preferred substituents include halo and especially —$OC_{1-3}$ alkyl (e.g. —O-methyl), where the latter is substituted by fluoro, so forming for example a —$OCF_3$ group.

The combined ring systems, i.e. Ring A and Ring B may be represented as follows:

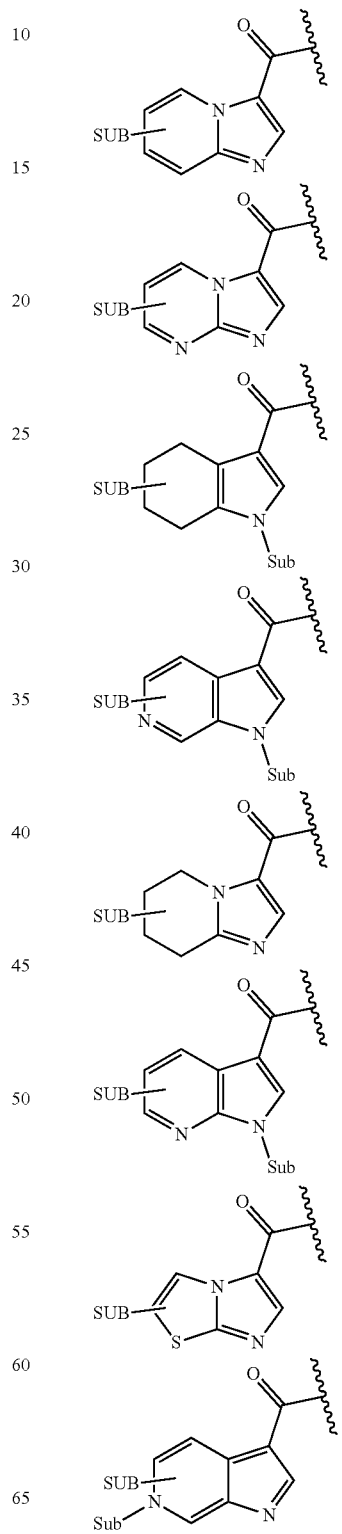

-continued

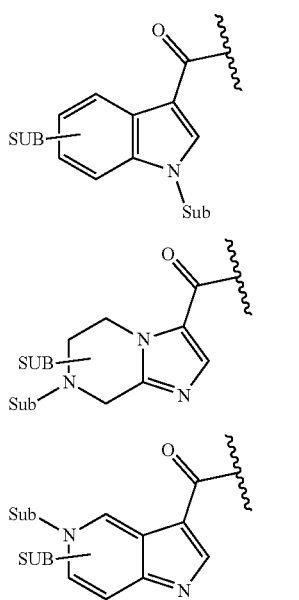

where "SUB" represents one or more possible substituents on the bicycle (i.e. on ring A and/or on ring B) and "Sub" represents a possible optional substituent on the N atom of the bicycle (unsubstituted in this context would mean "NH").

Other combined ring A and ring B systems that may be mentioned include the following:

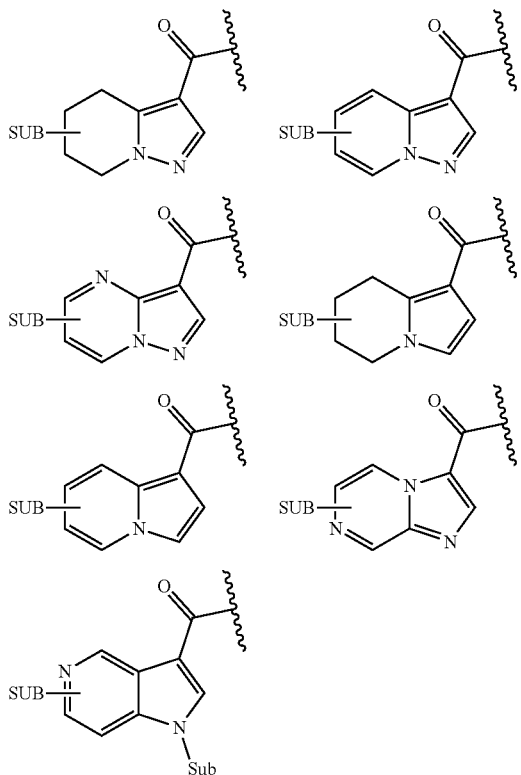

The combined ring A and ring B systems that may be mentioned when ring A is attached to the amido moiety via the "central" atom of the 5-membered A ring include the following:

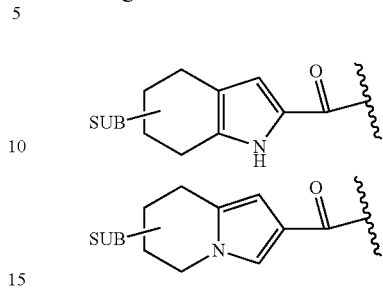

The following compounds of formula (IA) are preferred:

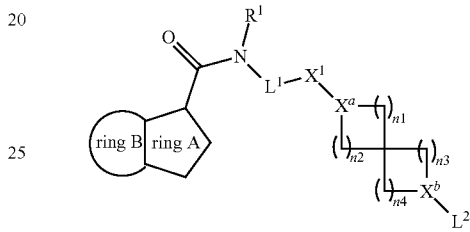

wherein
the integers are as hereinbefore defined, and where, preferably:
n1, n2, n3 and n4 independently represent 1;
at least one of $X^a$ and $X^b$ represents N and the other represents CH or N.

Certain compounds of the invention are mentioned (e.g. hereinbefore) for use in the treatment of tuberculosis. Certain of such compounds mentioned herein may also be novel per se. And certain of such compounds mentioned herein may be novel as medicaments/pharmaceuticals (or novel as a component of a pharmaceutical composition/formulation). Hence, in further aspects of the invention, there is provided the following compounds per se or following compounds for use as pharmaceuticals/medicaments (in the latter case such compounds may be components of a pharmaceutical composition/formulation):

(I) Compounds of formula (IB) as depicted below:

(IB)

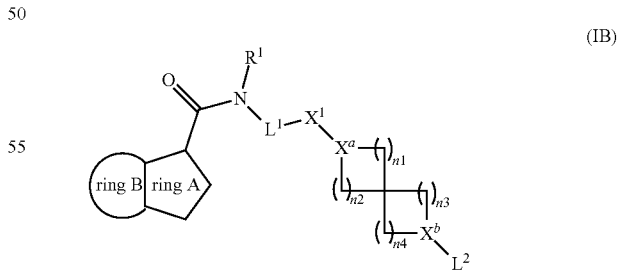

wherein
the integers are as hereinbefore defined, and where, preferably:
n1, n2, n3 and n4 independently represent 1;
at least one of $X^a$ and $X^b$ represents N and the other represents CH or N;

(II) Compounds of formula (IA) as hereinbefore defined and in which:
  $L^1$ represents —$CH_2$—;
  $X^1$ is not present;
  at least one of $X^a$ and $X^b$ represents N and the other represents $C(R^c)$, N or (in the case of $X^b$) O;
  the $X^a$ and $X^b$-containing spiro-cycle 3- to 6-membered ring attached to a 4- to 6-membered ring;
  in one aspect $L^2$ represents an aromatic group (as defined herein) optionally substituted as defined herein, and/or, in another aspect $L^2$ represents —$OR^f$ in which $R^f$ represents an aryl group (as defined herein) optionally substituted as defined herein;
  when $L^2$ represents an (optionally substituted) aromatic group, it may be phenyl or a 5- or 6-membered heterocyclic group (e.g. containing at least one nitrogen atom, so forming a pyridyl, thiazolyl or triazolyl ring; in a major embodiment the heterocyclic group is a pyridyl), where the optional substituents are as defined herein;
  optional substituents on aromatic $L^2$ groups are selected from halo, $C_{1-6}$alkyl, —$CF_3$, —$OC_{1-6}$alkyl and —$OCF_3$;
  when $R^f$ represents an aryl group, then it is preferably phenyl optionally substituted by $C_{1-3}$ alkyl, itself optionally substituted by fluoro);
  ring A and ring B together represent a 8 or 9-membered bicyclic ring (ring A is a 5-membered ring and ring B may be a 5 or 6-membered ring, in which both rings are preferably aromatic) containing at least one nitrogen atom (and in a major embodiment, at least one nitrogen atom that is common to both rings); optional substituents on ring A and ring B are halo, $C_{1-3}$ alkyl and —$OC_{1-3}$alkyl;

(III) Compounds of formula (IA) as hereinbefore defined and in which:
  $L^1$ represents —$CH_2$—;
  $X^1$ represents a carbocyclic aromatic linker group;
  when $X^1$ represents a carbocyclic linker group it represents phenylene (e.g. a 1,4-phenylene) for instance:

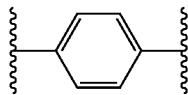

at least one of $X^a$ and $X^b$ represents N and the other represents $C(R^c)$, N or (in the case of $X^b$) O;
  the $X^a$ and $X^b$-containing spiro-cycle 3- to 6-membered ring attached to a 4- to 6-membered ring;
  in one aspect $L^2$ represents an aromatic group (as defined herein) optionally substituted as defined herein, and/or, in another aspect $L^2$ represents —$OR^f$ in which $R^f$ represents an aryl group (as defined herein) optionally substituted as defined herein;
  when $L^2$ represents an (optionally substituted) aromatic group, it may be phenyl or a 5- or 6-membered heterocyclic group (e.g. containing at least one nitrogen atom, so forming a pyridyl, thiazolyl or triazolyl ring; in a major embodiment the heterocyclic group is a pyridyl), where the optional substituents are as defined herein;
  optional substituents on aromatic $L^2$ groups are selected from halo, $C_{1-6}$alkyl, —$CF_3$, —$O_{1-6}$ alkyl and —$OCF_3$;
  when $R^f$ represents an aryl group, then it is preferably phenyl optionally substituted by $C_{1-3}$ alkyl, itself optionally substituted by fluoro); ring A and ring B together represent a 8 or 9-membered bicyclic ring (ring A is a 5-membered ring and ring B may be a 5 or 6-membered ring, in which both rings are preferably aromatic) containing at least one nitrogen atom (and in a major embodiment, at least one nitrogen atom that is common to both rings); optional substituents on ring A and ring B are halo, $C_{1-3}$ alkyl and —$OC_{1-3}$ alkyl;

(IV) Compounds as hereinbefore defined (e.g. at (I), (II) or (III) above) and further in which:
  $q^1$ represents —$CH_2$—, —$CH_2$—$CH_2$—, —O—$CH_2$— or "-" (i.e. in the latter case, n1=0, $X^c$ is not present and $X^d$ is not present);
  $q^2$ represents —$CH_2$— or —$CH_2$—$CH_2$—;
  $q^1$ represents —$CH_2$— or —$CH_2$—$CH_2$—;
  $q^4$ represents —$CH_2$— or —$CH_2$—$CH_2$—;

(V) Compounds as hereinbefore defined (e.g. at (I), (II), (III) or (IV) above) and further in which the $X^a$ and $X^b$-containing rings are represented as defined herein or more particularly as follows:

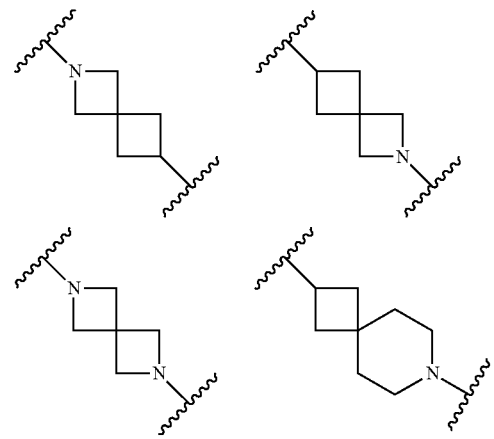

(or any one of the above-mentioned representations); and/or (VI) Compounds as hereinbefore defined (e.g. at (I), (II), (III), (IV) or (V) above) and further in which the ring A and ring B bicycles are represented as defined herein or more particularly as follows:

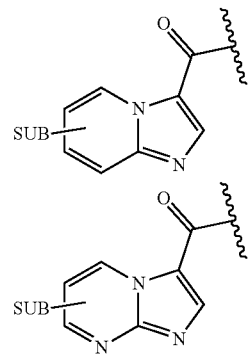

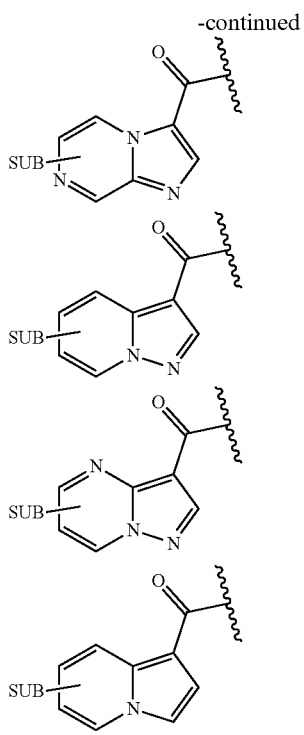

(or any one of the above-mentioned representations).

Pharmacology

The compounds according to the invention have surprisingly been shown to be suitable for the treatment of a bacterial infection including a mycobacterial infection, particularly those diseases caused by pathogenic mycobacteria such as *Mycobacterium tuberculosis* (including the latent and drug resistant form thereof). The present invention thus also relates to compounds of the invention as defined hereinabove, for use as a medicine, in particular for use as a medicine for the treatment of a bacterial infection including a mycobacterial infection.

Such compounds of the invention may act by interfering with ATP synthase in *M. tuberculosis*, with the inhibition of cytochrome $bc_1$ activity being the primary mode of action. Cytochrome $bc_1$ is an essential component of the electron transport chain required for ATP synthesis.

Further, the present invention also relates to the use of a compound of the invention, as well as any of the pharmaceutical compositions thereof as described hereinafter for the manufacture of a medicament for the treatment of a bacterial infection including a mycobacterial infection.

Accordingly, in another aspect, the invention provides a method of treating a patient suffering from, or at risk of, a bacterial infection, including a mycobacterial infection, which comprises administering to the patient a therapeutically effective amount of a compound or pharmaceutical composition according to the invention.

The compounds of the present invention also show activity against resistant bacterial strains.

Whenever used hereinbefore or hereinafter, that the compounds can treat a bacterial infection it is meant that the compounds can treat an infection with one or more bacterial strains.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight, even more preferably from 0.1 to 50% by weight of the active ingredient(s), and, from 1 to 99.95% by weight, more preferably from 30 to 99.9% by weight, even more preferably from 50 to 99.9% by weight of a pharmaceutically acceptable carrier, all percentages being based on the total weight of the composition.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The daily dosage of the compound according to the invention will, of course, vary with the compound employed, the mode of administration, the treatment desired and the mycobacterial disease indicated. However, in general, satisfactory results will be obtained when the compound according to the invention is administered at a daily dosage not exceeding 1 gram, e.g. in the range from 10 to 50 mg/kg body weight.

Given the fact that the compounds of formula (Ia) or Formula (Ib) are active against bacterial infections, the present compounds may be combined with other antibacterial agents in order to effectively combat bacterial infections.

Therefore, the present invention also relates to a combination of (a) a compound according to the invention, and (b) one or more other antibacterial agents.

The present invention also relates to a combination of (a) a compound according to the invention, and (b) one or more other antibacterial agents, for use as a medicine.

The present invention also relates to the use of a combination or pharmaceutical composition as defined directly above for the treatment of a bacterial infection.

A pharmaceutical composition comprising a pharmaceutically acceptable carrier and, as active ingredient, a therapeutically effective amount of (a) a compound according to the invention, and (b) one or more other antibacterial agents, is also comprised by the present invention.

The weight ratio of (a) the compound according to the invention and (b) the other antibacterial agent(s) when given as a combination may be determined by the person skilled in the art. Said ratio and the exact dosage and frequency of administration depends on the particular compound according to the invention and the other antibacterial agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of the invention and another antibacterial agent may range from 1/10 to 10/1, more in particular from 1/5 to 5/1, even more in particular from 1/3 to 3/1.

The compounds according to the invention and the one or more other antibacterial agents may be combined in a single preparation or they may be formulated in separate preparations so that they can be administered simultaneously, separately or sequentially. Thus, the present invention also relates to a product containing (a) a compound according to the invention, and (b) one or more other antibacterial agents, as a combined preparation for simultaneous, separate or sequential use in the treatment of a bacterial infection.

The other antibacterial agents which may be combined with the compounds of the invention are for example antibacterial agents known in the art. For example, the compounds of the invention may be combined with antibacterial agents known to interfere with the respiratory chain of *Mycobacterium tuberculosis*, including for example direct inhibitors of the ATP synthase (e.g. bedaquiline, bedaquiline fumarate or any other compounds that may have be disclosed in the prior art, e.g. compounds disclosed in WO2004/011436), inhibitors of ndh2 (e.g. clofazimine) and inhibitors of cytochrome bd. Additional mycobacterial agents which may be combined with the compounds of the invention are for example rifampicin (=rifampin); isoniazid; pyrazinamide; amikacin; ethionamide; ethambutol; streptomycin; para-aminosalicylic acid; cycloserine; capreomycin; kanamycin; thioacetazone; PA-824; delamanid; quinolones/ fluoroquinolones such as for example moxifloxacin, gatifloxacin, ofloxacin, ciprofloxacin, sparfloxacin; macrolides such as for example clarithromycin, amoxycillin with clavulanic acid; rifamycins; rifabutin; rifapentin; as well as others, which are currently being developed (but may not yet be on the market; see e.g. http://www.newtbdrugs.org/pipeline.php).

General Preparation

The compounds according to the invention can generally be prepared by a succession of steps, each of which may be known to the skilled person or described herein.

EXPERIMENTAL PART

Compounds of formula I may be prepared in accordance with the techniques employed in the examples hereinafter (and those methods know by those skilled in the art), for example by using the following techniques.

Compounds of formula (I) or (IA) in which $X^b$ represents N may be prepared by:

(i) reaction of a compound of formula (II),

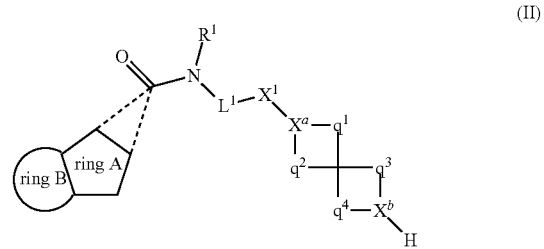

(II)

in which the integers are hereinbefore defined, with a compound of formula (III),

LG$^1$-L$^2$ (III)

wherein L$^2$ is as hereinbefore defined (for instance when L$^2$ is not hydrogen, halo or linked to O or S), and LG$^1$ is a suitable leaving group such as chloro, bromo, iodo or a sulfonate group, which reaction may require specific conditions (e.g. nucleophilic aromatic substitution reaction conditions, such as described herein);

(ii) reaction of a compound of formula (IV), (IV)

wherein the integers are as hereinbefore defined, or a suitable derivative thereof, such as a carboxylic acid ester derivative, with a compound of formula (V)

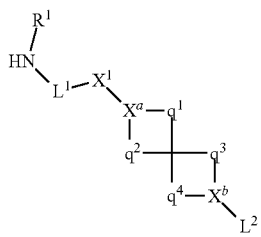
(V)

wherein the integers are as hereinbefore defined, under amide coupling reaction conditions, for example in the presence of a suitable coupling reagent (e.g. 1,1'-carbonyldiimidazole, N,N'-dicyclohexylcarbodiimide, 1-(3-dimethylaminopropyl)-3-ethylcarbodiimide (or hydrochloride thereof) or N,N'-disuccinimidyl carbonate), optionally in the presence of a suitable base (e.g. sodium hydride, sodium bicarbonate, potassium carbonate, pyridine, triethylamine, dimethylaminopyridine, diisopropylamine, sodium hydroxide, potassium tert-butoxide and/or lithium diisopropylamide (or variants thereof) and an appropriate solvent (e.g. tetrahydrofuran, pyridine, toluene, dichloromethane, chloroform, acetonitrile, dimethylformamide, trifluoromethylbenzene, dioxane or triethylamine). Alternatively, the carboxylic acid group of the compound of formula (IV) may first be converted under standard conditions to the corresponding acyl chloride (e.g. in the presence of $POCl_3$, $PCl_5$, $SOCl_2$ or oxalyl chloride), which acyl chloride is then reacted with a compound of formula (V), for example under similar conditions to those mentioned above; (iii) coupling of a compound of formula (VI),

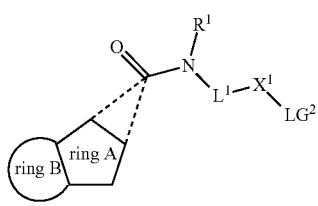
(VI)

wherein the integers are as hereinbefore defined, and $LG^2$ represents a suitable leaving group, such as iodo, bromo, chloro or a sulfonate group (for example a type of group that may be deployed for a coupling), with a compound of formula (VI),

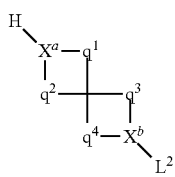
(VII)

wherein the integers are as hereinbefore defined, under standard conditions, for example optionally in the presence of an appropriate metal catalyst (or a salt or complex thereof) such as $Pd(dba)_2$, $Pd(OAc)_2$, Cu, $Cu(OAc)_2$, CuI, $NiCl_2$ or the like, with an optional additive such as $Ph_3P$, X-phos or the like, in the presence of an appropriate base (e.g. t-BuONa, or the like) in a suitable solvent (e.g. dioxane or the like) under reaction conditions known to those skilled in the art;

(iv) coupling of a compound of formula (VIII),

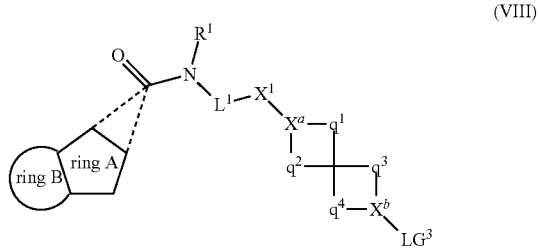
(VIII)

wherein the integers are as hereinbefore defined, and $LG^3$ represents a suitable leaving group as described hereinbefore with respect to $LG^2$ (and may particularly represent chloro, bromo or iodo), with a compound of formula (IX), $$LG^4\text{-}L^2 \qquad (IX)$$

wherein $L^2$ is as hereinbefore defined (for instance when $L^2$ is not hydrogen, halo or linked to O or S), and $LG^4$ is a suitable group such as $-B(OH)_2$, $-B(OR^{wx})_2$ or $-SN(R^{wx})_3$, in which each $R^{wx}$ independently represents a $C_{1-6}$ alkyl group, or, in the case of $-B(OR^{wx})_2$, the respective $R^{wx}$ groups may be linked together to form a 4- to 6-membered cyclic group, thereby forming e.g. a pinacolato boronate ester group (or $LG^4$ may represent iodo, bromo or chloro, provided that $LG^3$ and $LG^4$ are mutually compatible), and wherein the reaction may be performed in the presence of a suitable catalyst system, e.g. a metal (or a salt or complex thereof) such as Pd, CuI, Pd/C, $PdCl_2$, $Pd(OAc)_2$, $Pd(Ph_3P)_2Cl_2$, $Pd(Ph_3P)_4$, $Pd_2(dba)_3$ and/or $NiCl_2$ (or the like) and a ligand such as $PdCl_2(dppf).DCM$, $t\text{-}Bu_3P$, $(C_6H_{11})_3P$, $Ph_3P$ or the like, in a suitable solvent and under reaction conditions known to those skilled in the art.

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC, chiral chromatography. Individual diastereoisomers or individual enantiomers can also be obtained by Supercritical Fluid Chromatography (SCF).

The starting materials and the intermediates are compounds that are either commercially available or may be prepared according to conventional reaction procedures generally known in the art.

Synthesis of Compound 1

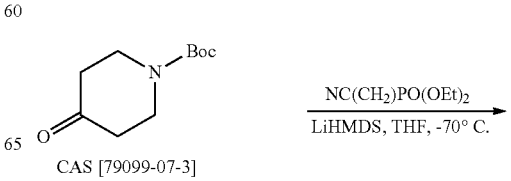

CAS [79099-07-3]

$NC(CH_2)PO(OEt)_2$
———————————
LiHMDS, THF, -70° C.

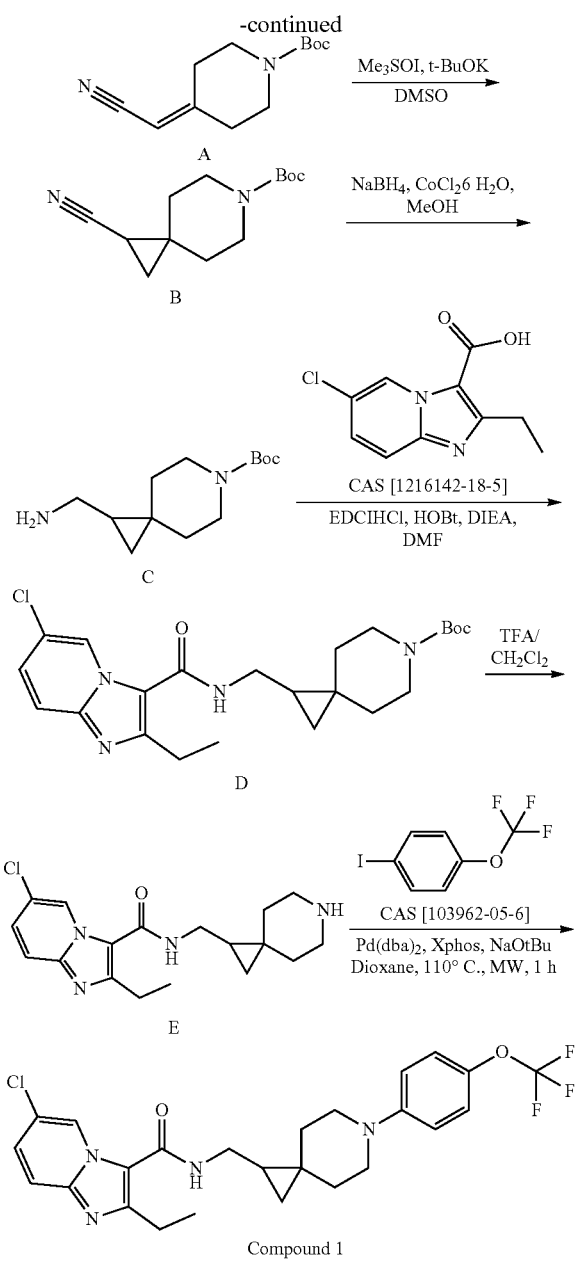

Preparation of Intermediate A

LiHMDS (50 mL, 1M in THF) was added to a mixture of N-tert-Butoxycarbonyl-4-piperidone (CAS [79099-07-3], 8.86 g, 50.0 mmol) in THF (180 mL) at −70° C. under $N_2$ flow. The mixture was stirred for 10 minutes. Diethyl cyanomethyl phosphonate (9 g, 45.2 mmol) was added to the mixture at −70° C. The mixture was stirred for 1 hour. The mixture was quenched with $NH_4Cl$ solution, extracted with ethyl acetate, washed with brine, dried over $MgSO_4$ and filtered. The filtrate was concentrated to give A, 10.0 g, 90.0%.

Preparation of Intermediate B

Me₃SOI (10.9 g, 49.5 mmol) was added slowly to a solution of t-BuOK (5.55 g, 49.5 mmol) in DMSO (60 mL). The mixture was stirred for 1.5 hours. A solution of A (10.0 g, 45.0 mmol) in DMSO (80 mL) was added to the mixture. The mixture was stirred 24 hours at 45° C. Saturated $NH_4Cl$ solution was added to the mixture and stirred for 0.5 hours. The mixture was extracted with ethyl acetate. The organic layers were washed with brine, dried over $MgSO_4$ and filtered. The filtrate was concentrated to give B, 10.0 g, 93%.

Preparation of Intermediate C

To a solution of B (460 mg, 1.95 mmol) in MeOH (10 mL) was added $CoCl_2 \cdot 6 H_2O$ (463 mg, 1.95 mmol). The mixture was stirred at −10° C. for 10 min. $NaBH_4$ (368 mg, 9.74 mmol) was added above the mixture in portions. Then the mixture was stirred for another 1 h. 1M HCl aqueous solution was added and the solid was dissolved. The aqueous phase was basified with aqueous $NH_3 \cdot H_2O$ till pH=9 and extracted with ethyl acetate. The combined organic layers were dried over $Na_2SO_4$ and concentrated in vacuum. The residue was triturated with an oxalic acid solution in ethyl acetate and filtered to afford a white solid. The solid was basified with 1N aqueous NaOH solution and extracted with dichloromethane. The combined organic layers were dried over $Na_2SO_4$ and concentrated in vacuum to give C, 120 mg, 26%.

Preparation of Intermediate D

HOBt (55.1 mg, 0.408 mmol), 6-chloro-2-ethylimidazo[3,2-a]pyridine-3-carboxylic acid (CAS [1216142-18-5], 91.7 mg, 0.408 mmol), DIEA (105 mg, 0.816 mmol) and EDCI.HCl (117 mg, 0.612 mmol) were added to a stirred solution of C (100 mg, 0.416 mmol) in DMF (10 mL). The mixture was stirred and heated at 60° C. for 16 hours. The mixture was concentrated. The residue was dissolved in ethyl acetate. The organic layer was washed with $H_2O$, dried over $MgSO_4$ and filtered. The filtrate was concentrated to give D, 100 mg, 51%.

Preparation of Intermediate E

TFA (5 mL) was added to a mixture of D (90 mg, 0.201 mmol) in $CH_2Cl_2$ (5 mL) at 0° C. The mixture was stirred for 5 hours at room temperature. The mixture was concentrated under vacuum. The residue was dissolved in $CH_2Cl_2$ and the mixture was adjust to pH=7 with $NaHCO_3$ solution. The organic layer was separated and concentrated. The crude product was purified by column chromatography over silica gel (eluent: ethyl acetate/petroleum ether from 0 to 1). The product fractions were collected and concentrated to give E, 70 mg, 90%.

Preparation of Compound 1

A solution of E (20 mg, 0.058 mmol), 1-iodo-4-(trifluoromethoxy)benzene (CAS [103962-05-6], 16.7 mg, 0.058 mmol), Pd(dba)₂ (3.34 mg, 0.006 mmol), Xphos (4.57 mg, 0.009 mmol) and t-BuONa (22.3 mg, 0.232 mmol) in 1,4-dioxane (5 mL) was irradiated under microwave at 110° C. for 1 hour under $N_2$. The mixture was concentrated under vacuum. The residue was purified by high performance liquid chromatography over Gemini (eluent: $NH_3$ water/acetonitrile 30/70 to 70/30). The desired fractions were collected and concentrated to give Compound 1, 19.3 mg, 64%.

¹H NMR (400 MHz, CDCl₃) δ ppm 9.47 (s, 1H) 7.54 (d, J=9.29 Hz, 1H) 7.30 (dd, J=9.41, 1.83 Hz, 1H) 7.10 (d, J=8.80 Hz, 2H) 6.91 (d, J=9.05 Hz, 2H) 5.87 (br. s., 1H) 3.51-3.60 (m, 2H) 3.30-3.42 (m, 2H) 3.08-3.17 (m, 2H) 3.02 (q, J=7.58 Hz, 2H) 1.86-1.94 (m, 1H) 1.73-1.82 (m, 1H) 1.64-1.69 (m, 1H) 1.43 (t, J=7.58 Hz, 3H) 1.36 (d, J=13.45 Hz, 1H) 1.01-1.10 (m, 1H) 0.70 (dd, J=8.44, 4.77 Hz, 1H) 0.38 (t, J=4.89 Hz, 1H)

Synthesis of Compound 2

Preparation of Intermediate F

A mixture of intermediate R (364 mg, 2.47 mmol), trans-2-amino-cyclohexanol (28.5 mg, 0.248 mmol) and Nickel iodine (38.7 mg, 0.124 mmol) in i-PrOH (4 mL) was stirred at 25° C. for 30 minutes under nitrogen flow. NaHMDS (2.48 mL, 1 M in THF) was added, and the mixture was stirred for 10 minutes under nitrogen flow. A solution of 4-cyanophenylboronic acid (CAS [126747-14-

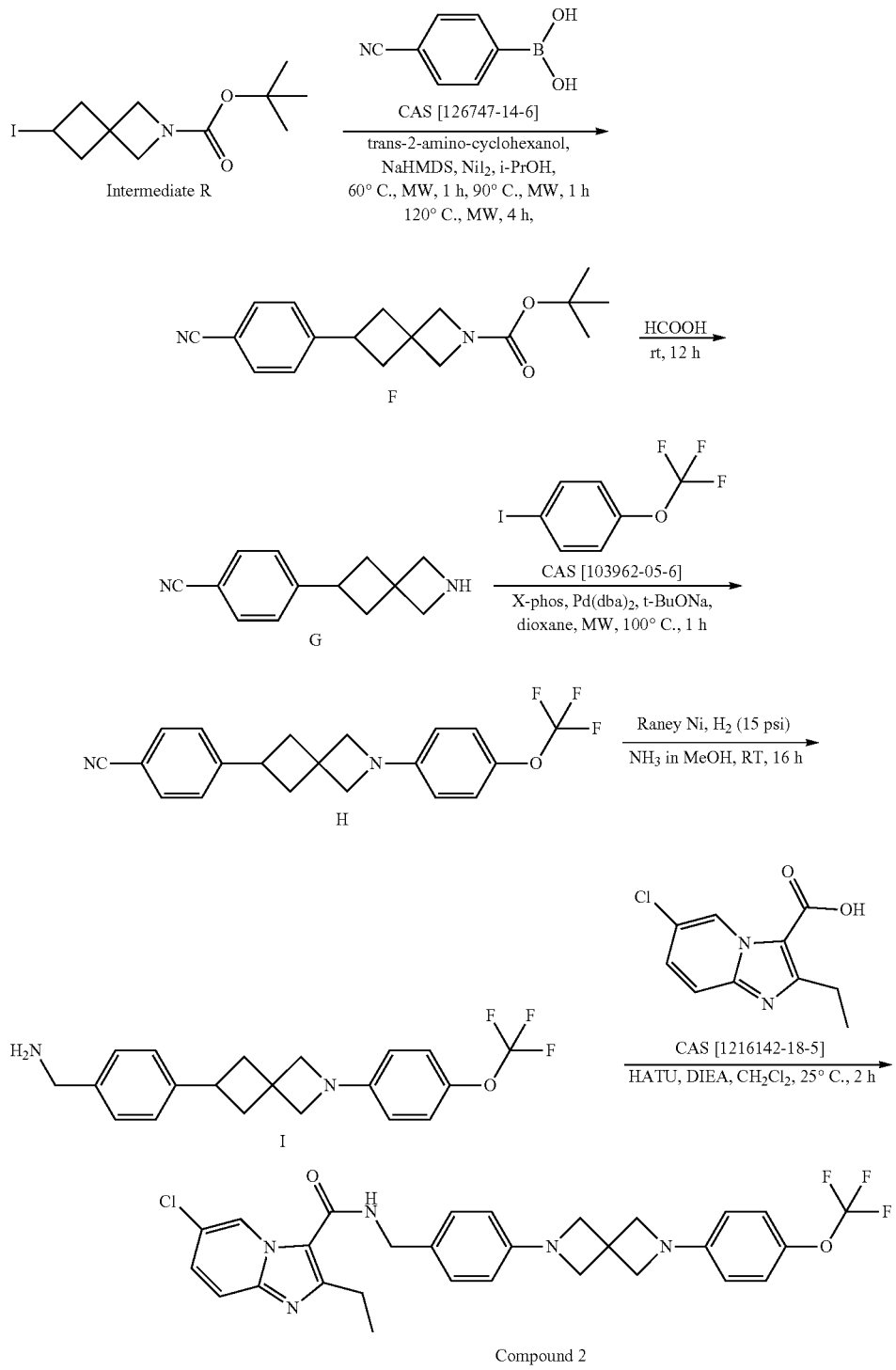

6], 400 mg, 1.24 mmol) in i-PrOH (4 mL) was added and the mixture was stirred at 60° C. under microwave for 1 hour, at 90° C. for 1 hour and at 120° C. for 4 hours. The mixture was diluted with dichloromethane (50 mL), washed with water (2×50 mL) and brine (20 mL). The organic layer was dried over sodium sulfate, filtered and concentrated under vacuum. The residue was purified by column chromatography over silica gel (eluent: petroleum ether/ethyl acetate 5/1) to give intermediate F (300 mg, yield: 37%).

Preparation of Intermediate G

A mixture of intermediate F (300 mg, 1.01 mmol) in formic acid (5 mL) was stirred at room temperature for 12 hours. The mixture was concentrated and $CH_2Cl_2$ (30 mL) was added to the mixture. The mixture was washed with $Na_2CO_3$ solution (20 mL). The organic layer was separated, dried over $Na_2SO_4$ and filtered. The filtrate was concentrated to give intermediate G (150 mg, yield: 64%).

Preparation of Intermediate H

A solution of intermediate G (100 mg, 0.504 mmol), 1-iodo-4-(trifluoromethoxy)benzene (CAS [103962-05-6], 145 mg, 0.504 mmol), X-Phos (28.8 mg, 0.06 mmol), $Pd(dba)_2$ (17.4 mg, 0.03 mmol) and t-BuONa (194 mg, 2.02 mmol) in dioxane (4 mL) was irradiated under microwave at 100° C. for 1 hour under $N_2$. The mixture was concentrated. The crude product was purified by column chromatography over silica gel (eluent: ethyl acetate/petroleum ether from 0 to 1/1). The desired fractions were collected and concentrated to give intermediate H (100 mg, yield: 55%).

Preparation of Intermediate I

A mixture of intermediate H (70.0 mg, 0.195 mmol) in $NH_3$.MeOH (7M in methanol, 20 mL) was hydrogenated (15 psi) with Raney Nickel (7 mg) as catalyst at 25° C. for 16 hours. After uptake of H2, the catalyst was filtered off and the filtrate was concentrated to give intermediate I (50.0 mg, yield: 71%).

Preparation of Compound 2

A solution of 6-chloro-2-ethylimidazo[3,2-a]pyridine-3-carboxylic acid (CAS [1216142-18-5], 22.5 mg, 0.100 mmol), HATU (49.4 mg, 0.130 mmol), DIEA (33.6 mg, 0.260 mmol) in $CH_2Cl_2$ (20 mL) was stirred for 30 minutes at 25° C. Intermediate I (40.0 mg, 0.110 mmol) was added to the mixture and the mixture was stirred for 2 hours at 25° C. The mixture was concentrated under vacuum. The crude product was purified by high performance liquid chromatography over Gemini (eluent: 0.05% ammonia in water/methanol 20/80 to 5/95). The desired fractions were collected and concentrated to give Compound 2 (9.80 mg, yield: 17%).

1H NMR (400 MHz, $CDCl_3$) δ=ppm 9.54 (s, 1H) 7.55 (d, J=9.26 Hz, 1H) 7.27-7.37 (m, 3H) 7.22 (d, J=7.94 Hz, 2H) 7.00-7.10 (m, 2H) 6.40 (d, J=8.82 Hz, 2H) 6.11 (br. s., 1H) 4.68 (d, J=5.73 Hz, 2H) 4.01 (s, 2H) 3.80 (s, 2H) 3.48 (q, J=8.93 Hz, 1H) 2.98 (q, J=7.50 Hz, 2H) 2.59-2.71 (m, 2H) 2.35 (td, J=9.70, 2.65 Hz, 2H) 1.36-1.47 (m, 3H)

Synthesis of Compound 3

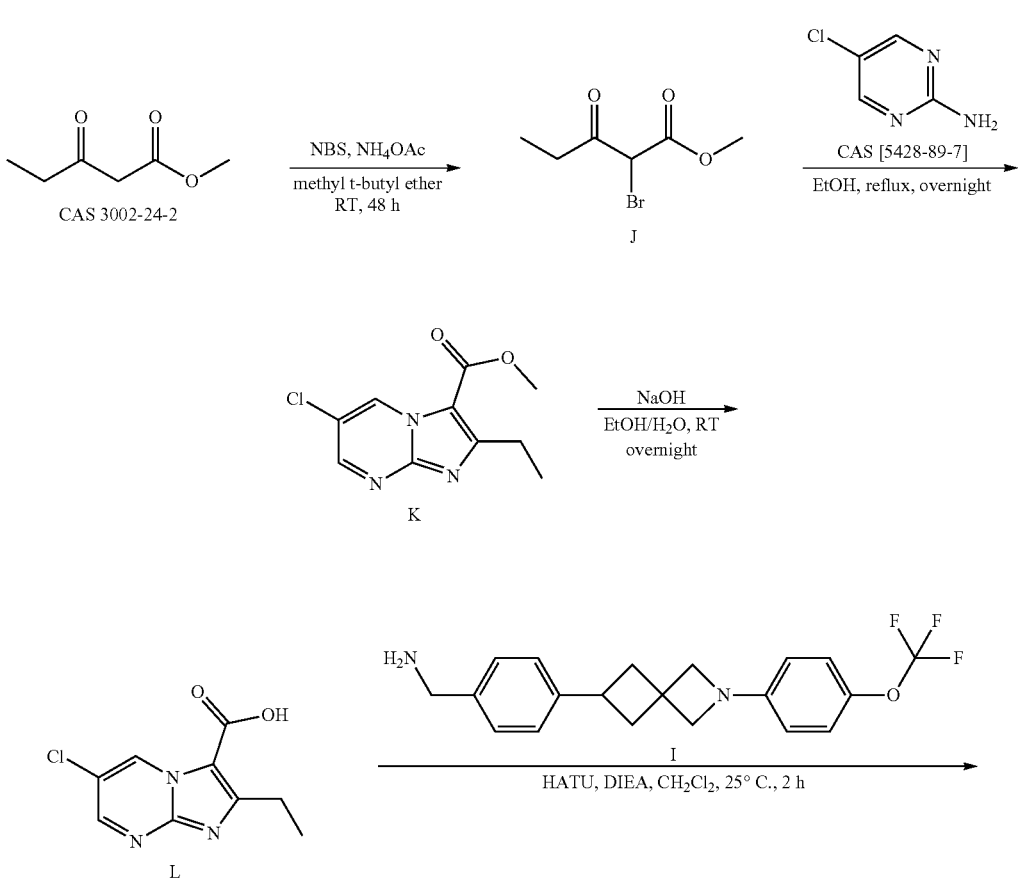

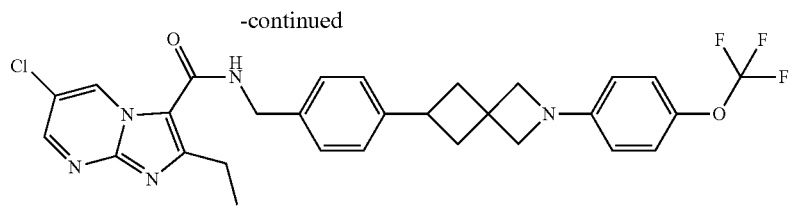

Compound 3

Preparation of Intermediate J

NBS (45.1 g, 254 mmol) and NH₄OAc (5.33 g, 69.2 mmol) were added to a solution of methyl-3-oxovalerate (CAS[30414-53-0], 30 g, 231 mmol) in methyl t-butylether (600 mL). The mixture was stirred at room temperature for 48 h. The mixture was filtered and washed with H₂O, dried over Na₂SO₄ and filtered. The filtrate was concentrated under vacuum. The residue was purified by column chromatography over silica gel (eluent: petroleum ether/ethyl acetate 20/1) to give intermediate J (20.0 g, yield: 35%).

Preparation of Intermediate K

A solution of 5-Chloro-2-pyridinamine (CAS [5428-89-7], 12.0 g, 93.0 mmol) and intermediate J (25.0 g, 112 mmol) in ethanol (60 mL) was refluxed overnight. The mixture was concentrated under vacuum. The residue was dissolved into ethyl acetate (100 mL). The solution was washed with water (2×100 mL), brine (100 mL), dried over sodium sulfate, filtered and concentrated under vacuum. The residue was purified by column chromatography over silica gel (eluent: petroleum ether/ethyl acetate 3/1) to give intermediate K (700 mg, yield: 3%).

Preparation of Intermediate L

A mixture of intermediate K (700 mg, 2.10 mmol) and sodium hydroxide (252 mg, 6.30 mmol) in ethanol (2 ml) and H₂O (2 mL) was stirred overnight at room temperature. Water (20 mL) was added and the solution was acidified with 2 M aqueous hydrochloride to pH ~3. The solution was lyophilized to give crude intermediate L (2 g).

Preparation of Compound 3

Accordingly, Compound 3 was prepared in the same way as Compound 2 starting from intermediate L and intermediate I, yielding 9.60 mg, yield: 8%.

1H NMR (400 MHz, CDCl₃) δ ppm 9.84 (d, J=2.51 Hz, 1H) 8.57 (d, J=2.76 Hz, 1H) 7.30-7.35 (m, 2H) 7.22 (d, J=8.03 Hz, 2H) 7.06 (d, J=8.03 Hz, 2H) 6.37-6.43 (m, 2H) 6.14-6.20 (m, 1H) 4.68 (d, J=5.77 Hz, 2H) 4.01 (s, 2H) 3.80 (s, 2H) 3.48 (q, J=8.85 Hz, 1H) 3.02 (q, J=7.53 Hz, 2H) 2.61-2.70 (m, 2H) 2.31-2.40 (m, 2H) 1.45 (t, J=7.53 Hz, 3H)

Synthesis of Compound 4

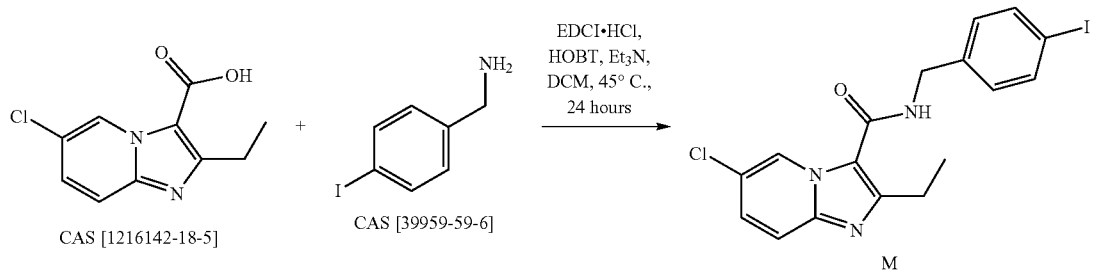

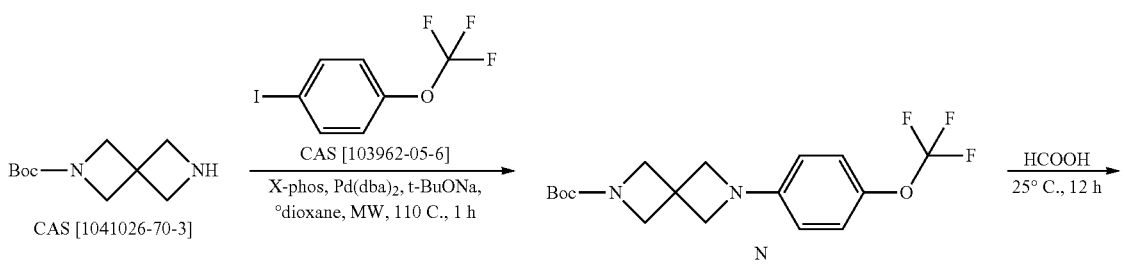

-continued

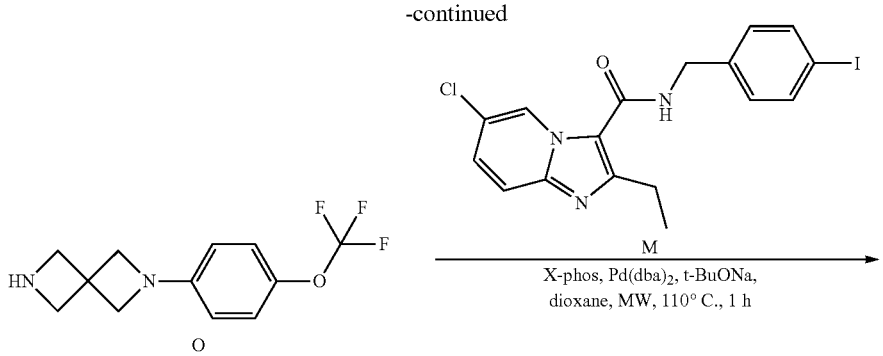

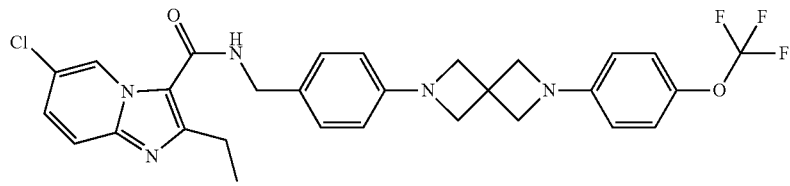

Compound 4

Preparation of Intermediate M

A solution of 6-chloro-2-ethylimidazo[3,2-a]pyridine-3-carboxylic acid (CAS [12161242-18-5], 1 g, 4.45 mmol), 4-iodobenzenemethanamine (CAS [39959-59-6], 1.09 g, 4.67 mmol), EDCI.HCl (1.28 g, 6.68 mmol), HOBT (0.601 g, 4.45 mmol) and triethylamine (1.24 mL, 9 mmol) in dichloromethane (8 mL) was stirred and heated at 45° C. for 24 hours. The solution was cooled down to 15° C. The solid was collected by filtration, washed with water and acetonitrile and the solid was dried (vacuum, 45° C., 1 hour) to give intermediate M, 1.2 g, 55%.

Preparation of Intermediate N

A solution of tert-butyl 2,6-diazaspiro[3.3]heptane-2-carboxylate (CAS [1041026-70-3], 500 mg, 2.52 mmol), 1-iodo-4-(trifluoromethoxy)benzene (CAS [103962-05-6], 726 mg, 2.52 mmol), X-phos (240 mg, 0.504 mmol), Pd(dba)$_2$ (145 mg, 0.252 mmol) and t-BuONa (969 mg, 10.1 mmol) in dioxane (8 mL) was irradiated under microwave at 110° C. for 1 hour under N$_2$. Water was added to the mixture and the mixture was extracted with ethyl acetate (50 mL×2). The organic layers were washed brine, dried over MgSO$_4$ and filtered. The filtrate was concentrated. The crude product was purified by column chromatography over silica gel (eluent: ethyl acetate/hexane from 0 to 1/5). The desired fractions were collected and concentrated to give N, 500 mg, 50%.

Preparation of Intermediate O

A mixture of N (100 mg, 0.279 mmol) in HCOOH (5 mL) was stirred for 12 hours. The mixture was concentrated and was used for the next step without further purification.

Preparation of Compound 4

A solution of intermediate O (72 mg, 0.279 mmol), intermediate M (123 mg, 0.279 mmol), X-Phos (26.6 mg, 0.056 mmol), Pd(dba)$_2$ (16.0 mg, 0.028 mmol) and t-BuONa (107 mg, 1.12 mmol) in dioxane (8 mL) was irradiated under microwave at 110° C. for 1 hour under N$_2$. The mixture was concentrated. The crude product was purified by high performance liquid chromatography over Gemini (eluent: ammonia in water/acetonitrile 50/50 to 20/80). The desired fractions were collected and concentrated to give Compound 4, 35.8 mg, 22%.

1H NMR (400 MHz, CDCl$_3$) δ ppm=9.53 (d, J=1.25 Hz, 1H) 7.56 (d, J=9.79 Hz, 1H) 7.31 (dd, J=9.54, 2.01 Hz, 1H) 7.24 (s, 2H) 7.08 (d, J=8.53 Hz, 2H) 6.49 (d, J=8.53 Hz, 2H) 6.42 (d, J=9.03 Hz, 2H) 6.01 (br. s., 1H) 4.59 (d, J=5.27 Hz, 2H) 4.04 (s, 4H) 4.02 (s, 4H) 2.96 (q, J=7.36 Hz, 2H) 1.39 (t, J=7.53 Hz, 3H)

Synthesis of Compound 5

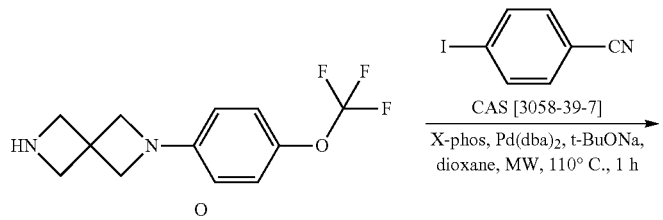

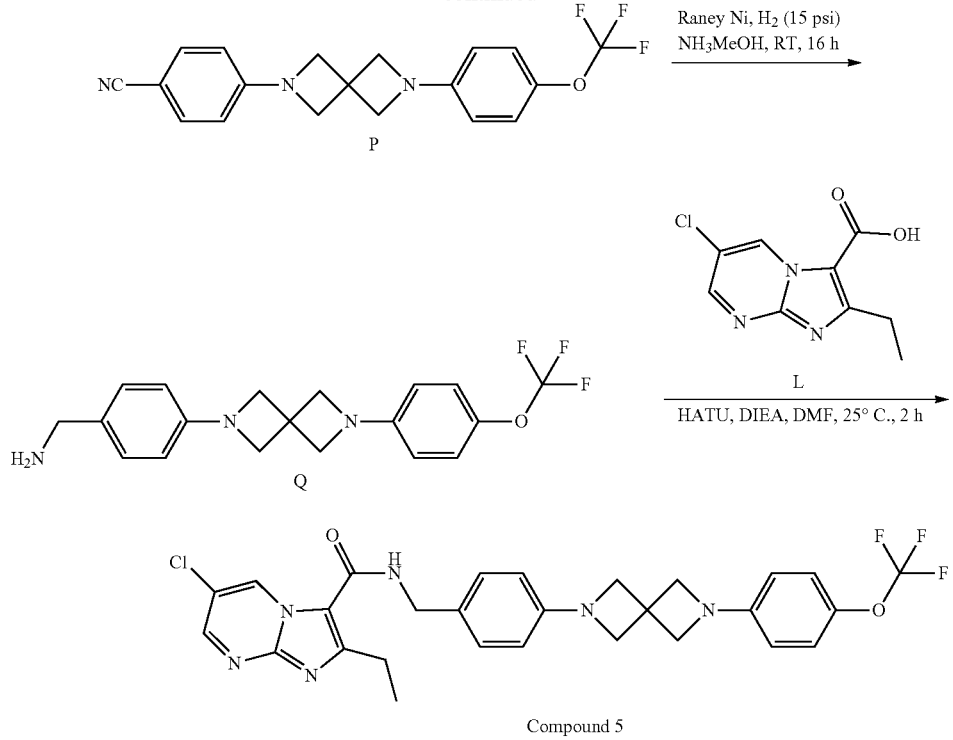

Preparation of Intermediate P

A solution of intermediate O (100 mg, 0.387 mmol), 4-iodobenzonitrile (CAS [3058-39-7], 115 mg, 0.503 mmol), X-phos (22.0 mg, 46.2 mmol), Pd(dba)$_2$ (13.3 mg, 23.1 mmol) and t-BuONa (149 mg, 1.55 mmol) in dioxane (5 mL) was irradiated under microwave at 110° C. for 1 hour under N$_2$. The mixture was concentrated under vacuum. The crude product was purified by high performance liquid chromatography over Gemini (eluent: 0.05% ammonia in water/methanol 30/70 to 5/95). The desired fractions were collected and concentrated to give intermediate P (60.0 mg, yield: 35%).

Preparation of Intermediate Q

Accordingly, intermediate Q was prepared as the same way as intermediate I starting from intermediate P, yielding 60.0 mg, yield: 99%.

Preparation of Compound 5

A solution of intermediate L (28.3 mg, 0.125 mmol), HATU (61.8 mg, 0.162 mmol), DIEA (42.0 mg, 0.325 mmol) in DMF (5 mL) was stirred for 30 minutes at 25° C. Intermediate Q (50.0 mg, 0.138 mmol) was added to the mixture and the mixture was stirred for 2 hours at 25° C. The mixture was concentrated under vacuum. The crude product was purified by high performance liquid chromatography over Gemini (eluent: 0.05% ammonia in water/methanol 25/75 to 5/95). The desired fractions were collected and concentrated to give Compound 5 (10.3 mg, yield: 14%).

1H NMR (400 MHz, CDCl$_3$) δ=ppm 9.84 (d, J=2.51 Hz, 1H) 8.56 (d, J=2.51 Hz, 1H) 7.25 (d, J=8.53 Hz, 2H) 7.08 (d, J=8.78 Hz, 2H) 6.49 (d, J=8.28 Hz, 2H) 6.43 (d, J=9.03 Hz, 2H) 6.06 (s, 1H) 4.59 (d, J=5.27 Hz, 2H) 4.05 (s, 4H) 4.03 (s, 4H) 2.99 (q, J=7.45 Hz, 2H) 1.43 (t, J=7.53 Hz, 3H)

Synthesis of Compound 6

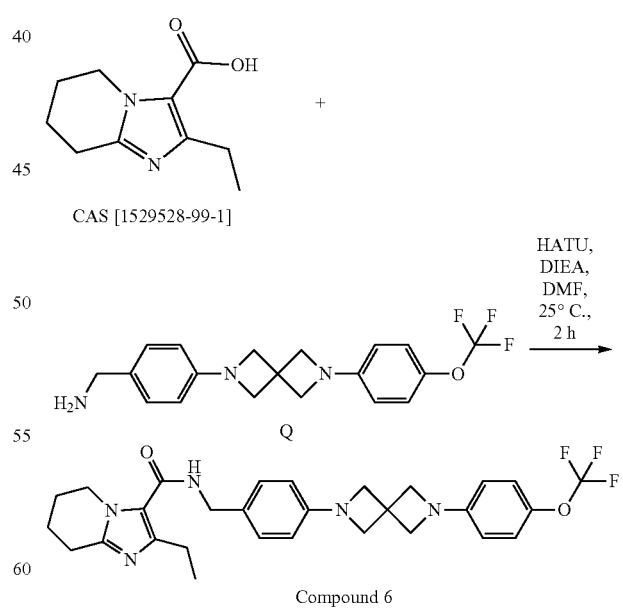

Accordingly, Compound 6 was prepared in the same way as Compound 5 starting from 2-ethyl-5H,6H,7H,8H-imidazo[1,2-a]pyridine-3-carboxylic acid CAS [1529528-99-1] and intermediate Q, yielding 153.90 mg, yield: 32%.

1H NMR (400 MHz, CDCl$_3$) δ ppm 7.21 (d, J=8.28 Hz, 2H) 7.08 (d, J=8.03 Hz, 2H) 6.47 (d, J=8.53 Hz, 2H) 6.40-6.45 (m, 2H) 5.83 (br. s., 1H) 4.50 (d, J=5.52 Hz, 2H) 4.23 (t, J=5.77 Hz, 2H) 4.04 (s, 8H) 2.86 (t, J=6.40 Hz, 2H) 2.68 (q, J=7.53 Hz, 2H) 1.83-2.01 (m, 4H) 1.23 (t, J=7.53 Hz, 3H)

Synthesis of Compound 7

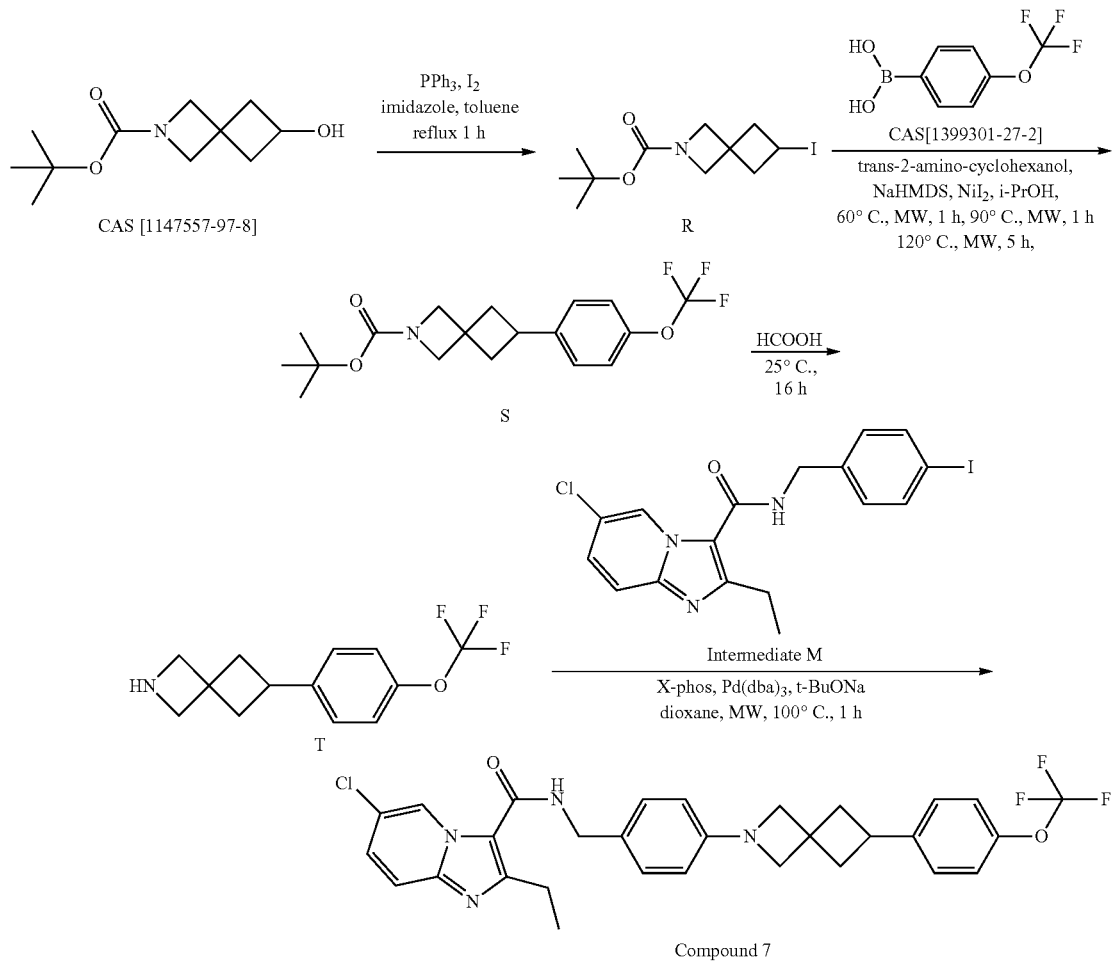

Preparation of Intermediate R

Triphenylphosphine (1.89 g, 7.20 mmol), imidazole (735 mg, 10.8 mmol) and iodine (1.37 g, 5.40 mmol) were added to a solution of tert-butyl 6-hydroxy-2-azaspiro[3.3]heptane-2-carboxylate (CAS [1147557-97-8], 768 mg, 3.60 mmol) in toluene (50 mL). The resulting mixture was refluxed for 1 hour. The mixture was cooled to 25° C., washed with water (100 mL) and brine (50 mL). The separated organic layer was dried, filtered and the filtrate was concentrated under vacuum. The residue was purified by flash column chromatography over silica gel (eluent: petroleum ether/ethyl acetate 1/0 to 1/1) to give intermediate R (1.20 g, yield: 93%).

Preparation of Intermediate S

A mixture of 4-(Trifluoromethoxy)phenylboronic acid (CAS [139301-27-2], 510 mg, 2.48 mmol), trans-2-amino-cyclohexanol (23.0 mg, 0.200 mmol) and nickel iodine (62.5 mg, 0.200 mmol) in isopropanol (4 mL) was stirred at 25° C. for 30 minutes under nitrogen flow. NaHMDS (2.47 ml, 1 M in THF, 2.47 mmol) was added, and the mixture was stirred for 10 minutes under nitrogen flow. Intermediate R (400 mg, 1.24 mmol) in isopropanol (1 mL) was added and the mixture was stirred at 60° C. under microwave for 1 hour, at 90° C. for 1 hour and at 120° C. for 5 hours. The mixture was diluted with dichloromethane (50 mL), washed with water (2×50 mL) and brine (20 mL). The organic layer was dried over sodium sulfate, filtered and concentrated under vacuum. The residue was purified by column chromatography over silica gel (eluent: petroleum ether/ethyl acetate 5/1) to give intermediate S (230 mg, yield: 52%).

Preparation of Intermediate T

Intermediate S (220 mg, 0.616 mmol) was added to formic acid (5 mL) at 0° C. under nitrogen atmosphere. The mixture was stirred at 25° C. for 5 hours. The mixture was concentrated under vacuum. The residue was dissolved into dichloromethane (20 mL). The solution was washed with saturated aqueous sodium carbonate solution (20 mL), brine (20 mL), dried over sodium sulfate, filtered and concentrated under vacuum to give Intermediate T (150 mg, yield: 85%).

Preparation of Compound 7

A solution of intermediate T (110 mg, 0.428 mmol), Intermediate M (226 mg, 0.514 mmol), Pd(dba)$_2$ (14.8 mg, 0.0260 mol), X-phos (20.4 mmol, 0.0430 mmol) and sodium tert-butoxide (165 mg, 1.71 mmol) in 1,4-dioxane (5 mL) was irradiated under microwave at 100° C. for 1 h under N$_2$ atmosphere. Ethyl acetate (30 mL) was added and the mixture was washed with water (10 mL) and brine (20 mL). The organic layer was dried over sodium sulfate, filtered and concentrated under vacuum. The residue was purified by column chromatography over silica gel (eluent: petroleum ether/ethyl acetate 1/0 to 0/1) to give crude compound. It was further purified by high performance liquid chromatography over Phenomenex Gemini C18 200×25 mm×10 μm (eluent: 0.5% ammonia in water/acetonitrile 80/20 to 14.5/85.5). The desired fractions were collected and lyophilized to give Compound 7 (84.60 mg, yield: 35%).

$^1$H NMR (400 MHz, CDCl$_3$) δ=9.52 (d, J=1.8 Hz, 1H), 7.53 (d, J=9.5 Hz, 1H), 7.29 (dd, J=2.0, 9.5 Hz, 1H), 7.26-7.18 (m, 4H), 7.18-7.12 (m, 2H), 6.47 (d, J=8.5 Hz, 2H), 5.99 (br.s., 1H), 4.58 (d, J=5.3 Hz, 2H), 4.02 (s, 2H), 3.80 (s, 2H), 3.47 (q, J=8.9 Hz, 1H), 2.94 (q, J=7.5 Hz, 2H), 2.70-2.61 (m, 2H), 2.38-2.29 (m, 2H), 1.38 (t, J=7.5 Hz, 3H)

Synthesis of Compound 8

Preparation of Intermediate U

Accordingly, intermediate U was prepared in the same way as intermediate H, starting from intermediate T and 4-iodobenzonitrile CAS [3058-39-7], yielding 120 mg, yield: 40%.

Preparation of Intermediate V

Accordingly, intermediate V was prepared in the same way as intermediate I, starting from intermediate U yielding 120 mg, yield: 92%.

Preparation of Compound 8

A mixture of intermediate V (125 mg, 0.222 mmol), intermediate L (80.5 mg, 0.222 mmol), HATU (110 mg, 0.289 mmol) and DIEA (74.6 mg, 0.577 mmol) in dichloromethane (10 mL) was stirred at 25° C. for 2 hours. Dichloromethane (50 mL) was added and the mixture was washed with water (50 mL) and brine (50 mL). The separated organic layer was dried over sodium sulfate, filtered and concentrated under vacuum. The residue was purified by column chromatography over silica gel (eluent: ethyl acetate) to give crude product. The crude product was further purified by high performance liquid chromatography over Gemini 150×25 5 μm (eluent: 0.05% ammonium water/

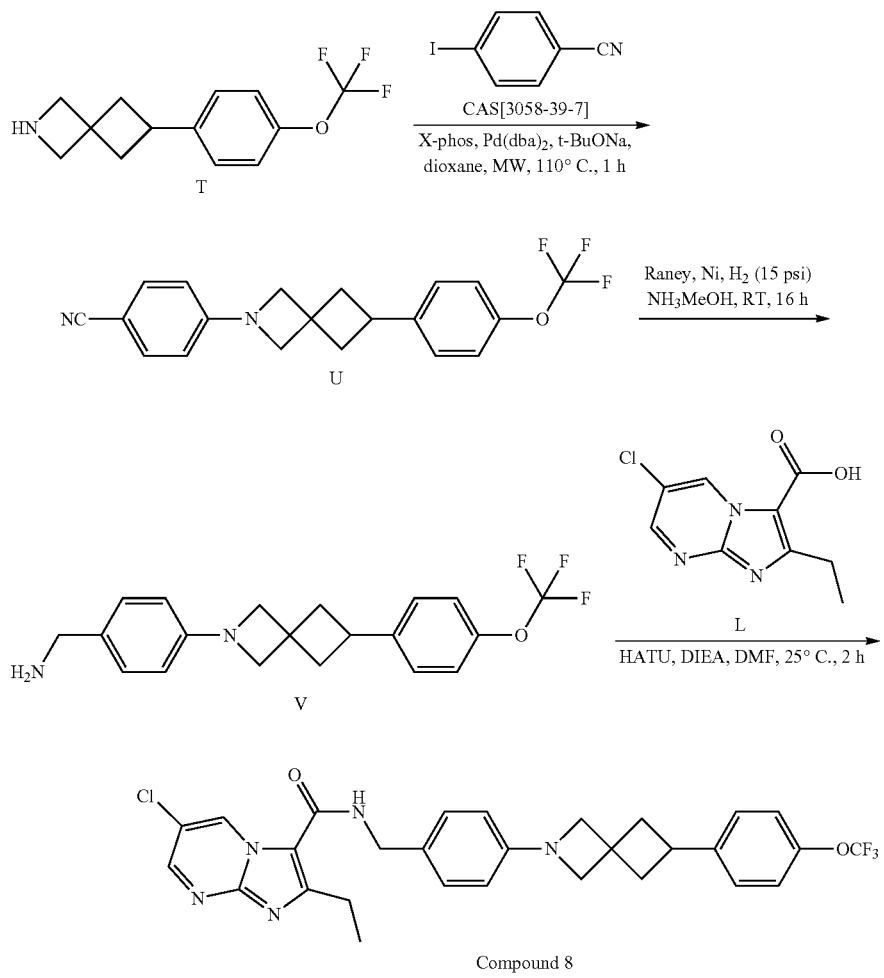

Compound 8 acetonitrile 21/79). The desired fractions were collected and lyophilized to give Compound 8 (36.6 mg, yield: 28%).

$^1$H NMR (400 MHz, CDCl$_3$) δ=9.83 (d, J=2.2 Hz, 1H), 8.55 (d, J=2.2 Hz, 1H), 7.25-7.08 (m, 6H), 6.46 (d, J=7.9 Hz, 2H), 6.06 (br. s., 1H), 4.58 (d, J=5.3 Hz, 2H), 4.02 (s, 2H), 3.81 (s, 2H), 3.47 (q, J=8.8 Hz, 1H), 2.98 (q, J=7.5 Hz, 2H), 2.73-2.59 (m, 2H), 2.41-2.27 (m, 2H), 1.42 (t, J=7.5 Hz, 3H).

Preparation of Intermediate W

Accordingly, intermediate W was prepared in the same way as intermediate H starting from intermediate AW (120 mg, 0.693 mmol) and 4-iodobenzonitrile (CAS [3058-39-7], 238 mg, 1.04 mmol) yielding 100 mg, 52%.

Preparation of Intermediate X

Accordingly, intermediate X was prepared in the same way as intermediate I starting from intermediate W (100 mg, 0.364 mmol yielding 100 mg, 94%.

Synthesis of Compound 9

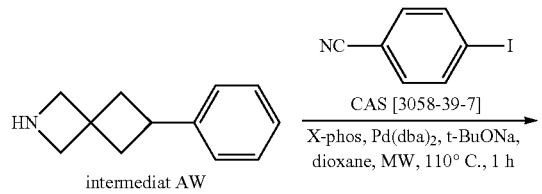

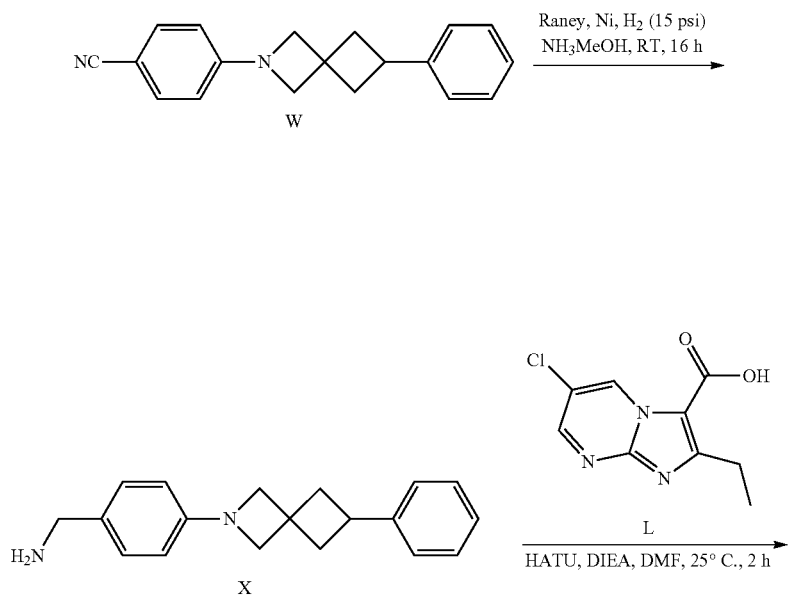

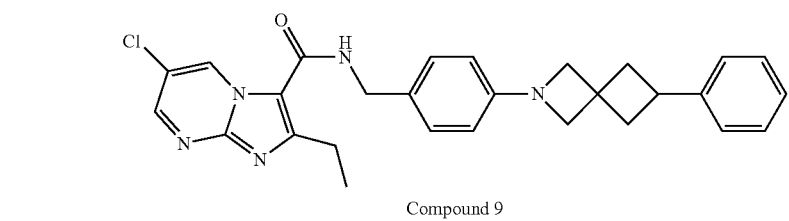

Compound 9

Preparation of Compound 9

A solution of intermediate L (50.0 mg, 0.222 mmol), HATU (110 mg, 0.289 mmol), DIEA (74.6 mg, 0.577 mmol) in DMF (5 mL) was stirred for 30 minutes at 25° C. Intermediate X (68.0 mg, 0.244 mmol) was added to the mixture and the mixture was stirred for 2 hours at 25° C. The mixture was concentrated under vacuum. The crude product was purified by high performance liquid chromatography over Gemini (eluent: gradient 0.05% ammonia in water/ methanol from 25/75 to 5/95). The desired fractions were collected and concentrated to give Compound 9 (34.7 mg, yield: 31%).

1H NMR (400 MHz, CDCl$_3$) δ ppm 9.82 (d, J=2.51 Hz, 1H) 8.55 (d, J=2.76 Hz, 1H) 7.28-7.35 (m, 2H) 7.18-7.23 (m, 5H) 6.41-6.50 (m, 2H) 6.08 (t, =5.02 Hz, 1H) 4.58 (d, J=5.52 Hz, 2H) 4.00-4.04 (m, 2H) 3.77-3.83 (m, 2H) 3.42-3.53 (m, 1H) 2.98 (q, J=7.36 Hz, 2H) 2.62-2.69 (m, 2H) 2.33-2.40 (m, 2H) 1.37-1.46 (m, 3H)

Synthesis of Compound 10

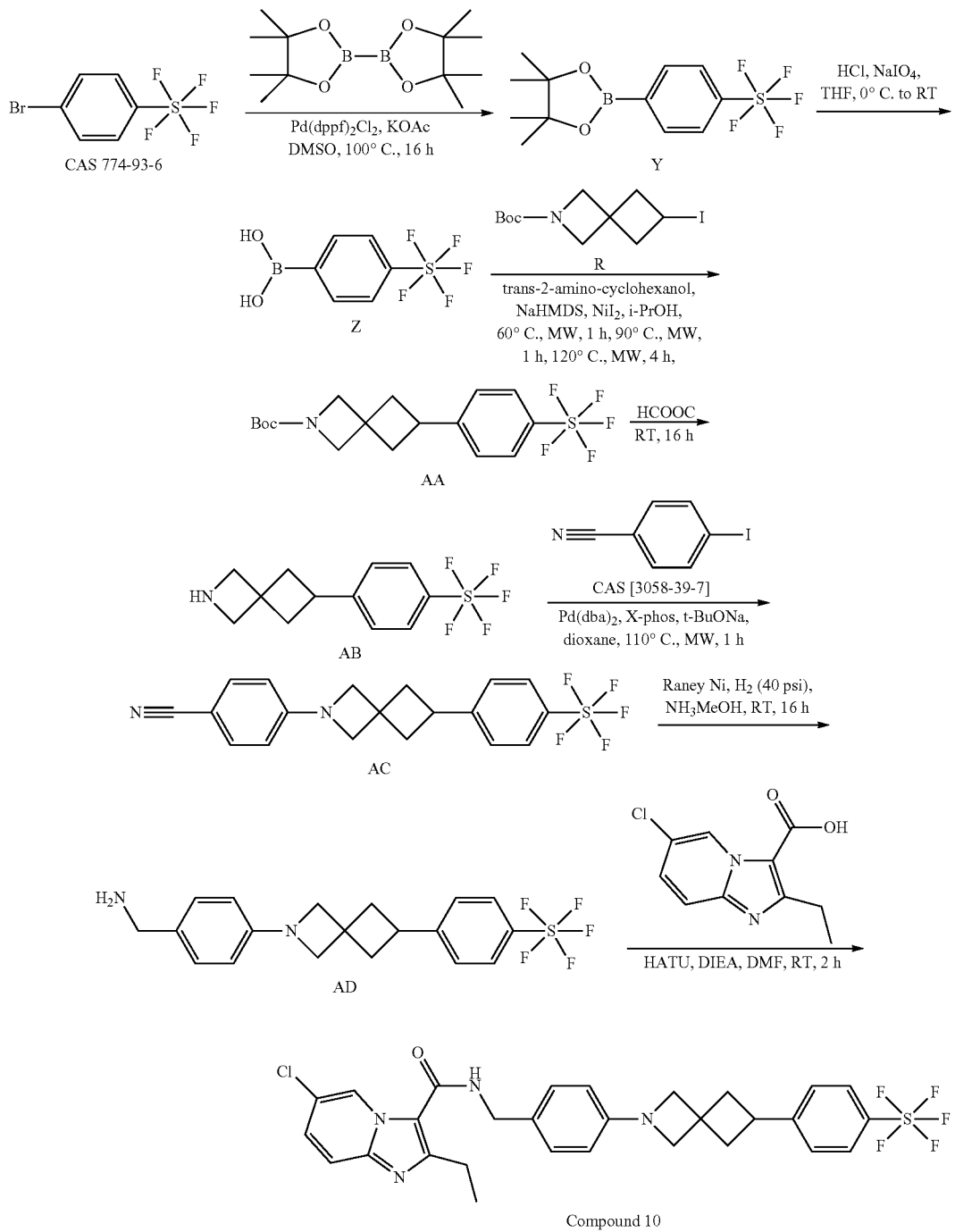

Preparation of Intermediate Y

A mixture of 4-bromophenylsulfur pentafluoride (CAS [774-93-6] 4 g, 14.1 mmol), bis(pinacolato)diboron (CAS [73183-34-3], 4.30 g, 16.9 mmol), potassium acetate (2.80 g, 28.5 mmol) and Pd(dppf)$_2$Cl$_2$ (0.946 g, 1.29 mmol) in 1,4-dioxane (50 mL) was stirred at 100° C. for 16 hours. Ethyl acetate (200 ml) was added and the mixture was washed with water (100 mL) and brine (100 mL). The separated organic layer was dried over sodium sulfate, filtered and concentrated under vacuum. The residue was purified by column chromatography over silica gel (eluent: petroleum ether/ethyl acetate 10/1) to give intermediate Y (4.60 g, yield: 89%).

Preparation of Intermediate Z

Sodium periodate (3.49 g, 16.3 mmol) was added portionwise to a solution of intermediate Y (1.80 g, 5.45 mmol) in concentrated hydrochloride (5 mL) and THF (20 mL) at 0° C. The mixture was stirred at room temperature for 3 hours. Ethyl acetate (50 mL) was added and the mixture was washed with saturated aqueous sodium sulfite solution (2×20 mL). The separated organic layer was washed with water (20 mL), brine (50 mL), dried over sodium sulfate, filtered and concentrated under vacuum to give intermediate Z (1 g, yield: 72%).).

Preparation of Intermediate AA

A mixture of intermediate Z (500 mg, 2.02 mmol), trans-3-amino-cyclohexanol (11.5 mg, 0.100 mmol) and nickel iodine (31.3 mg, 0.100 mmol) in isopropanol (7 ml) was stirred at room temperature for 30 minutes under nitrogen flow. NaHMDS (2.02 ml, 2.02 mmol, 1 M in THF) was added, and the mixture was stirred for 10 minutes under nitrogen flow. A solution of intermediate R (326 mg, 1.01 mmol) in isopropanol (3 ml) was added and the mixture was stirred at 60° C. under microwave for 1 hour, at 90° C. for 1 hour and at 120° C. for 4 hours. The mixture was diluted with dichloromethane (50 ml), washed with water (50 mL) and brine (50 mL). The organic layer was dried over sodium sulfate, filtered and concentrated under vacuum. The residue was purified by column chromatography over silica gel (eluent: petroleum ether/ethyl acetate 5/1) to give intermediate AA (170 mg, yield: 43%).

Preparation of Intermediate AB

Accordingly, intermediate AB was prepared in the same way as intermediate G, starting from intermediate AA (170 mg, 0.426 mmol) yielding 100 mg, 78%.

Preparation of Intermediate AC

Accordingly, intermediate AC was prepared in the same way as intermediate H, sorting from intermediate AB (80.0 mg, 0.267 mmol) and 4-iodobenzonitrile (CAS [3058-39-7], 91.6 mg, 0.4 mmol) yielding 90 mg, 71%.

Preparation of Intermediate AD

Accordingly, intermediate AD was prepared in the same way as intermediate I, starting from intermediate AC (80.0 mg, 0.200 mmol) yielding 80 mg, 99%.

Preparation of Compound 10

A mixture of 6-chloro-2-ethylimidazo[3,2-a]pyridine-3-carboxylic acid (CAS [1216142-18-5], 44.5 mg, 0.198 mmol), intermediate AD (80 mg, 0.198 mmol), HATU (97.9 mg, 0.257 mmol) and DIEA (76.8 mg, 0.594 mmol) in DMF (4 mL) was stirred at room temperature for 2 hours. The mixture was purified by high performance liquid chromatography over Waters Xbridge Prep OBD C18 150×30 5 μM (eluent: 0.05% ammonium water/methanol 15/85 to 5/95). The desired fractions were collected and lyophilized to give Compound 10 (36.6 mg, yield: 28%).

$^1$H NMR (400 MHz, CDCl$_3$) δ=9.52 (s, 1H), 7.69 (d, J=8.4 Hz, 2H), 7.54 (d, 0.1=9.3 Hz, 1H), 7.34-7.27 (m, 2H), 7.23 (br. s., 3H), 6.47 (d, J=7.9 Hz, 2H), 5.99 (br. s., 1H), 4.58 (d, J=4.4 Hz, 2H), 4.03 (s, 2H), 3.81 (s, 2H), 3.52 (quin, J=8.5 Hz, 1H), 2.94 (q, J=7.4 Hz, 2H), 2.69 (t, J=9.5 Hz, 2H), 2.36 (t, J=10.1 Hz, 2H), 1.38 (t, J=7.3 Hz, 3H).

Synthesis of Compound 11

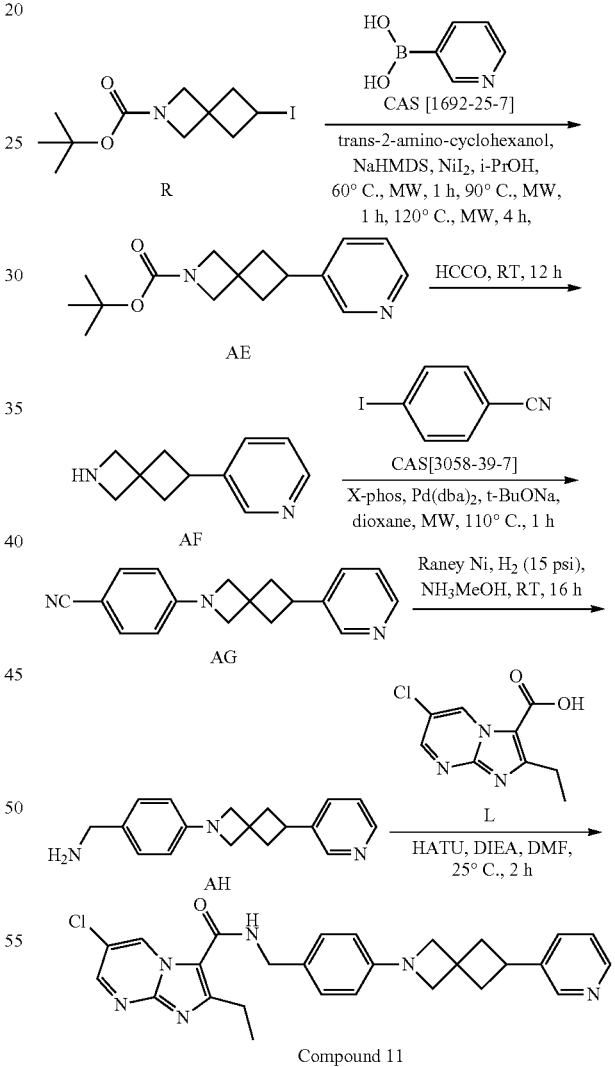

Preparation of Intermediate AE

A mixture of intermediate R (608 mg, 4.95 mmol), trans-2-amino-cyclohexanol (57.0 mg, 0.495 mmol) and NiI$_2$ (77.3 mg, 0.248 mmol) in i-PrOH (6 mL) was stirred at 25° C. for 30 minutes under nitrogen flow. NaHMDS (908 mg, 4.95 mmol) was added, and the mixture was stirred for 10 minutes under nitrogen flow. 3-Pyridineboronic acid (CAS [1692-25-7], 800 mg, 2.48 mmol) in i-PrOH (4 mL) was added and the mixture was stirred at 60° C. under microwave for 1 hour, at 90° C. for 1 hour and at 120° C. for 4 hours. The mixture was diluted with dichloromethane (50 mL), washed with water (50 mL) and brine (20 mL). The organic layer was dried over sodium sulfate, filtered and concentrated under vacuum. The residue was purified by column chromatography over silica gel (eluent: petroleum ether/ethyl acetate 1) to give intermediate AE (250 mg, yield: 37%).

Preparation of Intermediate AF

Accordingly, intermediate AF was prepared in the same way as intermediate G, starting from intermediate AE (200 mg, 0.729 mmol) yielding 120 mg, 94%.

Preparation of Intermediate AG

Accordingly, intermediate AG was prepared in the same way as intermediate AG, starting from intermediate AF (80.0 mg, 0.459 mmol) and 4-iodobenzonitrile (CAS [3058-39-7], 158 mg, 0.688 mmol) yielding 80.0 mg, 63%.

Preparation of Intermediate AH

Accordingly, intermediate AH was prepared in the same way as intermediate I, starting from intermediate AG (70.0 mg, 0.254 mmol) yielding 70.0 mg, 99%.

Preparation of Compound 11

A solution of intermediate L (51.4 mg, 0.228 mmol), HATU (113 mg, 0.296 mmol), DIEA (76.6 mg, 0.593 mmol) in DMF (10 mL) was stirred for 30 minutes at 25° C. Intermediate AH (70.0 mg, 0.251 mmol) was added to the mixture and the mixture was stirred for 2 hours at 25° C. The mixture was concentrated under vacuum. The crude product was purified by high performance liquid chromatography over Gemini (eluent: gradient 0.05% ammonia in water/methanol from 30/70 to 5/95). The desired fractions were collected and concentrated to give Compound 11 (10.5 mg, yield: 9%).

1H NMR (400 MHz, CDCl$_3$) δ ppm 9.83 (d, J=2.51 Hz, 1H) 8.55 (d, J=2.76 Hz, 1H) 8.42-8.49 (m, 2H) 7.53 (d, J=7.78 Hz, 1H) 7.23 (d, J=8.53 Hz, 3H) 6.47 (d, J=8.53 Hz, 2H) 6.06 (br. s., 1H) 4.58 (d, J=5.27 Hz, 2H) 4.04 (s, 2H) 3.83 (s, 2H) 3.50 (q, J=8.72 Hz, 1H) 2.99 (q, J=7.53 Hz, 2H) 2.65-2.74 (m, 2H) 2.33-2.43 (m, 2H) 1.42 (t, J=7.53 Hz, 3H)

Synthesis of Compound 12 and Compound 13

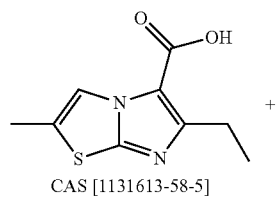

CAS [1131613-58-5]

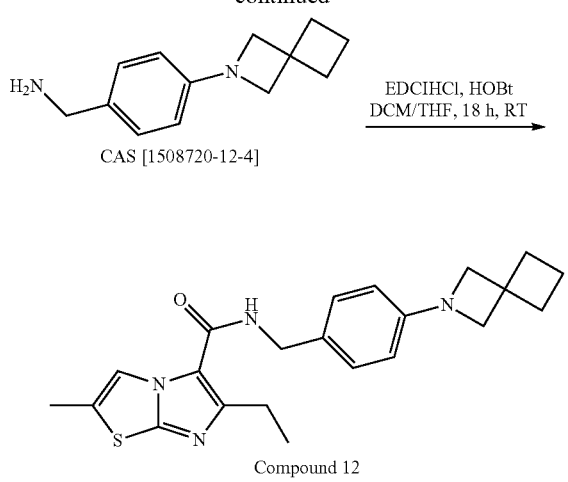

A solution of 6-ethyl-2-methylimidazo[2,1-b]thiazole-5-carboxylic acid (CAS [1131613-58-5], 40 mg, 0.19 mmol), (4-{2-azaspiro[3.3]heptan-2-yl}phenyl)methanamine (CAS [1508720-12-4], 46 mg, 0.23 mmol), EDCI.HCl (29 mg, 0.15 mmol), HOBt (26 mg, 0.19 mmol) and DIPEA (0.033 mL, 0.19 mmol) in dichloromethane (1.3 mL) and THF (1.3 mL) was stirred at room temperature for 18 h. The mixture was extended with silica and evaporated in vacuo. The residue was purified by preparative LC (regular SiOH 30 μm, 12 g Interchim, dry loading, mobile phase gradient: heptane/EtOAc from 70/30 to 50/50) to give after evaporation 41 mg of Compound 12 as a white solid (55%).

$^1$H NMR (500 MHz, DMSO-d$_6$) δ ppm 1.19 (t, J=7.4 Hz, 2H) 1.70-1.86 (m, 2H) 2.15 (t, J=7.6 Hz, 4H) 2.42 (d, J=1.3 Hz, 3H) 2.84 (q, J=7.6 Hz, 2H) 3.72 (s, 4H) 4.34 (d, J=6.0 Hz, 2H) 6.36 (d, J=8.5 Hz, 2H) 7.14 (d, J=8.5 Hz, 2H) 7.88 (d, J=1.3 Hz, 1H) 8.02 (br t, J=6.0 Hz, 1H).

Compound 13

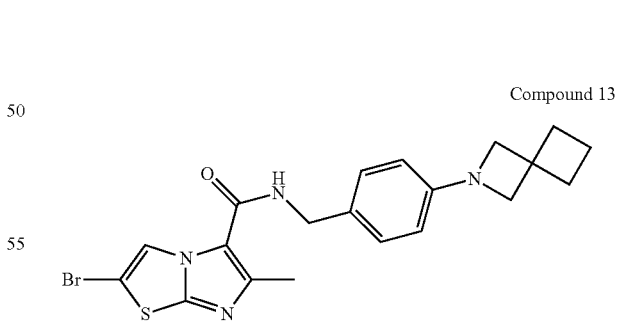

Compound 13

Accordingly, Compound 13 was prepared as the same way as Compound 12 starting from 2-bromo-6-methylimidazo[2,3-b][1,3]thiazole-5-carboxylic acid CAS [86933-04-2] and (4-{2-azaspiro[3.3]heptan-2-yl}phenyl)methanamine CAS [1508720-12-4], yielding 41 mg, 55%.

¹H NMR (500 MHz, DMSO-d₆) δ ppm 1.19 (t, J=7.4 Hz, 2H) 1.70-1.86 (m, 2H) 2.15 (t, J=7.6 Hz, 4H) 2.42 (d, J=1.3 Hz, 3H) 2.84 (q, J=7.6 Hz, 2H) 3.72 (s, 4H) 4.34 (d, J=6.0 Hz, 2H) 6.36 (d, J=8.5 Hz, 2H) 7.14 (d, J=8.5 Hz, 2H) 7.88 (d, J=1.3 Hz, 1H) 8.02 (br t, J=6.0 Hz, 1H).

Synthesis of Compound 14

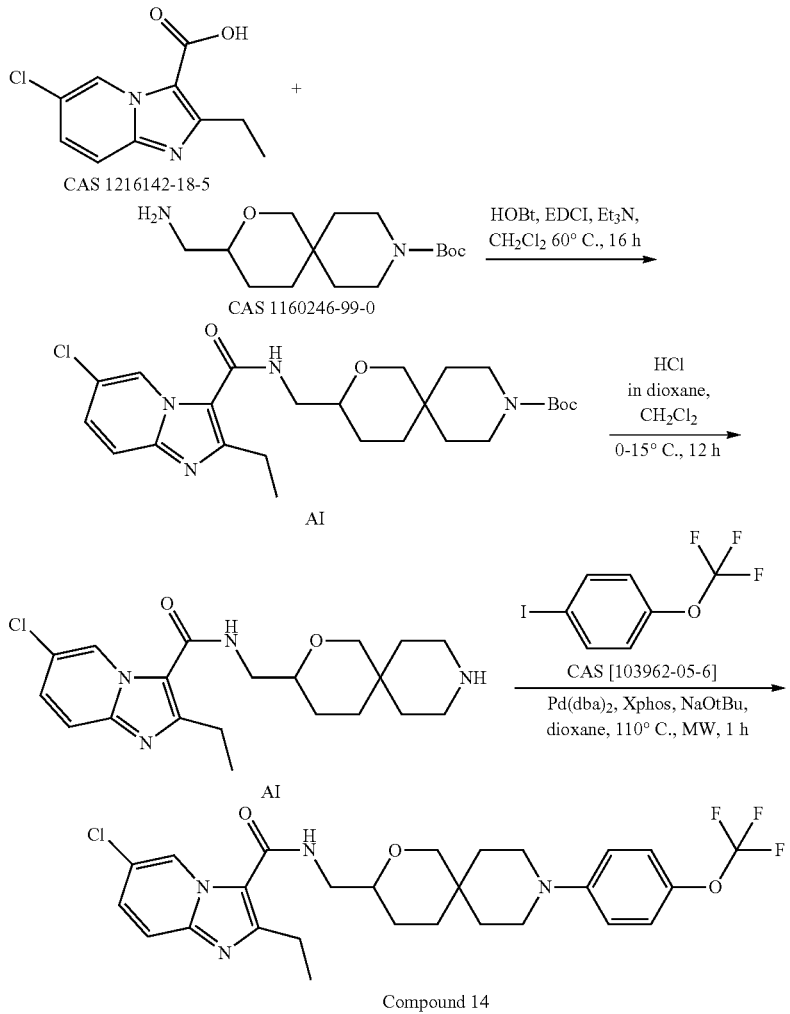

Preparation of Intermediate AI

Triethylamine (0.096 mL, 0.690 mmol), tert-butyl 3-(aminomethyl)-2-oxa-9-azaspiro[5.5]undecane-9-carboxylate (CAS [1160246-99-0], 100 mg, 0.352 mmol), HOBT (46.6 mg, 0.345 mmol) and EDCI.HCl (99.3 mg, 0.518 mmol) were added to a solution of 6-chloro-2-ethylimidazo[3,2-a]pyridine-3-carboxylic acid (CAS [1216142-18-5], 77.5 mg, 0.345 mmol) in dichloromethane (2 mL) in turn. After stirred at 60° C. for 16 hours, ethyl acetate (20 mL) was added. The mixture was washed with water (2×20 mL) and brine (20 mL). The separated organic layer was dried over sodium sulfate, filtered and the filtrate was concentrated under vacuum. The residue was purified by column chromatography over silica gel (eluent: petroleum ether/ethyl acetate 1/1 to 0/1) to give intermediate AI (160 mg, Yield: 86%).

Preparation of Intermediate AJ

Hydrochloride (2 mL, 8 mmol, 2 M in dioxane) was added to a solution of intermediate AI (120 mg, 0.244 mmol) in dichloromethane (2 mL) at 0° C. After stirred at 15° C. for 12 hours, the solvent was evaporated under vacuum. The residue was dissolved into water (20 mL) and then basified with saturated aqueous sodium carbonate to pH~10. The solution was extracted with dichloromethane/methanol (10/1, 2×20 mL). The combined organic layers were washed with brine (20 mL), dried over sodium sulfate, filtered and the filtrated was concentrated under vacuum to give intermediate AJ (50 mg, yield: 56%).

Preparation of Compound 14

A solution of intermediate AJ (30.0 mg, 0.0770 mmol), 1-iodo-4-(trifluoromethoxy) benzene (CAS [103962-05-6], 22.2 mg, 0.0770 mmol), Pd(dba)₂ (4.60 mg, 8.00 μmol, X-phos (7.63 mg, 16.0 μmol) and sodium tert-butoxide (29.6 mg, 0.308 mmol) in dioxane (4 mL) was irradiated under microwave at 110° C. for 1 h under N₂ atmosphere. The mixture was filtered and the filtrate was concentrated under reduced pressure. The residue was dissolved in ethyl acetate, washed with water, brine, dried over Na₂SO₄, filtered and concentrated to dryness under reduced pressure. The residue was purified by column chromatography over silica gel (petroleum ether/ethyl acetate 10/1 to 0/1) to give crude compound. It was further purified by high performance liquid chromatography over Gemini C18 150×25 mm×10 μl (eluent: 0.5% ammonia in water/acetonitrile 45/55 to 15/85). The desired fractions were collected and lyophilized to give Compound 14 (1.30 mg, yield: 3%).

$^1$H NMR (400 MHz, CDCl$_3$) δ=9.50 (d, J=1.3 Hz, 1H), 7.54 (d, J=9.5 Hz, 1H), 7.29 (dd, J=2.1, 9.4 Hz, 1H), 7.10 (d, J=8.5 Hz, 2H), 6.89 (d, J=9.3 Hz, 2H), 6.35 (br. s., 1H), 3.93-3.85 (m, 2H), 3.51 (br. s., 1H), 3.30 (m, 1H), 3.24 (d, J=11.3 Hz, 1H), 3.21-3.07 (m, 4H), 3.03 (q, J=7.5 Hz, 2H), 1.94-1.85 (m, 2H), 1.79 (d, J=7.0 Hz, 1H), 1.66-1.62 (m, 1H), 1.61-1.59 (m, 2H), 1.50-1.47 (m, 2H), 1.44 (t, J=7.5 Hz, 3H)

Synthesis of Compound 15

Preparation of Intermediate AK

Sodium tert-butoxide (481 mg, 5.01 mmol) in dimethoxyethane (5 mL) and butanol (5 mL) was added to a solution of 7-Boc-7-azaspiro[3.5]nonan-2-one (CAS [203661-69-2], 600 mg, 2.51 mmol) and Tosmic (548 mg, 2.81 mmol) in dimethoxyethane (5 mL) under nitrogen atmosphere at 10 to 15° C. over 1 hour. After stirring of the mixture at 20° C. for 12 hours, the reaction mixture was poured into ice water, and then extracted with ethyl acetate. The extract was washed with brine, dried, and evaporated. The residue was purified by column chromatography over silica gel (20% ethyl acetate-hexane) to give intermediate AK (50.0 mg, yield: 8%).

Preparation of Intermediate AL

A solution of intermediate AK (50 mg, 0.200 mmol) in NH$_3$.MeOH (7 M in methanol, 10 mL) was hydrogenated at

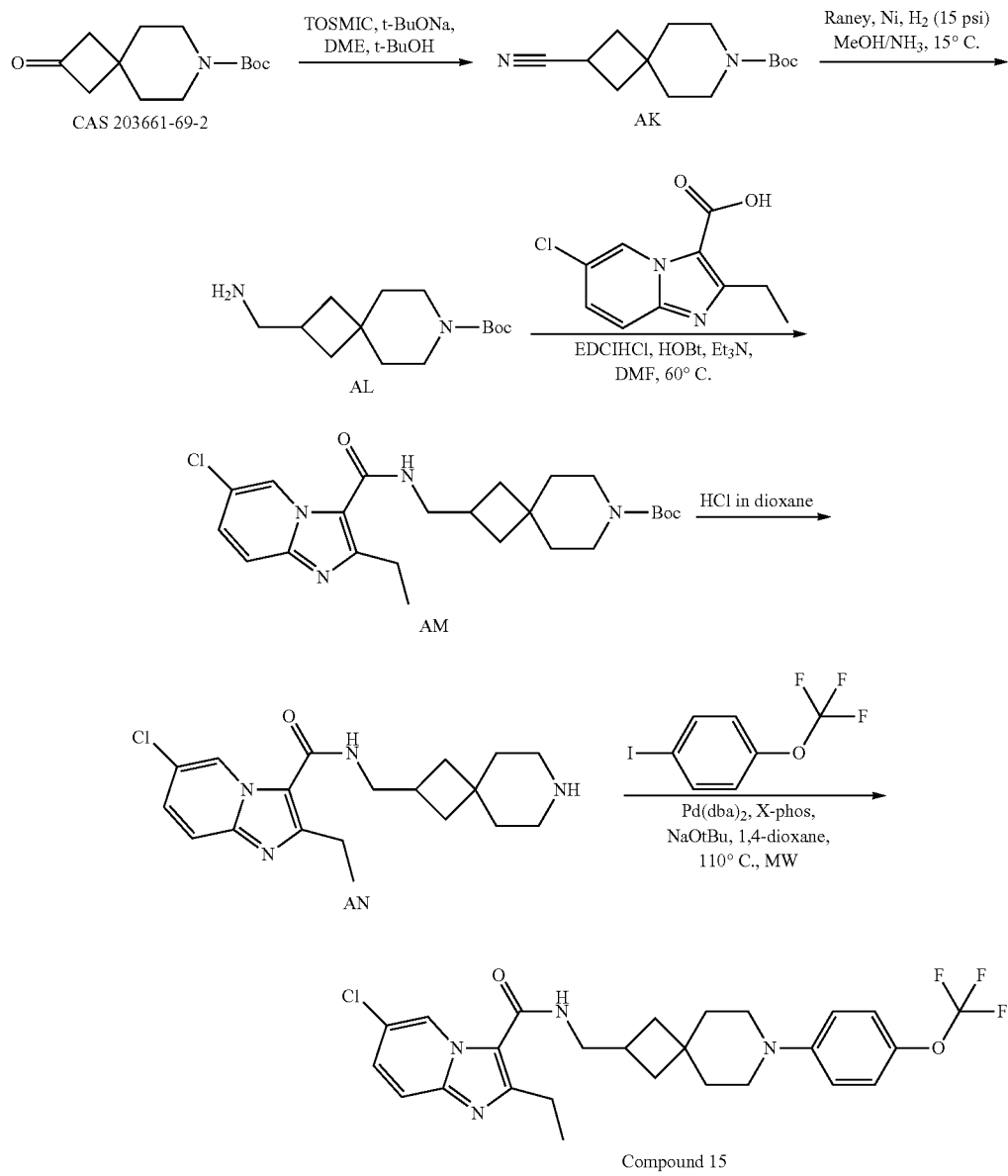

Compound 15

15° C. (H₂, 15 psi) with Raney Nickel (25 mg) as a catalyst for 16 hours. The catalyst was filtered off and the filtrate was concentrated under vacuum to give intermediate AL (50.9 mg, Yield: 95%).

Preparation of Intermediate AM

A solution of intermediate AL (44.9 mg, 0.200), 6-chloro-2-ethylimidazo[3,2-a]pyridine-3-carboxylic acid (CAS [1216142-18-5], 50.9 mg, 0.200 mmol), HOBt (27.0 mg, 0.200 mmol), EDCI (57.5 mg, 0.300 mmol) and triethylamine (0.056 ml, 0.400 mmol) in DMF (2 ml) was stirred at 60° C. for 16 hours. Ethyl acetate (20 mL) was added and the mixture was washed with brine, dried, filtered and the filtrate was concentrated. The residue was purified by column chromatography over silica gel (petroleum/ethyl acetate 1/1) to give intermediate AM (50.0 mg, yield: 51%).

Preparation of Intermediate AN

Hydrochloride (1.00 mL, 4.00 mmol, 4 M in ethyl acetate) was added to a solution of intermediate AM (50.0 mg, 0.108 mmol) in C at 0° C. The mixture was warmed up to 20° C. and stirred for 16 hours. The mixture was neutralized with saturated sodium carbonate to pH ~10 and diluted with ethyl acetate (10 mL). The organic layer was washed with brine (10 mL), dried over sodium sulfate, filtered and concentrated under vacuum. The residue was purified by thin layer chromatography over silica gel (eluent: dichloromethane/methanol 10/1) to give intermediate AN (35.0 mg, yield: 81%).

Preparation of Compound 15

A solution of intermediate AN (15.0 mg, 0.0420 mmol), 1-iodo-4-(trifluoromethoxy) benzene (CAS [103962-05-6], 12.1 mg, 0.042 mmol), Pd(dba)₂ (3.66 mg, 6.37 µmol), X-phos (3.81 mg, 8.00 mmol) and sodium tert-butoxide (16.1 mg, 0.168 mmol) in 1,4-dioxane (2 mL) was irradiated under microwave at 110° C. for 60 min under N₂ atmosphere. The mixture was filtered and then the filtrate was concentrated under reduced pressure. The residue was purified by column chromatography over silica gel (eluent: petroleum ether/ethyl acetate 1/1) to give crude compound. It was further purified by high performance liquid chromatography over Gemini C18 150×25 mm×10 µl (eluent: ammonia in water/acetonitrile 30/70 to 0/100). The desired fractions were collected and lyophilized to give Compound 15 (2.30 mg, yield: 10%).

¹H NMR (400 MHz, CDCl₃) δ=9.47 (s, 1H), 7.54 (d, J=9.5 Hz, 1H), 7.29 (dd, J=2.0, 9.5 Hz, 1H), 7.08 (d, J=9.0 Hz, 2H), 6.89 (d, J=9.0 Hz, 2H), 5.80 (br. s., 1H), 3.57 (t, J=6.5 Hz, 2H), 3.17-3.09 (m, 2H), 3.09-3.03 (m, 2H), 3.00 (q, J=7.5 Hz, 2H), 2.61 (td, J=8.3, 16.1 Hz, 1H), 2.11-1.99 (m, 2H), 1.83-1.75 (m, 2H), 1.71 (d, J=5.5 Hz, 2H), 1.60-1.54 (m, 2H), 1.45 (t, J=7.7 Hz, 3H)

Synthesis of Compound 16, Compound 17, Compound 18 and Compound 19

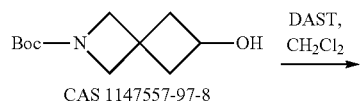

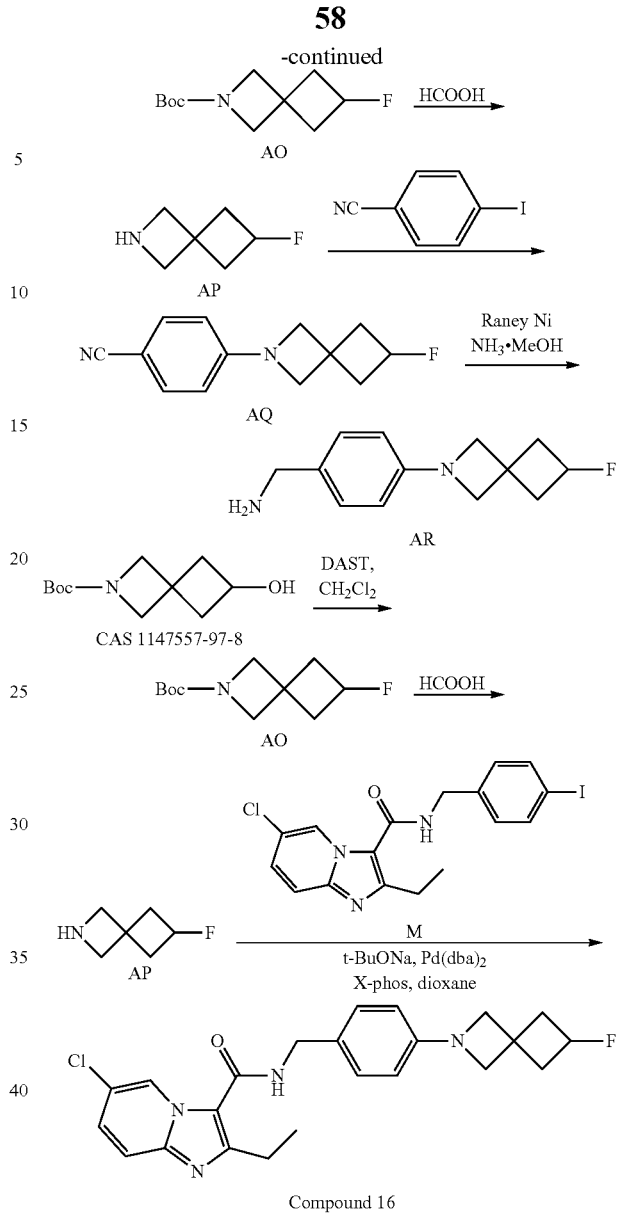

Compound 16

Preparation of Intermediate AO

DAST (0.507 mL, 3.84 mmol) was added dropwise to a solution of tert-butyl 6-hydroxy-2-azaspiro[3.3]heptane-2-carboxylate (CAS [63711570], 700 mg, 3.28 mmol) in dry dichloromethane (5 mL) under nitrogen atmosphere at 0° C. The mixture was slowly warmed up to 40° C. and stirred overnight. The resulting mixture was washed with water and brine. The organic layer was dried over magnesium sulfate, filtered and concentrated under vacuum. The residue was purified by column chromatography over silica gel to give intermediate AO (200 mg, yield: 27%).

Preparation of Intermediate AP

A mixture of intermediate AO (200 mg, 0.929 mmol) in formic acid (5 mL) was stirred at 25° C. for 16 hours. The mixture was concentrated under vacuum to give intermediate AP (149 mg, yield: 100%).

Preparation of Compound 16

A solution of intermediate AP (59.4 mg, 0.369 mmol), intermediate M (195 mg, 0.443 mmol), Pd(dba)$_2$ (21.2 mg, 0.037 mmol), X-phos (35.2 mg, 0.074 mmol) and sodium tert-butoxide (177 mg, 1.85 mmol) in 1,4-dioxane (8 ml) was irradiated under microwave at 110° C. for 60 min under N$_2$. Dichloromethane (50 mL) was added and the mixture was washed with water (50 mL) and brine (50 mL). The organic layer was dried over sodium sulfate, filtered and the filtrate was concentrated under vacuum. The residue was purified by column chromatography over silica gel (eluent: petroleum ether/ethyl acetate 1/0 to 0/1). The desired fractions were collected and concentrated. The residue was further purified by high performance liquid chromatography over Waters Xbridge C18 150×20 mm×5 μm (eluent: 0.5% NH$_3$ water/methanol 35/65 to 5/95). The desired fractions were collected and lyophilized to give Compound 16 (33.30 mg, yield: 21%).

$^1$H NMR (400 MHz, CDCl$_3$) δ=9.52 (d, J=1.5 Hz, 1H), 7.53 (d, J=9.5 Hz, 1H), 7.29 (dd, J=2.1, 9.4 Hz, 1H), 7.22 (d, J=8.3 Hz, 2H), 6.43 (d, J=8.3 Hz, 2H), 5.99 (br. s., 1H), 5.10-4.85 (m, 1H), 4.57 (d, =5.4 Hz, 2H), 3.87 (d, =16.4 Hz, 4H), 2.94 (q, J=7.6 Hz, 2H), 2.71-2.59 (m, 2H), 2.52-2.36 (m, 2H), 1.38 (t, J=7.6 Hz, 3H).

Preparation of Intermediate AO

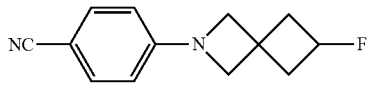 [SMILES: N#Cc1ccc(N2CC3(CC(F)C3)C2)cc1]

A solution of intermediate AP (400 mg, 3.47 mmol), 4-iodobenzonitrile (1.19 g, 5.21 mmol), X-phos (199 mg, 0.42 mmol), Pd(dba)$_2$ (120 mg, 0.208 mmol) and t-BuONa (1.34 g, 13.9 mmol) in dioxane (20 mL) was irradiated under microwave at 110° C. for 1 hour under N$_2$. The mixture was concentrated. The crude product was purified by column chromatography over silica gel (eluent: ethyl acetate/petroleum ether from 0 to 1/5). The desired fractions were collected and concentrated to give intermediate AQ (450 mg, yield: 60%).

Preparation of Intermediate AR

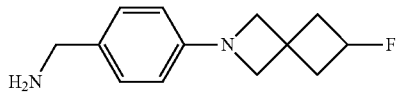

A mixture of intermediate AQ (450 mg, 2.08 mmol) in NH$_3$.MeOH (7M in methanol, 20 mL) was hydrogenated (15 psi) with Raney Nickel (50 mg) as catalyst at 25° C. for 16 hours. After uptake of H2, the catalyst was filtered off and the filtrate was concentrated to give intermediate AR (450 mg, yield: 98%).

Preparation of Compound 17

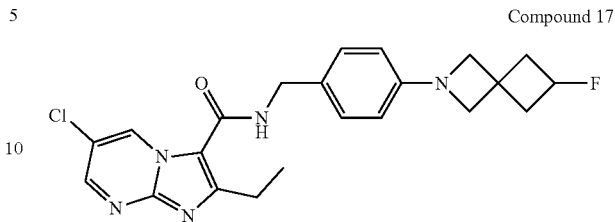

Compound 17

Accordingly, Compound 17 was prepared as the same way as Compound 11, starting from intermediate AR and intermediate L, yielding 5.20 mg, yield: 3%.

1H NMR (400 MHz, CDCl$_3$) δ ppm 9.82 (d, J=2.51 Hz, 1H) 8.55 (d, J=2.51 Hz, 1H) 7.21 (d, J=8.28 Hz, 2H) 6.43 (d, J=8.53 Hz, 2H) 6.05 (br. s., 1H) 5.05-4.9 (m, 1H) 4.57 (d, J=5.52 Hz, 2H) 3.89 (s, 2H) 3.85 (s, 2H) 2.98 (q, J=7.53 Hz, 2H) 2.61-2.69 (m, 2H) 2.38-2.50 (m, 2H) 1.42 (t, J=7.53 Hz, 3H)

Preparation of Compound 18

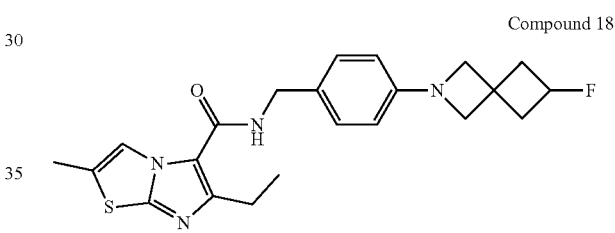

Compound 18

Accordingly, Compound 18 was prepared as the same way as Compound 11, starting from intermediate AR and 6-ethyl-2-methylimidazo[2,1-b]thiazole-5-carboxylic acid CAS[1131613-58-5], yielding 41.8 mg, yield: 27%.

$_1$H NMR (400 MHz, CDCl$_3$) δ ppm 7.99 (d, J=1.26 Hz, 1H) 7.20 (d, J=8.28 Hz, 2H) 6.40-6.45 (m, 2H) 5.84 (br. s., 1H) 5.05-4.9 (m, 1H) 4.54 (s, 2H) 3.88 (s, 2H) 3.84 (s, 2H) 2.82 (q, J=7.70 Hz, 2H) 2.60-2.70 (m, 2H) 2.37-2.52 (m, 5H) 1.29-1.36 (m, 3H).

Preparation of Compound 19

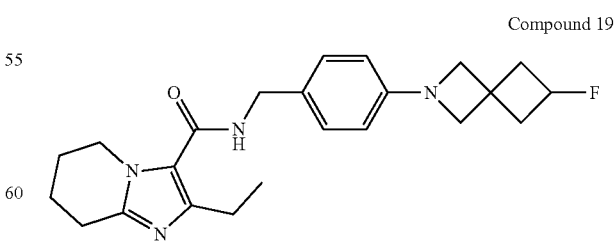

Compound 19

Accordingly, Compound 19 was prepared as the same way as Compound 11, starting from intermediate AR and 2-ethyl-5H,6H,7H,8H-imidazo[1,2-a]pyridine-3-carboxylic acid CAS [1529528-99-1], yielding 32.0 mg, yield: 21.5%.

1H NMR (400 MHz, CDCl$_3$) δ ppm 7.18 (d, J=8.28 Hz, 2H) 6.41 (d, J=8.53 Hz, 2H) 5.81 (br. s., 1H) 4.86-5.10 (m, 1H) 4.48 (d, J=5.52 Hz, 2H) 4.22 (t, J=5.90 Hz, 2H) 3.88 (s, 2H) 3.84 (s, 2H) 2.85 (t, J=6.40 Hz, 2H) 2.60-2.70 (m, 4H) 2.37-2.51 (m, 2H) 1.83-1.99 (m, 4H) 1.22 (t, J=7.65 Hz, 3H)

Synthesis of Compound 20 and Compound 21

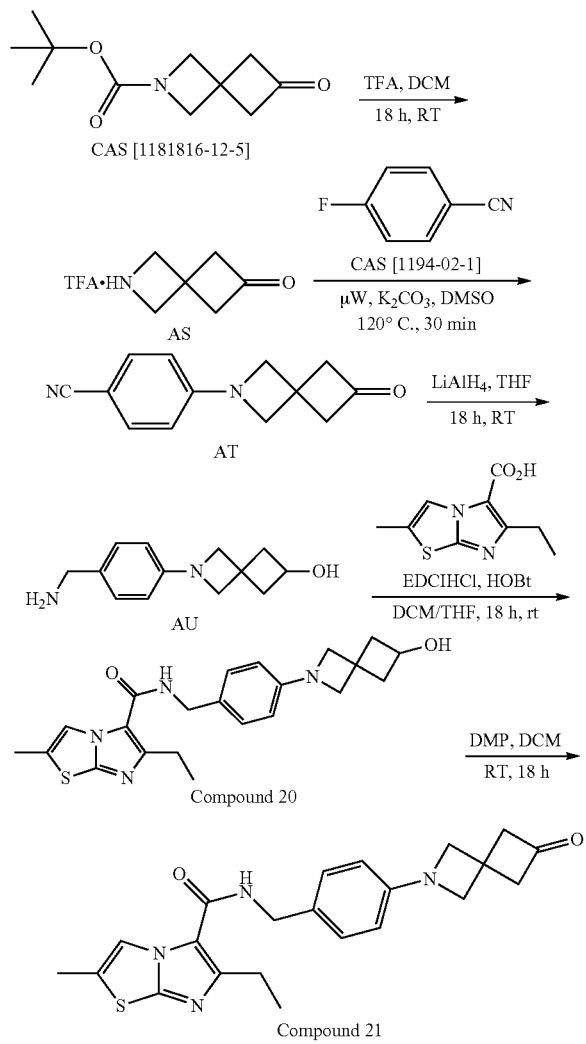

Preparation of Intermediate AS

TFA (1.6 mL, 21 mmol) was added to a solution of tert-butyl 6-oxo-2-azaspiro[3.3]heptane-2-carboxylate (CAS [1181816-12-5], 0.3 g, 1.4 mmol) in dichloromethane (9.8 mL) and the mixture was stirred at room temperature for 18 h. The reaction mixture was evaporated under vacuum, and coevaporated twice with toluene to afford 320 mg of Intermediate AS as a colorless oil (100%).

Preparation of Intermediate AT

A solution of intermediate AS (0.34 g, 1.5 mmol), 4-fluorobenzonitrile (CAS [1194-02-1], 0.37 g, 3.0 mmol) and K$_2$CO$_3$ (0.62 g, 4.5 mmol) in DMSO (5.4 mL) was heated at 120° C. using a single mode microwave (Biotage initiator60) with a power output ranging from 0 to 400 W for 30 min. Brine and EtOAc were added. The organic layer was extracted, dried over MgSO$_4$, filtered and evaporated. Purification of the residue was carried out by preparative LC (Interchim, 12 g, 30 μm, Heptane/EtOAc 90/10). Pure fractions were collected and evaporated to give 60 mg of intermediate AT as a white solid (19%).

Preparation of Intermediate AU

A solution of intermediate AT (60 mg, 0.28 mmol) in dry THF (1.1 mL) was added dropwise to a mixture of LiAlH$_4$ (64 mg, 1.7 mmol) in dry THF (1.2 mL) at 0° C. The mixture was slowly let come back to room temperature and stirred overnight. Water (0.24 mL) then dichloromethane (30 mL) were added very slowly and stirred for 20 min. MgSO$_4$ was added, the insoluble was filtered on a pad of celite, and the filtrate was evaporated until dryness to give 57 mg of intermediate AU as a white solid (92%).

Preparation of Compound 20

A solution of 6-ethyl-2-methylimidazo[2,1-b]thiazole-5-carboxylic acid (CAS [1131613-58-5], 46 mg, 0.22 mmol), intermediate AU (57 mg, 0.26 mmol), EDCI.HCl (34 mg, 0.22 mmol), HOBt (29 mg, 0.22 mmol) and DIPEA (0.038 mL, 0.22 mmol) in dichloromethane (1.5 mL) and THF (1.5 mL) was stirred at room temperature for 18 h. The mixture was extended with silica and evaporated in vacuo. The residue was purified by preparative LC (regular SiOH 30 μm, 12 g, dry loading, mobile phase gradient: DCM/MeOH from 99/1 to 96/4) to give after evaporation, trituration in Et$_2$O and a second evaporation, 53 mg of Compound 20 as a beige solid (59%).

$^1$H NMR (400 MHz, DMSO-d$_6$) δ ppm 1.19 (t, J=7.6 Hz, 3H) 1.89-2.02 (m, 2H) 2.38-2.45 (m, 2H) 2.41 (s, 3H) 2.83 (q, J=7.6 Hz, 2H) 3.67 (s, 2H) 3.72 (s, 2H) 3.90-4.08 (m, 1H) 4.34 (d, J=5.6 Hz, 2H) 5.01 (d, J=6.6 Hz, 1H) 6.34 (d, J=8.6 Hz, 2H) 7.13 (d, 0.1=8.1 Hz, 2H) 7.87 (d, J=1.0 Hz, 1H) 7.99 (t, J=6.1 Hz, 1H).

Preparation of Compound 21

Under nitrogen, DMP (15%) in dichloromethane (0.20 mL, 94 μmol) was added to a solution of Compound 20 (35 mg, 85 μmol) in dichloromethane (2.7 mL) and the mixture was stirred at room temperature for 72 h. The mixture was extended with silica and evaporated in vacuo. The residue was purified by preparative LC (regular SiOH 30 μm, 12 g, dry loading, mobile phase gradient: DCM/MeOH from 99/1 to 97/3) to give after evaporation, trituration in Et$_2$O and evaporation, 18 mg of a beige solid. This solid was purified via Reverse phase (Stationary phase: X-Bridge-C18 5 μm 30*150 mm, Mobile phase: Gradient from 75% aq. NH$_4$HCO$_3$ (0.5%), 25% MeCN to 35% aq. NH$_4$HCO$_3$ (0.5%), 65% MeCN) to give 5 mg of Compound 21 as a beige solid (14%).

$^1$H NMR (400 MHz, DMSO-d$_6$) δ ppm 1.19 (t, J=7.6 Hz, 3H) 2.41 (s, 3H) 2.84 (q, J=7.6 Hz, 2H) 3.32 (s, 4H) 3.95 (s, 4H) 4.35 (d, J=5.6 Hz, 2H) 6.43 (d, J=8.1 Hz, 2H) 7.17 (d, J=8.6 Hz, 2H) 7.88 (s, 1H) 8.02 (t, J=5.6 Hz, 1H).

Synthesis of Compound 23 and Compound 22

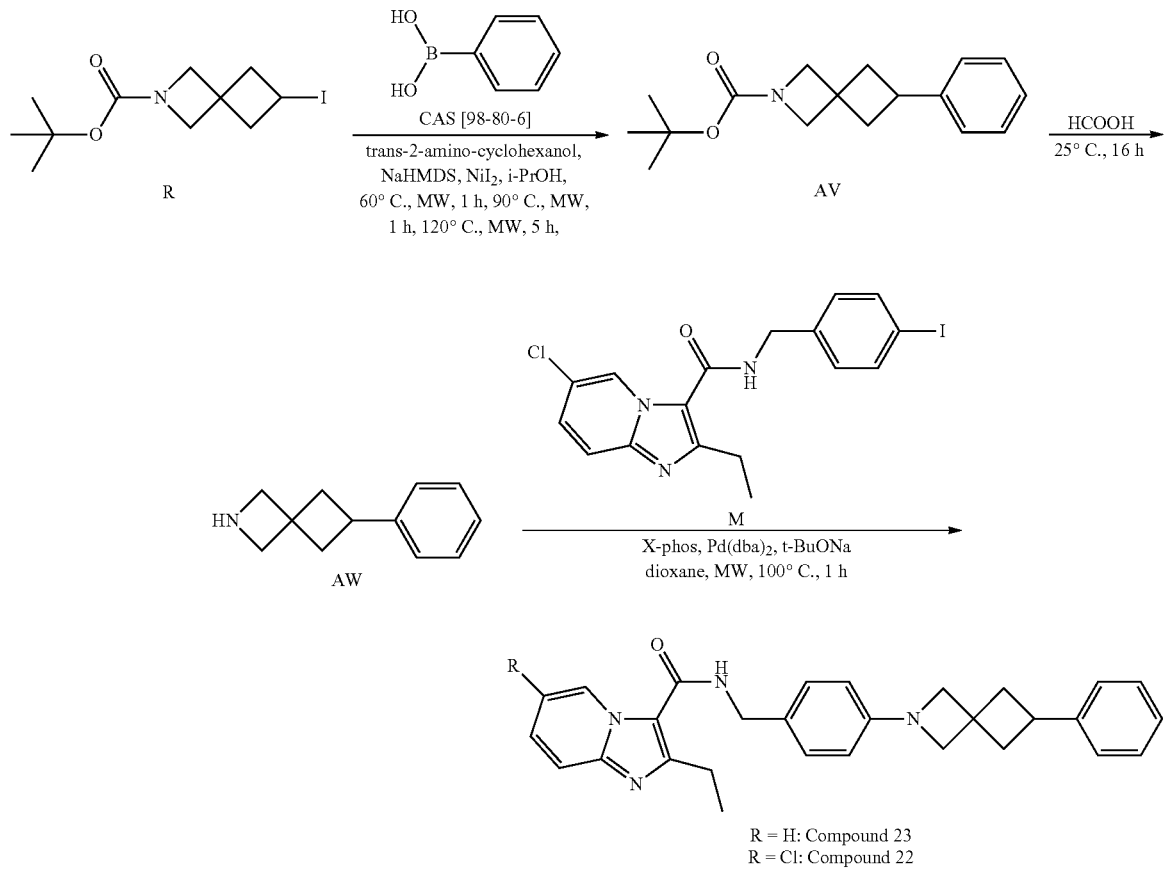

Preparation of Intermediate AV

Accordingly, intermediate AV was prepared in the same way as intermediate S, starting from intermediate R and Phenylboronic acid CAS [98-80-6], yielding 0.3 g, 62%.

Preparation of Intermediate AW

Accordingly, intermediate AW was prepared in the same way as intermediate T, starting from intermediate AV, yielding 0.27 g, 99'%.

Preparation of Compound 22 and Compound 23

Accordingly, Compound 22 was prepared in the same way as Compound 7 starting from intermediate AW and intermediate M. Yielding Compound 22, 0.031 g, 16% and Compound 23, as by product, 0.0071 g, 13%.

Compound 22 $^1$H NMR (400 MHz, CHLOROFORM-d) δ=9.53 (d, J=2.0 Hz, 1H), 7.57-7.49 (m, 1H), 7.28 (d, J=2.3 Hz, 3H), 7.24 (s, 1H), 7.23-7.17 (m, 4H), 6.47 (d, J=8.3 Hz, 2H), 5.98 (br. s., 1H), 4.58 (d, J=5.5 Hz, 2H), 4.02 (s, 2H), 3.81 (s, 2H), 3.48 (quin, =8.9 Hz, 1H), 2.94 (q, J=7.5 Hz, 2H), 2.69-2.60 (m, 2H), 2.41-2.32 (m, 2H), 1.38 (t, J=7.7 Hz, 3H).

Compound 23 $^1$H NMR (400 MHz, CHLOROFORM-d) δ ppm 9.40 (d, J=7.28 Hz, 1H) 7.60 (d, J=9.03 Hz, 1H) 7.34-7.31 (m, 3H) 7.29-7.20 (m, 5H) 6.88-6.95 (m, 1H) 6.47 (d, J=8.28 Hz, 2H) 5.97 (br. s., 1H) 4.59 (d, J=5.27 Hz, 2H) 4.02 (s, 2H) 3.81 (s, 2H) 3.38-3.54 (m, 1H) 2.96 (q, J=7.61 Hz, 2H) 2.59-2.74 (m, 2H) 2.31-2.42 (m, 2H) 1.39 (t, J=7.53 Hz, 3H)

Synthesis of Compound 24

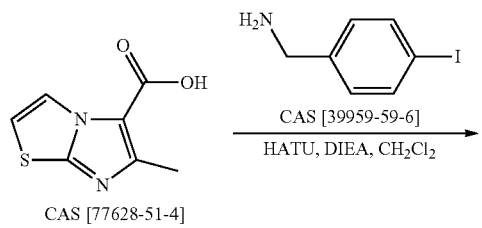

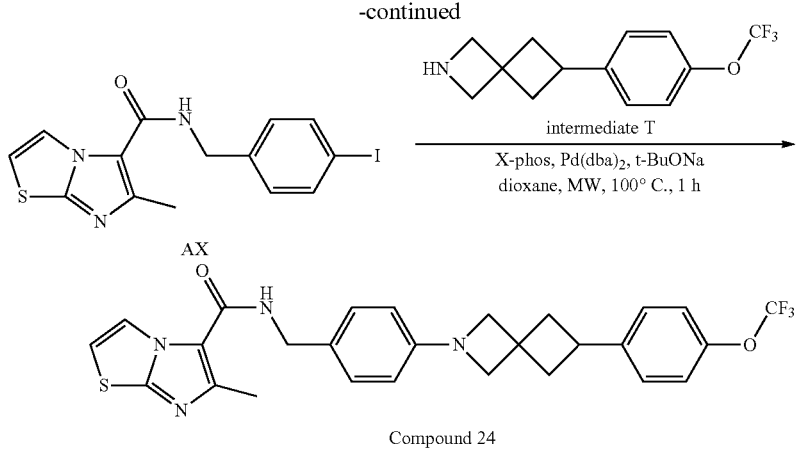

Compound 24

Preparation of Intermediate AX

A mixture of 6-methylimidazo[2,1-B][1,3]thiazole-5-carboxylic acid (CAS [77628-51-4], 200 mg, 1.10 mmol), 4-iodobenzenemethanamine (CAS [39959-59-6], 256 mg, 1.10 mmol), HATU (544 mg, 1.43 mmol), and diisopropylethylamine (425 mg, 3.29 mmol) in dichloromethane (5 ml) was stirred at 25° C. for 2 hours. The mixture was diluted with dichloromethane (100 ml). The solution was washed with water (50 mL), brine (50 mL), dried over sodium sulfate, filtered and concentrated under vacuum. The residue was purified by column chromatography over silica gel (eluent: petroleum ether/ethyl acetate 0/1) to give intermediate AX (220 mg, yield: 47.3%).

Preparation of Compound 24

Accordingly, Compound 24 was prepared in the same way as Compound 7 starting from intermediate AX and intermediate T, yielding 0.029 g, 17%.

$^1$H NMR (400 MHz, CHLOROFORM-d) δ ppm 8.29 (d, J=4.5 Hz, 1H), 7.24-7.18 (m, 4H), 7.18-7.13 (m, 2H), 6.88 (d, J=4.5 Hz, 1H), 6.46 (d, J=8.5 Hz, 2H), 5.85 (br. s., 1H), 4.56 (d, J=5.5 Hz, 2H), 4.02 (s, 2H), 3.80 (s, 2H), 3.47 (quin, J=8.9 Hz, 1H), 2.70-2.61 (m, 2H), 2.56 (s, 3H), 2.38-2.29 (m, 2H)

Synthesis of Compound 25 and Compound 26

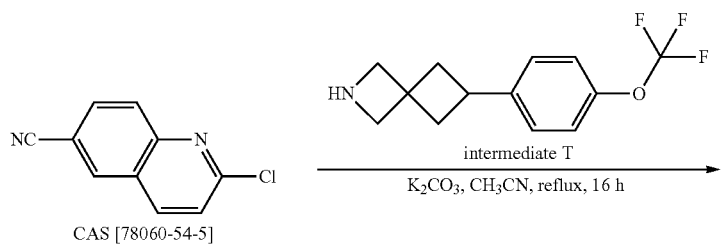

CAS [78060-54-5]

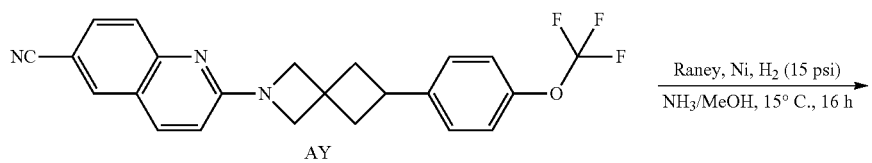

AY

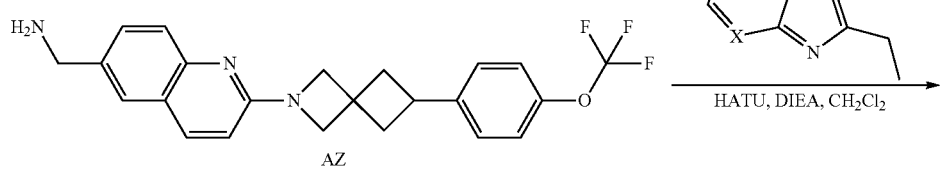

AZ

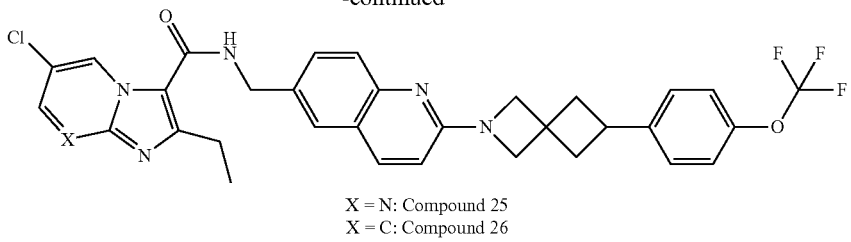

X = N: Compound 25
X = C: Compound 26

Preparation of Intermediate AY

A mixture of 2-chloro-6-quinolinecarbonitrile (CAS [78060-54-5], 14.7 mg, 0.078 mmol), Intermediate T (20.0 mg, 0.078 mmol) and potassium carbonate (21.6 mg, 0.156 mmol) in acetonitrile (5 mL) was refluxed for 16 hours. The solvent was evaporated under vacuum.

The residue was purified by column chromatography over silica gel (eluent: petroleum ether/ethyl acetate 1/1) to give intermediate AY (20.0 mg, yield: 62.8%).

Preparation of Intermediate AZ

A solution of intermediate AY (20.0 mg, 0.049 mmol) in $NH_3$·MeOH (20 mL, 7 M $NH_3$ in MeOH) was hydrogenated at 15° C. (15 psi) with Raney nickel (3 mg) as a catalyst for 16 hours. The catalyst was filtered off and the filtrate was concentrated under vacuum to give intermediate AZ (20.0 mg, yield: 91.84%).

Preparation of Compound 26

A solution of 6-chloro-2-ethylimidazo[3,2-a]pyridine-3-carboxylic acid (CAS [1216142-18-5], 9.79 mg, 0.044 mmol), HATU (21.7 mg, 0.057 mmol), DIEA (14.8 mg, 0.114 mmol) in $CH_2Cl_2$ (10 mL) was stirred for 30 minutes at 25° C. Intermediate AZ (20 mg, 0.048 mmol) was added to the mixture and the mixture was stirred for 2 hours at 25° C.

The mixture was concentrated under vacuum. The crude product was purified by high performance liquid chromatography over Gemini (eluent: 0.05% ammonia in water/methanol 35/65 to 5/95). The desired fractions were collected and concentrated to give Compound 26 (4.30 mg, 15.91%).

1H NMR (400 MHz, CHLOROFORM-d) δ ppm 9.56 (s, 1H) 7.84 (d, J=8.80 Hz, 1H) 7.74 (d, J=8.56 Hz, 1H) 7.59 (s, 1H) 7.55 (d, J=9.29 Hz, 2H) 7.31 (d, J=9.78 Hz, 1H) 7.22 (d, J=8.40 Hz, 2H) 7.16 (d, J=8.40 Hz, 2H) 6.59 (d, J=9.05 Hz, 1H) 6.13 (br. s., 1H) 4.79 (d, J=5.62 Hz, 2H) 4.33 (s, 2H) 4.11 (s, 2H) 3.50 (t, J=8.68 Hz, 1H) 2.97 (q, J=7.42 Hz, 2H) 2.65-2.76 (m, 2H) 2.33-2.44 (m, 2H) 1.38 (t, J=7.58 Hz, 3H)

Preparation of Compound 25

Accordingly, Compound 25 was prepared in the same way as Compound 26 starting from intermediate L and intermediate AZ, yielding 0.037 g, 25%.

1H NMR (400 MHz, CHLOROFORM-d) δ ppm 9.83 (d, J=2.51 Hz, 1H) 8.55 (d, J=2.51 Hz, 1H) 7.83 (d, J=8.78 Hz, 1H) 7.75 (d, J=8.53 Hz, 1H) 7.55 (d, J=9.20 Hz, 1H) 7.53 (d, J=6.80 Hz, 1H) 7.22 (d, J=8.80 Hz, 2H) 7.15 (d, 0.1=8.40 Hz, 2H) 6.58 (d, J=8.78 Hz, 1H) 6.26 (t, J=5.27 Hz, 1H) 4.77 (d, J=5.60 Hz, 2H) 4.33 (s, 2H) 4.11 (s, 2H) 3.50 (quin, J=8.85 Hz, 1H) 3.01 (q, J=7.53 Hz, 2H) 2.65-2.74 (m, 2H) 2.33-2.43 (m, 2H) 1.41 (t, J=7.53 Hz, 3H)

The following compounds were also prepared in accordance with the procedures described herein:

| Compound No | Structure |
|---|---|
| 27 | 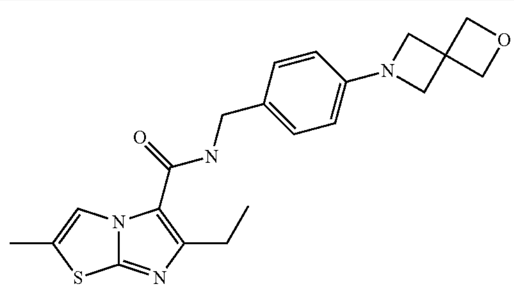 [SMILES: CCc1nc2sc(C)cn2c1C(=O)NCc1ccc(N2CC3(COC3)C2)cc1] |
| 28 | 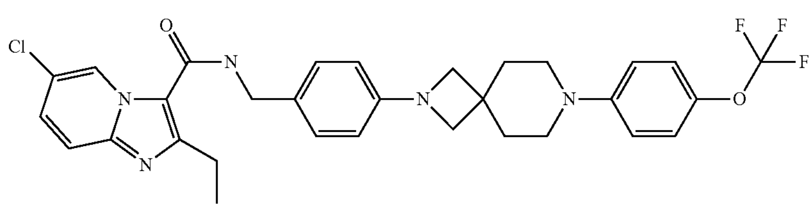 [SMILES: CCc1nc2ccc(Cl)cn2c1C(=O)NCc1ccc(N2CC3(CCN(c4ccc(OC(F)(F)F)cc4)CC3)C2)cc1] |

-continued
| Compound No | Structure |
|---|---|
| 29 | 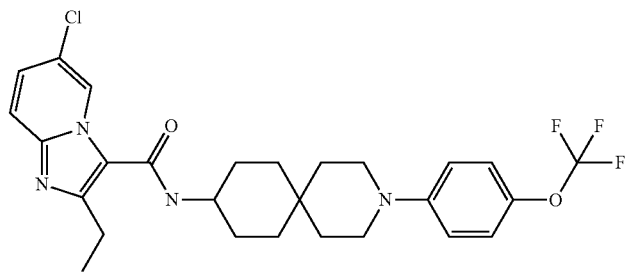 [SMILES: CCc1nc2ccc(Cl)cn2c1C(=O)NC1CCC2(CC1)CCN(c1ccc(OC(F)(F)F)cc1)CC2] |
| 30 | 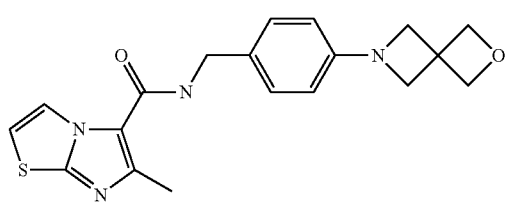 [SMILES: Cc1nc2sccn2c1C(=O)NCc1ccc(N2CC3(COC3)C2)cc1] |
| 31 | 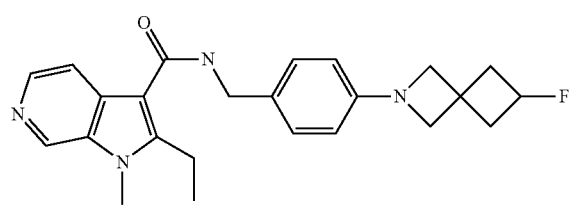 [SMILES: CCc1c(C(=O)NCc2ccc(N3CC4(CC(F)C4)C3)cc2)c2ccncc2n1C] |
| 32 | 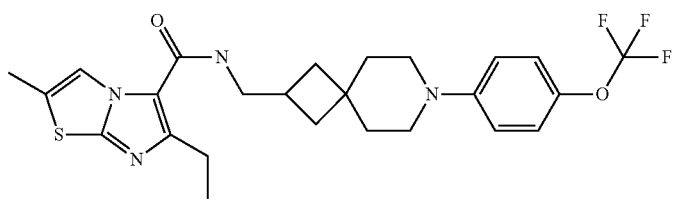 [SMILES: CCc1nc2sc(C)cn2c1C(=O)NCC1CC2(CCN(c3ccc(OC(F)(F)F)cc3)CC2)C1] |
| 33 | 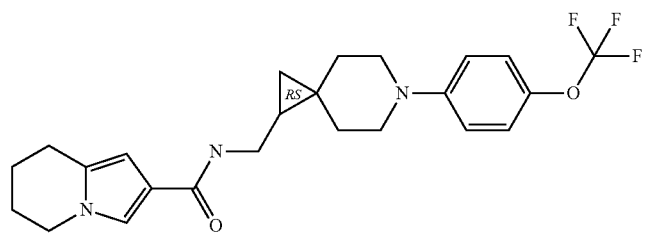 [SMILES: O=C(NCC1CC12CCN(c1ccc(OC(F)(F)F)cc1)CC2)c1cc2n(c1)CCCC2] |
| 34 | 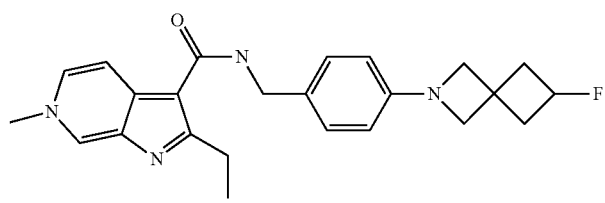 [SMILES: CCc1nc2cn(C)ccc-2c1C(=O)NCc1ccc(N2CC3(CC(F)C3)C2)cc1] |

-continued
| Compound No | Structure |
|---|---|
| 35 | 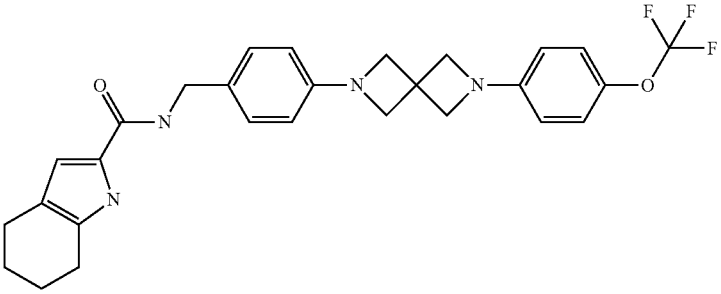 [SMILES: O=C(NCc1ccc(N2CC3(C2)CN(c2ccc(OC(F)(F)F)cc2)C3)cc1)c1cc2c([nH]1)CCCC2] |
| 36 | 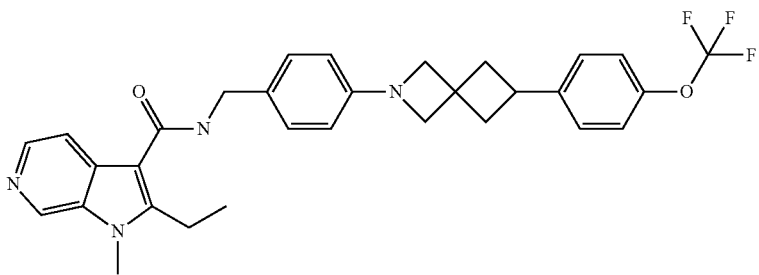 [SMILES: CCc1c(C(=O)NCc2ccc(N3CC4(CC(c5ccc(OC(F)(F)F)cc5)C4)C3)cc2)c2ccncc2n1C] |
| 37 | 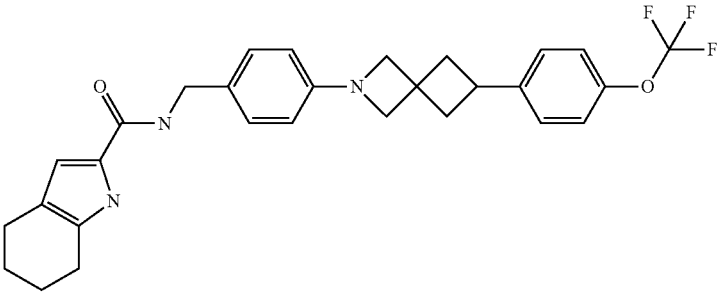 [SMILES: O=C(NCc1ccc(N2CC3(CC(c4ccc(OC(F)(F)F)cc4)C3)C2)cc1)c1cc2c([nH]1)CCCC2] |
| 38 | 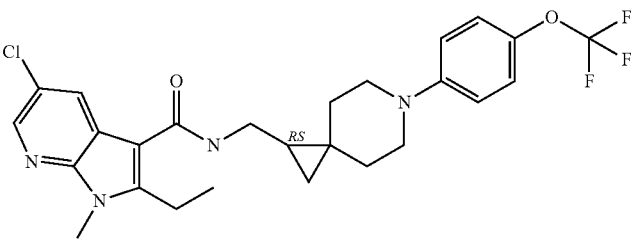 [SMILES: CCc1c(C(=O)NCC2CC23CCN(c2ccc(OC(F)(F)F)cc2)CC3)c2cc(Cl)cnc2n1C] |
| 39 | 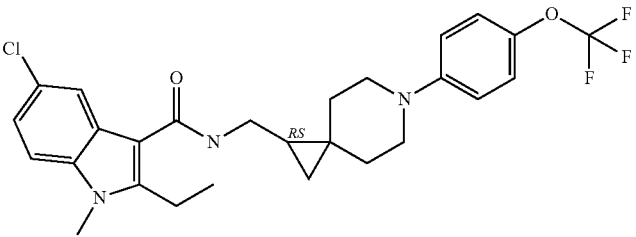 |

-continued

| Compound No | Structure |
|---|---|
| 40 | 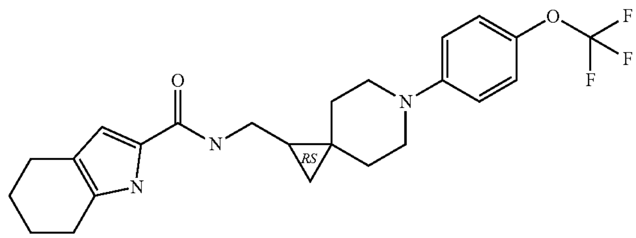 [SMILES: O=C(NCC1CC12CCN(c1ccc(OC(F)(F)F)cc1)CC2)c1cc2c([nH]1)CCCC2] |
| 41 | 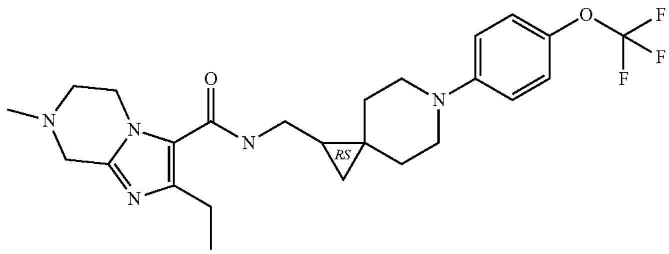 [SMILES: CCc1nc2n(c1C(=O)NCC1CC13CCN(c1ccc(OC(F)(F)F)cc1)CC3)CCN(C)C2] |
| 42 | 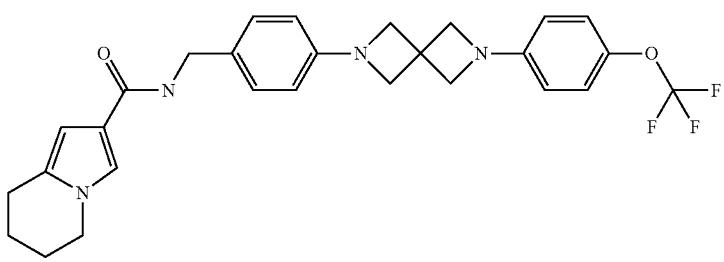 [SMILES: O=C(NCc1ccc(N2CC3(C2)CN(c2ccc(OC(F)(F)F)cc2)C3)cc1)c1cc2n(c1)CCCC2] |
| 43 | 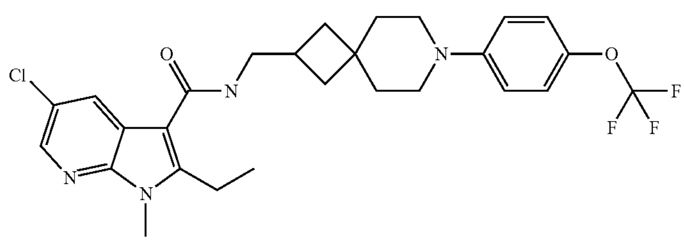 [SMILES: CCc1c(C(=O)NCC2CC3(CCN(c4ccc(OC(F)(F)F)cc4)CC3)C2)c2cc(Cl)cnc2n1C] |
| 44 | 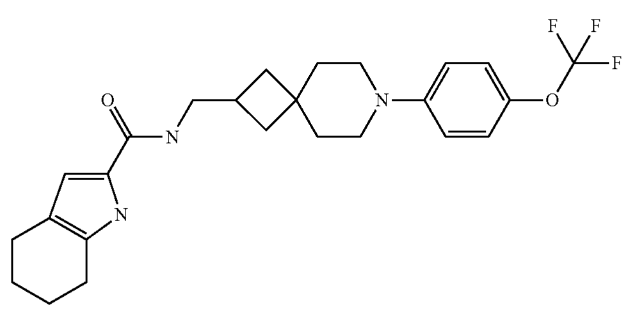 [SMILES: O=C(NCC1CC2(CCN(c3ccc(OC(F)(F)F)cc3)CC2)C1)c1cc2c([nH]1)CCCC2] |

-continued
| Compound No | Structure |
|---|---|
| 45 | 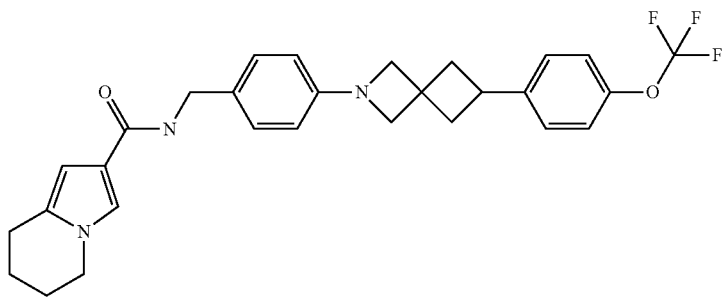 [SMILES: O=C(NCc1ccc(N2CC3(CC(c4ccc(OC(F)(F)F)cc4)C3)C2)cc1)c1cc2n(c1)CCCC2] |
| 46 | 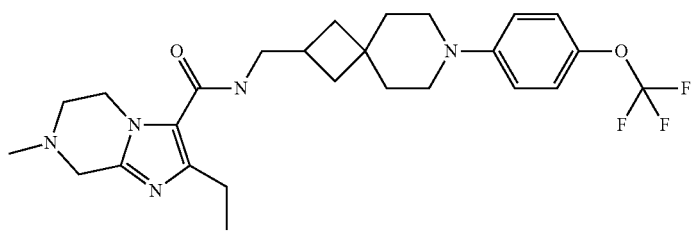 [SMILES: CCc1nc2n(c1C(=O)NCC1CC3(CCN(c4ccc(OC(F)(F)F)cc4)CC3)C1)CCN(C)C2] |
| 47 | 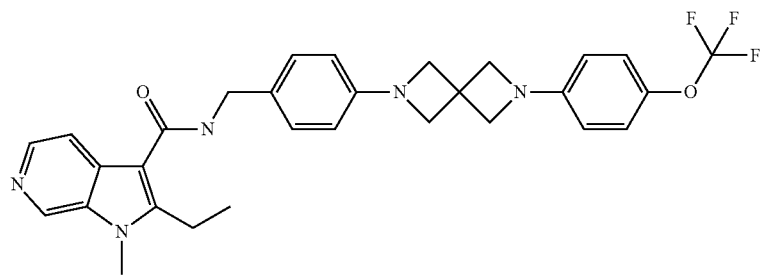 |
| 48 | 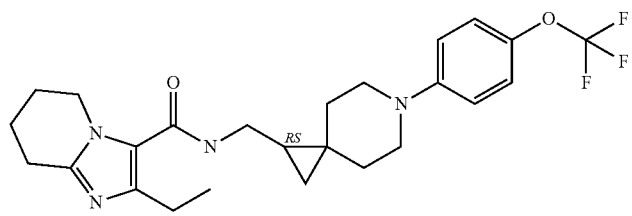 [SMILES: CCc1nc2n(c1C(=O)NCC1CC13CCN(c1ccc(OC(F)(F)F)cc1)CC3)CCCC2] |
| 49 | 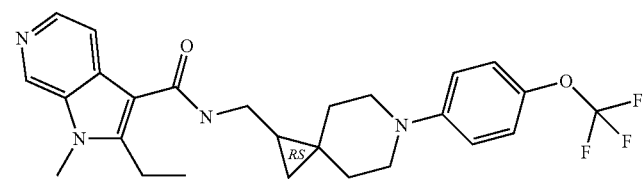 [SMILES: CCc1c(C(=O)NCC2CC23CCN(c2ccc(OC(F)(F)F)cc2)CC3)c2ccncc2n1C] |
| 50 | 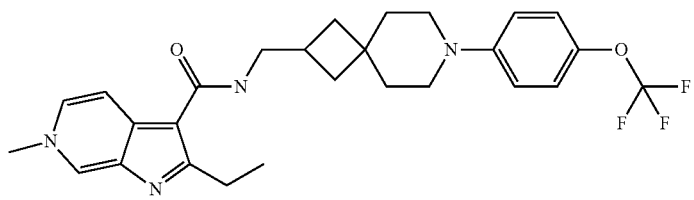 [SMILES: CCc1nc2cn(C)ccc-2c1C(=O)NCC1CC2(CCN(c3ccc(OC(F)(F)F)cc3)CC2)C1] |

| Compound No | Structure |
|---|---|
| 51 | 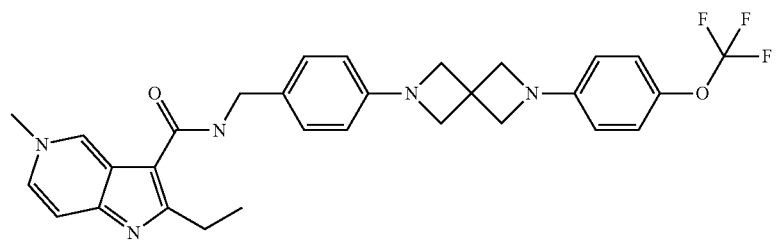 [SMILES: CCc1nc2ccn(C)cc-2c1C(=O)NCc1ccc(N2CC3(C2)CN(c2ccc(OC(F)(F)F)cc2)C3)cc1] |
| 52 | 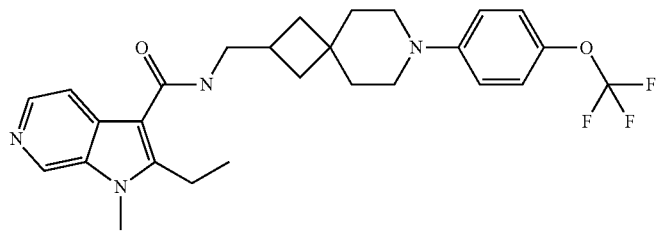 [SMILES: CCc1c(C(=O)NCC2CC3(CCN(c4ccc(OC(F)(F)F)cc4)CC3)C2)c2ccncc2n1C] |
| 53 | 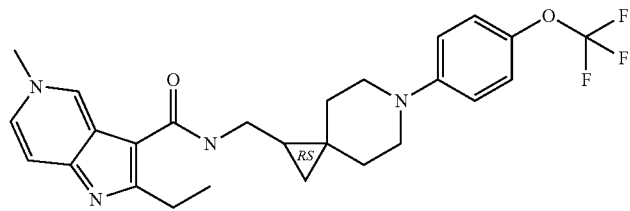 [SMILES: CCc1nc2ccn(C)cc-2c1C(=O)NCC1CC12CCN(c1ccc(OC(F)(F)F)cc1)CC2] |
| 54 | 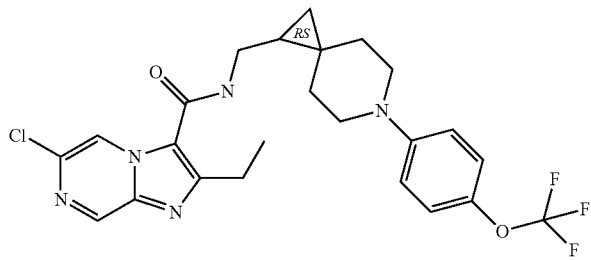 [SMILES: CCc1nc2cnc(Cl)cn2c1C(=O)NCC1CC12CCN(c1ccc(OC(F)(F)F)cc1)CC2] |
| 55 | 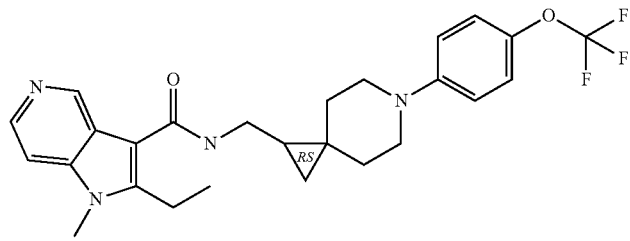 [SMILES: CCc1c(C(=O)NCC2CC23CCN(c2ccc(OC(F)(F)F)cc2)CC3)c2cnccc2n1C] |

Synthesis of Compound 56

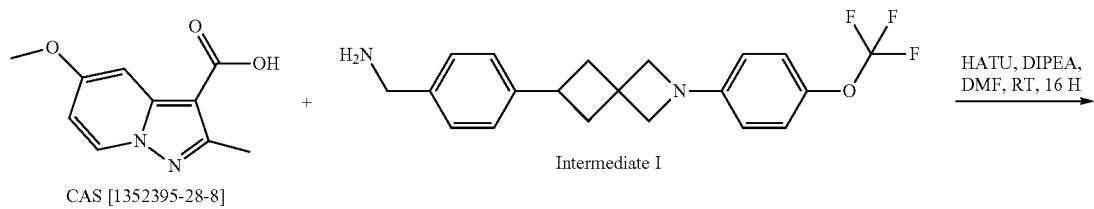

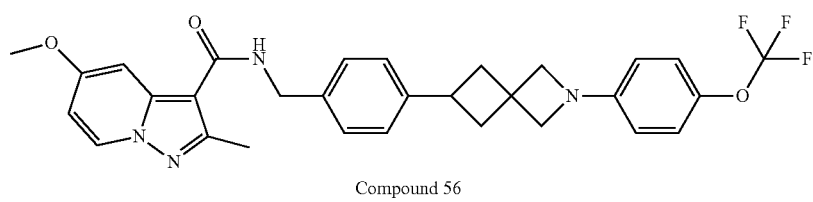

Compound 56

To a solution of 5-methoxy-2-methylpyrazolo[1,5-a]pyridine-3-carboxylic acid (CAS [1352395-28-8], 0.055 g mg, 0.26 mmol) in DMF (5 mL) was added intermediate I (0.08 g, 0.22 mmol), HATU (0.1 g, 0.26 mmol) and diisopropylethylamine (0.085 g, 0.66 mmol). The mixture was stirred at room temperature overnight. The solvent was removed in vacuum to dryness. The residue was purified by high performance liquid chromatography (Waters Xbridge Prep OBD C18 150×30×5μ, 25 mL/min, gradient water (containing 0.05% $NH_3.H_2O$)/Acetonitrile from 85/15 to 55/45). The desired fraction was collected and evaporated to remove off acetonitrile in vacuum. The residue was lyophilized to give Compound 56, 0.027 g, 21%.

$^1$H NMR (400 MHz, $CDCl_3$) δ=8.19 (d, J=7.5 Hz, 1H), 7.57 (d, J=2.2 Hz, 1H), 7.34 (d, J=7.5 Hz, 2H), 7.21 (d, J=7.9 Hz, 2H), 7.07 (d, J=8.4 Hz, 2H), 6.54 (dd, J=2.4, 7.3 Hz, 1H), 6.40 (d, J=8.8 Hz, 2H), 5.96 (br. s., 1H), 4.67 (d, J=5.3 Hz, 2H), 4.01 (s, 2H), 3.91 (s, 3H), 3.80 (s, 2H), 3.51-3.44 (m, 1H), 2.70-2.56 (m, 5H), 2.41-2.30 (m, 2H).

Synthesis of Compound 57

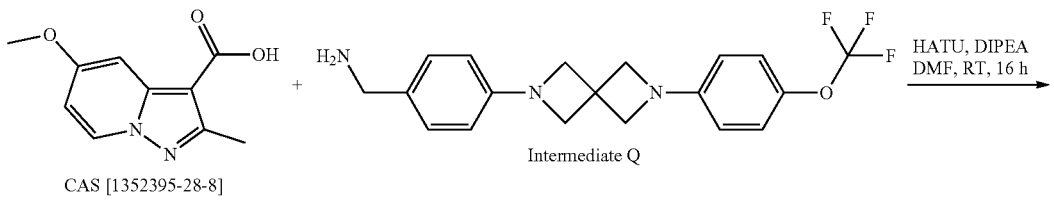

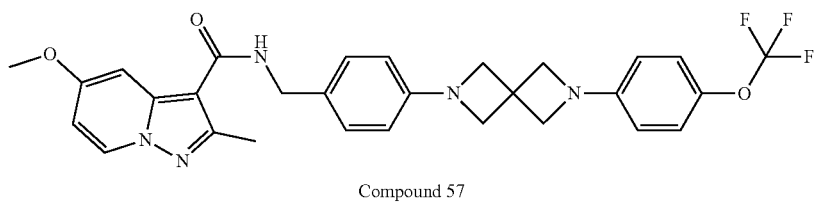

Compound 57

Accordingly, Compound 57 was prepared in the same way as Compound 56 starting from 5-methoxy-2-methylpyrazolo[1,5-a]pyridine-3-carboxylic acid CAS [1352395-28-8], and intermediate Q, yielding 0.027 g, 21%.

1H NMR (400 MHz, CDCl₃) δ=8.18 (d, J=7.5 Hz, 1H), 7.57 (d, J=2.6 Hz, 1H), 7.25 (br. s., 2H), 7.09 (d, J=8.8 Hz, 2H), 6.53 (dd, J=2.6, 7.5 Hz, 1H), 6.49 (d, J=8.4 Hz, 2H), 6.43 (d, J=8.8 Hz, 2H), 5.86 (br. s., 1H), 4.59 (d, J=5.3 Hz, 2H), 4.04 (s, 8H), 3.91 (s, 3H), 2.58 (s, 3H)

Synthesis of Compound 58

Preparation of Compound 58

Accordingly, Compound 58 was prepared in the same way as Compound 56 starting from intermediate BB and intermediate Q, yielding 0.05 g, 29%.

1H NMR (400 MHz, CDCl₃) δ=9.41 (s, 1H), 8.90 (s, 1H), 7.24 (d, J=7.9 Hz, 2H), 7.08 (d, J=8.4 Hz, 2H), 6.49 (d, J=8.4 Hz, 2H), 6.42 (d, J=8.8 Hz, 2H), 6.10 (br. s., 1H), 4.60 (d, J=5.3 Hz, 2H), 4.04 (d, J=3.5 Hz, 8H), 3.00 (q, J=7.5 Hz, 2H), 1.42 (t, J=7.5 Hz, 3H)

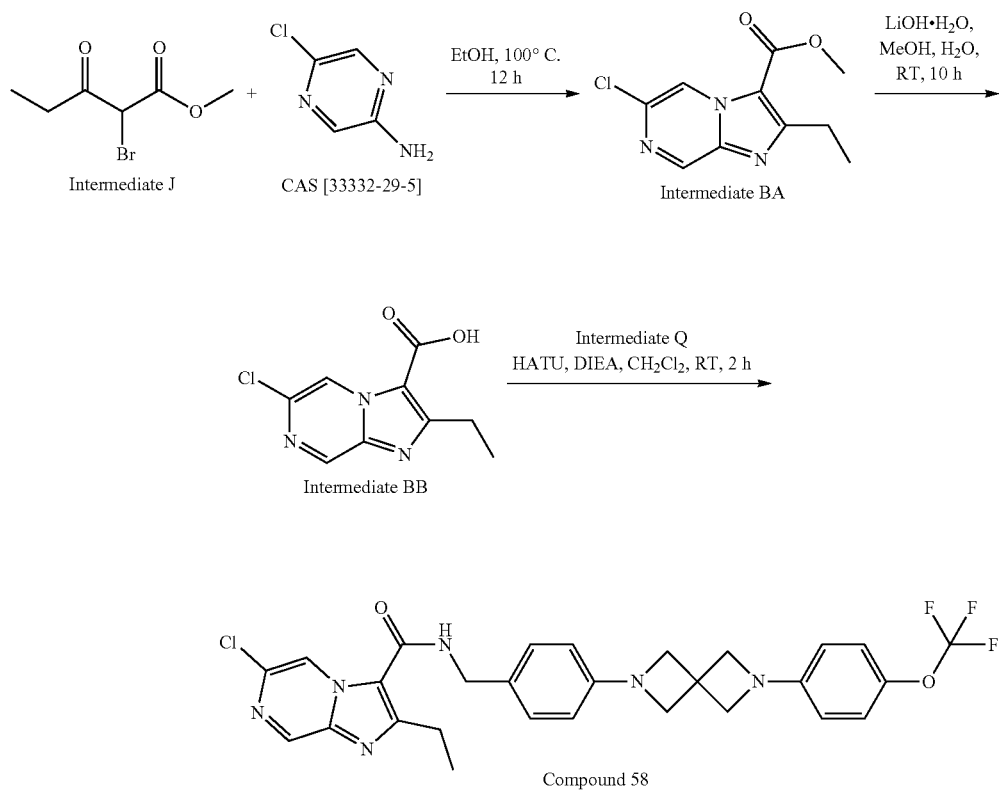

Preparation of Intermediate BA

A mixture of 2-Amino-5-chloropyrazine (CAS [33332-29-5], 6 g, 46.31 mmol) and intermediate J (14.52 g, 69.47 mmol) in EtOH (10 mL) was stirred at 100° C. for 12 h. The solvent was removed in vacuum. The residue was purified by column chromatography (petroleum ether/ethyl acetate=5/1). The product fractions were collected and the solvent was evaporated to give intermediate BA, 0.81 g, 7%.

Preparation of Intermediate BB

To a solution of intermediate BA (0.8 g, 3.34 mmol) in MeOH (30 mL) and water (6 mL) was added lithium hydroxide monohydrate (0.7 g, 16.69 mmol). The mixture was stirred at room temperature for 10 h. The solvent was removed in vacuum. The mixture was acidified with aqueous HCl 2N (5 mL) to pH=3-4. The resulting white precipitates were filtered, and washed with water (20 mL) to afford intermediate BB, 0.65 g, 86%.

Synthesis of Compound 59

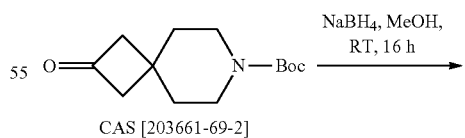

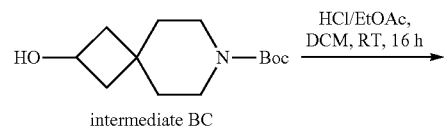

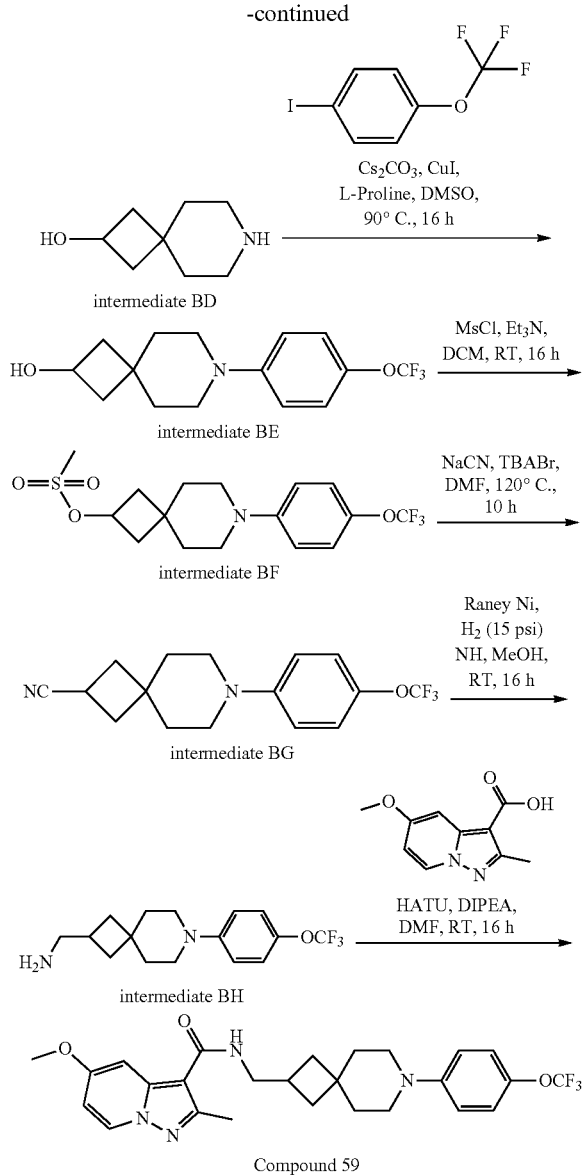

Preparation of Intermediate BE

To a solution of 1-iodo-4-(trifluoromethoxy)benzene (CAS [103962-05-6], 4.48 g, 15.54 mmol) in DMSO (50 mL) was added intermediate BD (1.84 g, 10.36 mmol), cesium carbonate (8.44 g, 25.9 mmol), L-Proline (0.48 g, 4.14 mmol) and copper iodide (0.39 g, 2.07 mmol). The mixture was heated at 90° C. for 18 h under argon atmosphere. The mixture was diluted with water (100 mL) and extracted with ethyl acetate (50 mL×3). The organic layer was washed with brine (50 mL), dried over $Na_2SO_4$, filtered and concentrated in vacuum. The residue was purified by column chromatography (petroleum ether/ethyl acetate=4/1) to give intermediate BE, 1.5 g, 48%.

Preparation of Intermediate BF

Methanesulfonyl chloride (0.77 mL, 9.96 mmol) was added to a solution of intermediate BE (1.5 g, 4.98 mmol) and triethylamine (2.78 mL, 19.91 mmol) in $CH_2Cl_2$ (20 mL). The reaction solution was stirred at room temperature overnight. The mixture was washed with water (100 mL) and concentrated under vacuum. The residue was purified by column chromatography over silica gel (petroleum ether/ethyl acetate 4/1). Pure fractions were collected and evaporated to give intermediate BF, 1.6 g, 85%.

Preparation of Intermediate BG

A mixture of intermediate BF (1.6 g, 4.22 mmol), sodium cyanide (0.83 g, 16.87 mmol) and tetrabutylammonium bromide (0.82 g, 2.53 mmol) in DMF (30 mL) was stirred at 120° C. for 10 h. The mixture was diluted with water (200 mL) and extracted with ethyl acetate (200 mL×3). The organic layers were washed with brine (200 mL), dried over $Na_2SO_4$, filtered and concentrated in vacuum. The residue was purified by column chromatography over silica gel (petroleum ether/ethyl acetate 4/1). The product fractions were collected and the solvent was evaporated affording intermediate BG, 1.3 g, 99%.

Preparation of Intermediate BH

A mixture of intermediate BG (1.3 g, 4.19 mmol) in $NH_3$.MeOH (7M in methanol, 20 mL) was hydrogenated (15 psi) with Raney Nickel (1 g) as catalyst at 25° C. for 16 hours. After uptake of H2, the catalyst was filtered off and the filtrate was concentrated to give intermediate BH, 1.3 g, 99/%.

Preparation of Compound 59

Accordingly, Compound 59 was prepared in the same way as Compound 56 starting from 5-methoxy-2-methylpyrazolo[1,5-a]pyridine-3-carboxylic acid CAS [1352395-28-8] and intermediate BH, yielding 0.048 g, 36%.

1H NMR (400 MHz, $CDCl_3$) δ=8.18 (d, J=7.5 Hz, 1H), 7.54 (d, J=2.6 Hz, 1H), 7.08 (d, J=8.8 Hz, 2H), 6.88 (d, J=8.8 Hz, 2H), 6.53 (dd, J=2.6, 7.5 Hz, 1H), 5.66 (br. s., 1H), 3.90 (s, 3H), 3.53 (t, J=6.4 Hz, 2H), 3.16-3.09 (m, 2H), 3.08-3.02 (m, 2H), 2.63-2.60 (m, 3H), 2.04 (t, J=10.4 Hz, 2H), 1.81-1.75 (m, 2H), 1.72-1.66 (m, 2H), 1.62 (br. s., 2H)

Preparation of Intermediate BC

Sodium borohydride (2.13 g, 56.41 mmol) was added to a solution of 7-Boc-7-azaspiro[3.5]nonan-2-one (CAS [203661-69-2], 2.5 g, 10.45 mmol) in MeOH (30 mL).

The mixture was stirred at 25° C. for 16 hours. The mixture was concentrated under vacuum. The residue was diluted with ethyl acetate (50 mL), washed with water (2×50 mL) and brine (50 mL). The separated organic layer was dried over anhydrous sodium sulfate and concentrated under vacuum to give intermediate BC, 2.5 g, 99/0.

Preparation of Intermediate BD

A solution HCl 4M in EtOAc (5.18 mL, 20.72 mmol) was added to a solution of intermediate BC (2.5 g, 10.36 mmo) in $CH_2Cl_2$ (100 mL) at 0° C. The solution was stirred at room temperature overnight. The solvent was concentrated under vacuum affording intermediate BD as an hydrochloride salt, 1.84 g, 100%.

Synthesis of Compound 60

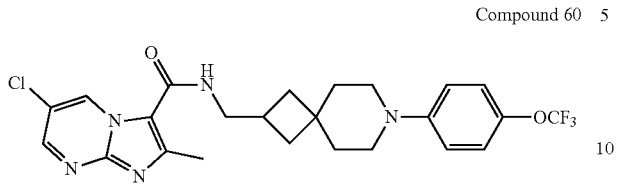

Compound 60

Accordingly, Compound 60 was prepared in the same way as Compound 59 starting from intermediate L and intermediate BH, yielding 0.075 g, 45%.

$^1$H NMR (400 MHz, CDCl$_3$) δ=9.79 (d, J=2.2 Hz, 1H), 8.56 (d, J=2.2 Hz, 1H), 7.09 (d, J=8.8 Hz, 2H), 6.89 (d, J=8.8 Hz, 2H), 5.86 (br. s., 1H), 3.57 (t, J=6.4 Hz, 2H), 3.17-3.11 (m, 2H), 3.10-3.00 (m, 4H), 2.61 (td, J=8.0, 16.2 Hz, 1H), 2.11-2.01 (m, 2H), 1.83-1.77 (m, 2H), 1.75-1.68 (m, 2H), 1.64 (m, 2H), 1.49 (t, J=7.5 Hz, 3H).

Synthesis of Compound 61

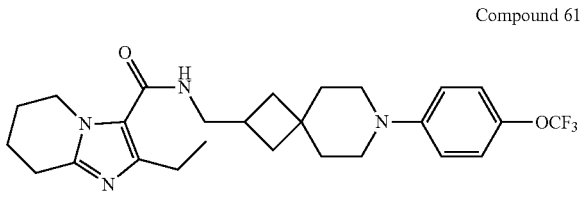 [SMILES: CCc1nc2n(c1C(=O)NCC1CC3(CCN(c4ccc(OC(F)(F)F)cc4)CC3)C1)CCCC2]

Compound 61

Accordingly, Compound 61 was prepared in the same way as Compound 59 starting from 2-ethyl-5H,6H,7H, 8H-imidazo[1,2-a]pyridine-3-carboxylic acid CAS [1529528-99-1] and intermediate BH, yielding 0.082 g, 65%.

$^1$H NMR (400 MHz, CDCl$_3$) δ=7.09 (d, J=8.5 Hz, 2H), 6.96-6.85 (m, 2H), 5.64 (br. s., 1H), 4.20 (t, J=5.9 Hz, 2H), 3.47 (dd, J=5.8, 7.3 Hz, 2H), 3.16-3.09 (m, 2H), 3.08-3.02 (m, 2H), 2.86 (t, J=6.3 Hz, 2H), 2.73 (q, J=7.6 Hz, 2H), 2.55 (td, J=7.9, 16.0 Hz, 1H), 2.05-1.98 (m, 2H), 1.97-1.85 (m, 4H), 1.82-1.74 (m, 2H), 1.71-1.67 (m, 2H), 1.61-1.52 (m, 2H), 1.30 (t, J=7.7 Hz, 3H).

Synthesis of Compound 62

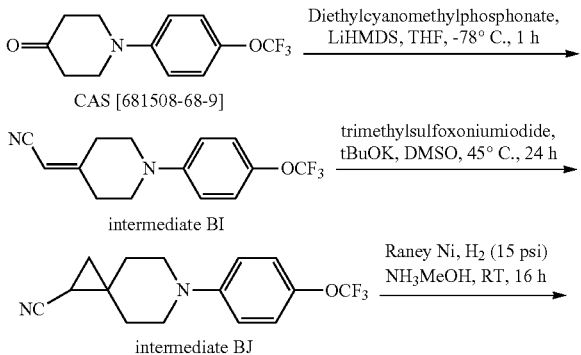

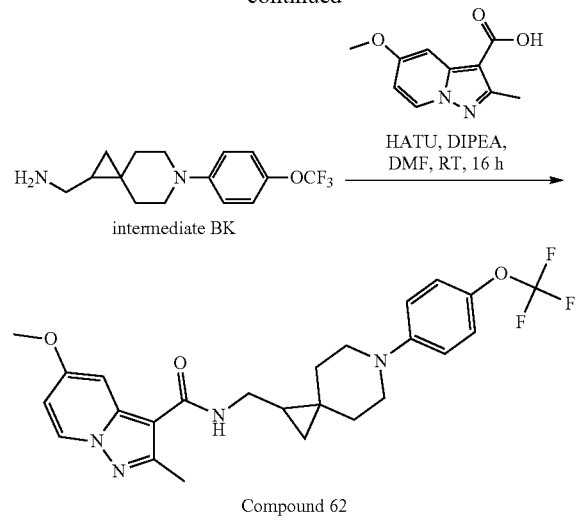

Compound 62

Preparation of Intermediate BI

LiHMDS (19.27 mL, 19.27 mmol) was added to a mixture of Diethylcyanomethyl phosphonate (3.41 g, 19.27 mmol) in THF (180 mL) at −70° C. under N$_2$ flow. The mixture was stirred for 10 minutes. 1-[4-(trifluoromethoxy)phenyl]-4-piperidinone (CAS [681508-68-9], 4.5 g, 17.36 mmol) was added to the mixture at −78° C. The mixture was stirred for 1 hour at −78° C. The mixture was quenched with NH$_4$Cl solution, extracted with ethyl acetate (300 mL), washed with brine (200 mL), dried over MgSO$_4$ and filtered. The filtrate was concentrated. The crude product was purified by column chromatography over silica gel (ethyl acetate/petroleum ether from 0 to 1/3). The desired fractions were collected and concentrated to give intermediate BI, 7.8 g, 72%.

Preparation of Intermediate BJ

Trimethylsulfoxonium iodide (5.83 g, 26.5 mmol) was added slowly to a solution of potassium tert-butoxide (2.97 g, 26.5 mmol) in DMSO (50 mL). The mixture was stirred for 1.5 hours at room temperature. A solution of intermediate BI (6.8 g, 24.09 mmol) in DMSO (50 mL) was added to the mixture. The mixture was stirred 24 hours at 45° C. Saturated NH$_4$Cl solution was added to the mixture and stirred for 0.5 hours. The mixture was extracted with ethyl acetate (100 mL). The organic layer was washed with brine (70 mL), dried over MgSO$_4$ and filtered. The filtrate was concentrated. The crude product was purified by column chromatography over silica gel (ethyl acetate/petroleum ether from 0 to 1/3). The desired fractions were collected and concentrated to give intermediate BJ, 4.5 g, 63%.

Preparation of Intermediate BK

Accordingly intermediate BK was prepared by the same way as intermediate BH, starting from intermediate BJ affording, 0.18 g,

Preparation of Compound 62

Accordingly, Compound 62 was prepared in the same way as Compound 56 starting from 5-methoxy-2-methylpyrazolo

[1,5-a]pyridine-3-carboxylic acid CAS [1352395-28-8] and intermediate BK, yielding 0.04 g, 9%.

1H NMR (400 MHz, CDCl₃) δ=8.18 (d, J=7.1 Hz, 1H), 7.53 (d, J=2.2 Hz, 1H), 7.10 (d, J=8.8 Hz, 2H), 6.91 (d, J=9.3 Hz, 2H), 6.52 (dd, J=2.4, 7.3 Hz, 1H), 5.73 (br. s., 1H), 3.89 (s, 3H), 3.60-3.48 (m, 2H), 3.34 (t, J=13.0 Hz, 2H), 3.17-3.09 (m, 2H), 2.63 (s, 3H), 1.93-1.84 (m, 1H), 1.80-1.73 (m, 1H), 1.66-1.58 (m, 1H), 1.42-1.34 (m, 1H), 1.10-1.00 (m, 1H), 0.67 (dd, J=4.6, 8.2 Hz, 1H), 0.36 (t, J=4.9 Hz, 1H)

Synthesis of Compound 63

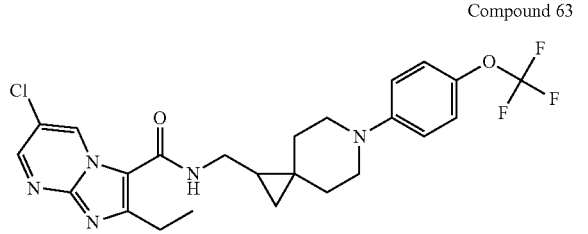 [SMILES: CCc1nc2ncc(Cl)cn2c1C(=O)NCC1CC12CCN(c1ccc(OC(F)(F)F)cc1)CC2]

Compound 63

Accordingly, Compound 63 was prepared in the same way as Compound 62 starting from intermediate L and intermediate BK, yielding 0.019 g, 16%.

1H NMR (400 MHz, CDCl₃) δ ppm 9.78 (d, J=2.76 Hz, 1H) 8.56 (d, J=2.76 Hz, 1H) 7.11 (d, J=8.28 Hz, 2H) 6.86-6.96 (m, 2H) 5.92 (br. s., 1H) 3.57 (dd, J=7.65, 5.40 Hz, 2H) 3.30-3.43 (m, 2H) 3.09-3.17 (m, 2H) 3.06 (q, J=7.53 Hz, 2H) 1.90 (ddd, J=12.92, 9.16, 3.26 Hz, 1H) 1.74-1.83 (m, 1H) 1.63 (br. s., 1H) 1.47 (t, J=7.65 Hz, 3H) 1.30-1.41 (m, 1H) 0.99-1.10 (m, 1H) 0.71 (dd, J=8.28, 4.77 Hz, 1H) 0.38 (t, J=5.02 Hz, 1H)

Synthesis of Compound 64

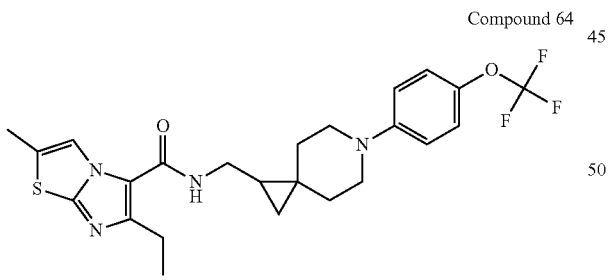

Compound 64

Accordingly, Compound 64 was prepared in the same way as Compound 62 starting from 6-ethyl-2-methylimidazo[2,1-b]thiazole-5-carboxylic acid CAS [1131613-58-5], and intermediate BK, yielding 0.048 g, 32%.

1H NMR (400 MHz, CDCl₃) δ ppm 7.95 (d, J=1.51 Hz, 1H) 7.10 (d, J=8.53 Hz, 2H) 6.91 (d, J=8.53 Hz 2H) 5.72 (br. s., 1H) 3.45-3.58 (m, 2H) 3.34 (t, J=13.05 Hz, 2H) 3.07-3.18 (m, 2H) 2.89 (q, J=7.53 Hz, 2H) 2.43 (d, J=1.51 Hz, 3H) 1.82-1.93 (m, 1H) 1.69-1.80 (m, 1H) 1.63 (br. s., 1H) 1.38 (t, J=7.65 Hz, 3H) 1.30 (t, J=7.65 Hz, 1H) 0.97-1.07 (m, 1H) 0.68 (dd, J=8.91, 4.39 Hz, 1H) 0.35 (t, J=4.89 Hz, 1H)

Synthesis of Compound 65

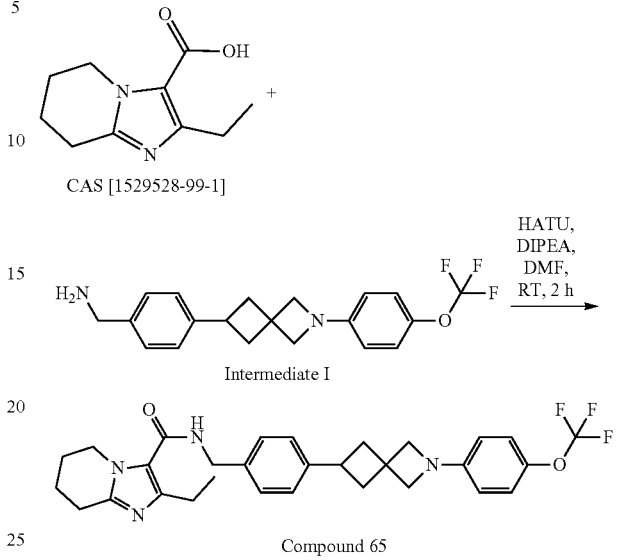

CAS [1529528-99-1]

Intermediate I

Compound 65

A solution of 2-ethyl-5H,6H,7H,8H-imidazo[1,2-a]pyridine-3-carboxylic acid (CAS [1529528-99-1], 0.18 g, 0.41 mmol), HATU (0.204 g, 0.54 mmol), diisopropylethylamine (0.139 g, 1.08 mmol) in DMF (5 mL) was stirred for 30 minutes at 25° C. Intermediate I (0.15 g, 0.41 mmol) was added to the mixture and the mixture was stirred for 2 hours at 25° C. The crude product was purified by high performance liquid chromatography over Waters Xbridge Prep OBD (eluent: 0.05% ammonia water/acetonitrile 25/75 to 5/95). The desired fractions were collected and lyophilized to give Compound 65 0.035 g, 29%.

1H NMR (400 MHz, CDCl₃) δ ppm 7.27-7.31 (m, 2H) 7.19 (d, J=8.03 Hz, 2H) 7.06 (d, J=8.28 Hz, 2H) 6.37-6.42 (m, 2H) 5.92 (br. s., 1H) 4.58 (d, J=5.77 Hz, 2H) 4.23 (t, J=5.77 Hz, 2H) 4.01 (s, 2H) 3.79 (s, 2H) 3.47 (quin, J=8.72 Hz, 1H) 2.86 (t, J=6.40 Hz, 2H) 2.71 (q, J=7.70 Hz, 2H) 2.61-2.68 (m, 2H) 2.31-2.39 (m, 2H) 1.83-2.00 (m, 4H) 1.25 (t, J=7.65 Hz, 3H)

Synthesis of Compound 66

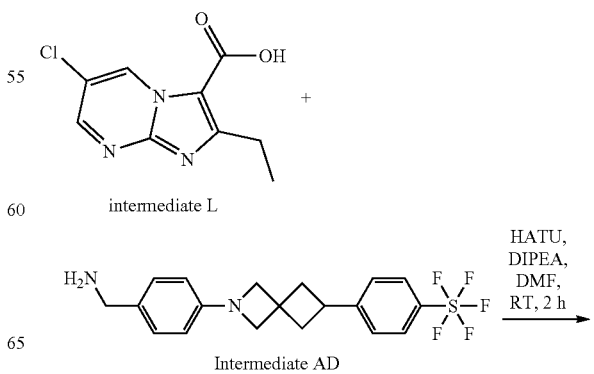

intermediate L

Intermediate AD

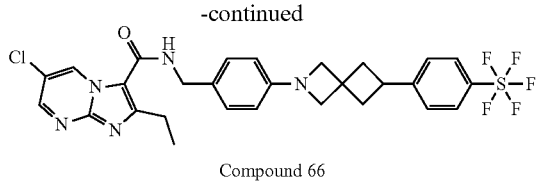

Compound 66

A mixture of intermediate L (0.011 g, 0.049 mmol), intermediate AD (0.02 g, 0.049 mmol), HATU (0.024 g, 0.063 mmol), and diisopropylethylamine (0.032 g, 0.245 mmol) in dichloromethane (1 mL) was stirred at room temperature for 2 hours. The mixture was concentrated under vacuum. Ethyl acetate (20 mL) was added and the mixture was washed with water (2×20 mL) and brine (20 mL). The separated organic layer was dried over magnesium sulfate, filtered and concentrated under vacuum. The residue was purified by high performance liquid chromatography over Phenomenex Gemini C18 250×21.2 mm×5 μm (eluent: water (0.05% ammonia hydroxide v/v)/methanol 25/75 to 5/95). The desired fractions were collected and lyophilized to give Compound 66, 0.011 g, 37%.

Synthesis of Compound 67

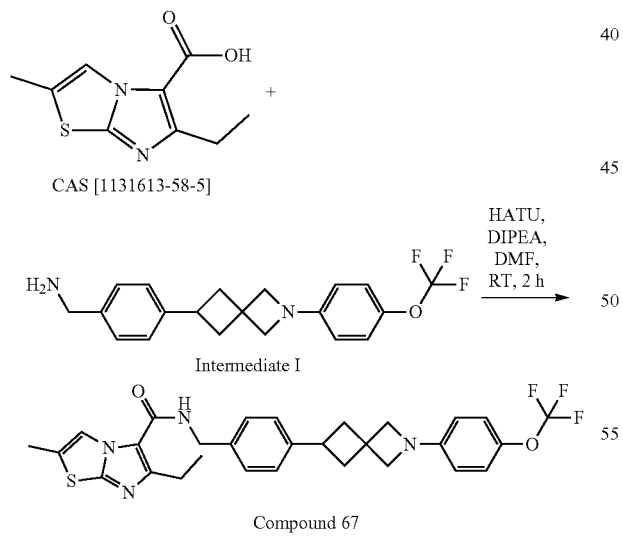

CAS [1131613-58-5]

Intermediate I

Compound 67

A mixture of 6-ethyl-2-methylimidazo[2,1-b]thiazole-5-carboxylic acid (CAS [1131613-58-5], 0.038 g, 0.18 mmol), HATU (0.082 g, 0.22 mmol), and diisopropylethylamine (0.056 g, 0.43 mmol) in DMF (20 mL) was stirred for 30 minutes at 25° C. Intermediate I (0.06 g, 0.17 mmol) was added to the mixture and the mixture was stirred for 2 hours at 25° C. The mixture was concentrated under vacuum. The crude product was purified by high performance liquid chromatography over Phenomenex Gemini (water(0.05% HCl)/ACN 60/40 to 30/70). The desired fractions were collected and lyophilized to give Compound 67, 0.036 g, 33%.

$^1$H NMR (400 MHz, CHLOROFORM-d) δ=7.98 (s, 1H), 7.28 (d, J=7.5 Hz, 2H), 7.18 (d, J=7.9 Hz, 2H), 7.04 (d, J=8.8 Hz, 2H), 6.38 (d, J=8.8 Hz, 2H), 5.96 (br. s., 1H), 4.62 (d, J=5.7 Hz, 2H), 3.99 (s, 2H), 3.77 (s, 2H), 3.45 (quin, J=8.8 Hz, 1H), 2.84 (q, J=7.5 Hz, 2H), 2.67-2.59 (m, 2H), 2.47-2.38 (m, 3H), 2.36-2.29 (m, 2H), 1.40-1.29 (m, 3H)

Synthesis of Compound 68

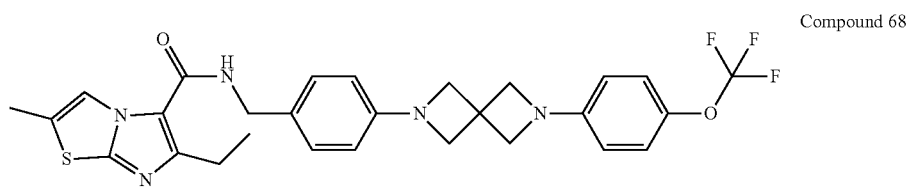

Compound 68

Diisopropylethylamine (0.512 mL; 2.98 mmol) and HATU (0.588 g; 1.55 mmol) were added successively to a solution of 6-ethyl-2-methylimidazo[2,1-b]thiazole-5-carboxylic acid (CAS [1131613-58-5], 0.25 g, 1.19 mmol) in DMF (30 mL). The resulting mixture was stirred at room temperature for 30 min, before the addition of intermediate Q (0.432 g, 1.19 mmol) and the mixture was stirred at room temperature for 4 h. The reaction mixture was evaporated in vacuo until dryness, diluted with EtOAc and washed with brine (twice). The organic layer was dried over MgSO$_4$, filtered and evaporated to give 1.1 g as brown oil. The crude product was purified by preparative LC (Regular SiOH 30 μm, 40 g Interchim, dry loading (Celite®), mobile phase gradient: from CH$_2$Cl$_2$/MeOH 100:0 to 95:5) to obtain 0.203 g as an off-white foam which was triturated in Et$_2$O, filtered and dried under high vacuum to give 0.151 g of Compound 68 as an off-white solid (23%).

$^1$H NMR (400 MHz, DMSO-d$_6$) δ ppm 8.02 (t, J=5.8 Hz, 1H), 7.87 (d, J=1.5 Hz, 1H), 7.16 (dd, J=8.6, 3.5 Hz, 4H), 6.49 (d, J=8.0 Hz, 2H), 6.42 (d, J=8.6 Hz, 2H), 4.35 (d, J=6.1 Hz, 2H), 3.94 (s, 4H) 4.00 (s, 4H), 2.84 (q, J=7.4 Hz, 2H), 2.41 (d, J=1.5 Hz, 3H), 1.19 (t, J=7.6 Hz, 3H).

Synthesis of Compound 69, Compound 70 and Compound 71

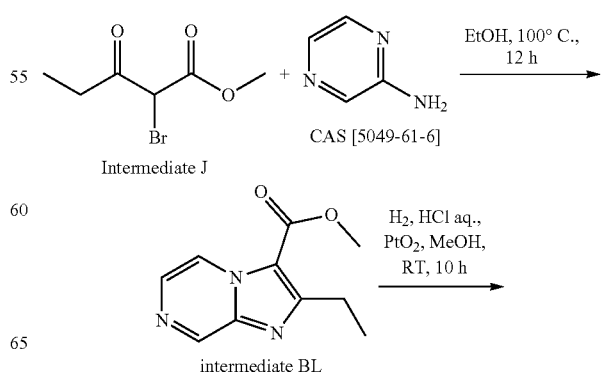

Intermediate J

CAS [5049-61-6]

intermediate BL

91

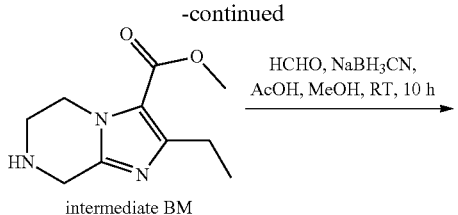

intermediate BM

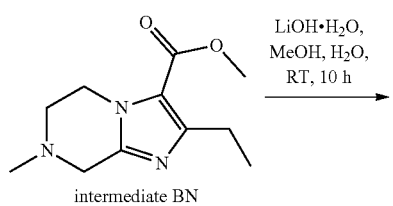

intermediate BN

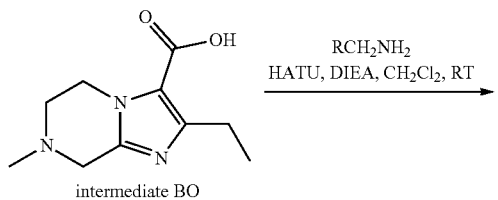

intermediate BO

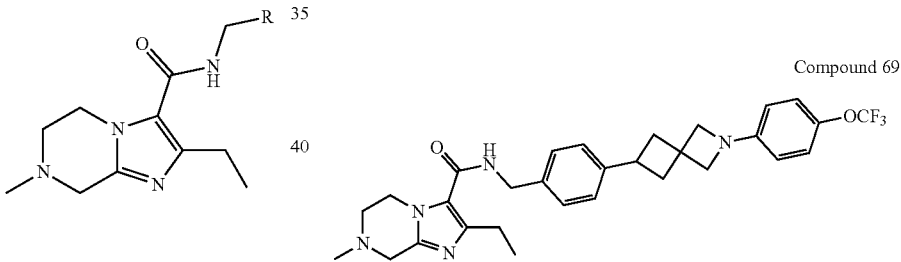

Preparation of Intermediate BL

A mixture of 2-aminopyrazine (CAS [5049-61-6], 12 g, 126.18 mmol) and intermediate J (39.6 g, 189.27 mmol) in EtOH (10 mL) was stirred at 100° C. for 12 h. The solvent was removed in vacuum. The crude product was purified by column chromatography (petroleum ether/ethyl acetate=5/1-1/1). The product fractions were collected and the solvent was evaporated to give intermediate BL, 2 g, 8%.

Preparation of Intermediate BM

To a solution of intermediate BL (5 g, 24.36 mmol) in MeOH (20 mL) was added platine dioxide (500 mg) under $N_2$, followed by addition a drop of con HCl. The suspension was degassed under vacuum and purged with $H_2$ several times. The mixture was stirred under $H_2$ (15 psi) at 25° C. for 10 hours. The suspension was filtered through a pad of Celite® and the pad was washed with methanol (50 mL). The combined filtrates were concentrated to dryness to give intermediate BM, 5 g, 98%.

92

Preparation of Intermediate BN

To a solution of intermediate BM (5 g, 23.89 mmol) in MeOH (75 mL) was added formaldehyde aqueous solution (9.7 g, 119.47 mmol, 37%) at 0° C., followed by addition sodium borocyanohydride (7.5 g, 119.47 mmol) and a drop of acetic acid (0.2 mL). Then the mixture was stirred at room temperature for overnight. 10% $NH_4Cl$ solution (25 mL) was added dropwise. The mixture was extracted with ethyl acetate, the combined organic layers were washed with brine, dried over $Na_2SO_4$, filtered and the solvent was evaporated under vacuum. The residue was purified by column chromatography over silica gel (dichloromethane/methanol=15:1 to 10:1) to give intermediate BN, 1.3 g, 24%.

Preparation of Intermediate BO

To a solution of intermediate BN (0.55 g, 2.46 mmol) in MeOH (25 mL) and water (5 mL) was added lithium hydroxide monohydrate (0.52 g, 12.32 mmol). The mixture was stirred at room temperature for 10 h. The solvent was removed in vacuum to dryness. The residue was purified by high performance liquid chromatography (DuraShell 150× 25 mm×5 μm, 25 ml/min, water (containing 0.05% HCl)/Acetonitrile from 100/0 to 70/30). The desired fraction was collected and evaporated to remove off acetonitrile in vacuum. The residue was lyophilized to give intermediate BO, 0.4 g 78%.

Preparation of Compound 69

Compound 69

Compound 69

A solution of intermediate BO (0.04 g, 0.19 mmol), HATU (0.095 g, 0.25 mmol), diisopropylethylamine (0.064 g, 0.5 mmol) in DMF (5 mL) was stirred for 30 minutes at 25° C. Intermediate I (0.069 g, 0.19 mmol) was added to the mixture and the mixture was stirred for 2 hours at 25° C. The crude product was purified by high performance liquid chromatography over Waters Xbridge Prep OBD (eluent: 0.05% ammonia water/acetonitrile from 50/50 to 20/80). The desired fractions were collected and lyophilized to give Compound 69, 0.053 g, 50%

1H NMR (400 MHz, $CDCl_3$) δ ppm 7.27-7.31 (m, 2H) 7.17-7.22 (m, 2H) 7.06 (d, J=8.28 Hz, 2H) 6.37-6.42 (m, 2H) 5.94 (br. s., 1H) 4.58 (d, J=5.52 Hz, 2H) 4.32 (t, J=5.65 Hz, 2H) 4.01 (s, 2H) 3.79 (s, 2H) 3.65 (s, 2H) 3.39-3.53 (m, 1H) 2.80 (t, J=5.65 Hz, 2H) 2.72 (q, J=7.70 Hz, 2H) 2.61-2.68 (m, 2H) 2.47 (s, 3H) 2.29-2.40 (m, 2H) 1.26 (t, J=7.53 Hz, 3H)

Preparation of Compound 70

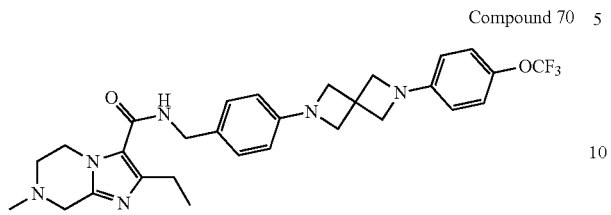
Compound 70

Accordingly, Compound 70 was prepared in the same way as Compound 69 starting from intermediate BO and intermediate Q affording 0.06 g, 50%.

$^1$H NMR (400 MHz, CDCl$_3$) δ=7.21 (d, J=8.3 Hz, 2H), 7.09 (d, J=8.3 Hz, 2H), 6.45 (dd, J=8.5, 17.8 Hz, 4H), 5.85 (br. s., 1H), 4.50 (d, J=5.5 Hz, 2H), 4.32 (t, J=5.4 Hz, 2H), 4.04 (s, 8H), 3.65 (s, 2H), 2.80 (t, J=5.6 Hz, 2H), 2.70 (q, J=7.4 Hz, 2H), 2.48 (s, 3H), 1.24 (t, J=7.5 Hz, 3H).

Preparation of Compound 71

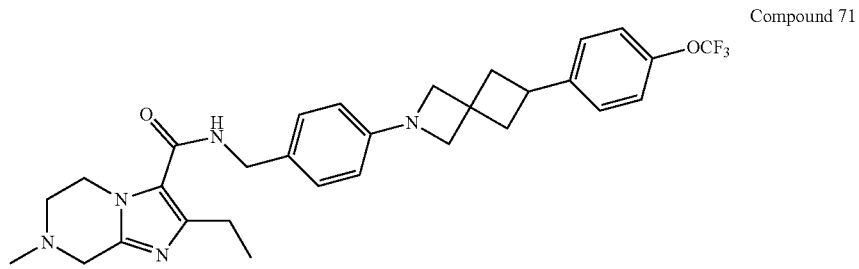 [SMILES: CCc1nc2n(c1C(=O)NCc1ccc(N3CC4(CC(c5ccc(OC(F)(F)F)cc5)C4)C3)cc1)CCN(C)C2]
Compound 71

Accordingly, Compound 71 was prepared in the same way as Compound 69 starting from intermediate BO and intermediate V affording 0.035 g, 38%.

1H NMR (400 MHz, CDCl$_3$) δ ppm 7.10-7.23 (m, 6H) 6.45 (d, J=7.94 Hz, 2H) 5.83 (br. s., 1H) 4.48 (d, J=5.29 Hz, 2H) 4.32 (t, J=5.51 Hz, 2H) 4.01 (s, 2H) 3.80 (s, 2H) 3.64 (s, 2H) 3.43-3.50 (m, 1H) 2.79 (t, J=5.51 Hz, 2H) 2.67 (dt, J=15.33, 7.99 Hz, 4H) 2.47 (s, 3H) 2.28-2.39 (m, 2H) 1.23 (t, J=7.50 Hz, 3H)

Synthesis of Compound 72, Compound 73 and Compound 74

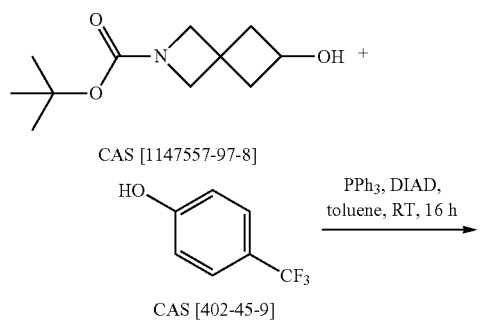

CAS [1147557-97-8]

CAS [402-45-9]

PPh$_3$, DIAD, toluene, RT, 16 h

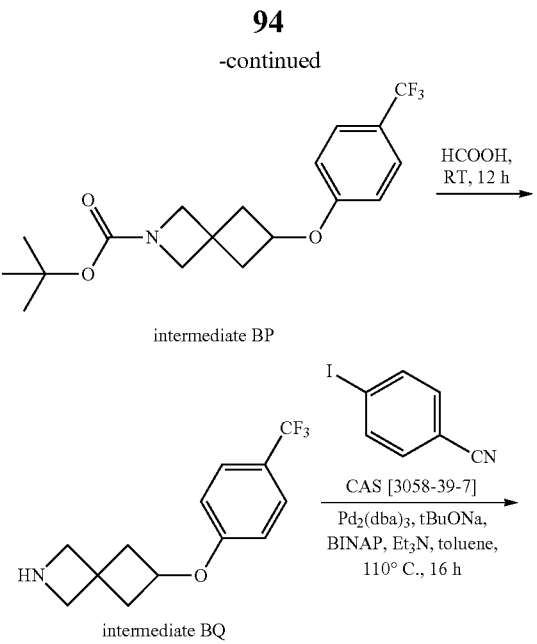

intermediate BP

HCOOH, RT, 12 h intermediate BQ

CAS [3058-39-7]
Pd$_2$(dba)$_3$, tBuONa, BINAP, Et$_3$N, toluene, 110° C., 16 h

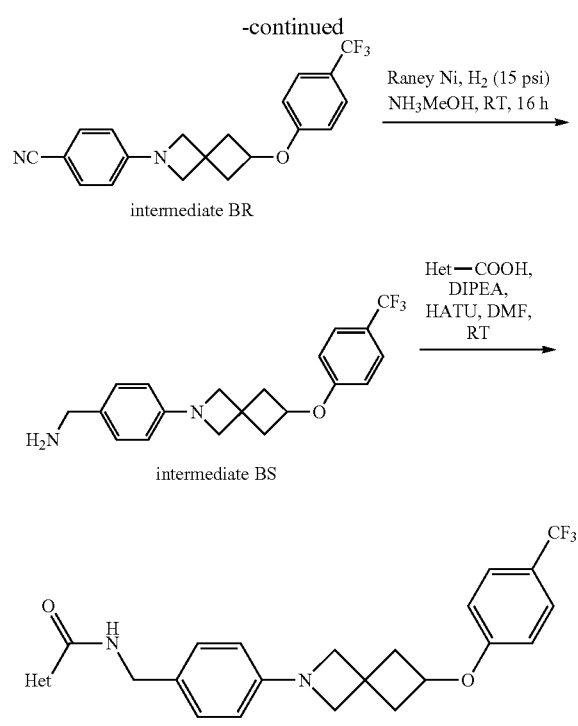

intermediate BR

Raney Ni, H$_2$ (15 psi)
NH$_3$MeOH, RT, 16 h intermediate BS

Het—COOH, DIPEA, HATU, DMF, RT

Preparation of Intermediate BP

DIAD (1.40 g, 6.92 mmol) in toluene (10 mL) was added to a solution of tert-butyl 6-hydroxy-2-azaspiro[3.3]heptane-2-carboxylate (CAS [1147557-97-8], 1.2 g, 5.63 mmol), 4-(trifluoromethyl)phenol (CAS [402-45-9], 1.10 g, 6.75 mmol), and triphenylphosphine (2.31 g, 8.80 mmol) in toluene (40 mL) at 0° C. under $N_2$ flow. The mixture was stirred overnight at room temperature. The mixture was concentrated. The crude product was purified by column chromatography over silica gel (petroleum ether/ethyl acetate from 1/0 to 3/1). The desired fraction was collected and concentrated to give intermediate BP, 2 g, 99%.

Preparation of Intermediate BO

A mixture of intermediate BP (2 g, 5.60 mmol) in formic acid (10 mL) was stirred for 12 hours. The mixture was concentrated to give intermediate BQ, 1.4 g, 97%.

Preparation of Intermediate BR

A solution of intermediate BQ (1.4 g, 5.44 mmol), 4-iodobenzonitrile (CAS [3058-39-7], 0.99 g, 5.44 mmol), BINAP (0.203 g, 0.33 mmol), $Pd_2(dba)_3$ (0.1 g, 0.11 mmol), sodium tert-butoxide (1.57 g, 16.33 mmol) and triethylamine (0.38 mL) in toluene (50 mL) was stirred overnight at 110° C. under $N_2$ flow. The mixture was concentrated. The residue was dissolved in $CH_2Cl_2$ (100 mL) and water (100 mL). The organic layer was washed with brine (100 mL), dried over $MgSO_4$ and filtered. The filtrate was concentrated. The crude product was purified by column chromatography over silica gel (ethyl acetate/petroleum ether from 0 to 1/5). The desired fractions were collected and concentrated to give intermediate BR, 1.8 g, 92%.

Preparation of Intermediate BS

A mixture of intermediate BR (0.2 g, 0.56 mmol) in ammonia 7N in methanol (20 mL) was hydrogenated with Raney Nickel (20 mg) as catalyst at 25° C. (15 Psi) for 16 hours. After uptake of H2, the catalyst was filtered off and the filtrate was concentrated to give intermediate BS, 0.2 g, 99%0.

Preparation of Compound 73

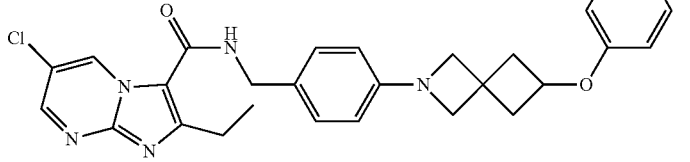

Compound 73

A solution of intermediate L (0.112 g, 0.25 mmol), HATU (0.122 g, 0.32 mmol), diisopropylethylamine (0.083 g, 0.65 mmol) in DMF (10 mL) was stirred for 30 minutes at 25° C. Intermediate BS (0.09 g, 0.25 mmol) was added to the mixture and the mixture was stirred for 2 hours at 25° C. The mixture was concentrated under vacuum. The crude product was purified by high performance liquid chromatography over Phenomenex Gemini (eluent: 0.05% ammonia water/acetonitrile 35/65 to 5/95). The desired fractions were collected and lyophilized to give Compound 73, 0.016 g, 110%.

1H NMR (400 MHz, $CDCl_3$) δ ppm 9.83 (d, J=2.65 Hz, 1H) 8.47-8.60 (m, 1H) 7.53 (d, J=8.38 Hz, 2H) 7.22 (d, J=7.94 Hz, 2H) 6.86 (d, =8.38 Hz, 2H) 6.45 (d, J=8.38 Hz, 2H) 6.05 (br. s., 1H) 4.63-4.71 (m, 1H) 4.58 (d, J=5.29 Hz, 2H) 3.95 (s, 2H) 3.90 (s, 2H) 2.98 (q, 1=7.50 Hz, 2H) 2.76-2.84 (m, 2H) 2.39-2.47 (m, 2H) 1.42 (t, J=7.50 Hz, 3H)

Preparation of Compound 72

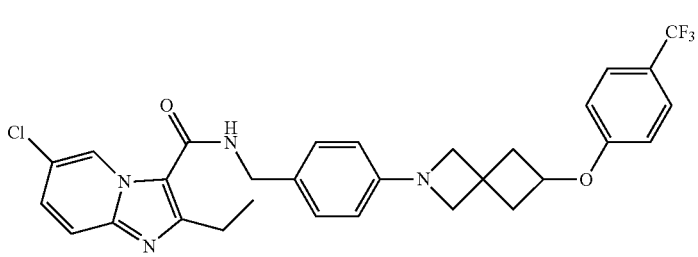

Compound 72

Accordingly, Compound 72 was prepared in the same way as Compound 73 starting from 6-chloro-2-ethylimidazo[3,2-a]pyridine-3-carboxylic acid CAS [1216142-18-5] and intermediate BS affording 0.035 g, 28%.

1H NMR (400 MHz, $CDCl_3$) δ ppm 9.52 (s, 1H) 7.53 (d, J=8.38 Hz, 3H) 7.29 (dd, J=9.48, 1.98 Hz, 1H) 7.23 (d, J=8.38 Hz, 2H) 6.86 (d, J=8.82 Hz, 2H) 6.46 (d, J=8.38 Hz, 2H) 5.99 (br. s., 1H) 4.64-4.70 (m, 1H) 4.58 (d, J=1=5.29 Hz, 2H) 3.95 (s, 2H) 3.90 (s, 2H) 2.94 (q, J=7.50 Hz, 2H) 2.80 (ddd, J=10.47, 6.95, 2.87 Hz, 2H) 2.43 (ddd, J=10.25, 6.73, 3.31 Hz, 2H) 1.38 (t, J=7.50 Hz, 3H)

Preparation of Compound 74
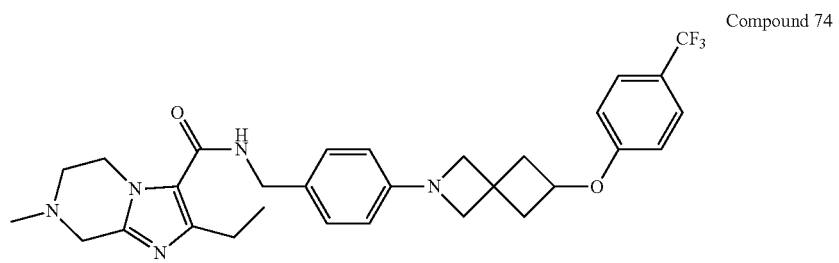 [SMILES: CCc1nc2n(c1C(=O)NCc1ccc(N3CC4(CC(Oc5ccc(C(F)(F)F)cc5)C4)C3)cc1)CCN(C)C2]
Accordingly, Compound 74 was prepared in the same way as Compound 73 starting from intermediate BO and intermediate BS affording 0.064 g, 70%.
Synthesis of Compound 75
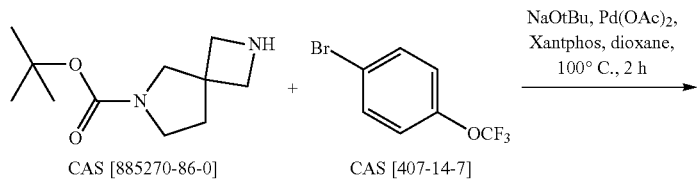
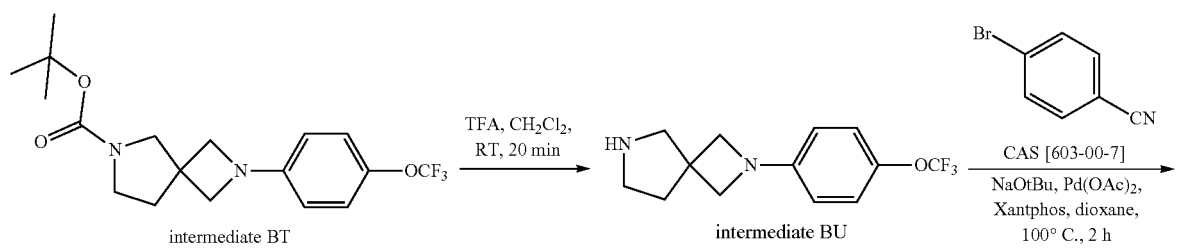
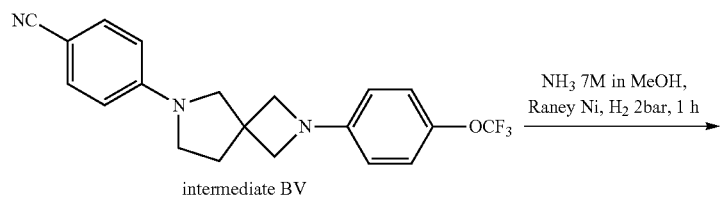
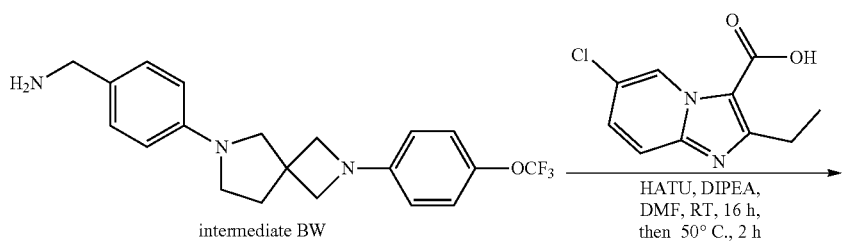

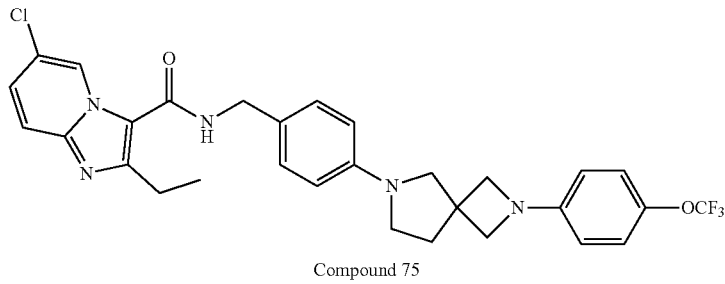

Compound 75

Preparation of Intermediate BT

In a Shlenck reactor, a solution of 6-Boc-2,6-diazaspiro[3.4]octane (CAS [885270-86-0], 0.5 g, 2.36 mmol), 1-Bromo-4-(trifluoromethoxy)benzene (CAS [407-14-7], 525 µL, 3.53 mmol) and sodium terbutoxide (0.453 g, 4.71 mmol) in 1,4-dioxane (25 mL) was purged with $N_2$. Then Palladium (II) acetate (52.9 mg, 0.236 mmol) and Xantphos (0.136 g, 0.236 mmol) were added, the mixture was purged again with $N_2$ and stirred at 100° C. for 2 h. The mixture was combined filtered on a pad of Celite®. The cake was washed with EtOAc and the filtrate was evaporated in vacuo to give 1.2 g as a brown solid. The residue was purified by preparative LC (irregular SiOH, 15-40 µm, 50 g, Merck, dry loading (Celite®), mobile phase gradient: from Heptane/EtOAc from 95/5 to 60/40) to give 0.756 g of intermediate BT as off-white solid (80%).

Preparation of Intermediate BU

To a solution of intermediate BT (0.706 g, 1.90 mmol) in $CH_2Cl_2$ (20 mL) was added trifluoroacetic acid (7.25 mL, 94.7 mmol) (reaction mixture turn brown) and the mixture was stirred at room temperature for 20 min. The mixture was poured into a sat. solution of $NaHCO_3$. The layers were separated and the aqueous layer was extracted with $CH_2Cl_2$. The combined organic layers were dried over $MgSO_4$, filtered off and evaporated in vacuo to give brown oil which was triturated in $Et_2O$ and filtered off to give 0.519 g of intermediate BU as a off-white powder (98%).

Preparation of Intermediate BV

In a sealed tube, a solution of intermediate BU (0.5 g, 1.84 mmol), 4-Bromobenzonitrile (CAS [623-00-7], 0.5 g, 2.76 mmol) and sodium terbutoxide (0.53 g, 5.51 mmol) in 1,4-dioxane (20 mL) was purged with $N_2$. Then Palladium (II) acetate (0.041 g, 0.184 mmol) and Xantphos (0.106 g, 0.184 mmol) were added, the mixture was purged again with $N_2$ and stirred at 100° C. for 3 h. The mixture was cooled down to room temperature, filtered on a pad of Celite® and the cake was washed with EtOAc. The filtrate was evaporated in vacuo to give a brown oil. The residue was purified by preparative LC (irregular SiOH, 15-40 µm, 40 g. Grace, dry loading (Celite®), mobile phase gradient: from Heptane/EtOAc from 95/5 to 50/50) to give 0.429 g of a yellow oil (which crystallized on standing). The oil was purified by Reverse phase (Stationary phase: YMC-actus Triart-C18 10 µm 30×150 mm, Mobile phase: Gradient from (aq. $NH_4HCO_3$ 0.2%)/CAN from 50/50 to 0/100) to give 0.328 g of intermediate BV as a yellow solid (48%).

Preparation of Intermediate BW

In an autoclave, to a solution of intermediate BV (0.28 g, 0.75 mmol) in Ammonia 7M in methanol (7.8 mL) was added Raney Nickel and the mixture was hydrogenated at room temperature under 2 bar for 1 h. The mixture was filtered on a pad of Celite® and the cake was washed with MeOH. The filtrate was evaporated in vacuo to give a black solid which was solubilized in EtOAc, filtered off and the filtrate was evaporated to provide 0.244 g of intermediate BW as a white solid (86%).

Preparation of Compound 75

A solution of 6-chloro-2-ethylimidazo[3,2-a]pyridine-3-carboxylic acid (CAS [1216142-18-5], 0.155 g, 0.647 mmol), intermediate BW (0.244 g, 0.647 mmol), HATU (0.271 g, 0.712 mmol) and diisopropylethylamine (0.286 mL, 1.68 mmol) in DMF (6.5 mL) was stirred at room temperature overnight. The mixture was heated at 50° C. for 2 h. The mixture was cooled down to room temperature and evaporated in vacuo to give 980 mg of black oil. The residue was purified by preparative LC (irregular SiOH, 15-40 µm, 50 g, Merck, dry loading (Celite®), mobile phase gradient: from Heptane/EtOAc from 95/5 to 50/50) to give 0.254 g of residue as a yellow solid.

The residue was purified by reverse phase (spherical C18, 25 µm, 40 g YMC-ODS-25, dry loading (Celite®), mobile phase gradient (aq. $NH_4HCO_3$ 0.2%)/MeCN from 30/70 to 0/100) to give a white solid which was triturated in pentane, filtered off and evaporated under vacuum (50° C., 16 h) affording 0.156 g of compound 75 as a white solid (41%).

$^1$H NMR (400 MHz, DMSO-$d_6$) δ ppm 9.06 (s, 1H), 8.35 (br t, J=5.8 Hz, 1H), 7.65 (d, J=9.6 Hz, 1H), 7.44 (dd, J=9.6, 2.0 Hz, 1H), 7.20 (br d, J=8.1 Hz, 2H), 7.16 (br d, J=8.6 Hz, 2H), 6.53 (br d, J=8.6 Hz, 2H), 6.49 (br d, J=8.6 Hz, 2H), 4.40 (d, J=6.1 Hz, 2H), 3.82 (s, 4H), 3.46 (s, 2H), 3.25-3.29 (m, 2H), 2.96 (q, J=7.4 Hz, 2H), 2.23 (t, J=6.8 Hz, 2H), 1.25 (t, J=7.6 Hz, 3H)

Synthesis of Compound 76

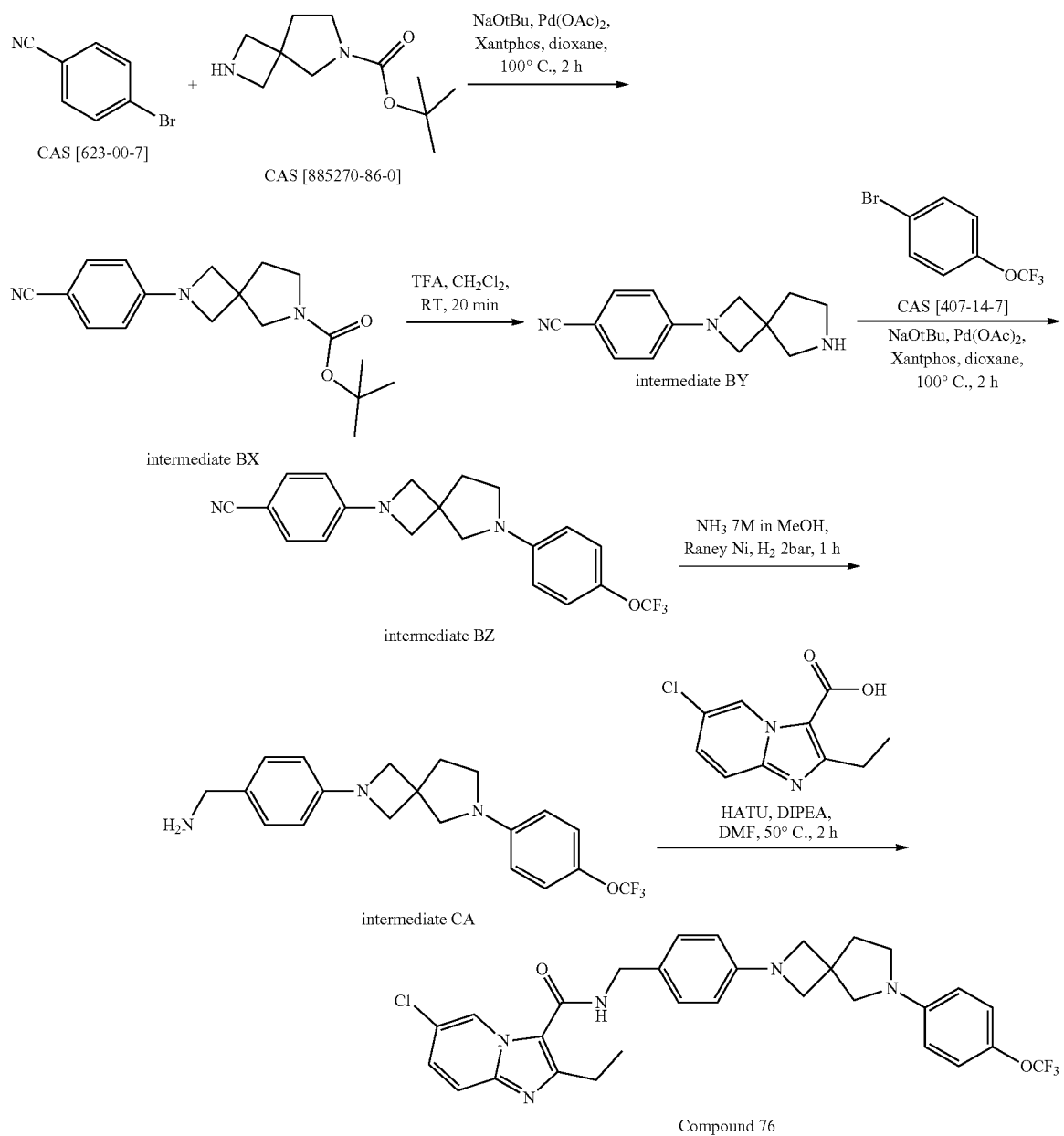

Preparation of Intermediate BX

Accordingly, intermediate BX was prepared in the same way as intermediate BT starting from 6-Boc-2,6-diazaspiro[3.4]octane CAS [885270-86-0] and 4-bromobenzonitrile CAS [623-00-7] affording 0.673 g, 84%.

Preparation of Intermediate BY

Accordingly, intermediate BY was prepared in the same way as intermediate BU starting from intermediate BX affording 0.312 g, 80%.

Preparation of Intermediate BZ

Accordingly, intermediate BZ was prepared in the same way as intermediate BV starting from intermediate BY and 1-bromo-4-(trifluoromethoxy)benzene CAS [407-14-7] affording 0.369 g, 73%.

Preparation of Intermediate CA

Accordingly, intermediate CA was prepared in the same way as intermediate BW starting from intermediate BZ affording 0.2 g, 56%.

Preparation of Compound 76

Accordingly, Compound 76 was prepared in the same way as Compound 75 starting from 6-chloro-2-ethylimidazo[3,2-a]pyridine-3-carboxylic acid CAS [1216142-18-5] and intermediate CA affording 0.078 g, 30%.

$^1$H NMR (500 MHz, DMSO-$d_6$) δ ppm 9.07 (s, 1H), 8.41 (t, J=6.2 Hz, 1H), 7.67 (d, J=9.5 Hz, 1H), 7.46 (dd, J=9.6, 1.7 Hz, 1H), 7.21 (m, J=8.2 Hz, 2H), 7.15 (br d, J=8.8 Hz, 2H), 6.57 (d, J=9.1 Hz, 2H), 6.46 (m, J=8.2 Hz, 2H), 4.42 (d, J=5.6 Hz, 2H), 3.79 (s, 4H), 3.47 (s, 2H), 3.30-3.33 (m, 2H), 2.97 (q, J=7.4 Hz, 2H), 2.24 (t, J=7.0 Hz, 2H), 1.26 (t, J=7.4 Hz, 3H)

Synthesis of Compound 77

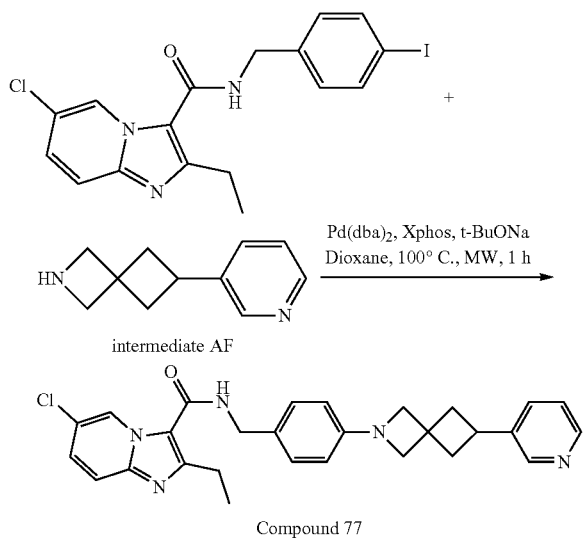

A solution of intermediate AF (0.1 g, 0.574 mmol), intermediate M (0.28 g, 0.631 mmol), X-phos (0.033 g, 0.069 mmol), Pd(dba)$_2$ (0.02 g, 0.034 mmol) and sodium tert-butoxide (0.221 g, 2.30 mmol) in dioxane (4 mL) was irradiated under microwave at 100° C. for 1 hour under N$_2$. The mixture was concentrated. The crude product was purified by high performance liquid chromatography over Gemini (eluent: NH$_3$ water/acetonitrile 45/55 to 45/55). The desired fractions were collected and concentrated to give Compound 77, 0.0076 g, 3%.

1H NMR (400 MHz, CHLOROFORM-d) δ ppm 9.53 (d, J=1.25 Hz, 1H) 8.47 (s, 2H) 7.50-7.56 (m, 2H) 7.30 (d, J=2.01 Hz, 1H) 7.28 (d, J=2.01 Hz, 1H) 7.25 (s, 1H) 7.23 (s, 1H) 6.47 (d, J=8.53 Hz, 2H) 5.99 (s, 1H) 4.59 (d, J=5.27 Hz, 2H) 4.04 (s, 2H) 3.83 (s, 2H) 3.50 (t, J=8.78 Hz, 1H) 2.95 (q, J=7.53 Hz, 2H) 2.63-2.75 (m, 2H) 2.30-2.44 (m, 2H) 1.39 (t, J=7.65 Hz, 3H)

Synthesis of Compound 78

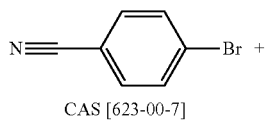

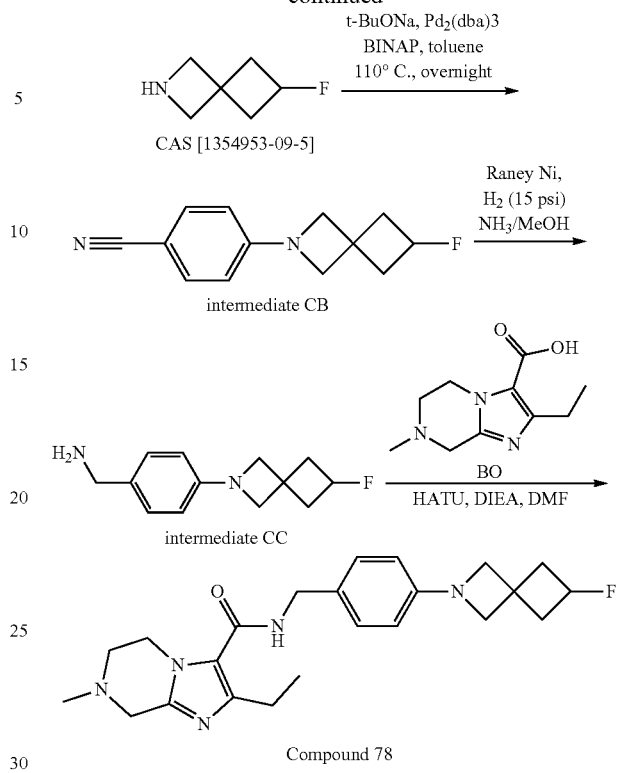

Preparation of Intermediate CB

A solution of 2-fluoro-6-azaspiro[3.3]heptane (CAS [1354953-09-5], 0.8 g, 6.95 mmol), 4-bromobenzonitrile (CAS [623-00-7], 1.265 g, 6.95 mmol), BINAP (0.26 g, 0.42 mmol), Pd$_2$(dba)$_3$ (0.127 g, 0.14 mmol), sodium tert-butoxide (2 g, 20.84 mmol) and triethylamine (0.48 mL) in toluene (50 mL) was stirred overnight at 110° C. under N$_2$ flow. The mixture was concentrated. The residue was dissolved in CH$_2$Cl$_2$ (300 mL) and water (150 mL). The organic layer was washed with brine (150 mL), dried over magnesium sulfate and filtered.

The filtrate was concentrated. The crude product was purified by column chromatography over silica gel (eluent: ethyl acetate/petroleum ether from 0 to 1/5). The desired fractions were collected and concentrated to give intermediate CB, 1 g, 66%.

Preparation of Intermediate CC

A mixture of intermediate CB (0.45 g, 2.08 mmol) in ammonia 7M in MeOH (20 mL) was hydrogenated with Raney Nickel (40 mg) as catalyst at 25° C. (H$_2$, 15 Psi) for 16 hours. After uptake of H2, the catalyst was filtered off and the filtrate was concentrated to give intermediate CC, 0.45 g, 98%.

Preparation of Compound 78

A solution of intermediate BO (0.048 g, 0.23 mmol), HATU (0.112 g, 0.3 mmol), diisopropylethylamine (0.076 g, 059 mmol) in DMF (10 mL) was stirred for 30 minutes at 25° C. Intermediate CC (0.05 g, 0.23 mmol) was added to the mixture and the mixture was stirred for 2 hours at 25° C. The crude product was purified by high performance liquid chromatography over Phenomenex Gemini (eluent: 0.05% ammonia water/methanol 30/70 to 0/100). The desired fractions were collected and lyophilized to give Compound 78, 0.0134 g, 14/%.

1H NMR (400 MHz, CHLOROFORM-d) δ ppm 7.18 (d, J=8.53 Hz, 2H) 6.38-6.45 (m, 2H) 5.83 (br. s., 1H) 4.86-5.09 (m, 1H) 4.48 (d, J=5.52 Hz, 2H) 4.31 (t, J=5.65 Hz, 2H) 3.88 (s, 2H) 3.84 (s, 2H) 3.64 (s, 2H) 2.79 (t, J=5.52 Hz, 2H) 2.67-2.71 (m, 2H) 2.60-2.67 (m, 2H) 2.38-2.50 (m, 5H) 1.22 (t, J=7.53 Hz, 3H)

Synthesis of Compound 79 column chromatography over silica gel (eluent: ethyl acetate/hexane from 0 to 1/1). The desired fractions were collected and concentrated to give intermediate CD, 2.5 g, 67%

Preparation of Intermediate CE

Sodium hydride (0.354 g, 8.85 mmol) was added to a solution of intermediate CD (2.2 g, 7.38 mmol) in THF (40 mL) at 0° C. After stirred for 30 minutes, methyl iodide (1.26 g, 8.85 mmol) was added. The mixture was warmed up to 25° C. and stirred for 3 hours. The mixture was poured into ice water. The mixture was extracted with ethyl acetate

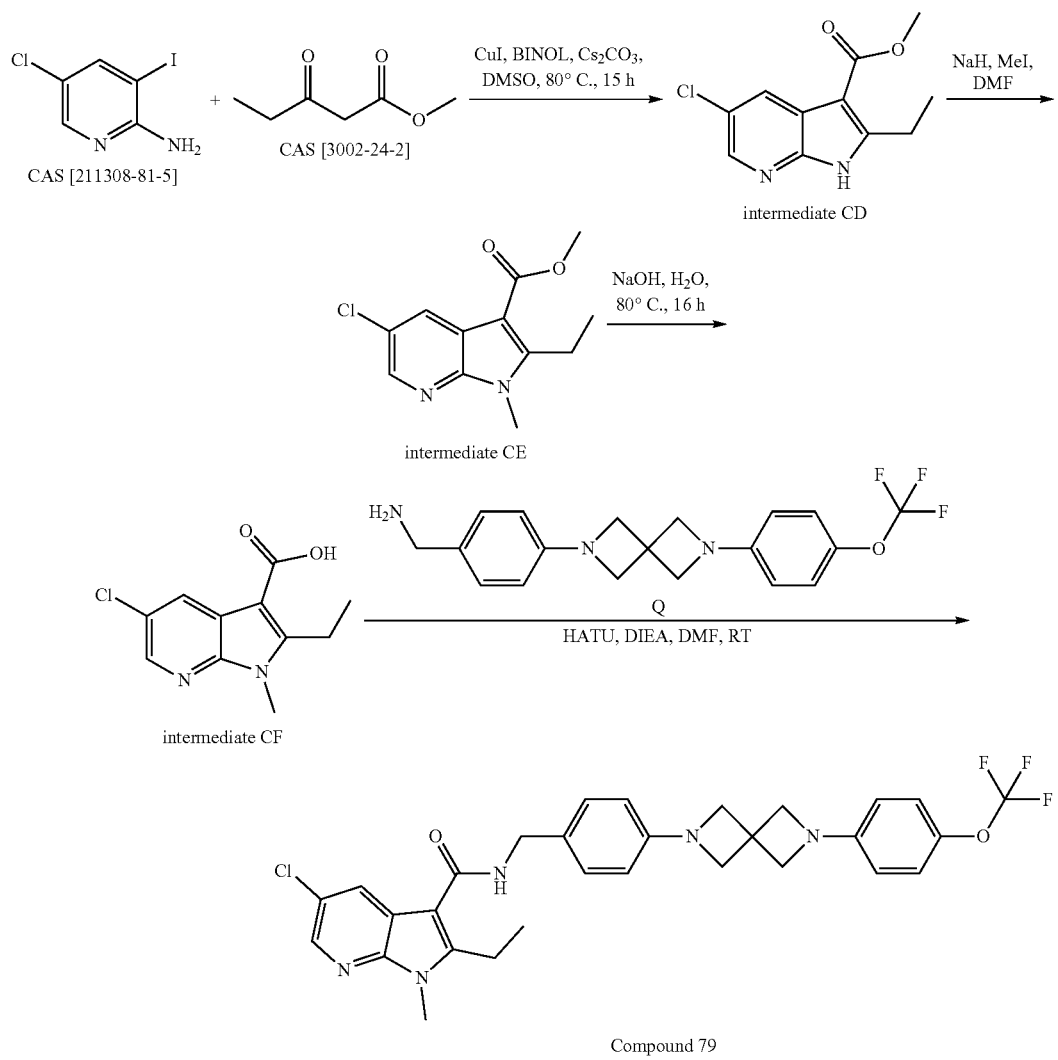

Preparation of Intermediate CD

A mixture of 5-chloro-3-iodopyridin-2-amine (CAS [211308-81-5], 4 g, 15.72 mmol), 2,4-Hexadione (CAS [3002-24-2], 4.50 g, 34.58 mmol), cesium carbonate (5.12 g, 15.71 mmol), BINOL (900.20 mg, 3.14 mmol) and copper iodide (299.39 mg, 1.57 mmol) in DMSO (50 mL) was stirred for 15 hours under N₂ flow. Brine and ethyl acetate were added to the mixture. The organic layer was separated, washed with brine, dried over MgSO₄ and filtered. The filtrate was concentrated. The crude product was purified by (50 mL×2). The organic layers were combined, washed with brine, dried over MgSO₄ and filtered. The filtrate was concentrated. The crude product was purified by column chromatography over silica gel (eluent: ethyl acetate/petroleum ether from 0 to 1/3). The filtrate was concentrated to give intermediate CE, 1.6 g, 86%.

Preparation of Intermediate CF

A mixture of intermediate CE (1.6 g, 6.33 mmol) in sodium hydroxide aqueous (5 g, 62.51 mmol, 50% in H₂O)

solution was stirred overnight at 80° C. Thin layer chromatography (eluent: ethyl acetate/petroleum ether=1/3) showed starting material was consumed. The mixture was concentrated. The mixture was extracted with methyl tert-butyl ether (25 mL×2). The water layers were extracted with solution (ethyl acetate/petroleum ether=1/3) (2×50 mL). The water layers were adjusted with 1 N HCl until pH was 4. The residue was filtered and concentrated to give intermediate CF, 1.3 g, 86%.

Preparation of Compound 79

A solution of intermediate CF (0.06 g, 0.25 mmol), HATU (0.123 g, 0.33 mmol), diisopropylethylamine (0.08 g, 0.62 mmol) in DMF (10 mL) was stirred for 30 minutes at 25° C. Intermediate Q (0.1 g, 0.28 mmol) was added to the mixture and the mixture was stirred for 2 hours at 25° C. The mixture was concentrated under vacuum. The crude product was purified by high performance liquid chromatography over Gemini (eluent: 0.05% ammonia/methanol 40/60 to 10/90). The desired fractions were collected and concentrated to give Compound 79, 0.052 g, 36%.

1H NMR (400 MHz, CHLOROFORM-d) δ ppm 8.22 (d, J=1.76 Hz, 1H) 7.91 (d, J=1.76 Hz, 1H) 7.28 (s, 2H) 7.08 (d, J=8.82 Hz, 2H) 6.49 (d, J=8.38 Hz, 2H) 6.42 (d, J=8.82 Hz, 2H) 5.89 (br. s., 1H) 4.59 (d, J=5.29 Hz, 2H) 4.04 (d, J=2.21 Hz, 7H) 3.83 (s, 3H) 3.21 (q, J=7.50 Hz, 2H) 1.33 (t, J=7.72 Hz, 3H)

Synthesis of Compound 80

A solution of 5-chloro-2-ethyl-1-methylindole-3-carboxylic acid (CAS [1784796-04-8], 0.131 g, 0.55 mmol), HATU (0.272 g, 0.72 mmol), diisopropylethylamine (0.185 g, 1.43 mmol) in DMF (10 mL) was stirred for 30 minutes at 25° C. Intermediate Q (0.1 g, 0.28 mmol) was added to the mixture and the mixture was stirred for 2 hours at 25° C. The mixture was concentrated under vacuum. The residue was purified by high performance liquid chromatography over Waters Xbridge Prep OBD C18 150×30×5μ (eluent: NH$_3$ water/acetonitrile from 70/65 to 40/95). The desired fractions were collected and lyophilized to give Compound 80, 0.0423 g, 13%.

1H NMR (400 MHz, CHLOROFORM-d) δ ppm 7.62 (d, J=1.76 Hz, 1H) 7.28 (d, J=8.53 Hz, 2H) 7.22-7.25 (m, 1H) 7.14-7.19 (m, 1H) 7.08 (d, J=8.78 Hz, 2H) 6.49 (d, J=8.53 Hz, 2H) 6.42 (d, J=9.03 Hz, 2H) 6.01 (br. s., 1H) 4.61 (d, J=5.52 Hz, 2H) 4.04 (s, 8H) 3.72 (s, 3H) 3.19 (q, J=7.19 Hz, 2H) 1.30 (t, J=7.53 Hz, 3H)

Synthesis of Compound 81

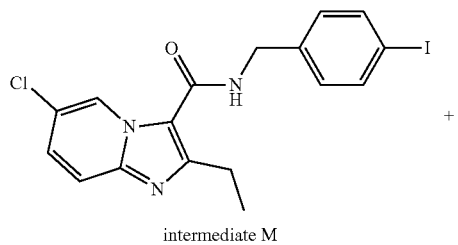

intermediate M

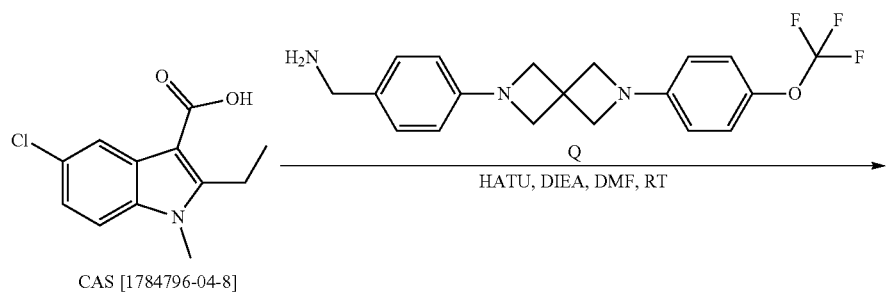

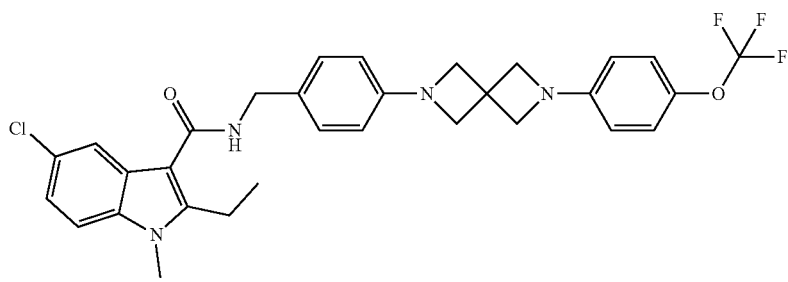

Compound 80

-continued

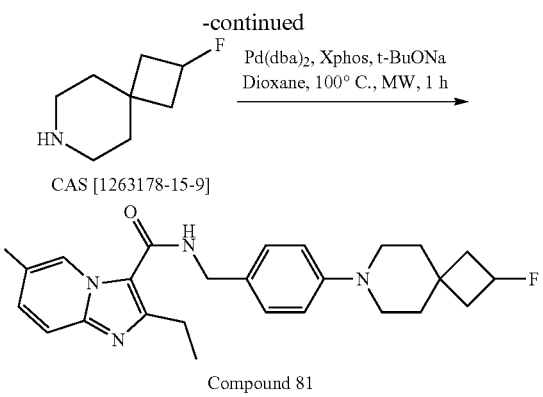

CAS [1263178-15-9]

Compound 81

A solution of intermediate M (0.1 g, 0.23 mmol), 2-fluoro-7-aza-spiro[3.5]nonane (CAS [1263178-15-9], 0.049 g, 0.23 mmol), X-phos (0.0105 g, 0.022 mmol), Pd(dba)₂ (0.0065 g, 0.011 mmol) and sodium tert-butoxide (0.055 g, 0.57 mmol) in dioxane (3 mL) was irradiated under microwave at 100° C. for 1 hour under N₂. The mixture was concentrated. The crude product was purified by high performance liquid chromatography over Gemini (C18 150×25 mm×10µ, 25 mL/min, eluent: NH₃ water/acetonitrile 45/55 to 45/55). The desired fractions were collected and concentrated to give Compound 81, 0.0073 g, 7%.

¹H NMR (400 MHz, CDCl₃) δ 9.53 (d, J=1.5 Hz, 1H), 7.54 (d, J=9.5 Hz, 1H), 7.33-7.26 (m, 3H), 6.95 (d, J=8.6 Hz, 2H), 6.02 (br. s., 1H), 5.86 (tdd, J=7.4, 10.0, 17.1 Hz, 1H), 5.20-5.08 (m, 2H), 4.61 (d, J=5.5 Hz, 2H), 3.50 (d, J=12.3 Hz, 2H), 3.10 (dt, J=2.4, 12.2 Hz, 2H), 2.96 (q, J=7.5 Hz, 2H), 2.47-2.34 (m, 2H), 1.99-1.63 (m, 4H), 1.39 (t, J=7.5 Hz, 3H)

Synthesis of Compound 82

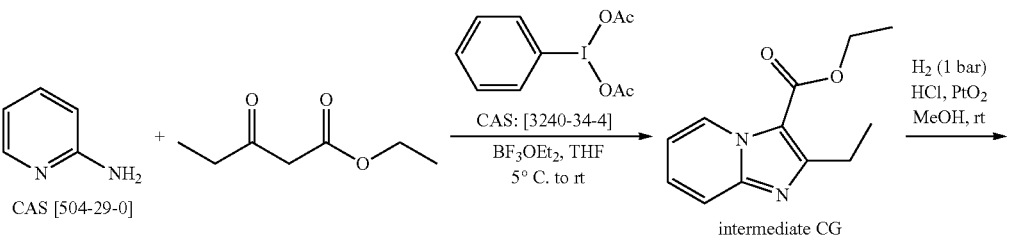

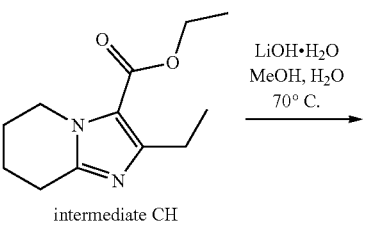

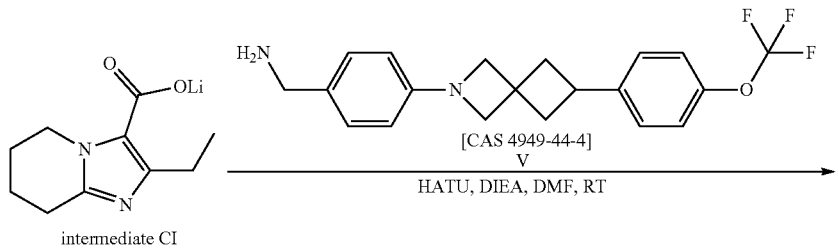

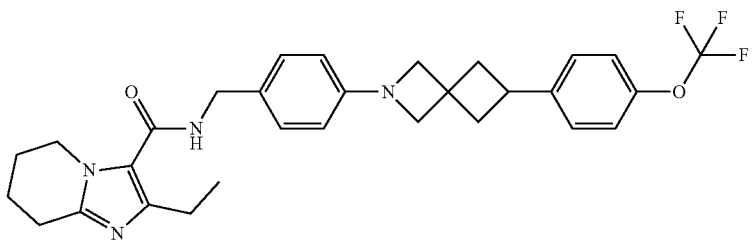

Compound 82

Preparation of intermediate CG A solution of 2-aminopyridine (CAS [504-29-0], 4.0 g; 42.5 mmol) in THF (220 mL) was cooled to 5° C., before the addition of ethyl propionylacetate (CAS [4949-44-4], 6.1 mL; 42.5 mmol), Iodobenzene Diacetate (CAS [3240-34-4], 13.7 g; 42.5 mmol) and BF$_3$.OEt$_2$(556 μL; 2.13 mmol). The resulting mixture was allowed to warm to rt, then stirred at rt overnight. The mixture was poured into saturated aqueous NaHCO$_3$and extracted with EtOAc. The combined organic layers were washed with brine, dried over MgSO$_4$, filtered and concentrated to give 18.8 g as an orange solid. The crude was taken-up in Et$_2$O, leading to precipitation. The precipitate was filtered to give 3.8 g of crude as an off-white solid (41%). The filtrate was purified by preparative LC (Regular silica 30 μm, 25 g, liquid loading (CH$_2$Cl$_2$), mobile phase gradient: from Heptane/EtOAc 100/0 to 50/50) to obtain 1.7 g of intermediate 30 as an off-white solid which was taken-up in Et$_2$O, the solid was filtered and dried under high vacuum to give 1.2 g of intermediate CG as a white solid (13%).

Preparation of intermediate CH

A solution of intermediate CG (1.2 g; 5.50 mmol) in MeOH (27 mL) was degassed by N$_2$ bubbling for 10 min before the addition of Platinum Oxide (125 mg; 0.55 mmol) and HCl (125 μL; 1.50 mmol). The resulting mixture was hydrogenated at rt under 1 bar overnight.

EtOAc was added and the mixture was filtered through a pad of Celite®, the filtrate was concentrated until dryness to give 1.4 g of intermediate CH as colourless oil (quant).

Preparation of Intermediate CI

Lithium hydroxide monohydrate (170 mg; 4.05 mmol) was added to a solution of intermediate CH (300 mg; 1.35 mmol) in MeOH (3 mL) and H$_2$O (158 μL). The resulting mixture was stirred at 50° C. for 48 h. The solvent was evaporated in vacuo until dryness to give an off-white gum which was azeotroped with toluene (twice), then dried under high vacuum to give 0.353 g of intermediate CI as an off-white solid (used as such in the next step).

Preparation of Compound 82

Diisopropylethylamine (0.232 mL; 1.35 mmol) and HATU (0.267 g; 0.70 mmol) were added successively to a solution of intermediate CI (0.108 g; 0.54 mmol) in DMF (10 mL). The resulting mixture was stirred at room temperature for 30 min, before the addition of intermediate V (0.196 g; 0.54 mmol) in DMF (7 mL). The mixture was stirred at room temperature for 4 h. The reaction mixture was evaporated in vacuo until dryness, then diluted with EtOAc and washed with brine (twice). The organic layer was dried over MgSO$_4$, filtered and evaporated to dryness to give 585 mg as a brown oil which was purified by preparative LC (Regular silica 30 μm, 12 g, dry loading (Celite®), mobile phase gradient Heptane/EtOAc/MeOH from 90/8/2 to 50/40/10) to obtain 0.131 g as an off-white solid. The solid was triturated in Et$_2$O, filtered and dried under high vacuum to give 97 mg of Compound 82 as a white solid (33% over 2 steps).

$^1$H NMR (400 MHz, DMSO-d$_6$) δ ppm 8.08 (t, J=6.1 Hz, 1H) 7.35 (d, J=8.6 Hz, 2H) 7.29 (d, J=8.1 Hz, 2H) 7.11 (d, J=8.6 Hz, 2H) 6.39 (d, J=8.1 Hz, 2H) 4.28 (d, J=6.1 Hz, 2H) 3.96 (t, J=5.6 Hz, 2H) 3.91 (s, 2H) 3.70 (s, 2H) 3.47 (quint, J=8.8 Hz, 1H) 2.66-2.72 (m, 2H) 2.52-2.62 (m, 4H) 2.26-2.34 (m, 2H) 1.74-1.87 (m, 4H) 1.08 (t, J=7.3 Hz, 3H)

Synthesis of Compound 83

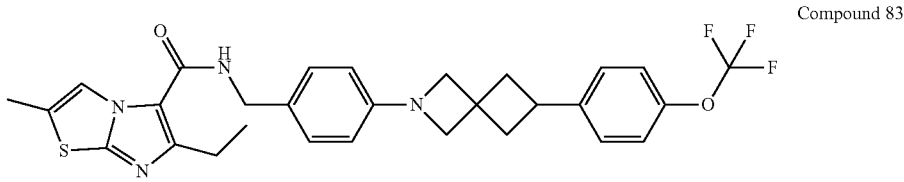 [SMILES: CCc1nc2sc(C)cn2c1C(=O)NCc1ccc(N2CC3(CC(c4ccc(OC(F)(F)F)cc4)C3)C2)cc1]

Compound 83

Diisopropylethylamine (0.31 mL, 1.78 mmol) and HATU (0.353 g, 0.927 mmol) were successively added to a solution of 6-Ethyl-2-methylimidazo[2,1-b]thiazole-5-carboxylic acid (CAS [1131613-58-5], 0.15 g, 0.713 mmol) in DMF (20 mL). The resulting mixture was stirred at room temperature for 30 min, before the addition of intermediate V (259 mg, 0.713 mmol) and the mixture was stirred at room temperature overnight. The reaction mixture was diluted with EtOAc and washed with an aq. sat. NaHCO$_3$ solution (twice) and brine (twice). The combined organic phases were dried over MgSO$_4$, filtered and evaporated to dryness. The crude was purified by preparative LC (Irregular silica 15-40 μm, 12 g, dry loading (silica), mobile phase gradient: from Heptane/EtOAc 90/10 to 50/50) and the obtained solid was triturated in pentane, filtered and dried under vacuo at 45° C. to obtain 0.167 g of Compound 83 as white solid (42%).

$^1$H NMR (400 MHz, DMSO-d$_6$) δ ppm 8.01 (t, J=5.8 Hz, 1H) 7.87 (s, 1H) 7.36 (d, J=8.6 Hz, 2H) 7.28 (d, J=8.6 Hz, 2H) 7.15 (d, J=8.1 Hz, 2H) 6.40 (d, 0.1=8.6 Hz, 2H) 4.35 (d, J=5.6 Hz, 2H) 3.91 (s, 2H) 3.70 (s, 2H) 3.47 (br t, J=8.6 Hz, 1H) 2.84 (q, J=7.2 Hz, 2H) 2.55-2.62 (m, 2H) 2.41 (s, 3H) 2.25-2.35 (m, 2H) 1.19 (t, J=7.58 Hz, 3H).

Synthesis of Compound 84 and Compound 85

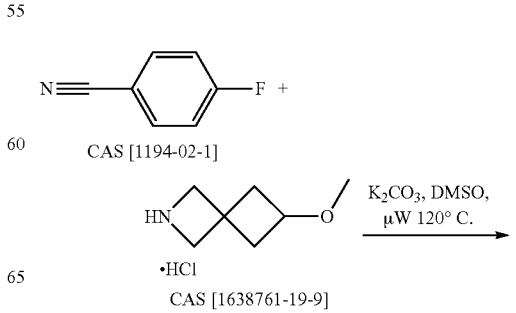

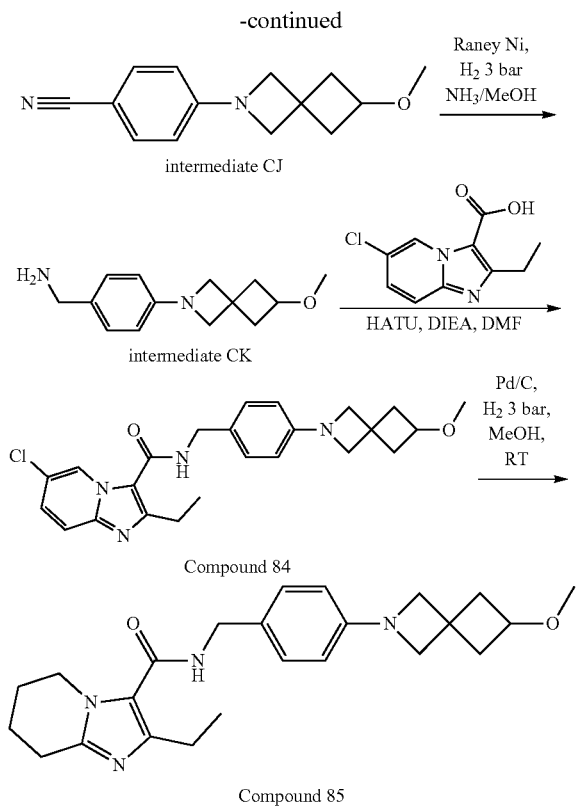

intermediate CJ intermediate CK

Compound 84

Compound 85

Preparation of Intermediate CJ

A suspension of 6-methoxy-2-azaspiro[3.3]heptane hydrochloride (CAS [1638761-19-9], 0.47 g, 2.36 mmol), 4-Fluorobenzonitrile (CAS [1194-02-1], 0.576 g, 4.71 mmol) and potassium carbonate (0.976 g, 7.07 mmol) in DMSO (11 mL) was heated at 120° C. using a single mode microwave (Biotage Initiator60) with a power output ranging from 0 to 400 W for 30 min [fixed hold time]. The reaction mixture was evaporated in a Genevac apparatus and purified by preparative LC (irregular silica, 15-40 μm, 50 g, dry loading (Celite®), mobile phase gradient Heptane/EtOAc from 95/5 to 70/30) to give 0.361 g of intermediate CJ as a white solid (67%).

Preparation of Intermediate CK

In an autoclave, Raney Nickel (0.8 g, 13.6 mmol) was added to a solution of intermediate CJ (0.713 g, 3.12 mmol) in ammonia 7N in MeOH (15 mL) and the mixture was stirred at room temperature under 3 bar of H2 overnight. The mixture was filtered over Celite® and evaporated in vacuo to give 0.717 g of intermediate CK as a blue oil (99%).

Preparation of Compound 84

Diisopropylethylamine (0.461 mL, 2.71 mmol) and HATU (436 mg, 1.15 mmol) were added successively to a solution of 6-chloro-2-ethylimidazo[3,2-a]pyridine-3-carboxylic acid (CAS [1216142-18-5], 0.25 g, 1.04 mmol) in DMF (10 mL). The resulting mixture was stirred at room temperature for 30 min., then a solution of intermediate CK (0.242 g, 1.04 mmol) in DMF (5 mL) was added and the mixture was stirred at room temperature for 1 h. The reaction mixture was evaporated in vacuo until dryness. The crude product was purified by preparative LC (irregular silica, 15-40 μm, 120 g, dry loading (silica), mobile phase gradient: from DCM 100%, MeOH 0% to DCM 90%, MeOH 10% in 20 CV) to give 0.5 g of an orange solid, which was successively triturated in Et$_2$O, Et$_2$O/EtOH (9:1), iPr$_2$O and EtOH to give 0.317 g of Compound 84 as a slightly orange solid (69%).

$^1$H NMR (400 MHz, DMSO-d$_6$) δ ppm 9.05 (d, J=1.5 Hz, 1H), 8.37 (t, J=5.8 Hz, 1H), 7.65 (d, J=9.6 Hz, 1H), 7.44 (dd, J=9.6, 2.0 Hz, 1H), 7.17 (d, J=8.6 Hz, 2H), 6.37 (d, J=8.6 Hz, 2H), 4.39 (d, J=6.1 Hz, 2H), 3.75 (s, 2H), 3.81-3.74 (m, 1H), 3.70 (s, 2H), 3.11 (s, 3H), 2.95 (q, J=7.4 Hz, 2H), 2.47-2.41 (m, 2H), 2.02 (ddd, J=10.0, 7.0, 2.8 Hz, 2H), 1.27-1.21 (m, 3H)

Preparation of Compound 85

A solution of Compound 84 (0.08 g; 114 mmol) in MeOH (3.5 mL) was degassed by N$_2$ bubbling for 5 min before the addition of Pd/C (0.0032 g; 3.01 μmol). The resulting mixture was hydrogenated at room temperature under 3 bar overnight. The mixture was filtered through a pad of Celite®, and the filtrate was evaporated under vacuum to dryness. The crude was purified by preparative LC (Regular silica 15-40 μm, 12 g, dry loading (Celite®), mobile phase gradient: from CH$_2$Cl$_2$/MeOH 100/0 to 95/5) to obtain 0.057 g of a solid which was triturated in heptane, filtered and dried under high vacuum at 50° C. during 72 h to give 0.043 g of Compound 85 as white solid (58%).

$^1$H NMR (500 MHz, DMSO-d$_6$) δ ppm 8.19 (br s, 1H) 7.10 (d, J=8.2 Hz, 2H) 6.36 (d, J=8.2 Hz, 2H) 4.28 (d, J=5.9 Hz, 2H) 3.98 (br t, J=5.5 Hz, 2H) 3.73-3.79 (m, 3H) 3.70 (s, 2H) 3.12 (s, 3H) 2.72 (br t, J=5.9 Hz, 2H) 2.58-2.65 (m, 2H) 2.41-2.48 (m, 2H) 2.03 (m, 2H) 1.85 (br d, J=4.7 Hz, 2H) 1.79 (br d, J=5.4 Hz, 2H) 1.09 (t, J=7.6 Hz, 3H).

Synthesis of Compound 86

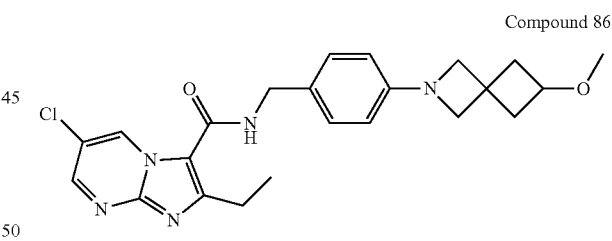

Compound 86

Diisopropylethylamine (0.293 mL, 1.73 mmol) and HATU (0.402 g, 1.06 mmol) were added successively to a solution of intermediate L (0.2 g, 0.704 mmol) in DMF (5 mL). The resulting mixture was stirred at room temperature for 30 min., then a solution of intermediate CK (0.135 g, 0.581 mmol) in DMF (2.3 mL) was added and the mixture was stirred at room temperature for 1 h. The reaction mixture was evaporated in vacuo until dryness to give 0.96 g as brown oil. The crude product was purified by preparative LC (Irregular silica 15-40 μm, 40 g, dry loading (Celite®), mobile phase gradient: from DCM 99.5%, MeOH/aq.NH$_3$ (95:5) 0.5% to DCM 94%, MeOH/aq.NH$_3$ (95:5) 6%) to obtain 0.516 g as an orange gum. The product was purified by Reverse phase (spherical C18 silica, 25 μm, 120 g YMC-ODS-25, dry loading (Celite®), mobile phase gradient: from 60% aq. (NH$_4$HCO$_3$ 0.2%), 40% MeCN to 20% aq. (NH₄HCO₃ 0.2%), 80% MeCN) to give 0.164 g of a pale yellow solid which was triturated in Et₂O, filtered and dried under high vacuum to afford 0.085 g of Compound 86 as a white solid (27%).

¹H NMR (400 MHz, DMSO-d₆) δ ppm 9.38 (d, J=2.5 Hz, 1H), 8.67 (d, J=2.5 Hz, 1H), 8.47 (t, J=5.8 Hz, 1H), 7.18 (d, J=8.6 Hz, 2H), 6.37 (d, J=8.1 Hz, 2H), 4.40 (d, J=5.6 Hz, 2H), 3.79-3.69 (m, 5H), 3.11 (s, 3H), 2.99 (q, J=7.6 Hz, 2H), 2.46-2.39 (m, 2H), 2.06-1.97 (m, 2H), 1.26 (t, J=7.6 Hz, 3H)

Synthesis of Compound 87

Preparation of Intermediate CL

In a flame-dried round-bottom flask under N₂, a solution of iPrMgCl·LiCl 1.3 M (7.14 mL, 9.28 mmol) was added to a solution of 4-Bromo-2-fluoroanisole (CAS [2357-52-0], 1.90 g, 9.28 mmol) in anhydrous THF (30 mL) at room temperature. The solution was stirred at room temperature for 5 h under a stream of N₂, then added dropwise (ca. 15 min.) to a solution of intermediate R (1.00 g, 3.09 mmol), N1,N1,N2,N2-tetramethylcyclohexane-1, 2-diamine (CAS [38383-49-2], 0.063 g, 0.37 mmol) and Cobalt II chloride (0.04 g, 0.31 mmol) in anhydrous THF (30 mL) under N₂,

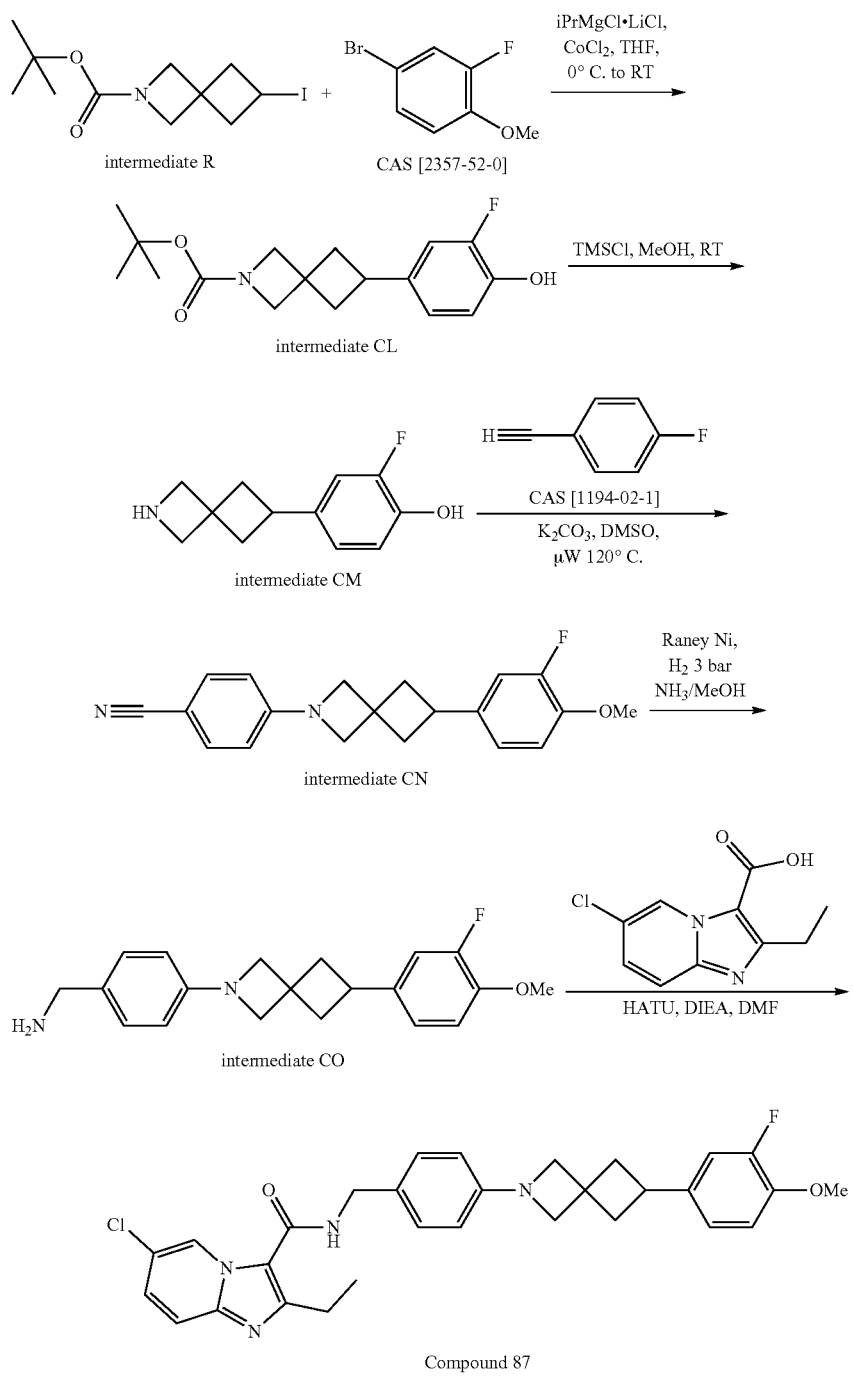

at 0° C. The resulting mixture was stirred at room temperature over week-end, hydrolyzed with aq. NH₄Cl 10% (40 mL) and extracted with ethyl acetate (2×40 mL). The combined organic phases were dried over MgSO₄, filtered and evaporated to dryness. The crude product was purified by preparative LC (irregular silica, 15-40 µm, 220 g, dry loading (silica), mobile phase gradient: from Heptane/EtOAc from 90/10 to 60/40) to give 0.619 g of intermediate CL as white solid (62%).

Preparation of Intermediate CM

Trimethylsilyl chloride (1.21 mL, 9.60 mmol) was added dropwise to a solution of intermediate CL (0.615 g, 1.91 mmol) in anhydrous methanol (20 mL) under N₂. The reaction mixture was stirred at room temperature overnight and then evaporated to dryness to give 0.447 g of intermediate CM as a white solid (91%).

Preparation of Intermediate CN

A mixture of intermediate CM (0.425 g, 1.65 mmol), 4-Fluorobenzonitrile (CAS [1194-02-1], 0.3 g, 2.47 mmol) and potassium carbonate (0.912 g, 6.60 mmol) in anhydrous DMSO (10 mL) was heated at 120° C. using a single mode microwave (Biotage Initiator60) with a power output ranging from 0 to 400 W for 1 h [fixed hold time]. The reaction mixture was quenched with water (40 mL) and extracted with ethyl acetate (2×50 mL). The combined organic phases were washed with water (2×50 mL) and brine (2×50 mL), dried over MgSO₄, filtered and evaporated to dryness. The crude product was purified by preparative LC (irregular silica, 15-40 µm, 120 g, dry loading (silica), mobile phase gradient: from Heptane/EtOAc from 90/10 to 40/60) to give 0.349 g of intermediate CN as a white solid (65%).

Preparation of Intermediate CO

In an autoclave, a mixture of intermediate CN (0.34 g, 1.06 mmol), and Raney Nickel (0.269 g, 4.58 mmol) in ammonia 7N in MeOH (11 mL) was stirred at room temperature under 3 bar of H2 overnight. The reaction mixture was then filtered through a pad of Celite® and evaporated to dryness to give 0.3 g of intermediate CO as off-white solid (87%).

Preparation of Compound 87

Diisopropylethylamine (0.19 mL, 1.09 mmol) and HATU (0.175 g, 0.46 mmol) were added successively to a solution of 6-chloro-2-ethylimidazo[3,2-a]pyridine-3-carboxylic acid (CAS [1216142-18-5], 0.1 g, 0.42 mmol) in DMF (7 mL). The resulting mixture was stirred at room temperature for 1 h, then intermediate CO (0.15 g, 0.46 mmol) was added and the mixture was stirred at room temperature for 2 h. The reaction mixture was evaporated in vacuo until dryness. The crude product was purified by preparative LC (irregular silica, 15-40 µm, 40 g, liquid loading, mobile phase gradient DCM/MeOH from 100/0 to 95/5) to give a yellow solid. That solid was triturated in Et₂O to give 0.132 g of a yellow solid which was dissolved in EtOH and evaporated to dryness to give 0.123 g of Compound 87 as a slightly yellow solid (55%).

¹H NMR (500 MHz, DMSO-d₆) δ ppm 9.05 (s, 1H), 8.39 (br t, J=5.7 Hz, 1H), 7.66 (d, J=9.5 Hz, 1H), 7.45 (br d, J=9.5 Hz, 1H), 7.19 (d, J=8.2 Hz, 2H), 7.13-7.04 (m, 2H), 6.99 (br d, J=8.5 Hz, 1H), 6.41 (d, J=8.2 Hz, 2H), 4.40 (br d, J=5.7 Hz, 2H), 3.90 (s, 2H), 3.80 (s, 3H), 3.70 (s, 2H), 3.40-3.33 (m, 1H), 2.96 (q, J=7.4 Hz, 2H), 2.28-2.23 (m, 2H), 1.25 (t, J=7.4 Hz, 3H)

Synthesis of Compound 88

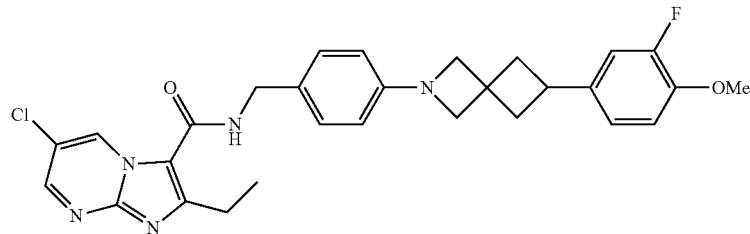

Compound 88

Diisopropylethylamine (0.171 mL, 1.01 mmol) and HATU (0.162 g, 0.43 mmol) were added successively to a solution of intermediate L (0.11 g, 0.39 mmol) in DMF (4 mL). The resulting mixture was stirred at room temperature for 45 min., then a solution of intermediate 38 (0.139 g, 0.43 mmol) in DMF (2 mL) was added and the mixture was stirred at room temperature for 1 h. The reaction mixture was evaporated in vacuo until dryness. The crude product was purified by preparative LC (irregular silica, 15-40 µm, 40 g, Grace, liquid loading, mobile phase gradient DCM/MeOH from 100/0 to 90/10) to give a brownish solid which was triturated in Et₂O and dried under high vacuum at 50° C. overnight to give 0.098 g of a yellowish solid. This solid was dissolved in ethanol and evaporated to dryness to give a yellowish solid which was triturated in iPr₂O to give 0.091 g of Compound 88 as a white solid (44%).

¹H NMR (400 MHz, DMSO-d₆) δ ppm 9.39 (s, 1H), 8.67 (s, 1H), 8.47 (br s, 1H), 7.19 (d, J=8.1 Hz, 2H), 7.13-7.03 (m, 2H), 7.02-6.96 (m, 1H), 6.40 (d, J=8.1 Hz, 2H), 4.41 (br d, J=5.6 Hz, 2H), 3.90 (s, 2H), 3.80 (s, 3H), 3.69 (s, 2H), 3.41-3.33 (m, 1H), 3.00 (q, J=7.2 Hz, 2H), 2.27-2.21 (m, 2H), 1.26 (br t, J=7.6 Hz, 3H)

Synthesis of Compound 89

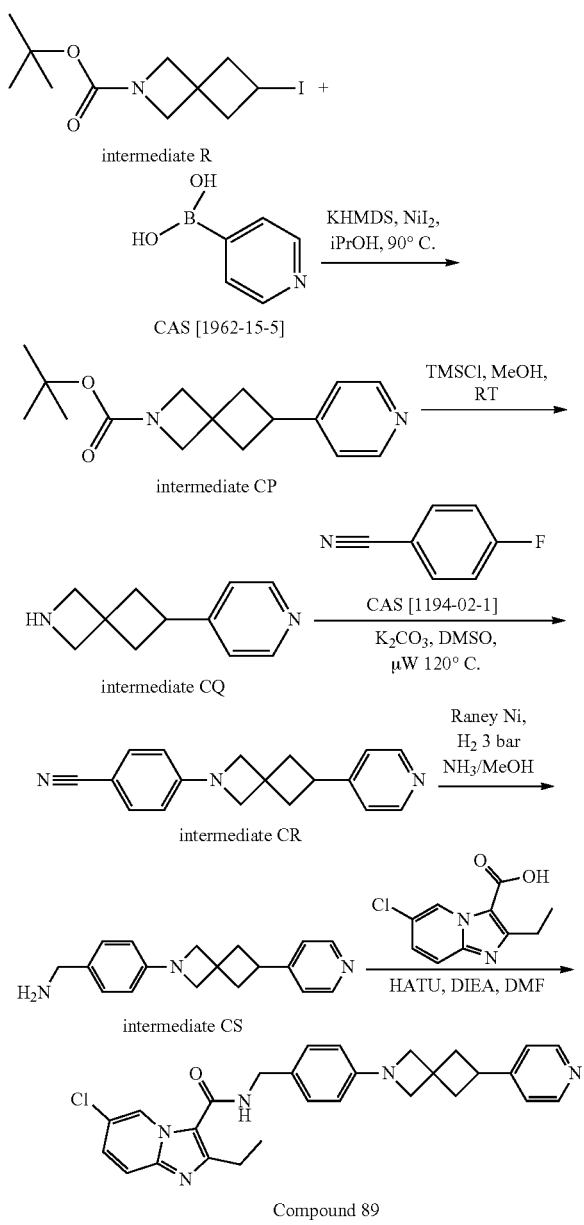

Preparation of Intermediate CP

A solution of Pyridine-4-boronic acid (CAS [1692-15-5], 0.571 g, 4.64 mmol), Potassium bis(trimethylsilyl)amide (1.14 g, 6.19 mmol), Nickel II iodide (0.097 g, 0.31 mmol) and trans-2-Aminocyclohexanol hydrochloride (CAS [5456-63-3], 0.036 g, 0.31 mmol) in iPrOH (20 mL) was stirred under $N_2$ for 5 min. at room temperature. Then, intermediate R (1.00 g, 3.09 mmol) was added and the reaction mixture was heated at 90° C. for 20 h. The reaction mixture was hydrolyzed with water (50 mL) and extracted with ethyl acetate (2×50 mL). The organic phases were combined and washed with brine (50 mL), dried over $MgSO_4$ and evaporated to dryness. The crude product was purified by preparative LC (irregular silica, 15-40 μm, 120 g, liquid loading, mobile phase gradient DCM/MeOH from 95/5 to 90/10) to give 0.251 g of intermediate 39 as a white solid (30%).

Preparation of Intermediate CQ

Trimethylsilyl chloride (0.52 mL, 4.15 mmol) was added dropwise to a solution of intermediate CP (0.227 g, 0.83 mmol) in anhydrous methanol (10 mL) under $N_2$. The reaction mixture was stirred at room temperature overnight and then evaporated to dryness to give 0.194 g of intermediate CQ as a white solid (quant.), used as such in the next step.

Preparation of Intermediate CR

A mixture of intermediate CQ (0.179 g), 4-Fluorobenzonitrile (CAS [1194-02-1], 0.206 g, 1.70 mmol) and potassium carbonate (0.587 g, 4.25 mmol) in anhydrous DMSO (5.5 mL) was heated at 120° C. using a single mode microwave (Biotage Initiator60) with a power output ranging from 0 to 400 W for 1 h [fixed hold time]. The reaction mixture was quenched with water and extracted with ethyl acetate (twice). The combined organic phases were washed with water (twice) and brine (twice), dried over $MgSO_4$, filtered and evaporated to dryness. The crude product was purified by preparative LC (irregular silica, 15-40 μm, 40 g, liquid loading, mobile phase gradient DCM/MeOH from 100/0 to 95/5) to give 0.095 g of intermediate CR as a white solid (41%).

Preparation of Intermediate CS

A mixture of intermediate CR (0.095 g, 0.35 mmol), and Raney Nickel 0.088 g, 1.5 mmol) in ammonia 7N in MeOH (4 mL) was stirred at room temperature under 3 bar of H2 overnight. The reaction mixture was then filtered through a pad of Celite® and evaporated until dryness to give 0.078 g of intermediate CS as a white solid (81%).

Preparation of Compound 89

Diisopropylethylamine (0.118 mL, 0.69 mmol) and HATU (0.112 g, 0.29 mmol) were added successively to a solution of 6-chloro-2-ethylimidazo[3,2-a]pyridine-3-carboxylic acid (CAS [1216142-18-5], 0.064 g, 0.27 mmol) in DMF (3 mL). The resulting mixture was stirred at room temperature for 45 min., then a solution of intermediate CS (0.078 g, 0.28 mmol) in DMF (2 mL) was added and the mixture was stirred at room temperature for 1 h. The reaction mixture was evaporated in vacuo until dryness. The crude product was purified by preparative LC (irregular silica, 15-40 μm, 40 g, liquid loading, mobile phase gradient DCM/MeOH from 100/0 to 90/10) to give a sticky solid. This solid was triturated in $Et_2O$, then dissolved in DCM and washed twice with water, dried over $MgSO_4$, filtered and evaporated to dryness to give 0.072 g of a white solid. That solid was dissolved in ethanol and evaporated to dryness, then successively triturated in $Et_2O$ and $iPr_2O$/EtOH (9:1). The resulting solid was purified by preparative LC (spherical C18 silica, 25 μm, 40 g YMC-ODS-25, dry loading (Celite®), mobile phase gradient: 0.2% aq. ($NH_4HCO_3$)/ MeCN from 30:70 to 0:100 in 6 CV) and finally triturated in $Et_2O$ to give 0.032 g of Compound 89 as a white solid (25%/).

$^1$H NMR (400 MHz, DMSO-$d_6$) δ ppm 9.06 (s, 1H), 8.47 (br d, J=5.6 Hz, 2H), 8.37 (br t, J=5.6 Hz, 1H), 7.66 (d, J=9.6

Hz, 1H), 7.44 (br d, J=9.6 Hz, 1H), 7.25 (d, J=4.8 Hz, 2H), 7.19 (d, J=8.0 Hz, 2H), 6.41 (br d, J=8.1 Hz, 2H), 4.41 (br d, J=5.6 Hz, 2H), 3.92 (s, 2H), 3.71 (s, 2H), 3.48-3.43 (m, 1H), 2.96 (q, J=7.6 Hz, 2H), 2.62-2.57 (m, 2H), 2.35-2.29 (m, 2H), 1.25 (br t, J=7.3 Hz, 3H)

Synthesis of Compound 90

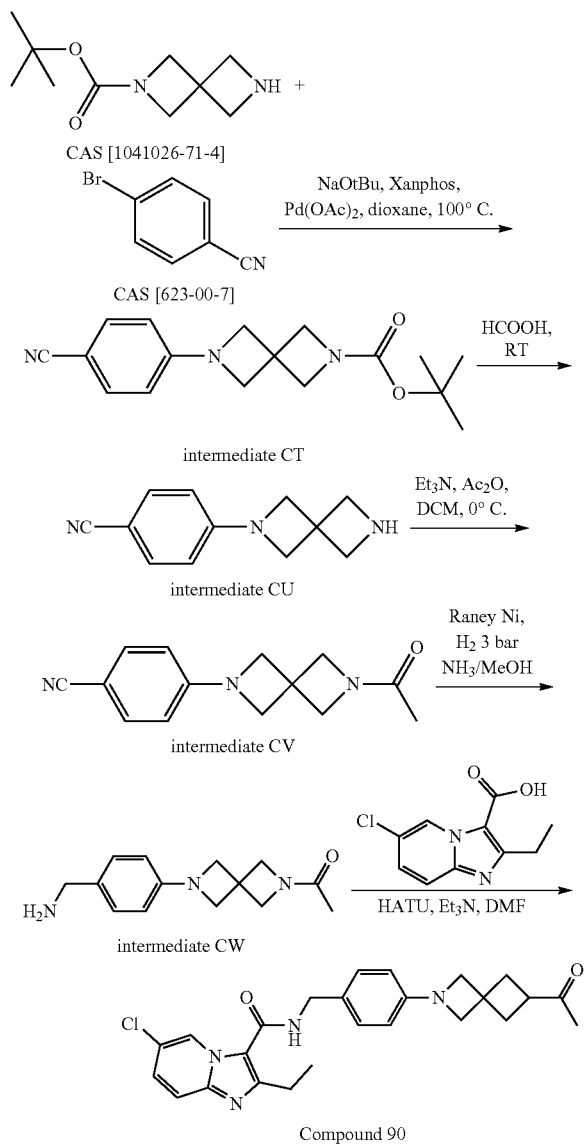

Preparation of Intermediate CT

A solution of 2-Boc-2,6-diazaspiro[3.3]heptane oxalate (CAS [1041026-71-4], 2.0 g, 6.73 mmol), 4-Bromobenzonitrile (CAS [623-00-7], 1.84 g, 10.1 mmol) and sodium terbutoxide (2.59 g, 26.9 mmol) in 1,4-dioxane (70 mL) was degassed. Then, palladium acetate (0.151 g, 0.673 mmol) and Xantphos (0.389 g, 0.673 mmol) were added, the mixture was purged again with $N_2$ and stirred at 100° C. for 3 h. The mixture was cooled down to room temperature and filtered on a pad of Celite®. The cake was washed with EtOAc and the filtrate was evaporated in vacuo. The crude product was purified by preparative LC (irregular silica, 15-40 μm, 120 g, dry loading (Celite®), mobile phase gradient Heptane/EtOAc from 95/5 to 60/40) to give 0.919 g of intermediate CT as a white solid (48%).

Preparation of Intermediate CU

A mixture of intermediate CT (0.5 g, 1.67 mmol) in formic acid (5 mL) was stirred at room temperature for 16 h. The mixture was evaporated in vacuo to give 0.526 g of intermediate 44 as an orange gum which crystallized on standing (quant.).

Preparation of Intermediate CV

To a solution of intermediate CU (0.25 mg, 0.715 mmol) and triethylamine (0.5 mL, 3.60 mmol) in DCM (7.5 mL) at 0° C. was added acetic anhydride (0.075 mL, 0.79 mmol) and the mixture was stirred at 0° C. for 2 h. The mixture was diluted with DCM and washed with water. The organic layer was dried over $MgSO_4$, filtered off and evaporated in vacuo. The crude product was purified by preparative LC (irregular silica, 15-40 μm, 24 g, liquid loading (DCM), mobile phase gradient DCM/MeOH from 99/1 to 94/6) to give 0.167 g of intermediate CV as a white solid (97%).

Preparation of Intermediate CW

In an autoclave, to a solution of intermediate CV (0.167 g, 0.69 mmol) in ammonia 7N in MeOH (4 mL) was added Raney Nickel 0.2 g, 3.4 mmol) and the mixture was stirred at room temperature under 3 bar of H2 for 2 h. The mixture was filtered off and evaporated in vacuo to give 0.153 g of intermediate CW as a white solid (90/%).

Preparation of Compound 90

Triethylamine (0.29 mL, 2.09 mmol) and HATU (0.285 g, 0.75 mmol) were added successively to a solution of 6-chloro-2-ethylimidazo[3,2-a]pyridine-3-carboxylic acid (CAS [1216142-18-5], 0.163 g, 0.68 mmol) in DMF (4 mL). The resulting mixture was stirred at room temperature for 30 min., then a solution of intermediate CW (0.178 g, 0.726 mmol) in DMF (3 mL) was added and the mixture was stirred at room temperature for 3 h.

The reaction mixture was evaporated in vacuo until dryness to give 0.717 g as a pale yellow solid. The crude product was purified by preparative LC (Irregular silica 15-40 μm, 50 g, dry loading (Celite®), mobile phase gradient DCM/MeOH from 99/1% to 95/5) to obtain 0.351 g as a yellow gum. The product was purified by Reverse phase (Stationary phase: YMC-actus Triart-C18 10 μm 30×150 mm, Mobile phase: Gradient from 70% aq. ($NH_4HCO_3$ 0.2%), 30% MeCN to 100% MeCN) to give 0.234 g of a white solid which was triturated in $Et_2O$, filtered and dried under high vacuum to afford 0.222 g of Compound 90 as a white solid (72%/).

$^1$H NMR (400 MHz, DMSO-$d_6$) δ ppm 9.06 (s, 1H), 8.41 (br s, 1H), 7.67 (d, J=9.5 Hz, 1H), 7.46 (d, J=9.0 Hz, 1H), 7.20 (d, J=8.2 Hz, 2H), 6.43 (d, J=8.2 Hz, 2H), 4.41 (br d, J=5.0 Hz, 2H), 4.28 (s, 2H), 4.00 (s, 2H), 3.91 (s, 4H), 2.96 (q, J=7.4 Hz, 2H), 1.75 (s, 3H), 1.25 (t, J=7.6 Hz, 3H)

Synthesis of Compound 91

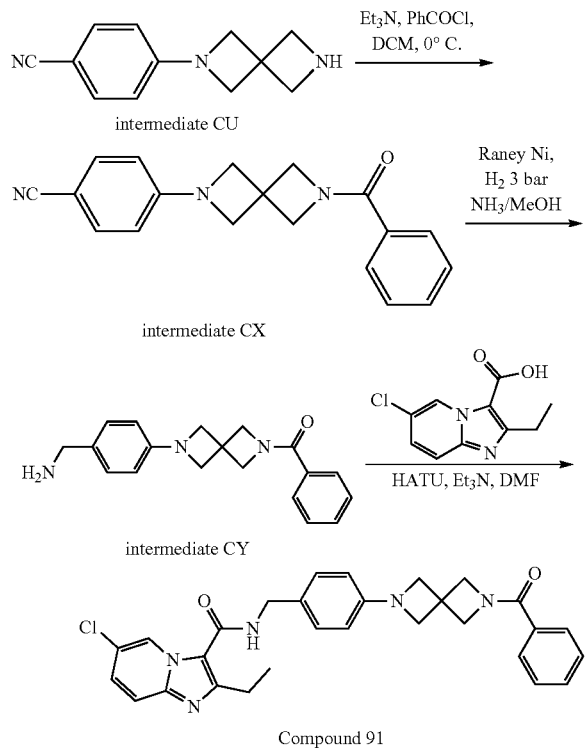

Preparation of Intermediate CX

To a solution of intermediate CU (0.25 g, 0.715 mmol) and triethylamine (0.50 mL, 3.60 mmol) in DCM (7.5 mL) at 0° C. was added benzoyl chloride (0.09 mL, 0.78 mmol) and the mixture was stirred at 0° C. for 2 h. The mixture was diluted with DCM and washed with water. The organic layer was dried over MgSO$_4$, filtered off and evaporated in vacuo.

The crude product was purified by preparative LC (irregular silica, 15-40 μm, 24 g, Grace, liquid loading (DCM), mobile phase gradient: from DCM 99%, MeOH 1% to DCM 96%, MeOH 4%) to give 0.128 g of intermediate CX as a white solid (59%).

Preparation of Intermediate CY

In an autoclave, to a solution of intermediate CX (0.128 g, 0.422 mmol) in ammonia 7N in MeOH (2.4 mL) was added Raney Nickel (0.12 g, 2.1 mmol) and the mixture was stirred at room temperature under 3 bar for 2 h. The mixture was filtered off and evaporated in vacuo to give 0.108 g of intermediate CY as a colourless oil which crystallized on standing (83%).

Preparation of Compound 91

Diisopropylethylamine (0.168 mL, 0.99 mmol) and HATU (0.168 g, 0.44 mmol) were added successively to a solution of 6-chloro-2-ethylimidazo[3,2-a]pyridine-3-carboxylic acid (CAS [1216142-18-5], 0.09 g, 0.38 mmol) in DMF (2.5 mL). The resulting mixture was stirred at room temperature for 30 min., then a solution of intermediate CY (0.13 g, 0.42 mmol) in DMF (1.7 mL) was added and the mixture was stirred at room temperature for 3 h. The reaction mixture was evaporated in vacuo until dryness to give 0.52 g as an orange gum. The crude product was purified by preparative LC (Irregular silica 15-40 μm, 40 g, dry loading (Celite®), mobile phase gradient DCM/MeOH from 99/1 to 94/6) to obtain 0.137 g as a yellow gum. The product was purified by Reverse phase (Stationary phase: YMC-actus Triart-C18 10 μm 30×150 mm, Mobile phase: Gradient from 60% aq. (NH$_4$HCO$_3$ 0.2%), 40% MeCN to 100% MeCN) to give 0.109 g of a colorless oil which was triturated in Et$_2$O, filtered and dried under high vacuum to afford 0.095 g of Compound 91 as a white solid (49%).

$^1$H NMR (500 MHz, DMSO-d$_6$) δ ppm 9.06 (s, 1H), 8.40 (br t, J=5.8 Hz, 1H), 7.68-7.62 (m, 3H), 7.54-7.44 (m, 4H), 7.20 (d, J=8.2 Hz, 2H), 6.43 (d, J=8.5 Hz, 2H), 4.49 (s, 2H), 4.41 (d, J=5.7 Hz, 2H), 4.24 (s, 2H), 3.99-3.90 (br q, 4H), 2.96 (q, J=7.4 Hz, 2H), 1.25 (t, J=7.4 Hz, 3H)

Synthesis of Compound 92

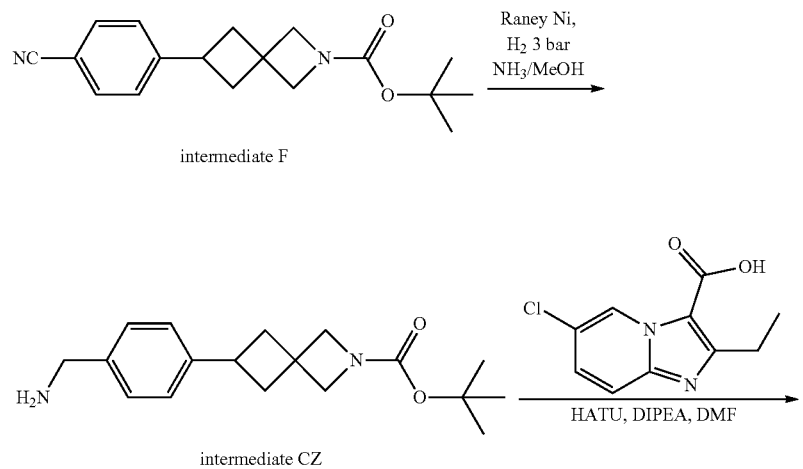

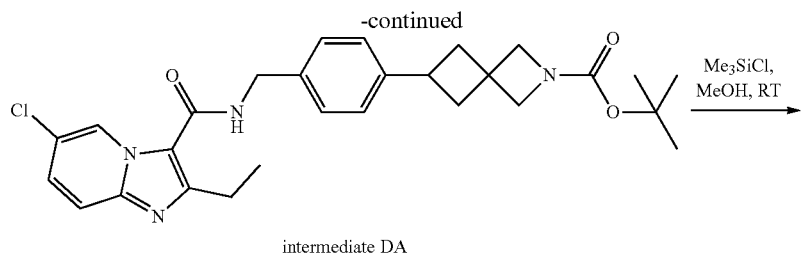

intermediate DA

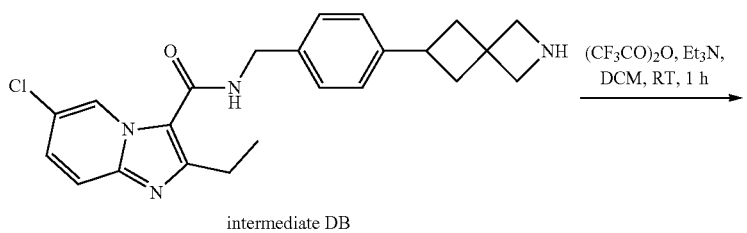

intermediate DB

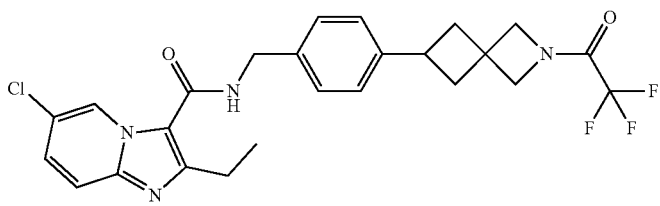

Compound 92

Preparation of Intermediate CZ

In an autoclave, to a solution of intermediate F (1.57 g, 5.26 mmol) in ammonia 7M in MeOH (50 mL) was added Raney Nickel (1.4 g, 23.9 mmol) and the mixture was hydrogenated at room temperature under 3 bar over the weekend (after 3 h, all hydrogen was consumed. The autoclave was refilled to 3 bar of H2). The mixture was filtered off and evaporated in vacuo. The residual grey gum was solubilized in EtOAc, stirred with SiliaMetS® Imidazole (1 eq. w/w) for 1 h then filtered over a pad of Celite®. The filtrate was evaporated in vacuo to afford 1.29 g of intermediate CZ as a white solid.

Preparation of Intermediate DA

To a solution of 6-chloro-2-ethylimidazo[3,2-a]pyridine-3-carboxylic acid (CAS [1216142-18-5], 0.4 g, 1.67 mmol) in diisopropylethylamine (0.74 mL, 4.35 mmol) and DMF (15 mL) was added HATU (0.7 g, 1.84 mmol) and the mixture was stirred at room temperature for 20 min. Intermediate CZ (505 mg, 1.67 mmol) was added then the mixture was stirred at room temperature for 1 h. The mixture was evaporated in vacuo to give a brown gum. The residue was purified by preparative LC (irregular SiOH, 15-40 μm, 50 g, dry loading (Celite®), Heptane/EtOAc/MeOH (9:1) from 85/15 to 35/65) to give 0.784 g of intermediate DA as a white solid (92%).

Preparation of Intermediate DB

To a solution of intermediate DA (0.784 g, 1.54 mmol) in MeOH (16 mL) was added Chlorotrimethylsilane (1 mL, 7.92 mmol) and the mixture was stirred at room temperature for 16 h. The mixture was evaporated in vacuo to afford 0.79 g of intermediate DA as pale yellow foam (crude used as such in next step).

Preparation of Compound 92

Trifluoroacetic anhydride (0.235 mL, 1.69 mmol) was added at 0° C. to a solution of intermediate DB (0.79 g, 80%, 1.54 mmol) and triethylamine (1.1 mL, 7.91 mmol) in DCM (9 mL). The reaction mixture was stirred at 0° C. for 1 h then, at room temperature for 1 h. The reaction mixture was quenched with NaHCO₃ sat. and extracted with DCM (twice). The organic layer was dried over MgSO₄, filtered off then evaporated in vacuo 0.75 g of an off-white foam. The residue was purified by preparative LC (irregular SiOH, 15-40 μm, 50 g, dry loading (Celite®), Heptane/EtOAc/MeOH (9:1) from 90/10 to 60/40) to give 0.643 g of a white foam.

The residue was purified by reverse phase (spherical C18, 25 μm, 120 g YMC-ODS-25, dry loading (Celite®), mobile phase gradient: from 35% aq.(NH4HCO3 0.2%), 65% MeCN to 100% MeCN) and clean fractions were directly freeze-dried. The fluffy solid was solubilized in MeCN then evaporated under vacuum to give a colorless oil. This oil was triturated in Et₂O and evaporated under vacuum to afford 0.593 g of Compound 92 as a white solid (76% over 2 steps).

$^1$H NMR (400 MHz, DMSO-d₆) δ ppm 9.07 (d, J=2.0 Hz, 1H), 8.46 (br t, J=5.8 Hz, 1H), 7.66 (d, J=9.6 Hz, 1H), 7.45 (dd, J=9.1, 2.0 Hz, 1H), 7.30 (d, J=8.1 Hz, 2H), 7.20 (d, J=8.1 Hz, 2H), 4.56 (s, 1H), 4.49 (d, J=5.6 Hz, 2H), 4.33 (s, 1H), 4.23 (s, 1H), 4.01 (s, 1H), 3.41-3.33 (m, 1H), 2.99 (q, J=7.6 Hz, 2H), 2.68-2.55 (m, 2H), 2.33-2.25 (m, 2H), 1.26 (t, J=7.6 Hz, 4H)

Synthesis of Compound 93

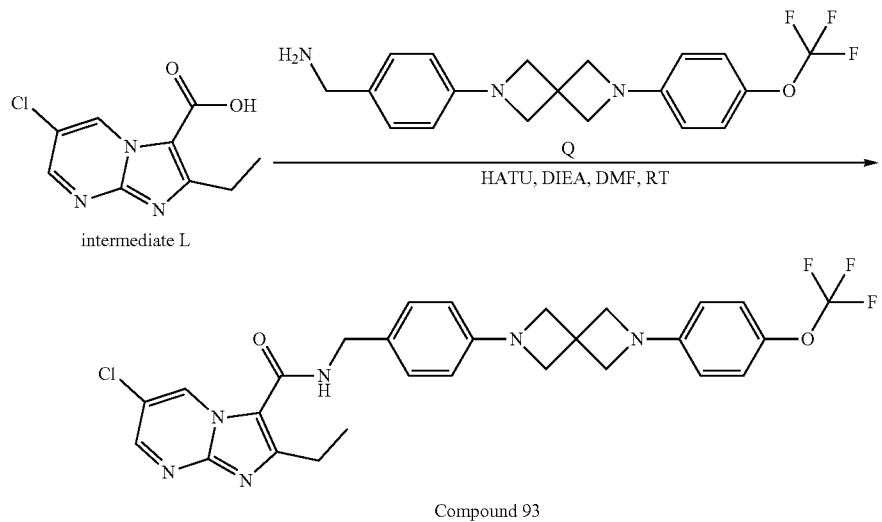

A solution of intermediate L (0.085 g, 0.299 mmol) and HATU (0.17 g, 0.447 mmol) in diisopropylethylamine (0.13 mL, 0.764 mmol) and DMF (2 mL) was stirred at room temperature for 30 min. Then, intermediate Q (0.085 g, 0.304 mmol) in DMF (1.4 mL) was added and the mixture was stirred at room temperature for 3 h. The mixture was evaporated in vacuo to give 0.543 g of a brown gum. The residue was purified by preparative LC (irregular SiOH, 15-40 μm, 30 g, dry loading (Celite®), Heptane/EtOAc/ MeOH (9:1) from 90/10 to 45/55) to give 0.088 g of a yellow gum (which crystallized on standing). The residue was triturated in Et$_2$O/EtOH (9:1), filtered off and dried under vacuum (50° C., 16 h) to give 0.064 g of Compound 93 as a pale yellow solid (36%).

$^1$H NMR (400 MHz, DMSO-d$_6$) δ ppm 9.38 (s, 1H), 8.67 (s, 1H), 8.51 (t, J=5.6 Hz, 1H), 7.21-7.15 (m, 4H), 6.68 (br t, J=7.1 Hz, 1H), 6.44 (br d, J=8.1 Hz, 4H), 4.41 (br d, J=5.6 Hz, 2H), 3.95 (br s, 8H), 3.00 (q, J=7.6 Hz, 2H), 1.26 (t, J=7.6 Hz, 3H).

Synthesis of Compound 94

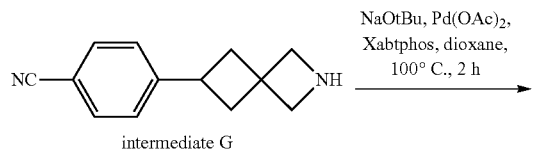

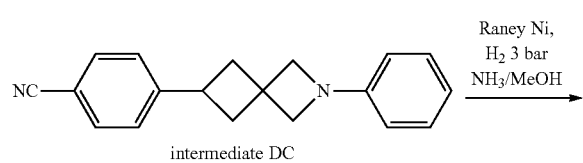

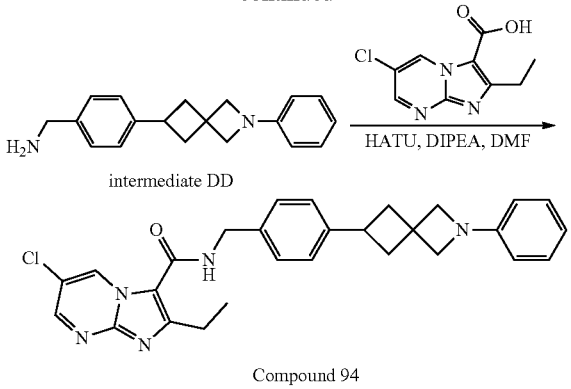

Preparation of Intermediate DC

Accordingly, intermediate DC was prepared in the same way as intermediate BV starting from intermediate G (0.315 g, 1.34 mmol) and bromobenzene affording 0.245 g, 66%.

Preparation of Intermediate DD

Accordingly, intermediate DD was prepared in the same way as intermediate CZ starting from intermediate DC (0.14 g, 0.51 mmol) to give 0.135 g, 83%.

Preparation of Compound 94

A solution of intermediate L (0.135 g, 0.475 mmol) and HATU (0.27 g, 0.71 mmol) in diisopropylethylamine (200 μL, 1.18 mmol) and DMF (2.5 mL) was stirred at room temperature for 30 min. Then, intermediate 52 (0.135 g, 0.485 mmol) in DMF (2.5 mL) was added and the mixture was stirred at room temperature for 3 h. The mixture was evaporated in vacuo to give 0.848 g of a brown oil. The residue was purified by preparative LC (irregular SiOH, 15-40 μm, 40 g, dry loading (Celite®), Heptane/EtOAc/

MeOH (9:1) from 80/20 to 35/65) to give 0.159 g of a pale yellow solid. The solid was triturated in Et₂O/EtOH (9:1), filtered off and dried under vacuum (50° C., 16 h) to give 0.118 g of a white solid. This solid was purified by Reverse phase (Stationary phase: YMC-actus Triart-Cl8 10 μm 30×150 mm, Mobile phase: Gradient from 40% aq. (NH₄HCO₃ 0.2%), 60% ACN to 100% ACN) then dried under vacuum (60° C., 16 h) to give 0.076 g of Compound 94 as a white solid (29%).

1H NMR (400 MHz, DMSO-d₆) δ ppm 9.40 (d, J=3.0 Hz, 1H), 8.68 (d, J=2.5 Hz, 1H), 8.57 (t, J=5.8 Hz, 1H), 7.32 (d, J=8.1 Hz, 2H), 7.22 (d, J=8.1 Hz, 2H), 7.15 (t, J=7.8 Hz, 2H), 6.65 (t, J=7.3 Hz, 1H), 6.41 (d, J=7.6 Hz, 2H), 4.51 (d, J=5.6 Hz, 2H), 3.93 (s, 2H), 3.71 (s, 2H), 3.42 (quin, J=8.7 Hz, 1H), 3.03 (q, J=7.6 Hz, 2H), 2.61-2.54 (m, 2H), 2.34-2.23 (m, 2H), 1.28 (t, J=7.6 Hz, 3H).

Synthesis of Compound 95 and Compound 96

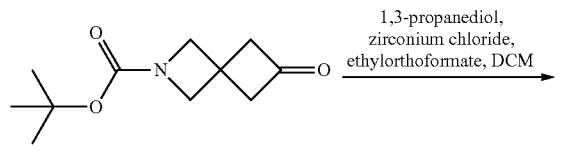

CAS [1147557-97-8]

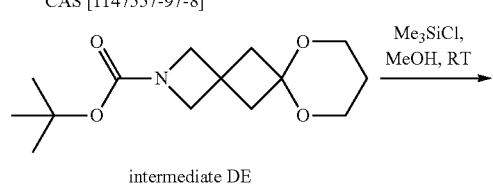

intermediate DE

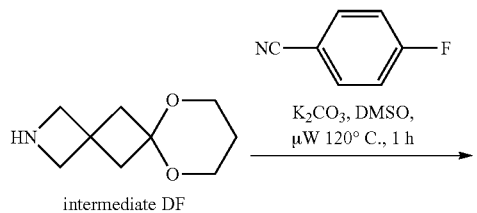

intermediate DF

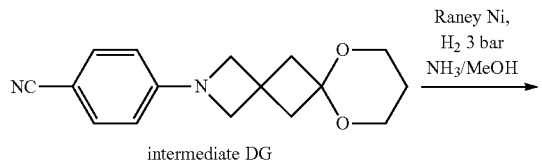

intermediate DG

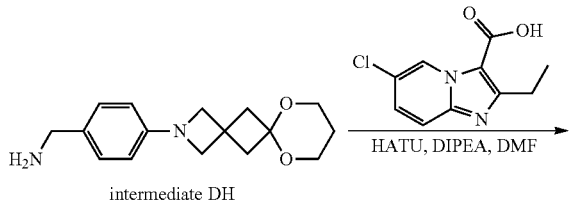

intermediate DH

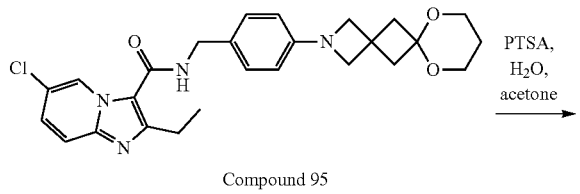

Compound 95

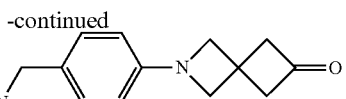

Compound 96

Preparation of Intermediate DE

A solution of 2-Boc-2-azaspiro[3.3]heptan-6-one (CAS [1181816-12-5], 0.5 g, 2.37 mmol), 1,3-propanediol (0.26 mL, 3.55 mmol), ethylorthoformate (0.39 mL, 2.37 mmol) and zirconium chloride (0.028 g, 0.118 mmol) in anhydrous DCM (10 mL) was stirred under N₂ for 2 h at room temperature. After 2 h, 0.25 eq of ethylorthoformate (0.099 mL, 0.59 mmol) and 0.5 eq. of 1,3-propanediol (0.09 mL, 1.18 mmol) were added. After 5 h: the reaction mixture was quenched with water (30 mL) and extracted with DCM (30 mL). The organic phase was washed with water, dried over MgSO₄, filtered and evaporated to dryness to give 0.633 g of intermediate DE as a colorless oil.

Preparation of Intermediate DF

Accordingly, intermediate DF was prepared in the same way as intermediate DB, starting from intermediate DE (0.63 g, 2.35 mmol) affording 0.431 g, 2.1 mmol as an hydrochloride salt.

Preparation of Intermediate DG

A mixture of intermediate DF (0.426 g, 2.07 mmol), 4-Fluorobenzonitrile (0.376 g, 3.11 mmol) and potassium carbonate (0.859 g, 6.21 mmol) in anhydrous DMSO (12 mL) was heated at 120° C. using a single mode microwave (Biotage initiator60) with a power output ranging from 0 to 400 W for 1 h [fixed hold time]. The reaction mixture was quenched with water (30 mL), extracted with EtOAc (2×30 mL). The combined organic phases were washed with water (2×30 mL) and brine (2×20 mL), dried over MgSO₄, filtered and evaporated to dryness to give a green solid. The residue was purified by preparative LC (irregular SiOH, 15-40 μm, 80 g, Grace, dry loading (Silica), Heptane/EtOAc from 90/10 to 50/50) to give 0.369 g of intermediate DG as white solid (66%).

Preparation of Intermediate DH

Accordingly, intermediate DH was prepared in the same way as intermediate CZ starting from intermediate DG (0.334 g, 1.24 mmol) to give 0.297 g, 88%.

Preparation of Compound 95

A solution of 6-chloro-2-ethylimidazo[3,2-a]pyridine-3-carboxylic acid (CAS [1216142-18-5], 0.225 g, 0.939 mmol) and HATU (0.39 g, 1.03 mmol) in triethylamine (0.39 mL, 2.81 mmol) and DMF (6 mL) was stirred at room temperature for 30 min. Then, intermediate DH (0.27 g, 0.984 mmol) in DMF (5 mL) was added and the mixture was stirred at room temperature for 3 hours. The mixture was evaporated in vacuo to give 1.22 g of an orange gum. The residue was purified by preparative LC (irregular SiOH, 15-40 µm, 50 g, merck, dry loading (Celite®), Heptane/EtOAc/MeOH (9:1) from 90/10 to 45/55) to give 0.483 g as a white foam (96%).

51 mg of the residue was solubilized in MeCN, washed with pentane (twice) and evaporated in vacuo. The residual colorless oil was triturated in Et$_2$O, filtered off and dried under high vacuum (50° C., 16 h) to afford 43 mg of Compound 95 as a white solid.

$^1$H NMR (400 MHz, DMSO-d$_6$) δ ppm 9.05 (s, 1H), 8.37 (t, J=5.8 Hz, 1H), 7.65 (d, J=9.6 Hz, 1H), 7.44 (dd, J=9.6, 2.0 Hz, 1H), 7.17 (d, J=8.1 Hz, 2H), 6.39 (d, J=8.6 Hz, 2H), 4.40 (d, J=6.1 Hz, 2H), 3.77-3.72 (m, 8H), 2.95 (q, J=7.6 Hz, 2H), 2.39 (s, 4H), 1.60-1.55 (m, 2H), 1.24 (t, J=7.6 Hz, 3H)

Preparation of Compound 96

A solution of Compound 95 (0.35 g, 0.673 mmol) and para-toluenesulfonic acid (0.013 g, 0.0673 mmol) in acetone (7.5 mL) and water (1.8 mL) was heated at 100° C. using a single mode microwave (Biotage initiator60) with a power output ranging from 0 to 400 W for 2 h [fixed hold time]. The mixture was heated again at 100° C. using a single mode microwave (Biotage initiator60) with a power output ranging from 0 to 400 W for 2 h [fixed hold time]. The mixture was diluted with EtOAc, washed with aq. NaHCO$_3$ sat., brine, dried over MgSO$_4$, filtered off and evaporated in vacuo to afford 0.301 g of a yellow solid. The residue was purified by preparative LC (irregular SiOH, 15-40 µm, 24 g, Grace, dry loading (Celite®), Heptane/EtOAc/MeOH (9:1) from 80/20 to 40/60) to give 0.275 g of an off-white solid. The solid was triturated in Et$_2$O (3 times) then in Et$_2$O/EtOH (9:1, twice) and filtered off to afford 0.256 g a white solid.

The solid was purified by preparative LC (irregular SiOH, 15-40 µm, 24 g, Grace, dry loading (Celite®), Heptane/EtOAc/MeOH (9:1) from 90/10 to 50/50) and clean fractions were directly combined to give 0.151 g of a white solid. The solid was purified by reverse phase (spherical C18, 25 µm, 40 g YMC-ODS-25, dry loading (Celite), mobile phase gradient: from 75% aq.(NH$_4$HCO$_3$ 0.2%), 25% MeCN to 35% aq.(NH$_4$HCO$_3$ 0.2%), 65% MeCN) and clean fractions were freeze-dried to afford 0.045 g of Compound 96 a white solid.

1H NMR (400 MHz, DMSO-d$_6$) δ ppm 9.06 (d, J=2.0 Hz, 1H), 8.39 (br s, 1H), 7.66 (d, J=9.6 Hz, 1H), 7.44 (dd, J=9.6, 2.0 Hz, 1H), 7.20 (d, J=8.08 Hz, 2H), 6.45 (d, J=8.59 Hz, 2H), 4.41 (br d, J=4.6 Hz, 2H), 3.96 (s, 4H), 3.35-3.29 (m, 4H), 2.96 (q, J=7.6 Hz, 2H), 1.25 (t, J=7.6 Hz, 3H)

The Following Compounds were also prepared in accordance with the procedures herein:

| Compound No | Structure |
|---|---|
| 97 | 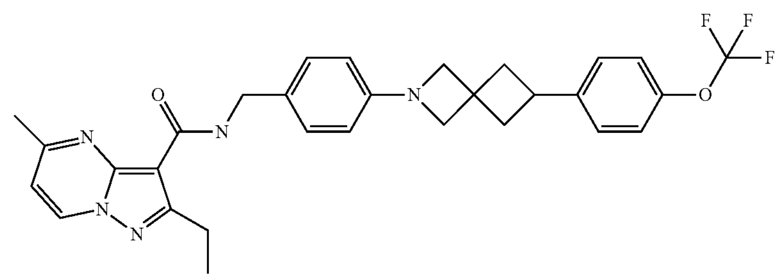 [SMILES: CCc1nn2ccc(C)nc2c1C(=O)NCc1ccc(N2CC3(CC(c4ccc(OC(F)(F)F)cc4)C3)C2)cc1] |
| 98 | 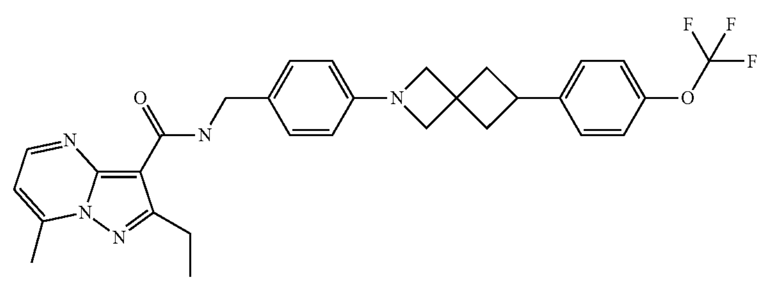 [SMILES: CCc1nn2c(C)ccnc2c1C(=O)NCc1ccc(N2CC3(CC(c4ccc(OC(F)(F)F)cc4)C3)C2)cc1] |
| 99 | 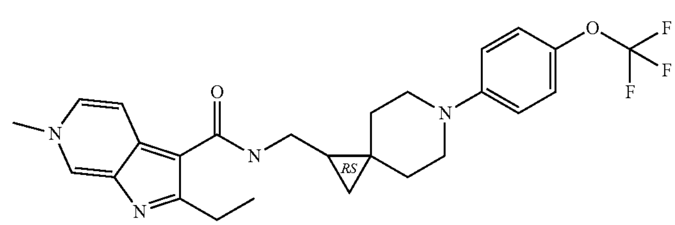 [SMILES: CCc1nc2cn(C)ccc-2c1C(=O)NCC1CC12CCN(c1ccc(OC(F)(F)F)cc1)CC2] |

-continued

| Compound No | Structure |
|---|---|
| 100 | 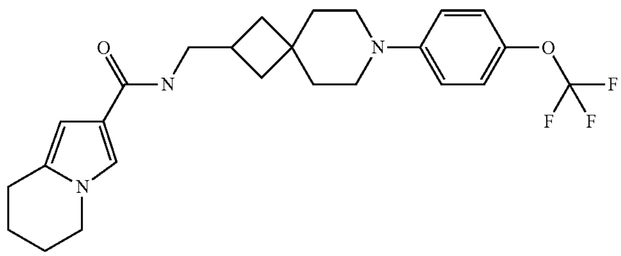 [SMILES: O=C(NCC1CC2(CCN(c3ccc(OC(F)(F)F)cc3)CC2)C1)c1cc2n(c1)CCCC2] |
| 101 | 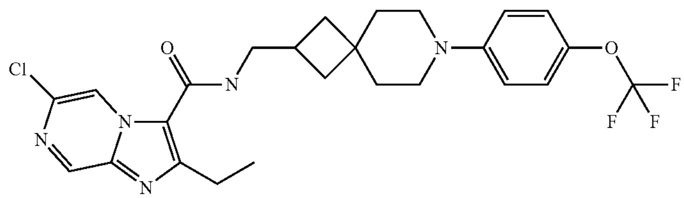 [SMILES: CCc1nc2cnc(Cl)cn2c1C(=O)NCC1CC2(CCN(c3ccc(OC(F)(F)F)cc3)CC2)C1] |
| 102 | 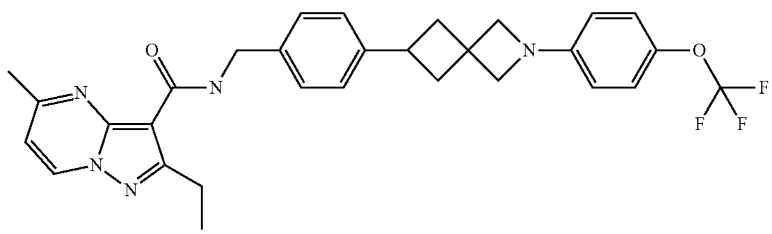 [SMILES: CCc1nn2ccc(C)nc2c1C(=O)NCc1ccc(C2CC3(C2)CN(c2ccc(OC(F)(F)F)cc2)C3)cc1] |
| 103 | 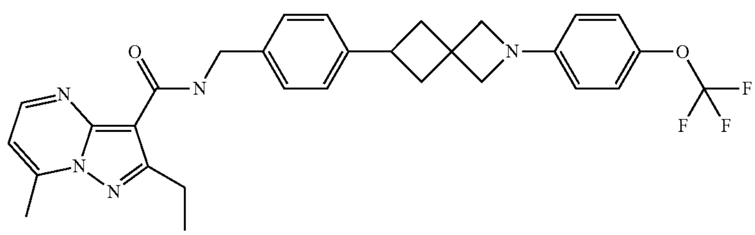 [SMILES: CCc1nn2c(C)ccnc2c1C(=O)NCc1ccc(C2CC3(C2)CN(c2ccc(OC(F)(F)F)cc2)C3)cc1] |
| 104 | 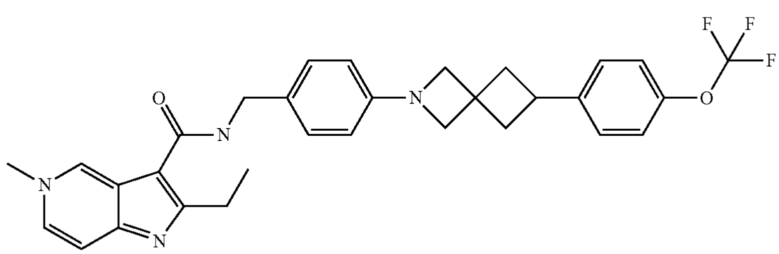 [SMILES: CCc1nc2ccn(C)cc-2c1C(=O)NCc1ccc(N2CC3(CC(c4ccc(OC(F)(F)F)cc4)C3)C2)cc1] |
| 105 | 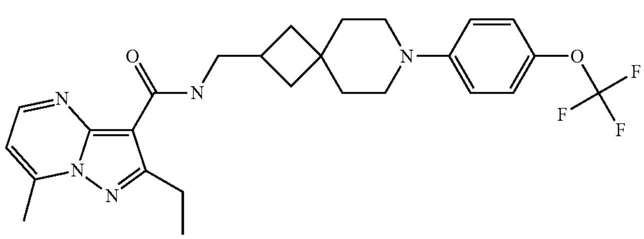 [SMILES: CCc1nn2c(C)ccnc2c1C(=O)NCC1CC2(CCN(c3ccc(OC(F)(F)F)cc3)CC2)C1] |

US 11,180,472 B2
135                                                                    136
-continued
| Compound No | Structure |
|---|---|
| 106 | 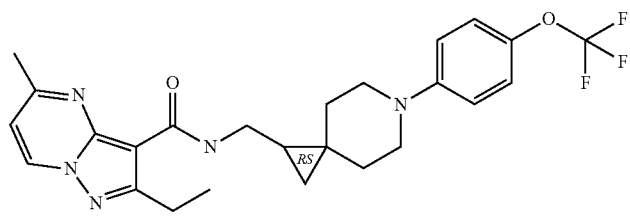 [SMILES: CCc1nn2ccc(C)nc2c1C(=O)NCC1CC12CCN(c1ccc(OC(F)(F)F)cc1)CC2] |
| 107 | 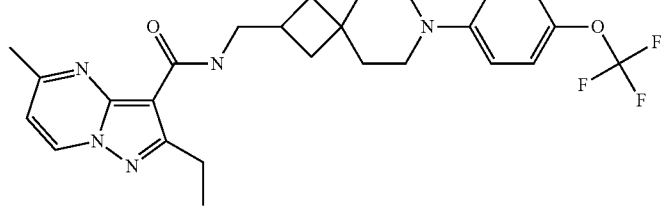 |
| 108 | 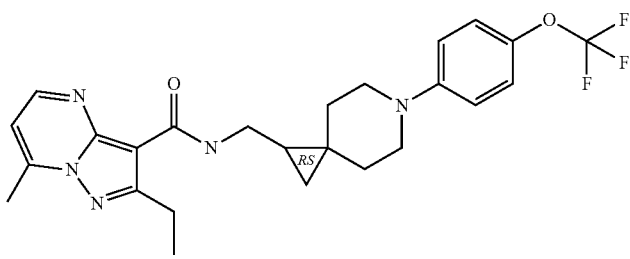 [SMILES: CCc1nn2c(C)ccnc2c1C(=O)NCC1CC12CCN(c1ccc(OC(F)(F)F)cc1)CC2] |
| 109 | 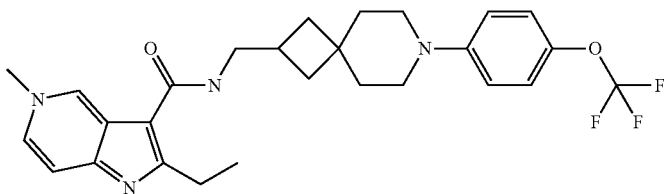 [SMILES: CCc1nc2ccn(C)cc-2c1C(=O)NCC1CC2(CCN(c3ccc(OC(F)(F)F)cc3)CC2)C1] |
| 110 | 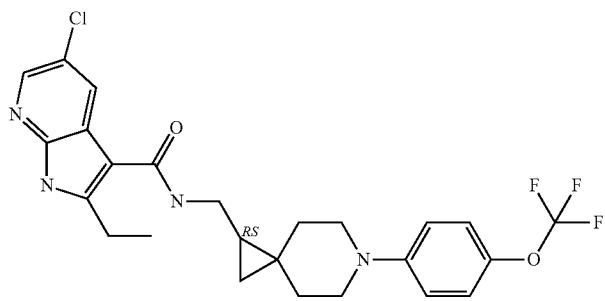 [SMILES: CCc1[nH]c2ncc(Cl)cc2c1C(=O)NCC1CC12CCN(c1ccc(OC(F)(F)F)cc1)CC2] |
| 111 | 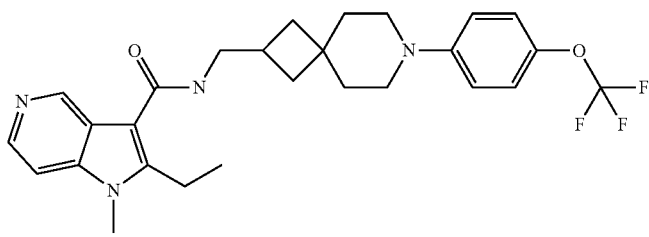 [SMILES: CCc1c(C(=O)NCC2CC3(CCN(c4ccc(OC(F)(F)F)cc4)CC3)C2)c2cnccc2n1C] |

-continued

| Compound No | Structure |
|---|---|
| 112 | 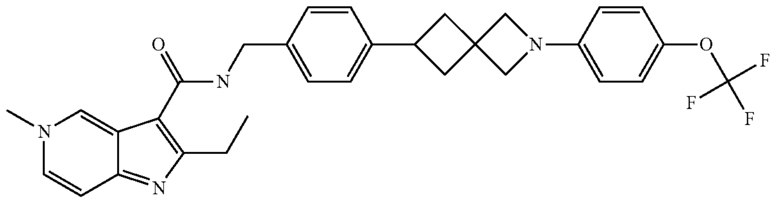 [SMILES: CCc1nc2ccn(C)cc-2c1C(=O)NCc1ccc(C2CC3(C2)CN(c2ccc(OC(F)(F)F)cc2)C3)cc1] |
| 113 | 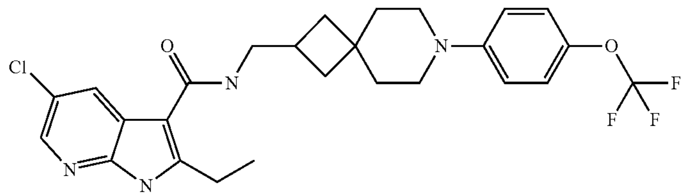 [SMILES: CCc1[nH]c2ncc(Cl)cc2c1C(=O)NCC1CC2(CCN(c3ccc(OC(F)(F)F)cc3)CC2)C1] |
| 114 | 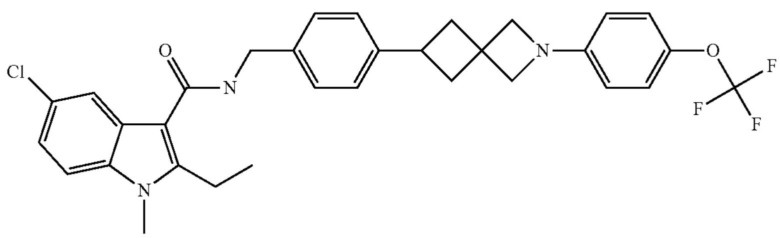 [SMILES: CCc1c(C(=O)NCc2ccc(C3CC4(C3)CN(c3ccc(OC(F)(F)F)cc3)C4)cc2)c2cc(Cl)ccc2n1C] |
| 115 | 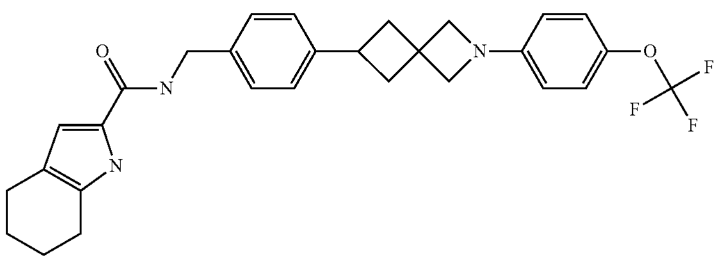 [SMILES: O=C(NCc1ccc(C2CC3(C2)CN(c2ccc(OC(F)(F)F)cc2)C3)cc1)c1cc2c([nH]1)CCCC2] |
| 116 | 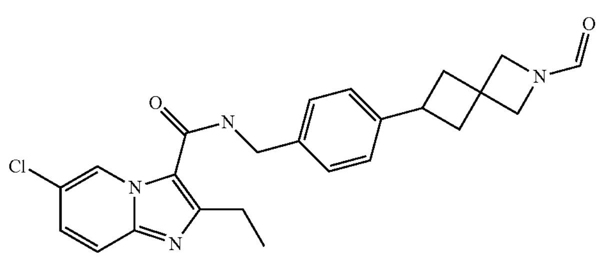 [SMILES: CCc1nc2ccc(Cl)cn2c1C(=O)NCc1ccc(C2CC3(C2)CN(C=O)C3)cc1] |
| 117 | 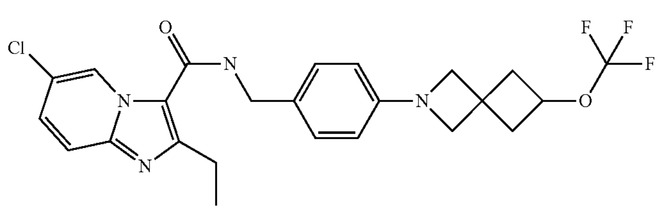 [SMILES: CCc1nc2ccc(Cl)cn2c1C(=O)NCc1ccc(N2CC3(CC(OC(F)(F)F)C3)C2)cc1] |
| 118 | 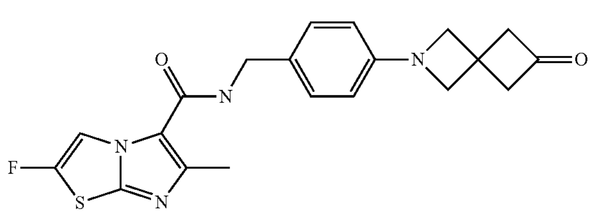 [SMILES: Cc1nc2sc(F)cn2c1C(=O)NCc1ccc(N2CC3(CC(=O)C3)C2)cc1] |

-continued
| Compound No | Structure |
|---|---|
| 119 | 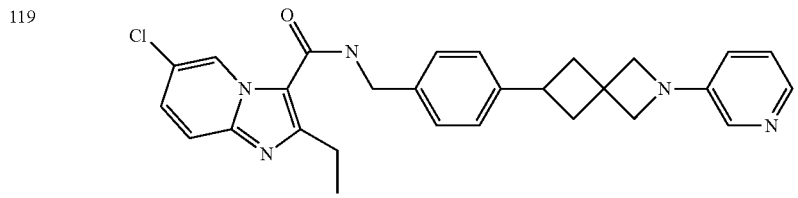 |
| 120 | 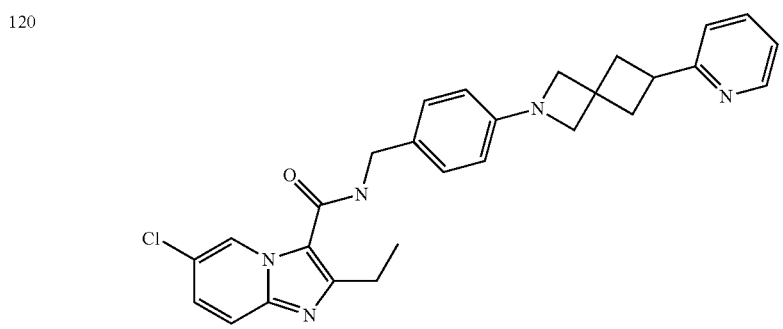 |
| 121 | 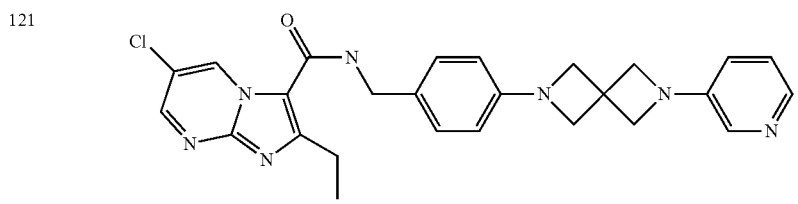 |
| 122 | 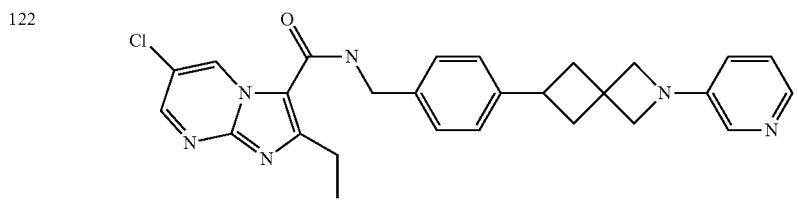 |
| 123 | 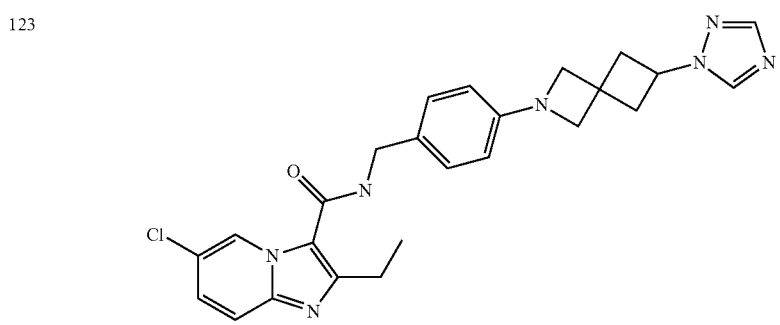 |

-continued
| Compound No | Structure |
|---|---|
| 124 | 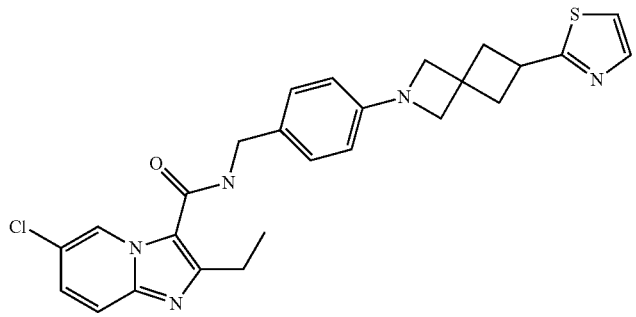 [SMILES: CCc1nc2ccc(Cl)cn2c1C(=O)NCc1ccc(N2CC3(CC(c4nccs4)C3)C2)cc1] |
| 125 | 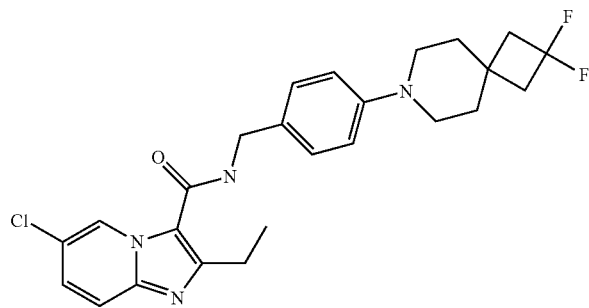 [SMILES: CCc1nc2ccc(Cl)cn2c1C(=O)NCc1ccc(N2CCC3(CC2)CC(F)(F)C3)cc1] |
| 126 | 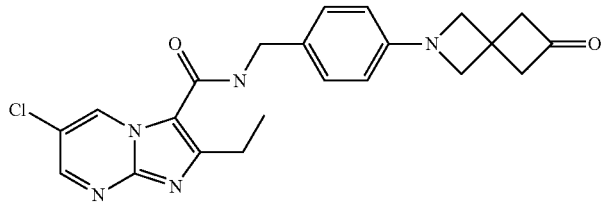 [SMILES: CCc1nc2ncc(Cl)cn2c1C(=O)NCc1ccc(N2CC3(CC(=O)C3)C2)cc1] |
| 127 | 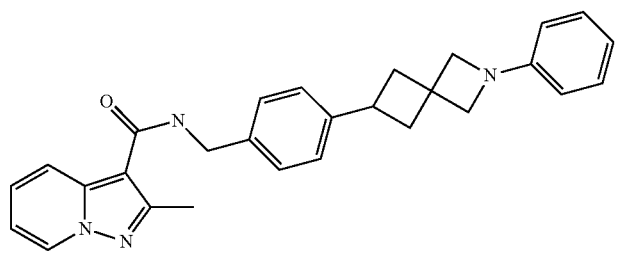 [SMILES: Cc1nn2ccccc2c1C(=O)NCc1ccc(C2CC3(C2)CN(c2ccccc2)C3)cc1] |
| 128 | 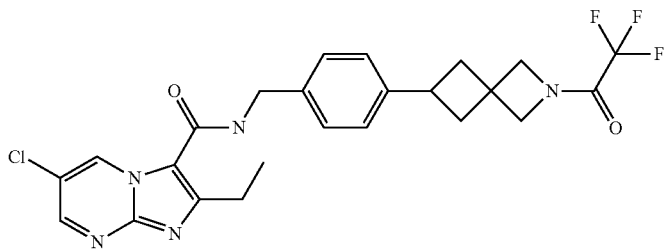 [SMILES: CCc1nc2ncc(Cl)cn2c1C(=O)NCc1ccc(C2CC3(C2)CN(C(=O)C(F)(F)F)C3)cc1] |

| Compound No | Structure |
|---|---|
| 129 | 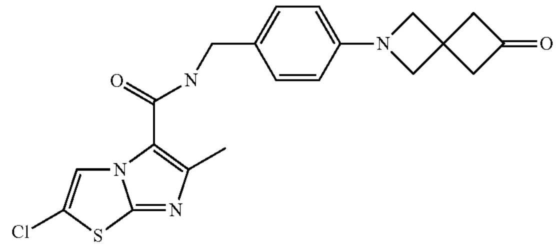 [SMILES: Cc1nc2sc(Cl)cn2c1C(=O)NCc1ccc(N2CC3(CC(=O)C3)C2)cc1] |

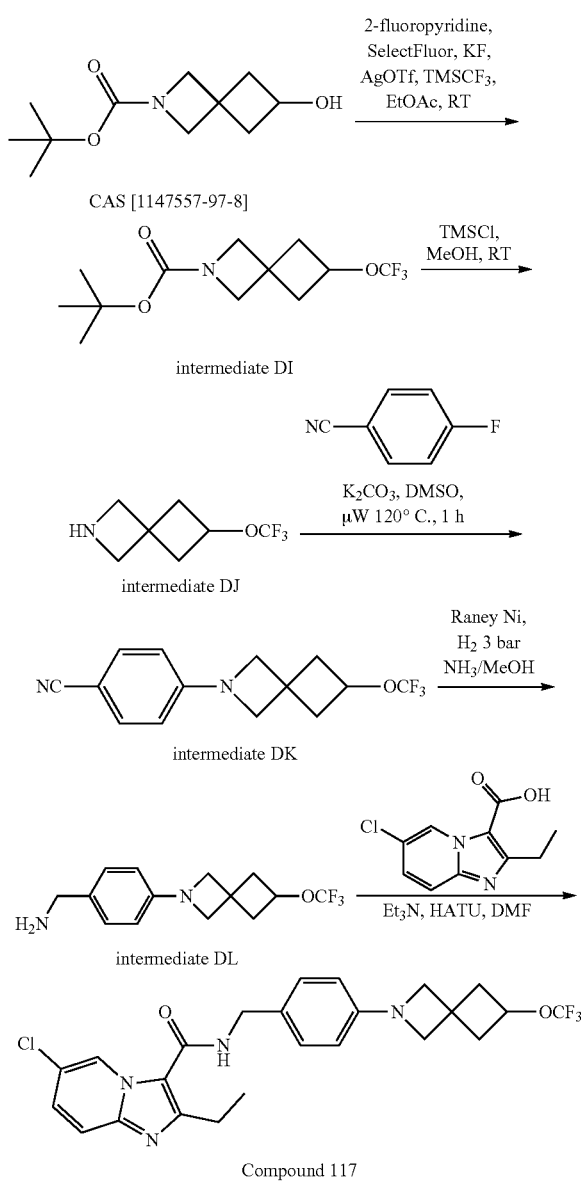

Synthesis of Compound 117, Compound 130 & Compound 131

Preparation of Intermediate DI

A suspension of silver triflate (3.6 g, 14.1 mmol), Selectfluor® (2.49 g, 7.03 mmol), potassium fluoride (1.09 g, 18.8 mmol) and 6-oxo-2-azaspiro[3.3]heptane-2-carboxylate (CAS [1147557-97-8], 1.00 g, 4.69 mmol) was purged with $N_2$. Then, EtOAc (24 mL), 2-fluoropyridine (1.21 mL, 14.1 mmol) and trifluoromethyltrimethylsilane 2M in THF (7.03 mL, 14.1 mmol) were added, the mixture was purged again and the resulting mixture was stirred at room temperature for 3 days. The reaction mixture was then filtered on Celite® and evaporated to dryness. The crude product was purified by preparative LC (irregular silica, 15-40 μm, 50 g, Merck, dry loading (Celite®), mobile phase gradient: Heptane/EtOAc from 90/10 to 50/50) to give 0.64 g of intermediate DI as a white crystals (49%).

Preparation of Intermediate DJ

Chlorotrimethylsilane (0.9 mL, 7.12 mmol) was added to a solution of intermediate DI (0.4 g, 1.42 mmol) in anhydrous methanol (9 mL) and the mixture was stirred at room temperature overnight. The mixture was evaporated in vacuo to give 0.308 g of intermediate DJ as a pale pink gum which crystallized on standing (quant.).

Preparation of Intermediate DK

A suspension of intermediate DJ (0.308 g, 1.42 mmol), 4-Fluorobenzonitrile (CAS [1194-02-1], 0.346 g, 2.83 mmol) and potassium carbonate (0.782 g, 5.66 mmol) in DMSO (7 mL) was heated at 120° C. using a single mode microwave (Biotage Initiator60) with a power output ranging from 0 to 400 W for 30 min [fixed hold time]. The mixture was diluted in EtOAc, washed with water (3×), brine (3×), dried over $MgSO_4$, filtered off and evaporated. The crude product was purified by preparative LC (irregular silica, 15-40 μm, 24 g, Grace, dry loading (Celite®), mobile phase gradient: Heptane/EtOAc from 95/5 to 60/40) to give 0.101 g of intermediate DK as a white solid (25%).

Preparation of Intermediate DL

In an autoclave, to a solution of intermediate DK (0.101 g, 0.36 mmol) in ammonia 7N in MeOH (1.8 mL) was added Raney Nickel (~0.1 g, 1.7 mmol) and the mixture was stirred at room temperature under 3 bar of H2 for 2 hours. The mixture was filtered off and evaporated in vacuo. The filtrate was taken-up in EtOAc and filtered on a pad of Celite®. The filtrate was evaporated in vacuo to give 0.09 g of intermediate DL as a colorless oil (87%).

Preparation of Compound 117

Diisopropylethylamine (0.132 mL, 0.78 mmol) and HATU (125 mg, 0.33 mmol) were added successively to a solution of 6-chloro-2-ethylimidazo[1,2-a]pyridine-3-carboxylic acid (CAS [1216142-18-5], 0.072 g, 0.30 mmol) in DMF (2 mL). The resulting mixture was stirred at room temperature for 30 min., then a solution of intermediate DL (0.09 g, 0.31 mmol) in DMF (1 mL) was added and the mixture was stirred at room temperature for 1 h. The reaction mixture was evaporated in vacuo until dryness to give 0.26 g as brown oil. The crude product was purified by preparative LC (Irregular silica 15-40 μm, 12 g Grace, dry loading (Celite®), mobile phase gradient Heptane/EtOAc/MeOH (9:1) from 90/10 to 50/50) to obtain 0.126 g as a yellow solid. The product was purified by Reverse phase (spherical C18, 25 μm, 120 g YMC-ODS-25, dry loading (Celite®), mobile phase gradient: from 30% aq. (NH$_4$HCO$_3$ 0.2%), 70% MeCN to 100% MeCN) to give 0.107 g of a white solid which was triturated in Et$_2$O, filtered and dried under high vacuum to afford 0.085 g of Compound 117 as a white solid (57%).

1H NMR (400 MHz, DMSO-d$_6$) δ ppm 9.05 (s, 1H), 8.37 (t, J=5.6 Hz, 1H), 7.65 (d, J=9.6 Hz, 1H), 7.44 (dd, J=9.6, 1.5 Hz, 1H), 7.18 (d, J=8.6 Hz, 2H), 6.38 (d, J=8.6 Hz, 2H), 4.79 (m, J=7.1 Hz, 1H), 4.40 (d, J=5.6 Hz, 2H), 3.78 (d, J=11.6 Hz, 4H), 2.95 (q, J=7.6 Hz, 2H), 2.68-2.55 (m, 2H), 2.45-2.38 (m, 2H), 1.24 (t, J=7.6 Hz, 3H)

Preparation of Compound 130

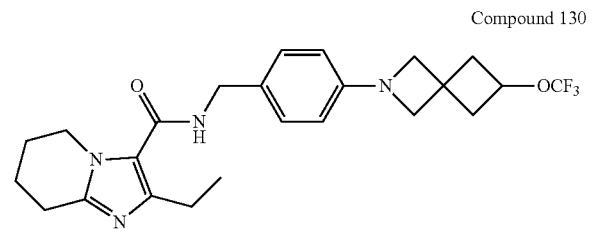 [SMILES: CCc1nc2n(c1C(=O)NCc1ccc(N3CC4(CC(OC(F)(F)F)C4)C3)cc1)CCCC2]

Compound 130

Compound 130 was prepared in the same way as Compound 117, starting from intermediate CI and intermediate DL. The crude product was purified by preparative LC (Regular SiOH 30 μm, 12 g Interchim, dry loading (Celite®), mobile phase gradient Heptane/EtOAc/MeOH from 70:25:5 to 40:50:10) to give 0.099 g of Compound 130 as an off-white solid (31%).

1H NMR (500 MHz, DMSO-d$_6$) δ ppm 8.09 (t, J=6.0 Hz, 1H), 7.11 (d, J=8.5 Hz, 2H), 6.36 (d, J=8.5 Hz, 2H), 4.79 (quint., J=7.3 Hz, 1H), 4.28 (d, J=6.0 Hz, 2H), 3.96 (t, J=5.8 Hz, 2H), 3.78 (s, 2H), 3.75 (s, 2H), 2.70-2.63 (m, 4H), 2.58 (q, J=7.6 Hz, 2H), 2.47-2.39 (m, 2H), 1.86-1.75 (m, 4H), 1.08 (t, J=7.6 Hz, 3H)

Preparation of Compound 131

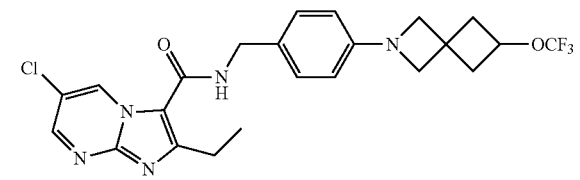 [SMILES: CCc1nc2ncc(Cl)cn2c1C(=O)NCc1ccc(N2CC3(CC(OC(F)(F)F)C3)C2)cc1]

To a solution of intermediate L (250 mg, 1.03 mmol) in triethylamine (0.4 mL, 2.88 mmol) and DCM (8.5 mL) were added EDCI (300 mg, 1.57 mmol) and HOBt (210 mg, 1.55 mmol) and the mixture was stirred at room temperature for 30 min. Intermediate DL (312 mg, 1.09 mmol) in DCM (2 mL) was added and the mixture was stirred at room temperature for 16 h. The mixture was then washed with water (2×) and brine. The organic layer was dried over MgSO$_4$, filtered, and evaporated to dryness. The crude product was purified by preparative LC (irregular SiOH, 15-40 μm, 40 g, Grace, dry loading (Celite®), mobile phase gradient Heptane/EtOAc from 80/20 to 20/80) to give a pale yellow solid, which was triturated in ethanol and filtered off to afford 0.248 g of Compound 131 as a white solid (49%).

1H NMR (500 MHz, DMSO-d$_6$) δ ppm 9.38 (d, J=2.5 Hz, 1H), 8.67 (d, J=2.8 Hz, 1H), 8.49 (t, J=5.8 Hz, 1H), 7.19 (d, J=8.2 Hz, 2H), 6.38 (d, J=8.5 Hz, 2H), 4.79 (quin, J=7.1 Hz, 1H), 4.40 (br d, J=5.7 Hz, 2H), 3.7 (s, 2H), 3.76 (s, 2H), 2.99 (q, J=7.4 Hz, 2H), 2.67-2.63 (m, 2H), 2.43-2.39 (m, 2H), 1.26 (t, J=7.6 Hz, 3H)

Synthesis of Compound 132

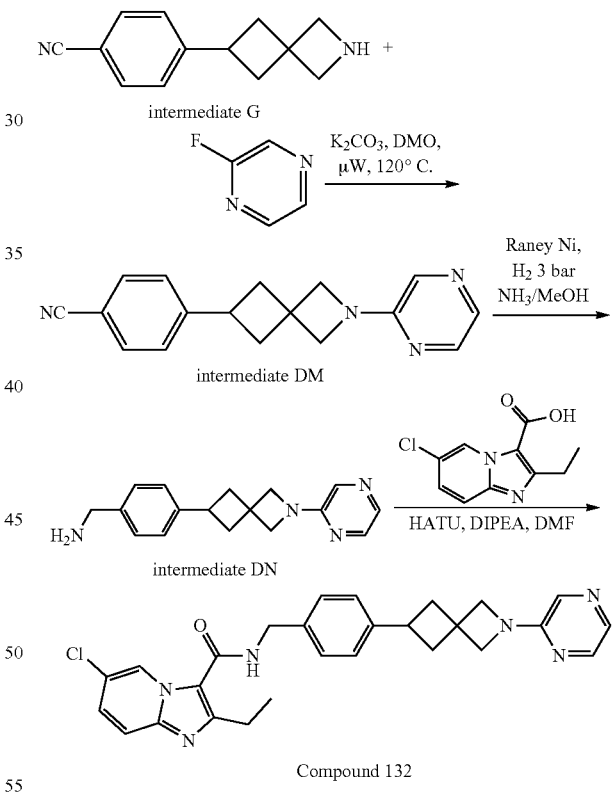

Preparation of Intermediate DM

A suspension of intermediate G (0.238 g, 1.01 mmol), 2-fluoropyrazine (0.123 mL, 1.52 mmol) and potassium carbonate (420 mg, 3.04 mmol) in DMSO (6.2 mL) was heated at 120° C. using a single mode microwave (Biotage initiator60) with a power output ranging from 0 to 400 W for 1 h [fixed hold time]. The reaction mixture was evaporated in Genevac and purified by preparative LC (irregular SiOH, 15-40 μm, 40 g, Merck, dry loading (silica), mobile phase gradient from DCM/MeOH from 100/0 to 90/10) to give 0.194 g of intermediate DM as a yellow solid (69%).

Preparation of Intermediate DN

Accordingly, intermediate DN was prepared in the same was as intermediate DL starting from intermediate DM, yielding 0.169 g, 88%.

Preparation of Compound 132

Diisopropylethylamine (0.24 mL, 1.41 mmol) and HATU (0.227 g, 0.60 mmol) were added successively to a solution of 6-chloro-2-ethylimidazo[1,2-a]pyridine-3-carboxylic acid (CAS [1216142-18-5], 0.125 g, 0.54 mmol) in DMF (3.2 mL). The resulting mixture was stirred at room temperature for 1 h, then a solution of intermediate DN (0.152 g, 0.54 mmol) in DMF (3.2 mL) was added and the mixture was stirred at room temperature for 1 h. The reaction mixture was evaporated to dryness. The residue was dissolved in DCM and washed with NaHCO$_3$ 1% (2×), water (2×) and brine, dried over MgSO$_4$, filtered and evaporated to dryness. The crude product was purified by preparative LC (irregular SiOH, 15-40 μm, 40 g, Grace, dry loading (Silica), mobile phase gradient DCM/MeOH from 100/0 to 90/10) to give a brown solid, which was triturated in Et$_2$O to afford 0.121 g of Compound 132 as an off-white solid (46%).

1H NMR (400 MHz, DMSO-d$_6$) δ ppm 9.07 (s, 1H), 8.48 (t, J=5.8 Hz, 1H), 8.02 (s, 1H), 7.85 (s, 1H), 7.82 (d, J=2.8 Hz, 1H), 7.67 (d, J=9.6 Hz, 1H), 7.46 (dd, J=9.6, 2.0 Hz, 1H), 7.31 (d, J=7.6 Hz, 2H), 7.23 (d, J=8.1 Hz, 2H), 4.50 (d, J=6.1 Hz, 2H), 4.17 (s, 2H), 3.96 (s, 2H), 3.42 (quin, J=8.9 Hz, 1H), 2.99 (q, J=7.6 Hz, 2H), 2.63-2.57 (m, 2H), 2.33-2.27 (m, 2H), 1.27 (t, J=7.6 Hz, 3H)

Synthesis of Compound 125 & Compound 133

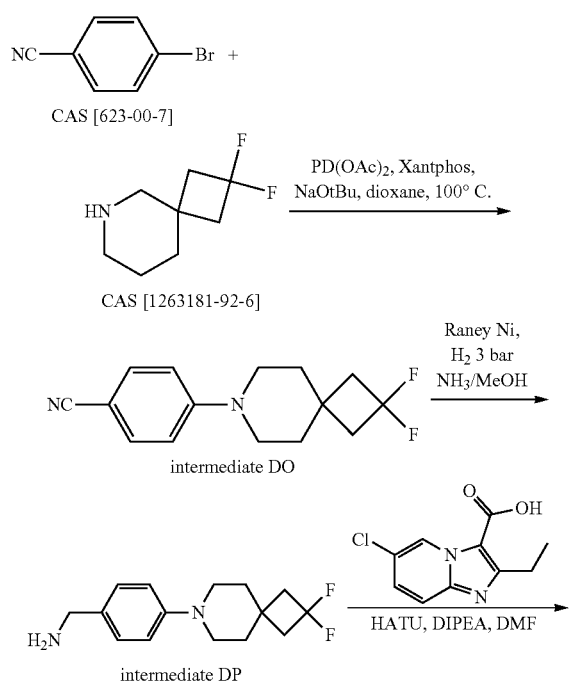

-continued

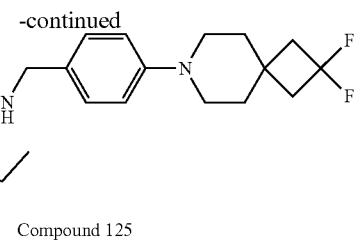

Compound 125

Preparation of Intermediate DO

A solution of 2,2-difluoro-7-azaspiro[3.5]nonane hydrochloride (CAS [1263181-82-5], 0.3 g, 1.52 mmol), 4-Bromobenzonitrile (0.414 g, 2.28 mmol) and sodium terbutoxide (0.583 g, 6.07 mmol) in 1,4-dioxane (16 mL) was degassed under N$_2$. Then, Palladium II acetate (0.034 g, 0.152 mmol) and Xantphos (0.088 g, 0.152 mmol) were added, the mixture was purged again with N$_2$ and heated to 120° C. overnight. The mixture was cooled to room temperature and filtered over a pad of Celite®. The cake was washed with EtOAc and the filtrate was evaporated in vacuo. The crude was purified by preparative LC (irregular SiOH, 15-40 μm, 24 g, Grace, dry loading (SiOH), mobile phase gradient Heptane/EtOAc from 90/10 to 50/50 to obtain 0.343 g of intermediate DO as yellow solid (86%).

Preparation of Intermediate DP

Accordingly, intermediate DP was prepared in the same was as intermediate DL starting from intermediate DO, yielding 0.312 g, 90%.

Preparation of Compound 125

Diisopropylethylamine (0.21 mL, 1.20 mmol) and HATU (238 mg, 0.625 mmol) were added successively to a solution of 6-chloro-2-ethylimidazo[1,2-a]pyridine-3-carboxylic acid (CAS [1216142-18-5], 0.111 g, 0.481 mmol) in DMF (13 mL). The resulting mixture was stirred at room temperature for 30 min, before the addition of intermediate DP (0.128 g, 0.481 mmol) and the mixture was stirred at room temperature for 1 h. The reaction mixture was diluted with EtOAc and washed with an aq. sat. NaHCO$_3$ solution (twice) and brine (twice). The organic phase was dried over MgSO$_4$, filtered and evaporated to dryness to give 0.269 g. The crude was purified by preparative LC (Irregular SiOH 15-40 μm, 40 g Grace Resolv, dry loading (SiOH), mobile phase gradient: Heptane/EtOAc from 90/10 to 50/50) to obtain 0.199 g as white brown solid. The residue was dissolved in EtOAc and washed with 1% aq. NaHCO$_3$ (2×), water and brine (2×), dried over MgSO$_4$, filtered and evaporated to obtain 0.183 g. It was triturated in iPr$_2$O, filtered and dried to obtain 0.146 g as white solid. It was dissolved in EtOH and evaporated to dryness (3×) and dried under vacuo overnight to obtain 0.144 g of Compound 125 as white solid (63%).

1H NMR (400 MHz, DMSO-d$_6$) δ ppm 9.06 (d, J=1.5 Hz, 1H), 8.40 (t, J=5.8 Hz, 1H), 7.66 (d, J=9.6 Hz, 1H), 7.45 (dd, J=9.3, 2.3 Hz, 1H), 7.21 (d, J=8.6 Hz, 2H), 6.92 (d, J=8.6 Hz, 2H), 4.42 (d, J=6.1 Hz, 2H), 3.10-3.07 (m, 4H), 2.96 (q, J=7.6 Hz, 2H), 2.39 (t, J=13.1 Hz, 4H), 1.70-1.67 (m, 4H), 1.25 (t, J=7.6 Hz, 3H)

149

Preparation of Compound 133

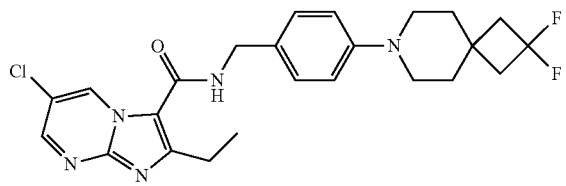 [SMILES: CCc1nc2ncc(Cl)cn2c1C(=O)NCc1ccc(N2CCC3(CC2)CC(F)(F)C3)cc1]

Compound 133 was prepared in the same way as Compound 125, starting from intermediate L and intermediate DP. The crude product was purified by preparative LCs (Irregular SiOH 15-40 µm, 40 g Grace, dry loading (silica), mobile phase gradient Heptane/(AcOEt/MeOH 9/1) from 90/10 to 60/40; then spherical C18 25 µm, 40 g YMC-ODS-25, dry loading (Celite®), mobile phase gradient: 0.2% aq. NH$_4$HCO$_3$/MeCN from 65/35 to 25/75) to give 0.083 g of Compound 133 as a white solid (36%).

1H NMR (500 MHz, DMSO-d$_6$) δ ppm 9.39 (d, J=2.5 Hz, 1H), 8.67 (d, J=2.5 Hz, 1H), 8.51 (t, J=5.7 Hz, 1H), 7.21 (d, J=8.5 Hz, 2H), 6.92 (d, J=8.8 Hz, 2H), 4.42 (d, J=5.7 Hz, 2H), 3.10-3.06 (m, 4H), 3.00 (q, J=7.4 Hz, 2H), 2.39 (t, J=13.5 Hz, 4H), 1.71-1.67 (m, 4H), 1.26 (t, J=7.4 Hz, 3H)

Synthesis of Compound 134

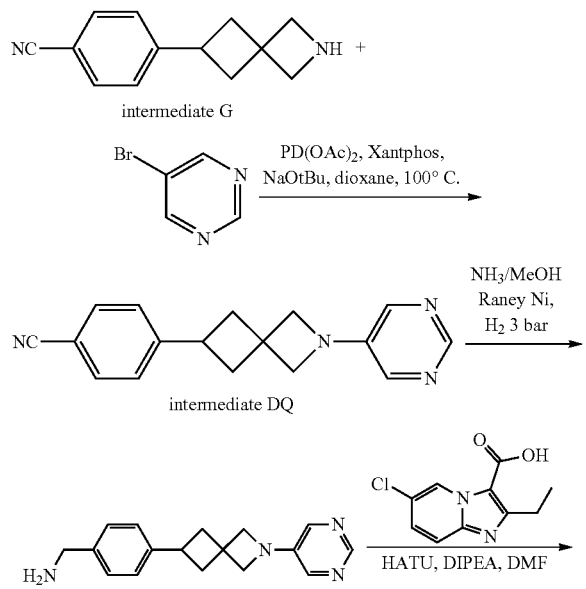

150

Preparation of Intermediate DO

Palladium acetate (0.107 g, 117 µmol) and Xantphos (0.182 g, 293 µmol) were added to a mixture of intermediate G (0.55 g, 2.34 mmol), 5-bromopyrimidine (0.373 g, 2.34 mmol) and sodium t-butoxide (0.676 g, 7.03 mmol) in 1,4-dioxane (8.3 mL). The atmosphere was evacuated and backfilled with N$_2$. The reaction mixture was heated at 100° C. for 5 h. After cooling to room temperature, the reaction mixture was diluted with AcOEt and DCM and filtered over a pad of Celite®. The filtrate was evaporated to dryness. The crude mixture was purified by preparative LC (irregular SiOH, 15-40 µm, 120 g, Grace, dry loading (silica), mobile phase gradient DCM/MeOH from 100/0 to 95/5) to Give 0.306 g of intermediate DQ as a yellow solid (47%).

Preparation of Intermediate DR

Accordingly, intermediate DR was prepared in the same was as intermediate DL starting from intermediate DQ, yielding 0.298 g, 96% as a yellow solid.

Preparation of Compound 134

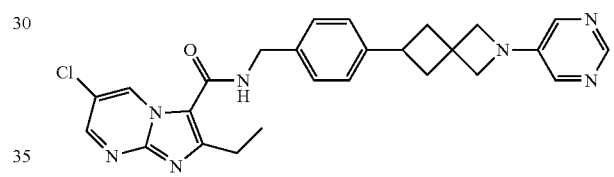

Compound 134 was prepared in the same way as Compound 132, starting from 6-chloro-2-ethylimidazo[1,2-a]pyridine-3-carboxylic acid CAS [1216142-18-5] and intermediate DR. The crude product was purified by preparative LC (irregular SiOH, 15-40 µm, 80 g, Grace, dry loading (silica), mobile phase gradient DCM/MeOH from 100/0 to 90/10) to give 0.268 g of Compound 134 as a white solid (56%).

1H NMR (500 MHz, DMSO-d$_6$) δ ppm 9.08 (s, 1H), 8.53 (s, 1H), 8.48 (t, J=5.6 Hz, 1H), 8.03 (s, 2H), 7.68 (d, J=9.5 Hz, 1H), 7.47 (dd, J=9.5, 1.9 Hz, 1H), 7.32 (d, J=7.9 Hz, 2H), 7.23 (d, J=7.88 Hz, 2H), 4.51 (d, J=5.6 Hz, 2H), 4.09 (s, 2H), 3.88 (s, 2H), 3.46-3.36 (m, 1H), 3.00 (q, J=7.6 Hz, 2H), 2.62-2.58 (m, 2H), 2.33-2.28 (m, 2H), 1.29-1.24 (t, J=7.6 Hz, 3H)

Synthesis of Compound 135 & Compound 136

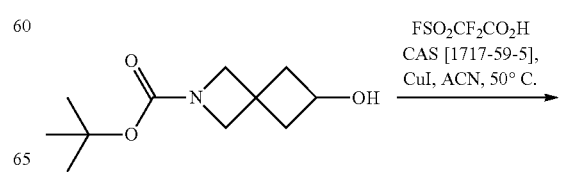

-continued

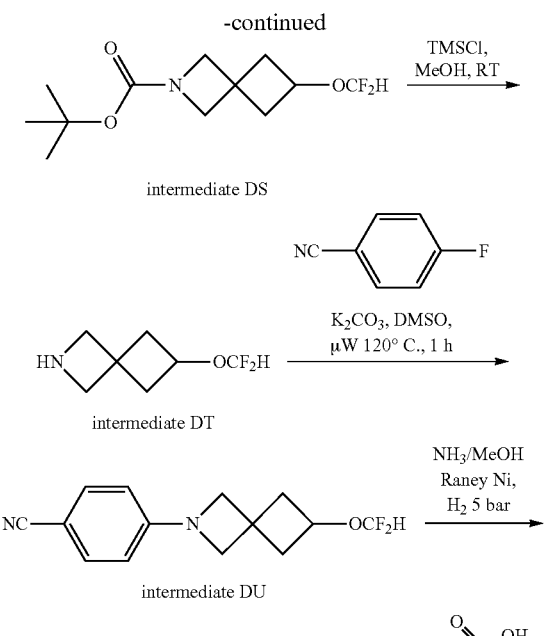

Preparation of Intermediate DS

A solution of 2,2-Difluoro-2-(fluorosulfonyl)acetic acid (CAS [1717-59-5], 1.25 g, 7.03 mmol) in Acetonitrile (6 mL) was added over 1 h30 to a solution of tert-Butyl 6-hydroxy-2-azaspiro[3.3]heptane-2-carboxylate (CAS [1147557-97-8], 1.00 g, 4.69 mmol) and copper iodide (0.179 g, 0.94 mmol) in acetonitrile (12 mL) at 50° C. under $N_2$. The reaction mixture was further stirred at 50° C. for 30 min, then evaporated to dryness. The crude product was purified by preparative LC (irregular SiOH, 15-40 μm, 80 g, Grace, dry loading (silica), mobile phase gradient Heptane/EtOAc from 100/0 to 70/30) to give 0.788 g of intermediate DS as a white solid (64%).

Preparation of Intermediate DT

Accordingly, intermediate DT was prepared in the same way as intermediate DJ starting from intermediate DS yielding 0.563 g, quantitative, as a colorless oil, used as such.

Preparation of Intermediate DU

Accordingly, intermediate DU was prepared in the same way as intermediate DK starting from intermediate DT yielding 0.445 g, 60% as a white solid.

Preparation of Intermediate DV

Accordingly, intermediate DV was prepared in the same was as intermediate DL starting from intermediate DU yielding 0.433 g, 96% as a colorless oil.

Preparation of Compound 135

Compound 135 was prepared in the same way as Compound 132, starting from 6-chloro-2-ethylimidazo[1,2-a]pyridine-3-carboxylic acid CAS [1216142-18-5] and intermediate DV. The crude product was purified by preparative LC (irregular SiOH, 15-40 μm, 80 g, Grace, dry loading (silica), mobile phase gradient: from DCM 100%, MeOH 0% to DCM 95%, MeOH 5% to give 0.176 g of Compound 135 as a white solid (53%).

1H NMR (500 MHz, DMSO-$d_6$) δ ppm 9.05 (s, 1H), 8.38 (br t, J=5.8 Hz, 1H), 7.66 (d, J=9.5 Hz, 1H), 7.45 (dd, J=9.5, 1.9 Hz, 1H), 7.18 (d, J=8.2 Hz, 2H), 6.62 (t, J=76 Hz, 1H), 6.38 (d, J=8.5 Hz, 2H), 4.54 (quin, J=7.2 Hz, 1H), 4.40 (d, J=6.0 Hz, 2H), 3.78 (s, 2H), 3.74 (s, 2H), 2.95 (q, J=7.6 Hz, 2H), 2.59-2.55 (m, 2H), 2.30-2.26 (m, 2H), 2.28, 1.24 (t, J=7.4 Hz, 3H)

Preparation of Compound 136

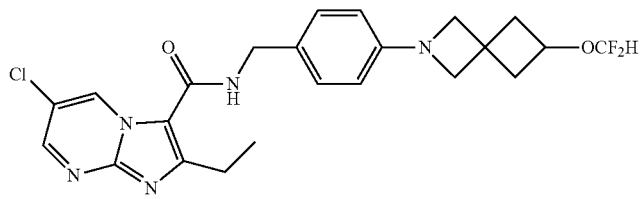

Compound 136

Compound 136 was prepared in the same way as Compound 135, starting from intermediate L and intermediate DV. The crude product was purified by preparative LC (irregular SiOH, 15-40 μm, 80 g, Grace, dry loading (silica), mobile phase gradient DCM/MeOH from 100/0 to 90/10) to give 0.127 g of Compound 136 as a white solid (38%).

1H NMR (400 MHz, DMSO-$d_6$) δ ppm 9.38 (d, J=2.5 Hz, 1H), 8.67 (d, J=2.5 Hz, 1H), 8.48 (t, J=5.8 Hz, 1H), 7.18 (d, J=8.6 Hz, 2H), 6.62 (t, J=76 Hz, 1H), 6.37 (t, J=8.4 Hz, 2H), 4.54 (t, J=7.1 Hz, 1H), 4.40 (d, J=6.1 Hz, 2H), 3.78 (s, 2H), 3.74 (s, 2H), 2.99 (q, J=7.4 Hz, 2H), 2.59-2.54 (m, 2H), 2.30-2.25 (m, 2H), 1.26 (t, J=7.6 Hz, 3H)

Synthesis of Compound 137

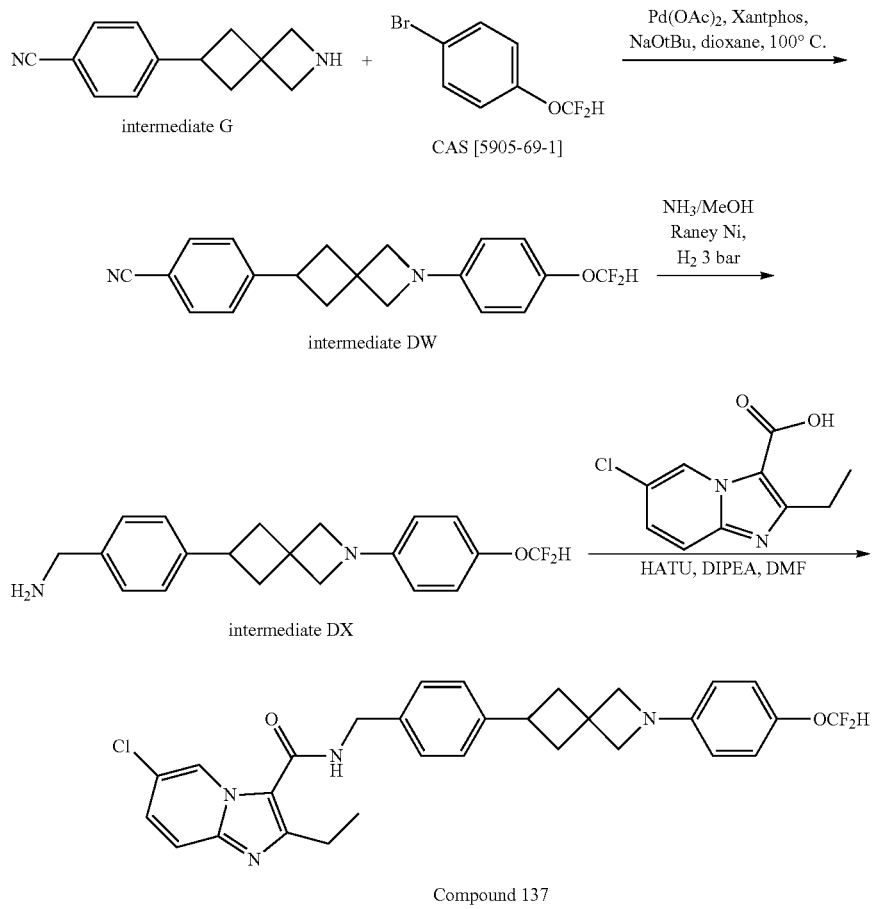

Preparation of Intermediate DW

Accordingly, intermediate DW was prepared in the same way as intermediate DQ starting from intermediate G and 4-bromodifluoromethoxybenzene CAS [5905-69-1], yielding 0.13 g as a white solid (30%).

Preparation of Intermediate DX

Accordingly, intermediate DX was prepared in the same way as intermediate DR starting from intermediate DW yielding 0.264 g as a white solid (90/%).

Preparation of Compound 137

Compound 137 was prepared in the same way as Compound 132, starting from 6-chloro-2-ethylimidazo[1,2-a]pyridine-3-carboxylic acid CAS [1216142-18-5] and intermediate DX. The crude product was purified by preparative LC (irregular SiOH, 15-40 μm, 40 g, Grace, dry loading (silica), mobile phase gradient DCM/MeOH from 100/0 to 90/10) to give 0.132 g of Compound 137 as a white solid (69%).

1H NMR (400 MHz, DMSO-$d_6$) δ ppm 9.07 (d, J=1.5 Hz, 1H), 8.47 (t, J=6.1 Hz, 1H), 7.67 (d, J=9.6 Hz, 1H), 7.46 (dd, J=9.6, 2.0 Hz, 1H), 7.31 (d, J=8.0 Hz, 2H), 7.22 (d, J=8.0 Hz, 2H), 6.98 (t, J=76 Hz, 1H), 6.98 (d, J=7.9 Hz, 2H), 6.43 (d, J=7.9 Hz, 2H), 4.50 (d, J=5.6 Hz, 2H), 3.92 (s, 2H), 3.71 (s, 2H), 3.46-3.36 (m, 1H), 2.99 (q, J=7.6 Hz, 2H), 2.59-2.54 (m, 2H), 2.30-2.25 (m, 2H), 1.27 (t, J=7.6 Hz, 3H)

Synthesis of Compound 138 & Compound 139

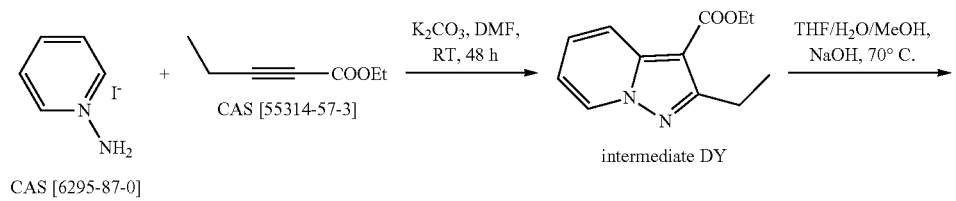

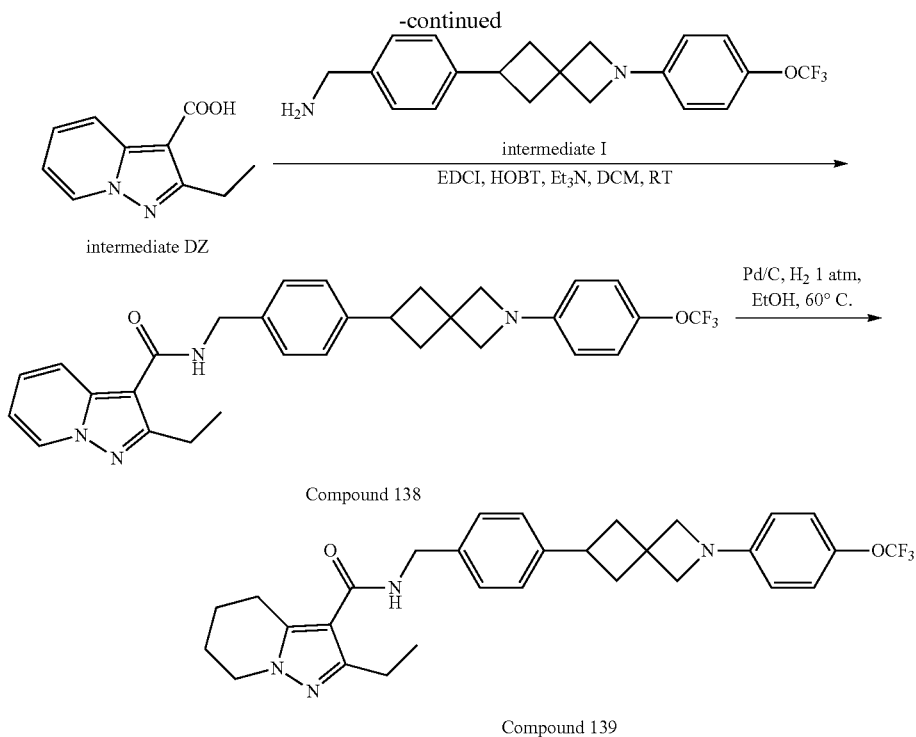

Preparation of Intermediate DY

Ethyl 2-pentynoate (18 mL, 135 mmol) was added to a solution of 1-aminopyridinium iodide (25 g, 113 mmol) and potassium carbonate (19 g, 135 mmol) in DMF (250 mL). The resulting mixture was stirred at room temperature for 48 h and evaporated to dryness. The residue was solubilized in EtOAc and washed with brine (3×). The organic layer was dried over $MgSO_4$, filtered and evaporated to dryness to give 14.5 g of a brown solid, which was triturated successively in $Et_2O$, and MeCN and filtered to give 8.1 g of intermediate DY as an off-white solid. The filtrate was evaporated to dryness and purified by preparative LC (Regular SiOH 30 μm, 120 g Interchim, dry loading (Celite®), mobile phase gradient Heptane/EtOAc from 100/0 to 70/30) to give additional 1.2 g of intermediate 73 as a white solid (global yield: 38%).

Preparation of Intermediate DZ

Aqueous sodium hydroxide 8M (20 mL, 164 mmol) was added to a solution of intermediate DY (7 g, 32.1 mmol) in THF (39 mL) and methanol (39 mL). The resulting mixture was stirred at 70° C. overnight. HCl (1M) was added to the mixture until pH-7-8.

The resulting precipitate was filtered and dried under high vacuum to give 5.3 g of intermediate DZ as an off-white solid (87%).

Preparation of Compound 138

To a solution of intermediate DY (0.1 g, 0.52 mmol) and triethylamine (0.188 mL, 1.36 mmol) in DCM (6 mL) were added EDCI (0.152 g, 0.78 mmol) and HOBt (0.108 g, 0.78 mmol). The resulting mixture was stirred at room temperature for 30 min before the addition of Intermediate I (0.202 g, 0.56 mmol), then stirred at room temperature for 4 h.

The reaction mixture was washed with water (2×). The organic layer was dried over $MgSO_4$, filtered and evaporated to dryness. The crude product was purified by preparative LCs (Regular SiOH 30 μm, 25 g Interchim, dry loading (Celite®), mobile phase: Heptane/AcOEt/MeOH 100:35:5; then spherical C18 25 μm, 40 g YMC-ODS-25, liquid loading (MeOH/MeCN), mobile phase gradient: 0.2% aq. $NH_4HCO_3$/MeCN from 50:50 to 0:100 then 100% MeCN) to give a white solid, further triturated in $Et_2O$ to give 0.145 g of Compound 138 as a white solid (52%).

1H NMR (500 MHz, DMSO-$d_6$) δ ppm 8.68 (d, J=6.9 Hz, 1H), 8.18 (t, J=6.0 Hz, 1H), 7.87 (d, J=8.8 Hz, 1H), 7.40-7.36 (m, 1H), 7.30 (d, J=8.2 Hz, 2H), 7.21 (d, J=7.9 Hz, 2H), 7.14 (d, J=8.5 Hz, 2H), 6.95 (td, J=6.9, 1.3 Hz, 1H), 6.45 (d, J=7.8 Hz, 2H), 4.45 (d, J=6.0 Hz, 2H), 3.96 (s, 2H), 3.75 (s, 2H), 3.45-3.35 (m, 1H), 3.01 (q, J=7.6 Hz, 2H), 2.59-2.55 (m, 2H), 2.31-2.25 (m, 2H), 1.25 (t, J=7.6 Hz, 3H)

Preparation of Compound 139

Compound 138 (0.1 g, 0.187 mmol) was dissolved in ethanol (1.3 mL) and treated with Pd/C 10% (10 mg). The reaction was stirred under H2 at atmospheric pressure at 60° C. for 16 h. The reaction mixture was filtered over Celite® and rinsed with EtOAc. The solvent was removed under reduced pressure. The crude product was purified by preparative LC (irregular SiOH, 15-40 μm, 24 g, Grace, dry loading (silica), mobile phase gradient Heptane/EtOAc from 70/30 to 10/90) and to give 0.065 g of Compound 139 as white solid (65%).

1H NMR (500 MHz, DMSO-$d_6$) δ ppm 7.69 (br t, J=6.0 Hz, 1H), 7.36 (d, J=8.8 Hz, 2H), 7.29 (d, J=8.5 Hz, 2H), 7.10 (d, J=8.2 Hz, 2H), 6.38 (d, J=8.2 Hz, 2H), 4.26 (d, J=5.7 Hz, 2H), 3.96 (br t, J=5.8 Hz, 2H), 3.91 (s, 2H), 3.69 (s, 2H), 3.50-3.43 (m, 1H), 2.84 (br t, J=6.1 Hz, 2H), 2.67 (q, J=7.5 Hz, 2H), 2.60-2.56 (m, 2H), 2.31-2.27 (m, 2H), 1.93-1.88 (m, 2H), 1.76-1.72 (m, 2H), 1.09 (t, J=7.6 Hz, 3H)

Synthesis of Compound 140, Compound 141 & Compound 142

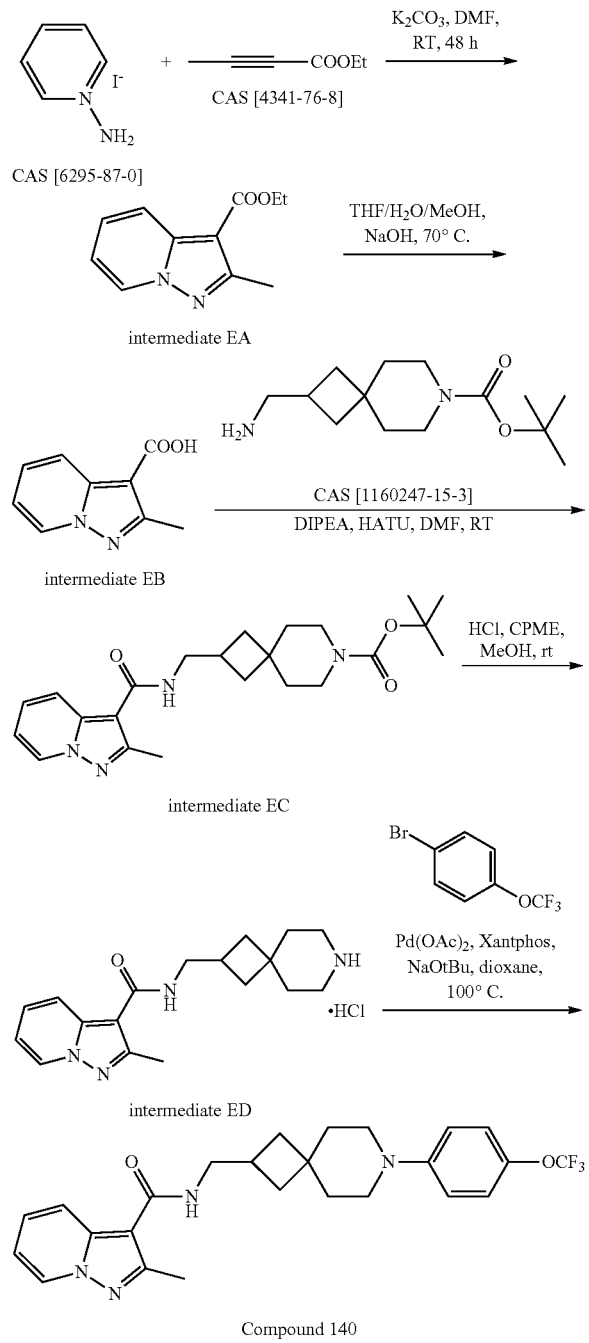

Preparation of Intermediate EA

Ethyl-2-butynoate (CAS [4341-76-8], 6.2 mL, 54.0 mmol) was added to a solution of 1-aminopyridinium iodide (CAS [6295-37-0], 10 g, 45 mmol) and potassium carbonate (7.5 g, 54 mmol) in DMF (100 mL). The resulting mixture was stirred at room temperature for 72 h. The mixture was evaporated to dryness and the residue was solubilized in EtOAc and washed with brine (3×). The organic layer was dried over MgSO$_4$, filtered and evaporated to dryness to give 5.1 g of intermediate EA as a brown solid (55%).

Preparation of Intermediate EB

Accordingly, intermediate EB was prepared in the same way as intermediate DZ starting from intermediate EA yielding 3.7 g as an off-white solid, 84%.

Preparation of Intermediate EC

A solution of intermediate EB (0.2 g, 1.14 mmol), HATU (0.475 g, 1.25 mmol) and diisopropylethylamine (0.47 mL, 3.41 mmol) in DMF (15 mL) was stirred at room temperature for 30 min before the addition of tert-butyl 2-(aminomethyl)-7-azaspiro[3.5]nonane-7-carboxylate (CAS [1160247-15-3], 0.303 g, 1.19 mmol) in DMF (5 mL). The resulting mixture was stirred at room temperature for 2 h. The mixture was evaporated to dryness and the residue was solubilized in EtOAc and washed with an aqueous solution of NaHCO$_3$ 1% (2×), water (2×) and brine (2×). The organic layer was dried over MgSO$_4$, filtered and evaporated to dryness. The crude product was purified by preparative LCs (Regular SiOH 30 μm, 12 g Interchim, dry loading (Celite®), mobile phase gradient: from Heptane/EtOAc/MeOH 100:0:0 to 70:25:5; then spherical C18 25 μm, 40 g YMC-ODS-25, dry loading (Celite®), mobile phase gradient: 0.2% aq. NH$_4$HCO$_3$/MeOH from 50:50 to 10:90 then 0.2% aq. NH$_4$HCO$_3$/MeOH 10:90) to give 0.318 g of intermediate EC as a colorless oil (68%).

Preparation of Intermediate ED

HCl 3M in CPME (0.77 mL, 2.31 mmol) was added to a solution of intermediate EC (0.318 g, 0.77 mmol) in methanol (6 mL) at 0° C. The resulting mixture was allowed to warm to room temperature overnight. Additional HCl 3M in CPME (0.51 mL, 1.54 mmol) was added at 0° C. and the mixture was allowed to warm to room temperature overnight. The mixture was evaporated to dryness to give 0.306 g of intermediate ED as a white solid (quant.).

Preparation of Compound 140

A mixture of intermediate ED (0.26 g, 0.745 mmol), 4-bromotrifluoromethoxybenzene (0.166 mL, 1.12 mmol) and sodium t-butoxide (0.286 g, 2.98 mmol) in 1,4-dioxane (10 mL) was degassed by N$_2$ bubbling for 10 min before the addition of palladium acetate (0.016 g, 75 μmol) and Xantphos (0.043 g, 75 μmol). The resulting mixture was stirred at 100° C. overnight, then cooled to room temperature and filtered through a pad of Celite®. The cake was washed with EtOAc and the filtrate was evaporated to dryness. The residue was solubilized in EtOAc and washed with brine (2×). The organic layer was dried over MgSO$_4$, filtered and concentrated to dryness. The crude product was purified by preparative LCs (Irregular SiOH 15-40 μm, 10 g Biotage, liquid loading (DCM), mobile phase gradient: from Heptane/EtOAc/MeOH 80:17:3 to 60:35:5; then spherical C18 25 μm, 40 g YMC-ODS-25, dry loading (Celite®), mobile phase gradient: 0.2% aq. NH$_4$HCO$_3$/MeCN from 70:30 to 0:100 in 10 CV, then 5 CV at 0.2% aq. NH$_4$HCO$_3$/MeCN 0:100) to give 0.062 g of Compound 140 as a white solid (18%).

1H NMR (500 MHz, DMSO-d$_6$) δ ppm 8.64 (d, J=6.6 Hz, 1H), 7.84 (d, J=8.8 Hz, 1H), 7.60 (t, J=5.7 Hz, 1H), 7.37 (td, J=7.9, 1.0 Hz, 1H), 7.15 (d, J=8.8 Hz, 2H), 7.00-6.93 (m, 3H), 3.37-3.30 (m, 2H), 3.17-3.12 (m, 2H), 3.07-3.05 (m, 2H), 2.58-2.50 (m, 1H), 2.54 (s, 3H), 1.93-1.88 (m, 2H), 1.69-1.65 (m, 2H), 1.63-1.54 (m, 4H)

Preparation of Compound 141

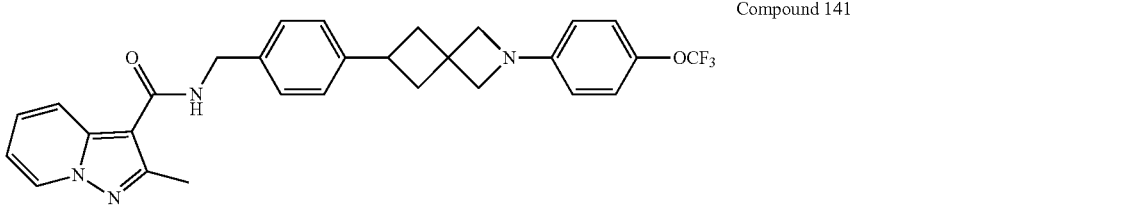

Compound 141

Compound 141 was prepared in the same way as Compound 140, starting from intermediate EB and intermediate I. The crude product was purified by preparative LC (irregular SiOH, 15-40 µm, 40 g, Grace, dry loading (silica), mobile phase gradient Heptane/EtOAc from 70/30 to 10/90) to give 0.056 g of Compound 141 as a white solid (43%).

1H NMR (500 MHz, DMSO-$d_6$) δ ppm 8.65 (d, J=6.9 Hz, 1H), 8.08 (t, J=6.0 Hz, 1H), 7.91 (d, J=9.1 Hz, 1H), 7.40-7.37 (m, 1H), 7.30 (d, J=8.2 Hz, 2H), 7.21 (d, J=7.9 Hz, 2H), 7.14 (d, J=8.5 Hz, 2H), 6.97-6.95 (m, 1H), 6.45 (d, J=8.8 Hz, 2H), 4.46 (d, J 10=5.7 Hz, 2H), 3.96 (s, 2H), 3.75 (s, 2H), 3.41 (quin, J=8.8 Hz, 1H), 2.60-2.55 (m, 2H), 2.57 (s, 3H), 2.30-2.26 (m, 2H)

Preparation of Compound 142

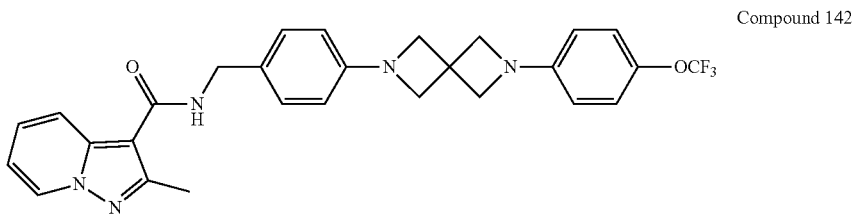 [SMILES: Cc1nn2ccccc2c1C(=O)NCc1ccc(C2CC3(C2)CN(c2ccc(OC(F)(F)F)cc2)C3)cc1]

Compound 142

Compound 142 was prepared in the same way as Compound 140, starting from intermediate EB and intermediate Q. The crude product was purified by preparative LC (irregular SiOH, 15-40 µm, 40 g, Grace, dry loading (silica), mobile phase gradient Heptane/EtOAc from 70/30 to 10/90) and yielding 0.165 g of Compound 142 as a white solid (62%).

1H NMR (400 MHz, DMSO-$d_6$) δ ppm 8.64 (d, J=6.6 Hz, 1H), 7.98 (t, J=5.8 Hz, 1H), 7.88 (d, J=9.1 Hz, 1H), 7.39-7.35 (m, 1H), 7.19 (d, J=8.0 Hz, 2H), 7.16 (d, J=8.0 Hz, 2H), 6.97-6.93 (m, 1H), 6.49 (d, J=8.6 Hz, 2H), 6.43 (d, J=8.6 Hz, 2H), 4.37 (d, J=5.6 Hz, 2H), 4.00 (s, 4H), 3.95 (s, 4H), 2.55 (s, 3H)

Preparation of Compound 143

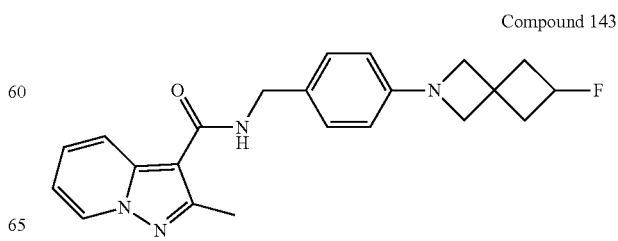

Compound 143

Compound 143 was prepared in the same way as Compound 140, starting from intermediate EB and intermediate CC. The crude product was purified by preparative LC (irregular SiOH, 15-40 μm, 40 g, Grace, dry loading (silica), mobile phase gradient Heptane/EtOAc from 70/30 to 10/90) to give 0.252 g of Compound 143 as a white solid (74%).

1H NMR (500 MHz, DMSO-d$_6$) δ ppm 8.64 (d, J=6.6 Hz, 1H), 7.98 (br t, J=5.8 Hz, 1H), 7.87 (d, J=8.8 Hz, 1H), 7.39-7.35 (m, 1H), 7.17 (d, J=8.5 Hz, 2H), 6.96-6.93 (m 1H), 6.37 (d, J=8.5 Hz, 2H), 5.01 (dquin, J=56, 6.5 Hz, 1H), 4.35 (d, J=6.0 Hz, 2H), 3.76 (s, 2H), 3.74 (s, 2H), 2.61-2.58 (m, 2H), 2.54 (s, 3H), 2.39-2.30 (m, 2H)

Synthesis of Compound 144 & Compound 145

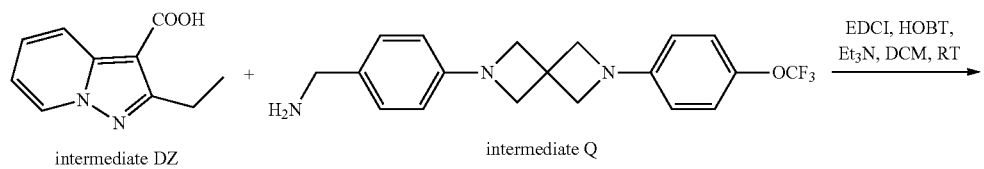

intermediate DZ        intermediate Q

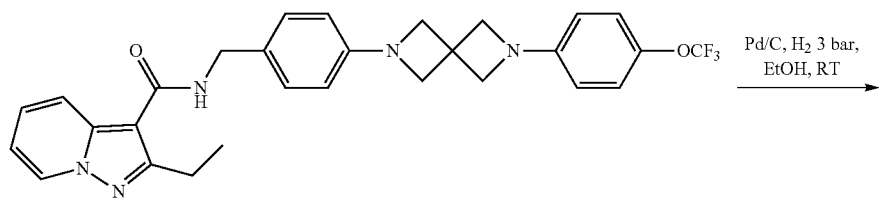

Compound 144

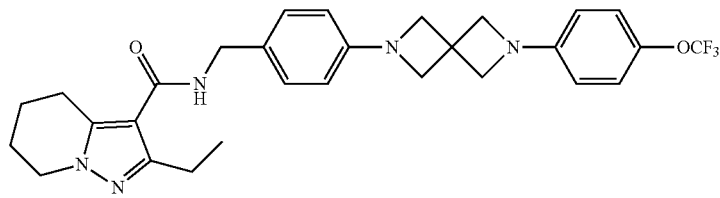

Compound 145

Preparation of Compound 144

Compound 144 was prepared in the same way as Compound 138, starting from intermediate DZ and intermediate Q. The crude product was purified by preparative LC (irregular SiOH, 15-40 μm, 40 g, Grace, dry loading (silica), mobile phase gradient Heptane/EtOAc from 70/30 to 10/90) to give 0.128 g of Compound 144 as a white solid (51%).

1H NMR (400 MHz, DMSO-d$_6$) δ ppm 8.66 (d, J=7.1 Hz, 1H), 8.06 (t, J=5.8 Hz, 1H), 7.84 (d, J=9.1 Hz, 1H), 7.38-7.34 (m, 1H), 7.19 (d, J=8.0 Hz, 2H), 7.15 (d, J=8.0 Hz, 2H), 6.95-6.92 (m, 1H), 6.49 (d, J=9.1 Hz, 2H), 6.43 (d, J=8.1 Hz, 2H), 4.37 (d, J=6.1 Hz, 2H), 4.00 (s, 4H), 3.95 (s, 4H), 2.99 (q, J=7.6 Hz, 2H), 1.24 (t, J=7.6 Hz, 3H)

Preparation of Compound 145

Compound 144 (0.32 g, 0.56 mmol) was dissolved in ethanol (5 mL) and treated with Pd/C 10% (0.064 g, 0.060 mmol). The reaction mixture was stirred under 3 bar of H2 at room temperature for 3 days, then filtered over a pad of Celite® and evaporated to dryness. The crude product was purified by preparative LCs (irregular SiOH, 15-40 μm, 24 g, Grace, liquid loading (DCM), mobile phase gradient Heptane/(EtOAc/MeOH) (9:1) from 90/0 to 20/80; then spherical C18, 25 μm, 40 g YMC-ODS-25, dry loading (Celite®), mobile phase gradient: from 50% (aq. NH$_4$HCO$_3$ 0.2%), 50% MeCN to 100% MeCN then MeCN 100%) to give 0.184 g of Compound 145 as a white solid (56%).

1H NMR (500 MHz, DMSO-d$_6$) δ ppm 7.69 (t, J=5.8 Hz, 1H), 7.16 (d, J=8.2 Hz, 2H), 7.12 (d, J=8.2 Hz, 2H), 6.49 (d, J=8.8 Hz, 2H), 6.41 (d, J=8.5 Hz, 2H), 4.27 (d, J=5.7 Hz, 2H), 4.0 (s, 4H), 3.99-3.94 (m, 2H), 3.94 (s, 4H), 2.85 (t, J=6.3 Hz, 2H), 2.67 (q, J=7.6 Hz, 2H), 1.94-1.88 (m, 2H), 1.77-1.72 (m, 2H), 1.09 (t, J=7.4 Hz, 3H)

Synthesis of Compound 146 & Compound 147

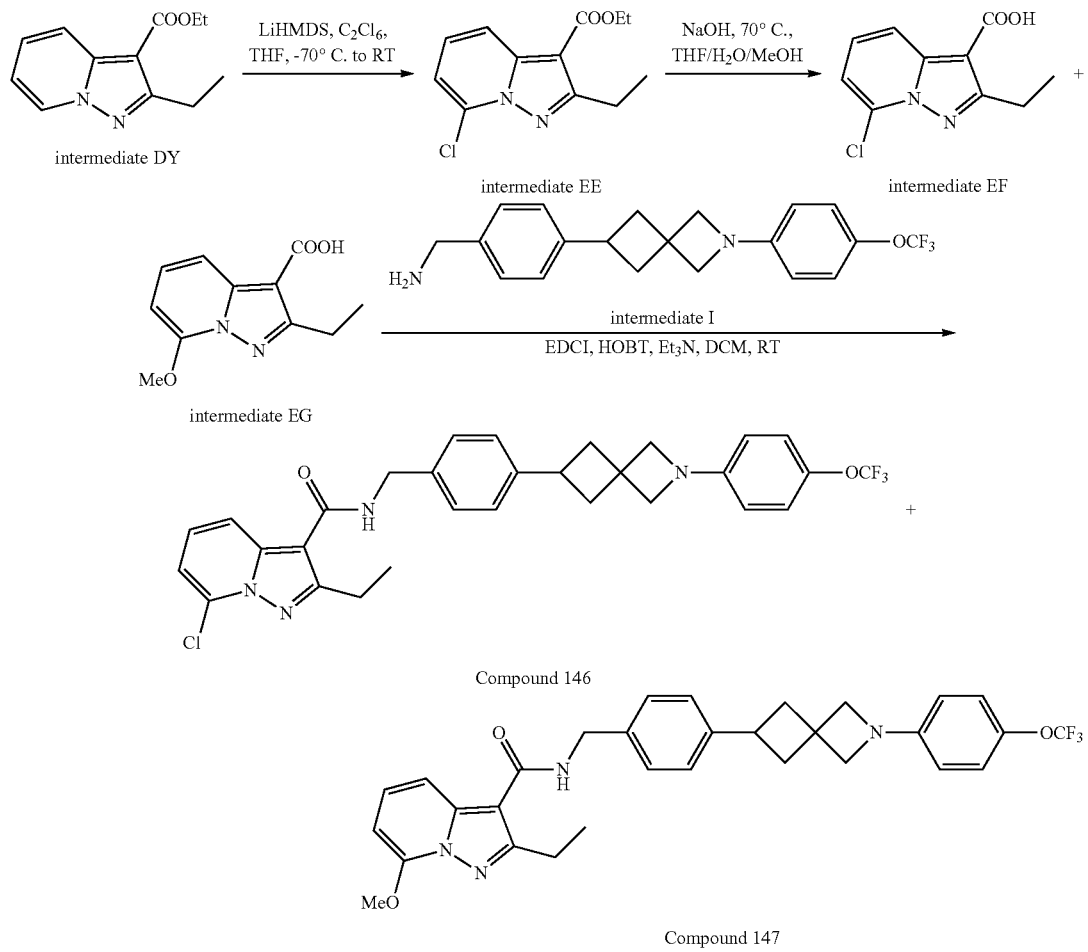

Preparation of Intermediate EE

LiHMDS 1.5 M (2.64 mL, 3.96 mmol) was added dropwise to a stirred solution of intermediate DY (0.721 g, 3.30 mmol) in THF (10 mL) at −70° C. under $N_2$. The reaction was stirred at −70° C. for 2 h, then hexachloroethane (0.938 g, 3.96 mmol) in THF (2 mL) was added dropwise. The reaction was allowed to stir at room temperature for 4 h and quenched with water and saturated aqueous $NH_4Cl$. The aqueous phase was extracted with EtOAc. The organic phase was dried over $MgSO_4$, filtered and evaporated to dryness to give 0.913 g of intermediate EE (quant.), used as such in the next step.

Preparation of Intermediate EF/EG

Sodium hydroxide 8M (2.05 mL, 16.4 mmol) was added to a solution of intermediate EE (813 mg, 3.22 mmol) in THF (3.9 mL) and MeOH (3.9 mL), the resulting mixture was stirred at 70° C. overnight. HCl (1 M) was added to the mixture until pH 1. The resulting precipitate was filtered and dried under high vacuum at 50° C. to give 0.612 g of a mixture of intermediate EF and EG, used as such in the next step.

Preparation of Compound 146 & Compound 147

Compounds 146 and 147 were prepared in the same way as Compound 138, starting from mixture of intermediate EF/EG and intermediate I. The crude products were purified by preparative LC (irregular SiOH, 15-40 μm, 24 g, Grace, dry loading (silica), mobile phase gradient Heptane/EtOAc from 70/30 to 10/90) to give 0.128 g (61%) of Compound 146 and 0.037 g (17%) of Compound 147, both as white solids.

Compound 146

1H NMR (400 MHz, DMSO-$d_6$) δ ppm 8.36 (t, J=5.8 Hz, 1H), 7.87 (d, J=8.6 Hz, 1H), 7.42-7.38 (m, 1H), 7.31-7.26 (m, 3H), 7.21 (d, J=8.1 Hz, 2H), 7.14 (d, J=8.6 Hz, 2H), 6.45 (d, J=9.1 Hz, 2H), 4.46 (d, J=5.6 Hz, 2H), 3.96 (s, 2H), 3.75 (s, 2H), 3.43-3.38 (m, 1H), 3.04 (q, J=7.6 Hz, 2H), 2.60-2.54 (m, 2H), 2.31-2.25 (m, 2H), 1.26 (t, J=7.3 Hz, 3H)

Compound 147

1H NMR (400 MHz, DMSO-$d_6$) δ ppm 8.14 (t, J=6.1 Hz, 1H), 7.47 (d, J=8.4 Hz, 1H), 7.40-7.36 (m, 1H), 7.29 (d, J=8.0 Hz, 2H), 7.21 (d, J=8.0 Hz, 2H), 7.14 (d, J=8.1 Hz, 2H), 6.46-6.44 (m, 3H), 4.44 (d, J=5.6 Hz, 2H), 4.09 (s, 3H), 3.96 (s, 2H), 3.75 (s, 2H), 3.46-3.38 (m, 1H), 3.00 (q, J=7.4 Hz, 2H), 2.60-2.54 (m, 2H), 2.31-2.25 (m, 2H), 1.23 (t, J=7.6 Hz, 3H)

Synthesis of Compound 148

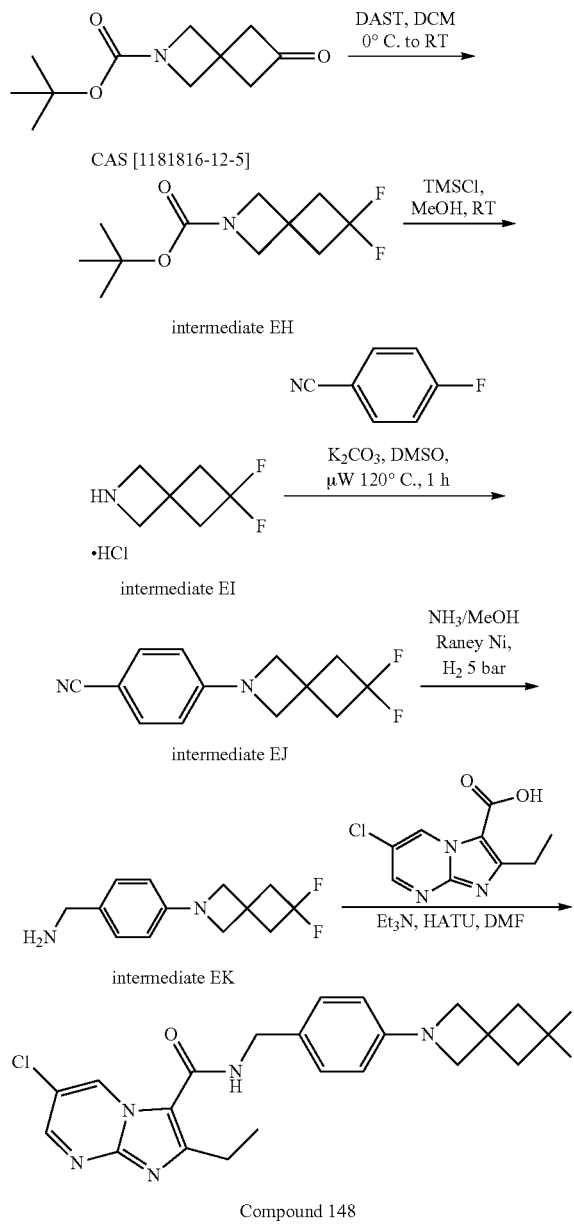

Preparation of Intermediate EH

To a solution of tert-Butyl 6-oxo-2-azaspiro[3.3]heptane-2-carboxylate (CAS [1181816-12-5], 1 g, 4.73 mmol) in dry DCM (50 mL) at 0° C. was added DAST (1.86 mL, 14.2 mmol), then the mixture was warmed to room temperature and stirred for 16 h. Additional DAST (0.62 mL, 1 eq., 4.73 mmol) was added, then the mixture was stirred at room temperature for 3 h. The mixture was quenched with sat. NaHCO$_3$, then stirred for 10 min. The layers were separated and the aqueous layer was extracted with DCM (2×). The combined organic layers were dried over MgSO$_4$, filtered off and evaporated to dryness to give 1.02 g of intermediate EH as a yellow solid (76%).

Preparation of Intermediate EI

Accordingly, intermediate 83 was prepared in the same way as intermediate DJ starting from intermediate EH yielding 0.764 g as a beige solid Preparation of Intermediate EJ Accordingly, intermediate EJ was prepared in the same way as intermediate DK and 4-fluorobenzonitrile starting from intermediate EI yielding 0.608 g as a white solid, 74%

Preparation of Intermediate EK

Accordingly, intermediate EK was prepared in the same way as intermediate DL starting from intermediate EJ yielding 0.559 g as a blue solid, 74%

Preparation of Compound 148

Compound 148 was prepared in the same way as Compound 117 (using triethylamine instead of DIPEA), starting from intermediate L and intermediate EK. The crude product was purified by preparative LC (irregular SiOH, 15-40 μm, 40 g, Grace, dry loading (Celite®), mobile phase gradient Heptane/(EtOAc/MeOH) (9:1) from 85/15 to 40/60) to give 0.285 g of Compound 148 as a white solid (70%).

1H NMR (500 MHz, DMSO-d$_6$) δ ppm 9.38 (d, J=2.5 Hz, 1H), 8.67 (d, J=2.5 Hz, 1H), 8.50 (t, J=5.8 Hz, 1H), 7.19 (d, J=8.2 Hz, 2H), 6.42 (d, J=8.2 Hz, 2H), 4.41 (d, J=5.7 Hz, 2H), 3.85 (s, 4H), 2.99 (q, J=7.5 Hz, 2H), 2.84 (t, J=12.6 Hz, 4H), 1.26 (t, J=7.6 Hz, 3H)

Synthesis of Compound 149

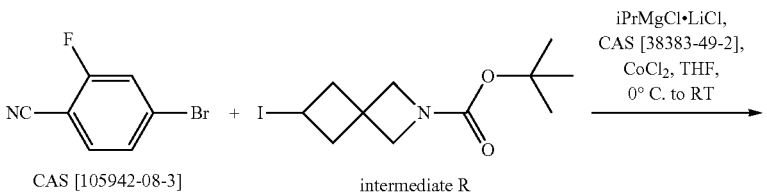

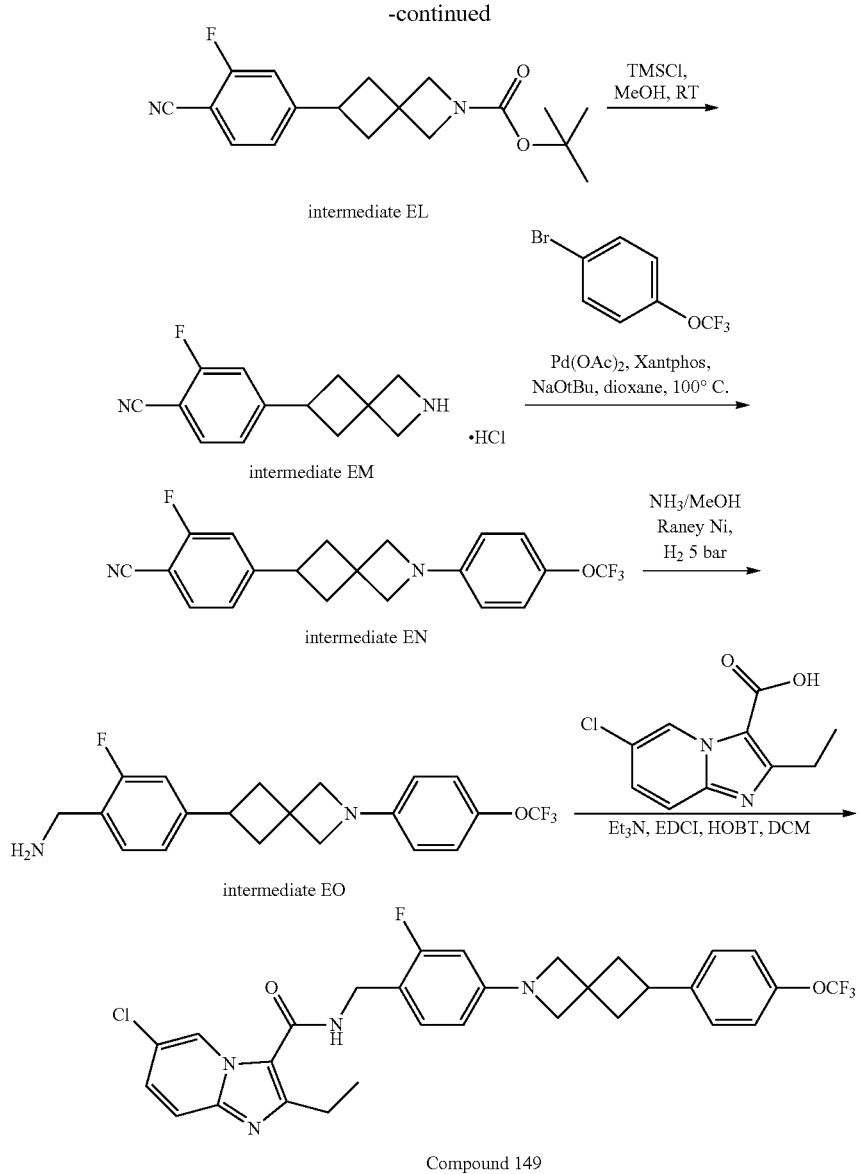

Preparation of Intermediate EL iPrMgCl.LiCl 1.3M (7.14 mL, 9.28 mmol) was added to a solution of 2-fluoro-4-bromobenzonitrile in anhydrous THF (25 mL) at 0° C. under $N_2$. The resulting solution was stirred at 0° C. for 4 h under a stream of $N_2$, before being cannulated (ca. 30 min) to a solution of intermediate R and N1,N1,N2,N2-tetramethylcyclohexane-1,2-diamine (CAS [38383-49-2], 0.063 g, 0.37 mmol) and $CoCl_2$ (0.04 g, 0.31 mmol) in anhydrous THF (25 mL) under $N_2$, at 0° C. The resulting mixture was stirred at room temperature for 18 h, then quenched with water. EtOAc was added, the aqueous layer was separated and extracted with EtOAc (2×). The combined organic layers were washed with brine, dried over $MgSO_4$, filtered off and evaporated to dryness. The crude mixture was purified by preparative LCs (regular SiOH, 30 µm, 80 g, Interchim, dry loading (Celite®), mobile phase gradient Heptane/EtOAc from 95/5 to 60/40; then spherical C18, 25 µm, 120 g YMC-ODS-25, dry loading (Celite®), mobile phase gradient: from 20/o (aq. $NH_4HCO_3$ 0.2%), 80% MeCN to 100% MeCN) to give 0.933-g of intermediate EL as a white solid, 95%.

Preparation of Intermediate EM

Accordingly, intermediate EM was prepared in the same way as intermediate DJ starting from intermediate EL yielding 0.608 g as a white solid, 74%

Preparation of Intermediate EN

Accordingly, intermediate EN was prepared in the same way as intermediate DW starting from intermediate EM and 4-bromotrifluoromethoxybenzene, yielding 0.478 g as a white solid, 44%.

Preparation of Intermediate EO

Accordingly, intermediate EO was prepared in the same way as intermediate DL starting from intermediate EN yielding 0.18 g as a blue solid, 89%

Preparation of Compound 149

Compound 149 was prepared in the same way as Compound 131, starting from 6-chloro-2-ethylimidazo[1,2-a]pyridine-3-carboxylic acid CAS [1216142-18-5], and intermediate EO. The crude product was purified by preparative LCs (irregular SiOH, 15-40 μm, 24 g, Grace, dry loading (Celite®), mobile phase gradient Heptane/(EtOAc/MeOH) (9:1) from 95/5 to 50/50; then spherical C18, 25 μm, 40 g YMC-ODS-25, dry loading (Celite®), mobile phase gradient: from 50/% (aq. $NH_4HCO_3$ 0.2%), 50% MeCN to 100% MeCN then 100% MeCN) to give 0.148 g of Compound 149 as a white solid (41%).

1H NMR (500 MHz, DMSO-$d_6$) δ ppm 9.06 (d, J=1.6 Hz, 1H), 8.46 (t, J=5.7 Hz, 1H), 7.67 (d, J=9.5 Hz, 1H), 7.46 (dd, J=9.5, 2.2 Hz, 1H), 7.36 (t, J=7.9 Hz, 1H), 7.15-7.06 (m, 4H), 6.45 (d, J=7.8 Hz, 2H), 4.54 (br d, J=5.7 Hz, 2H), 3.96 (s, 2H), 3.75 (s, 2H), 3.44 (quin, J=8.8 Hz, 1H), 2.98 (q, J=7.6 Hz, 2H), 2.59-2.55 (m, 2H), 2.32-2.28 (m, 2H), 1.26 (t, J=7.6 Hz, 3H)

Synthesis of Compound 150

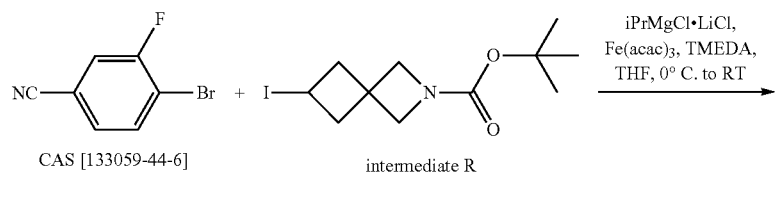

CAS [133059-44-6]    intermediate R

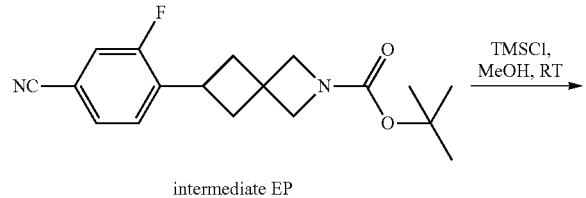

intermediate EP

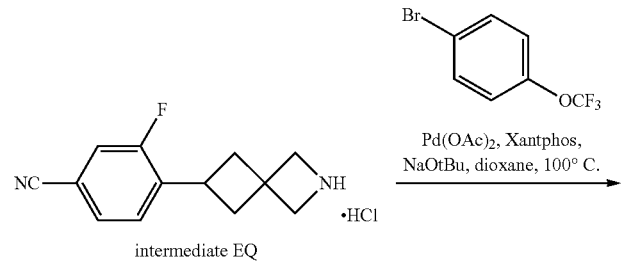

intermediate EQ

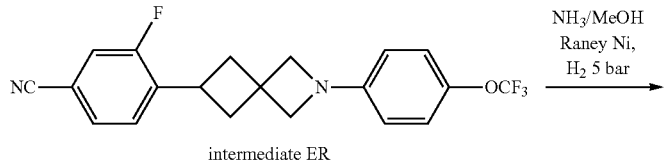

intermediate ER

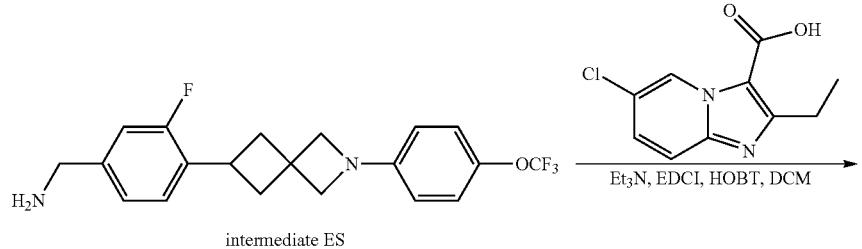

intermediate ES

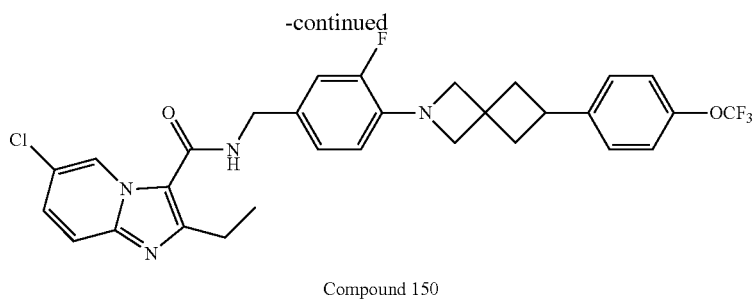

Compound 150

Preparation of Intermediate EP iPrMgCl.LiCl 1.3 M (10.5 mL, 13.7 mmol) was added to a solution of 4-bromo-3-fluorobenzonitrile (1.39 g, 6.96 mmol) in anhydrous THF (8 mL) at 0° C. under $N_2$. The resulting solution was stirred at 0° C. for 4 h under a stream of $N_2$. This solution was added dropwise over 1 h to a solution of intermediate R (0.75 g, 2.32 mmol), Fe(acac)$_3$ (0.082 g, 0.23 mmol) and TMEDA (0.84 mL, 5.57 mmol) in anhydrous THF (15 mL) under $N_2$, at 0° C. The resulting mixture was stirred at room temperature for 18 h, then quenched with $NH_4Cl$. EtOAc and water were added, the aqueous layer was separated and extracted with EtOAc. The combined organic layers were washed with brine, dried over $MgSO_4$, filtered and evaporated to dryness. The crude mixture was purified by preparative LC (irregular SiOH, 15-40 µm, 50 g, Merck, dry loading (Celite®), mobile phase gradient Heptane/EtOAc from 100/0 to 65/35) to give 0.391 g of intermediate EP as a yellow solid (53%).

Preparation of Intermediate EQ

Accordingly, intermediate EQ was prepared in the same way as intermediate EM starting from intermediate EP yielding 0.325 g as a green gum, quant.

Preparation of Intermediate ER

Accordingly, intermediate ER was prepared in the same way as intermediate EN starting from intermediate EQ and 4-bromotrifluoromethoxybenzene, yielding 0.385 g as a white solid, 81%.

Preparation of Intermediate ES

Accordingly, intermediate ES was prepared in the same way as intermediate EO starting from intermediate ER yielding 0.229 g as a grey solid, 59%

Preparation of Compound 150

Compound 150 was prepared in the same way as Compound 149, starting from 6-chloro-2-ethylimidazo[1,2-a]pyridine-3-carboxylic acid CAS [1216142-18-5] and intermediate ES. The crude product was purified by preparative LC (irregular SiOH, 15-40 µm, 24 g, Grace, dry loading (Celite®), mobile phase gradient Heptane/(EtOAc/MeOH) (9:1) from 95/5 to 50/50) to give 0.289 g of Compound 150 as a white solid (84%).

1H NMR (400 MHz, DMSO-d$_6$) δ ppm 9.08 (s, 1H), 8.48 (t, J=5.8 Hz, 1H), 7.67 (d, J=9.6 Hz, 1H), 7.46 (dd, J=9.6, 2.0 Hz, 1H), 7.33 (t, J=7.9 Hz, 1H), 7.19-7.11 (m, 4H), 6.45 (d, J=8.6 Hz, 2H), 4.51 (br d, J=5.6 Hz, 2H), 3.98 (s, 2H), 3.75 (s, 2H), 3.57 (quin, J=8.8 Hz, 1H), 3.00 (q, J=7.4 Hz, 2H), 2.61-2.56 (m, 2H), 2.37-2.31 (m, 2H), 1.27 (t, J=7.6 Hz, 3H)

Synthesis of Compound 151

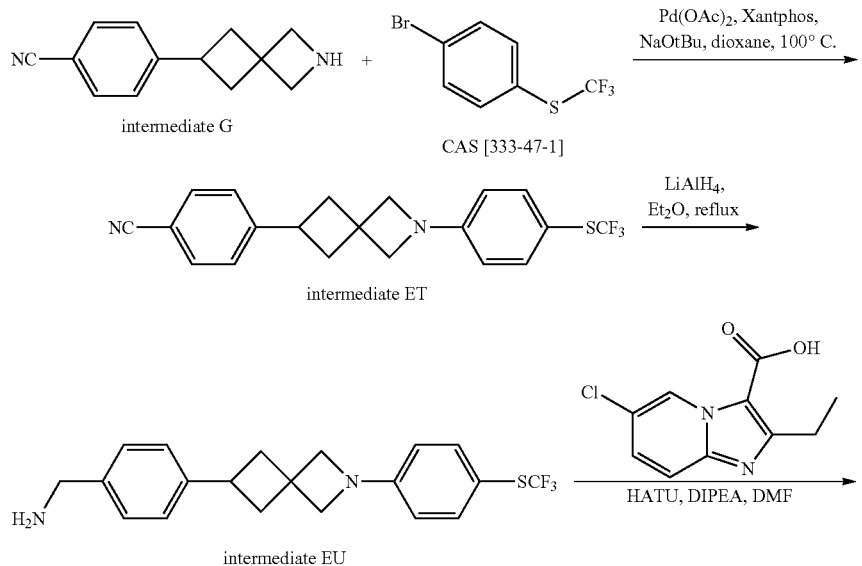

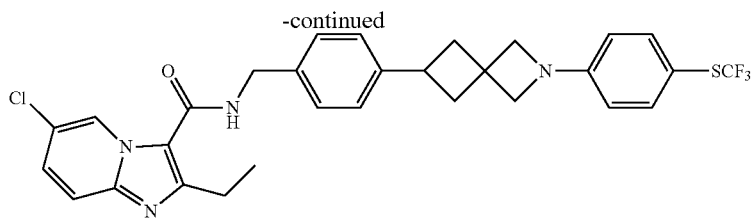

Compound 151

Preparation of Intermediate ET

Accordingly, intermediate ET was prepared in the same way as intermediate DQ starting from intermediate G and 1-Bromo-4-(Trifluoromethylthio)Benzene CAS [333-47-1] yielding 0.37 g as a reddish solid, 60%.

Preparation of Intermediate EU

Intermediate ET (0.32 g, 0.855 mmol) was added portionwise to a suspension of LiAlH$_4$ (0.04 g, 1.05 mmol) in dry Et$_2$O (8 mL) at 0° C. under N$_2$. The mixture was warmed to room temperature then refluxed for 3 h, and evaporated to dryness. The residue was taken-up in MeOH and filtered over a pad of Celite®. The cake was washed with MeOH and the filtrate was evaporated to dryness to give 0.328 g of intermediate EU as a pale yellow solid (quant.).

Preparation of Compound 151

Compound 151 was prepared in the same way as Compound 150, starting from 6-chloro-2-ethylimidazo[1,2-a]pyridine-3-carboxylic acid CAS [1216142-18-5] and intermediate EU. The crude product was purified by preparative LC (irregular SiOH, 15-40 µm, 30 g, Merck, dry loading (Celite®), mobile phase gradient Heptane/EtOAc from 90/10 to 10/90) to give 0.189 g of Compound 151 as a white solid (41%).

1H NMR (500 MHz, DMSO-d$_6$) δ ppm 9.08 (s, 1H), 8.47 (t, J=5.7 Hz, 1H), 7.67 (d, J=9.5 Hz, 1H), 7.49-7.41 (m, 3H), 7.32 (d, J=7.9 Hz, 2H), 7.23 (d, J=7.9 Hz, 2H), 6.48 (d, J=8.5 Hz, 2H), 4.50 (br d, J=5.7 Hz, 2H), 4.05 (s, 2H), 3.83 (s, 2H), 3.32 (quin, J=8.8 Hz, 1H), 2.99 (q, J=7.6 Hz, 2H), 2.66-2.62 (m, 2H), 2.33-2.27 (m, 2H), 1.27 (t, J=7.6 Hz, 3H)

Synthesis of Compound 152

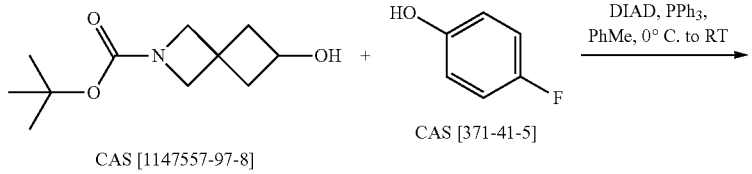

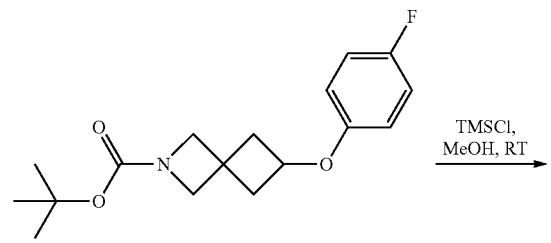

intermediate EV

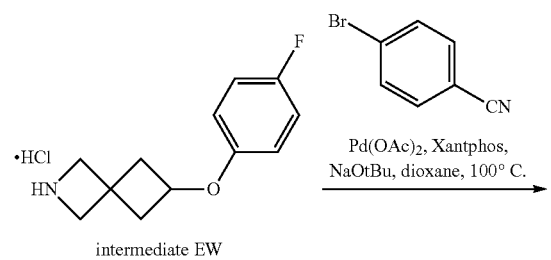

intermediate EW

-continued

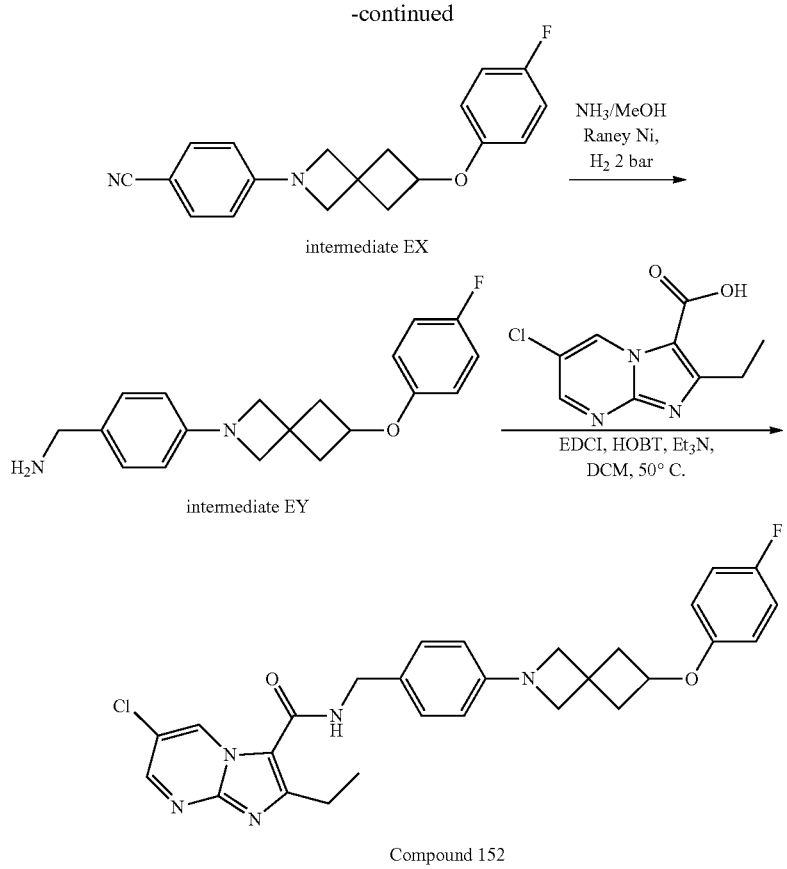

Compound 152

Preparation of Intermediate EV

A solution of DIAD (0.74 mL, 3.75 mmol) in toluene (5 mL) was added to a solution of 6-oxo-2-azaspiro[3.3]heptane-2-carboxylate (CAS [1147557-97-8], 0.8 g, 3.75 mmol), 4-fluorophenol (0.421 g, 3.75 mmol) and triphenylphosphine (1.48 g, 5.63 mmol) in toluene (35 mL) at 0° C. under $N_2$. The reaction mixture was then allowed to warm up to room temperature slowly overnight. Additional 4-fluorophenol (0.21 g, 1.88 mmol) was added and the reaction was stirred further at room temperature for 3 d. The reaction mixture was evaporated to dryness, then dissolved in a minimum of diethyl ether and cooled to 0° C. A large excess of heptane was added and the resulting mixture was evaporated under vacuum which induced the precipitation of $PPh_3O$, which was filtered off and washed with diethyl ether. The filtrate was evaporated to dryness and purified by preparative LC (irregular SiOH, 15-40 μm, 40 g, Grace, dry loading (silica), mobile phase gradient: Heptane/EtOAc from 90/10 to 50/50) to give 1.07 g of intermediate EV as a yellow solid (not obtained pure but engaged as such in the next step).

Preparation of Intermediate EW

A solution of intermediate EV (0.945 g, 3.08 mmol) and chlorotrimethylsilane (1.95 mL, 15.4 mmol) in anhydrous methanol (31 ml) was stirred under $N_2$ overnight. The reaction mixture was then evaporated to dryness and the residue triturated in $Et_2O$, filtered and dried to give 0.543 g of intermediate EW as beige solid (85%).

Preparation of Intermediate EX

A mixture of intermediate EW (0.393 g, 1.90 mmol), 4-bromobenzonitrile (0.518 g, 2.84 mmol) and sodium t-butoxide (0.729 g, 7.59 mmol) in 1,4-dioxane (20 mL) was degassed under $N_2$. Then, palladium acetate (0.043 g, 0.190 mmol) and Xantphos (0.11 g, 0.190 mmol) were added, the mixture was purged again with $N_2$ and heated to 120° C. overnight. The mixture was cooled to room temperature and filtered over a pad of Celite®. The cake was washed with EtOAc and the filtrate was evaporated to dryness. The crude product was purified by preparative LC (irregular SiOH, 15-40 μm, 80 g, Grace, dry loading (silica), mobile phase gradient Heptane/EtOAc from 90/10 to 50/50) to give 0.24 g of intermediate EX as yellow solid (41%).

Preparation of Intermediate EY

Accordingly, intermediate EY was prepared in the same way as intermediate ES starting from intermediate EX yielding 0.304 g as a white solid, 97%

Preparation of Compound 152

Compound 152 was prepared in the same way as Compound 131 (heating 50° C.), starting from intermediate L and intermediate EY. The crude product was purified by preparative LC (irregular SiOH, 15-40 μm, 40 g Grace, dry loading (silica), mobile phase gradient Heptane/EtOAc from 90/10 to 10/90) to give 0.157 g of Compound 152 as a yellow solid (67%).

1H NMR (500 MHz, DMSO-$d_6$) δ ppm 9.38 (d, J=2.5 Hz, 1H), 8.67 (d, J=2.8 Hz, 1H), 8.49 (t, J=5.8 Hz, 1H), 7.19 (d, J=8.2 Hz, 2H), 7.10 (t, J=8.8 Hz, 2H), 6.86 (dd, J=9.1, 4.4 Hz, 2H), 6.39 (d, J=8.2 Hz, 2H), 4.63 (quin, J=6.9 Hz, 1H), 4.40 (d, J=6.0 Hz, 2H), 3.84 (s, 2H), 3.76 (s, 2H), 2.99 (q, J=7.5 Hz, 2H), 2.75-2.72 (m, 2H), 2.26-2.22 (m, 2H), 1.26 (t, J=7.6 Hz, 3H)

Synthesis of Compound 153

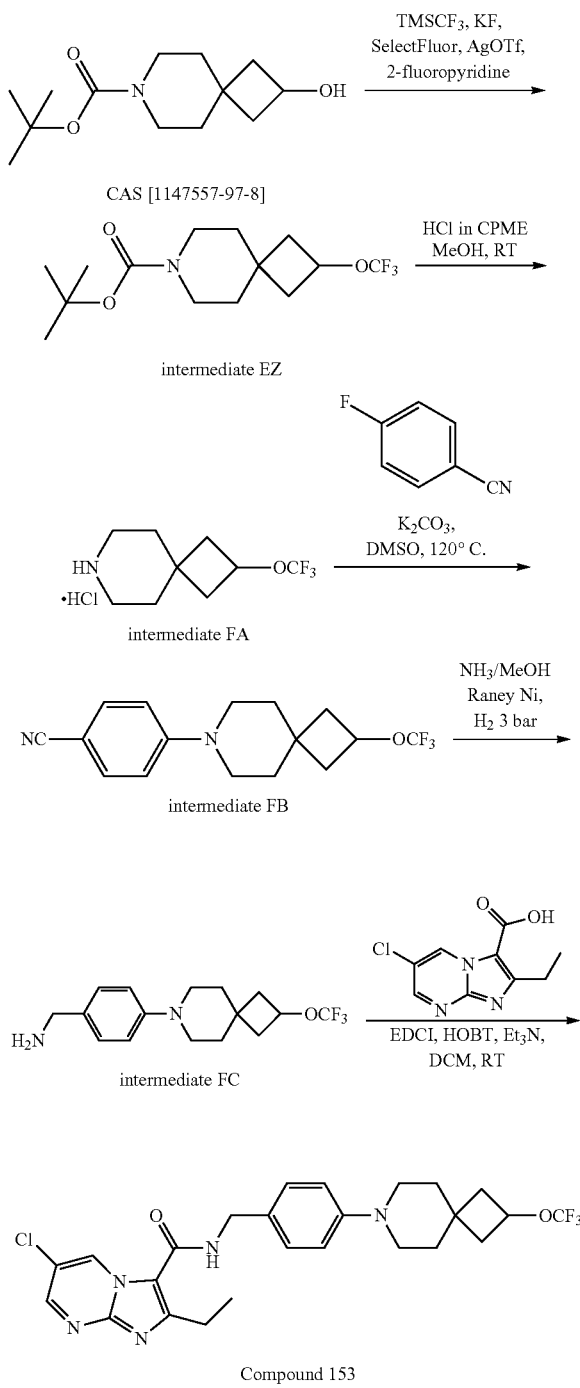

Preparation of Intermediate EZ

Silver triflate (4.79 g, 18.6 mmol), Selectfluor (3.30 g, 9.32 mmol), potassium fluoride (1.44 g, 24.9 mmol) and tert-Butyl 2-hydroxy-7-azaspiro[3.5]nonane-7-carboxylate (CAS [240401-28-9], 1.50 g, 6.22 mmol) were dissolved in ethyl acetate (33 mL). 2-fluoropyridine (1.60 mL) and trifluoromethyltrimethylsilane 2M (9.32 mL, 18.6 mmol) were added under $N_2$ and the resulting mixture was stirred at room temperature for 40 h. The reaction mixture was then filtered over Celite® and evaporated to dryness. The crude mixture was purified by preparative LC (irregular SiOH, 15-40 µm, 120 g, Grace, dry loading (Silica), mobile phase gradient: from Heptane/EtOAc from 90/10 to 80/20) to give 0.855 g of intermediate EZ as white solid (44%).

Preparation of Intermediate FA

Intermediate EZ (0.853 g, 2.76 mmol) was dissolved in methanol (21 mL) and treated with HCl 3M in CPME (4.6 mL, 13.8 mmol) at 0° C. The reaction was then stirred at room temperature overnight. The solvent was removed under reduced pressure to give 0.674 g of intermediate FA as white solid (99%).

Preparation of Intermediate FB

A suspension of intermediate FA (0.67 g, 3.21 mmol), 4-fluorobenzonitrile (0.79 g, 6.45 mmol) and potassium carbonate (3.53 g, 25.5 mmol) in DMSO (32 mL) was heated at 120° C. overnight. The reaction was quenched with water and extracted with EtOAc (3×). The combined organic phases were washed with water (3×) and brine (2×), dried over $MgSO_4$, filtered and evaporated to dryness. The crude product was purified by preparative LC (irregular SiOH 15-40 µm, 40 g Grace, dry loading (silica), mobile phase gradient Heptane/EtOAc from 90/10 to 70/30) to give 0.747 g of intermediate FB as white solid (70%).

Preparation of Intermediate FC

Accordingly, intermediate FC was prepared in the same way as intermediate ES starting from intermediate FB yielding 0.241 g as a white solid, 95%

Preparation of Compound 153

Compound 153 was prepared in the same way as Compound 152, starting from intermediate L and intermediate 103. The crude product was purified by preparative LC (irregular SiOH, 15-40 µm, 40 g, Grace, dry loading (silica), mobile phase gradient Heptane/EtOAc from 90/10 to 10/90) to give 0.222 g of Compound 153 as a yellow solid (59%).

1H NMR (500 MHz, DMSO-$d_6$) δ ppm 9.39 (d, J=2.8 Hz, 1H), 8.67 (d, J=2.5 Hz, 1H), 8.50 (t, J=5.8 Hz, 1H), 7.21 (d, J=8.5 Hz, 2H), 6.90 (d, J=8.5 Hz, 2H), 4.89 (quin, J=7.2 Hz, 1H), 4.42 (d, J=5.7 Hz, 2H), 3.09-3.07 (m, 2H), 3.04-3.02 (m, 2H), 3.00 (q, J=7.5 Hz, 2H), 2.36-2.32 (m, 2H), 1.98-1.94 (m, 2H), 1.66-1.64 (m, 4H), 1.27 (t, J=7.4 Hz, 3H)

Synthesis of Compound 154
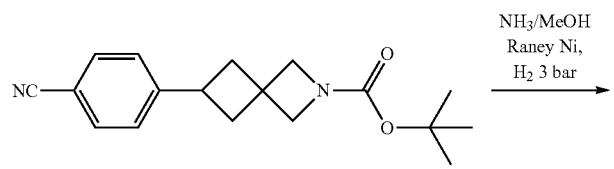
intermediate F
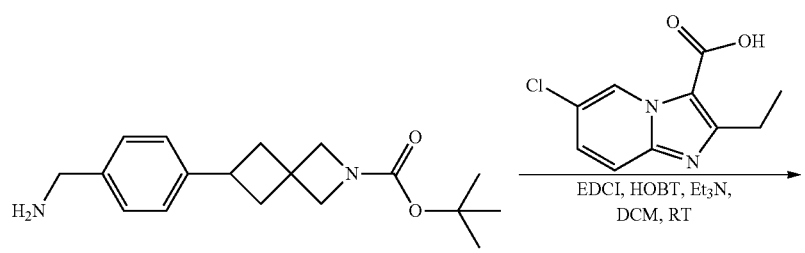
intermediate FD
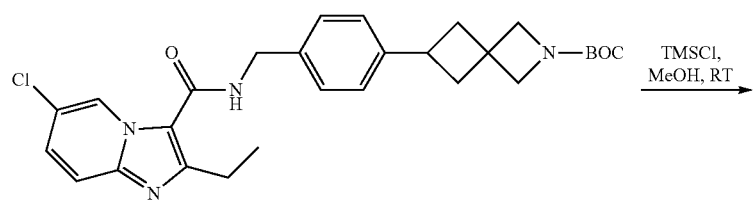
intermediate FE
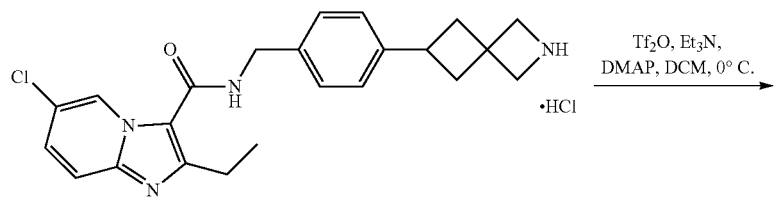
intermediate FF
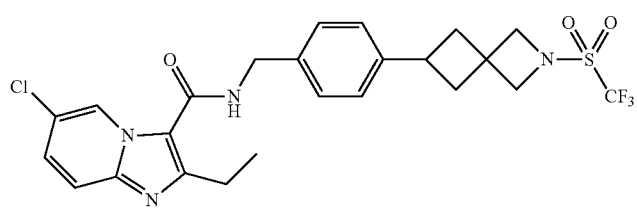
Compound 154

Preparation of Intermediate FD

Accordingly, intermediate FD was prepared in the same way as intermediate ES starting from intermediate F yielding 1.29 g as a white solid, 81%

Preparation of Intermediate FE

To a solution of 6-chloro-2-ethylimidazo[1,2-a]pyridine-3-carboxylic acid (CAS [1216142-18-5], 0.117 g, 0.504 mmol) in DCM (5.1 mL) and triethylamine (0.18 mL) were added EDCI (145 mg, 0.756 mmol) and HOBt (103 mg, 0.760 mmol) and the mixture was stirred at room temperature for 30 min. Intermediate FD (0.162 g, 0.536 mmol) was added and the mixture was stirred at room temperature for 4 h. The mixture was washed with water (2×). The organic layer was dried over MgSO$_4$, filtered and evaporated to dryness to give 0.293 g of intermediate FE as colourless oil (quant.), used as such in the next step.

Preparation of Intermediate FF

To a solution of intermediate FE (0.291 g, 0.572 mmol) in methanol (5.9 mL) was added trimethylchlorosilane (0.37 mL, 2.94 mmol) and the mixture was stirred at room temperature for 16 h. The mixture was evaporated to dryness to give 0.304 g of intermediate FF as a pale yellow foam (quant.).

Preparation of Compound 154

Trifluoromethanesulfonic anhydride (0.12 mL, 0.696 mmol) was added to a solution of intermediate FF (155 mg, 0.348 mmol) and DMAP (2.13 mg, 17.4 µmol) in triethylamine (0.39 mL, 2.78 mmol) and DCM (5.3 mL) at 0° C. The resulting mixture was stirred at 0° C. for 6 h. Water was added and the organic layer was washed with water, dried over MgSO$_4$, filtered and evaporated to dryness. The crude product was purified by preparative LC (irregular SiOH, 15-40 µm, 40 g, Grace, dry loading (silica), mobile phase gradient Heptane/EtOAc from 90/10 to 10/90) to obtain 186 mg of a pale yellow solid, which was triturated in heptane and purified by preparative LC (spherical C18 25 µm, 40 g YMC-ODS-25, dry loading (Celite®), mobile phase gradient: 0.2% aq. NH$_4$HCO$_3$/MeCN from 90/10 to 0/100) to give 0.112 g of Compound 154 as a white solid (59%).

1H NMR (400 MHz, DMSO-d$_6$) δ ppm 9.07 (s, 1H), 8.47 (br s, 1H), 7.67 (d, J=8.1 Hz, 1H), 7.46 (br d, J=9.1 Hz, 1H), 7.30 (br d, J=8.1 Hz, 2H), 7.20 (br d, J=7.6 Hz, 2H), 4.49 (br d, J=5.1 Hz, 2H), 4.41 (s, 2H), 4.18 (s, 2H), 3.39-3.31 (m, 1H), 2.98 (q, J=7.4 Hz, 2H), 2.63-2.58 (m, 2H), 2.34-2.29 (m, 2H), 1.26 (br t, J=7.3 Hz, 3H)

Synthesis of Compound 155 & Compound 156

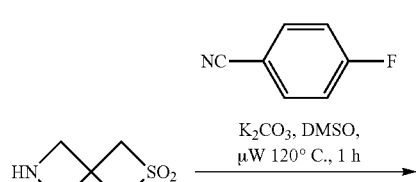

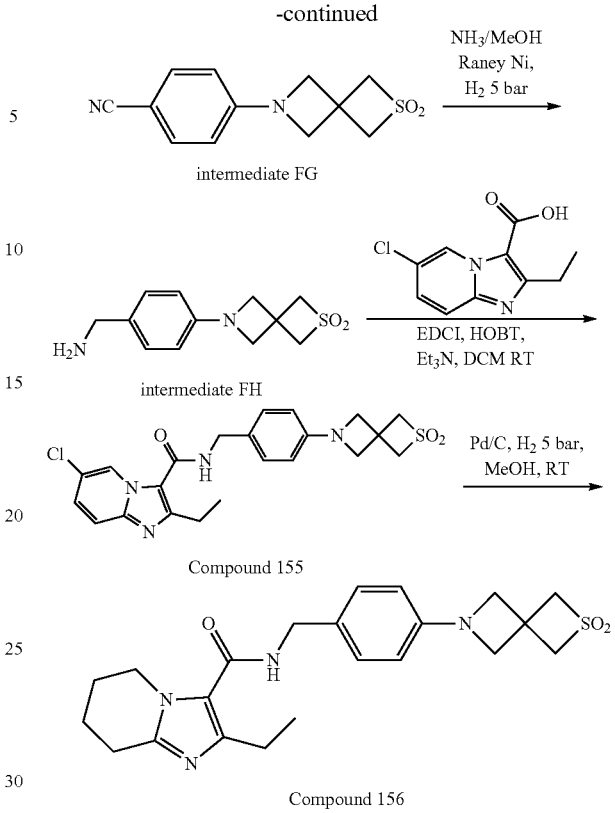

Preparation of Intermediate FG

Accordingly, intermediate FG was prepared in the same way as intermediate DK starting from 2-Thia-6-azaspiro[3.3]heptane 2,2-dioxide CAS [1263182-09-7] and 4-fluorobenzonitrile, yielding 0.206 g as a white solid, 51%

Preparation of Intermediate FH

Accordingly, intermediate FH was prepared in the same way as intermediate ES starting from intermediate FG yielding 0.208 g as a white solid, 93%

Preparation of Compound 155

Compound 155 was prepared in the same way as Compound 153, starting from 6-chloro-2-ethylimidazo[1,2-a]pyridine-3-carboxylic acid CAS [1216142-18-5] and intermediate FH. The crude product was purified by preparative LC (irregular SiOH, 15-40 µm, 24 g, Grace, dry loading (silica), mobile phase gradient Heptane/EtOAc from 90/10 to 10/90) and yielding 0.252 g of Compound 155 as a white solid (69%).

1H NMR (400 MHz, DMSO-d$_6$) δ ppm 9.05 (s, 1H), 8.40 (br s, 1H), 7.66 (d, J=8.6 Hz, 1H), 7.45 (d, J=9.6 Hz, 1H), 7.21 (d, J=7.1 Hz, 2H), 6.46 (d, J=8.1 Hz, 1H), 4.47 (d, J=1.5 Hz, 4H), 4.41 (br s, 2H), 3.99 (s, 4H), 2.96 (q, J=7.4 Hz, 2H), 1.25 (t, J=7.4 Hz, 3H)

Preparation of Compound 156

A solution of Compound 155 (0.117 g, 255 µmol) in methanol (5.6 mL) was degassed by N$_2$ bubbling for 5 min before the addition of Pd/C 10% (8.99 mg, 8.44 µmol). The resulting mixture was stirred at room temperature under 5 bar of H2 overnight. The mixture was filtered through a pad of Celite®, rinsed with EtOAc and evaporated to dryness. The crude product was purified by preparative LC (Regular SiOH 15-40 μm, 24 g Grace, dry loading (silica), mobile phase gradient Heptane/EtOAc from 70/30 to 0/100 then MeOH 100%) to give 0.095 g of Compound 156 as white solid (69%).

1H NMR (400 MHz, DMSO-$d_6$) δ ppm 8.10 (br t, J=5.6 Hz, 1H), 7.13 (d, J=8.6 Hz, 2H), 6.44 (d, J=8.1 Hz, 2H), 4.46 (s, 4H), 4.29 (br d, J=6.1 Hz, 2H), 3.98 (s, 4H), 3.97-3.94 (m, 2H), 2.71-2.68 (m, 2H), 2.58 (q, J=7.4 Hz, 2H), 1.83-1.78 (m, 4H), 1.08 (t, J=7.6 Hz, 3H)

Synthesis of Compound 157 filtered and evaporated to dryness. The crude mixture was purified by preparative LC (irregular SiOH, 15-40 μm, 120 g, Grace, liquid loading (DCM), mobile phase gradient Heptane/EtOAc from 90/10 to 70/30) to give 0.274 g of intermediate FI as white solid (65%).

Preparation of Intermediate FJ

To a solution of intermediate FI (0.172 g, 0.73 mmol) in water (2.4 mL) and ethanol (2.4 mL) was added sodium hydroxide (0.088 g, 2.19 mmol) and the mixture was stirred at room temperature overnight. The mixture was acidified to pH 3 with HCl (3N). EtOH was evaporated and the residue was basified with KOH solution. The resulting white precipitate was collected by filtration and acidified with HCl

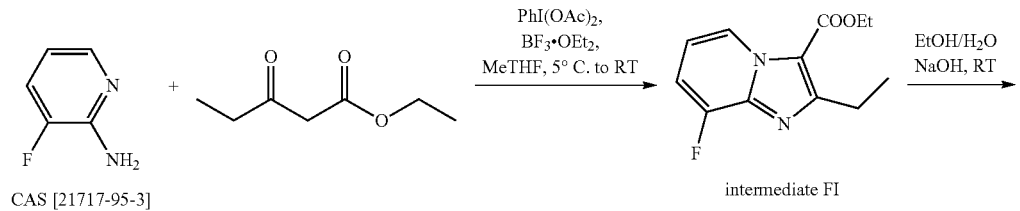

intermediate FI

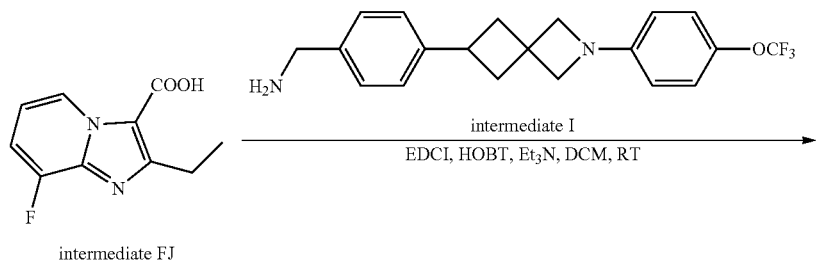

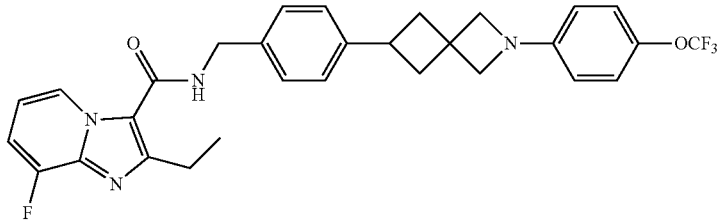

Compound 157

Preparation of Intermediate FI

A solution of 2-amino-3-fluoropyridine (CAS [21717-95-3], 0.2 g, 1.78 mmo) in Me-THF (9 mL) was cooled down to 5° C. Ethyl 3-oxovalerateethyl 3-oxovalerate (0.50 mL, 3.53 mmol), iodobenzene diacetate (0.578 g, 1.79 mmol) and boron trifluoride etherate (0.024 mL, 0.089 mmol) were added successively. The solution was stirred at the 5° C. for 2 h and then warmed to room temperature overnight. EtOAc and saturated aqueous NaHCO$_3$ were added. The layers were separated and the aqueous layer was extracted with EtOAc. The combined organic layers were dried over MgSO$_4$, (1M) to pH 1 and the white solid was filtered and dried to give 0.119 g of intermediate FJ as a white solid (79/%).

Preparation of Compound 157

Compound 157 was prepared in the same way as Compound 131, starting from intermediate FJ and intermediate I. The crude product was purified by preparative LC (irregular SiOH, 15-40 μm, 40 g, Grace, dry loading (silica), mobile phase gradient Heptane/EtOAc from 90/10 to 10/90) to give 0.091 g of JNJ-65053092-AAA as a white solid (42%).

1H NMR (500 MHz, DMSO-$d_6$) δ ppm 8.76 (d, J=6.9 Hz, 1H), 8.56 (br t, J=5.7 Hz, 1H), 7.32-7.27 (m, 3H), 7.22 (d, J=8.2 Hz, 2H), 7.14 (d, J=8.5 Hz, 2H), 7.00-6.96 (m, 1H), 6.45 (d, J=9.1 Hz, 2H), 4.50 (d, J=6.0 Hz, 2H), 3.96 (s, 2H), 3.75 (s, 2H), 3.45-3.38 (m, 1H), 2.99 (q, J=7.6 Hz, 2H), 2.60-2.55 (m, 2H), 2.30-2.26 (m, 2H), 1.27 (t, J=7.6 Hz, 3H)
The following compounds were also prepared in accordance with the procedures disclosed herein:
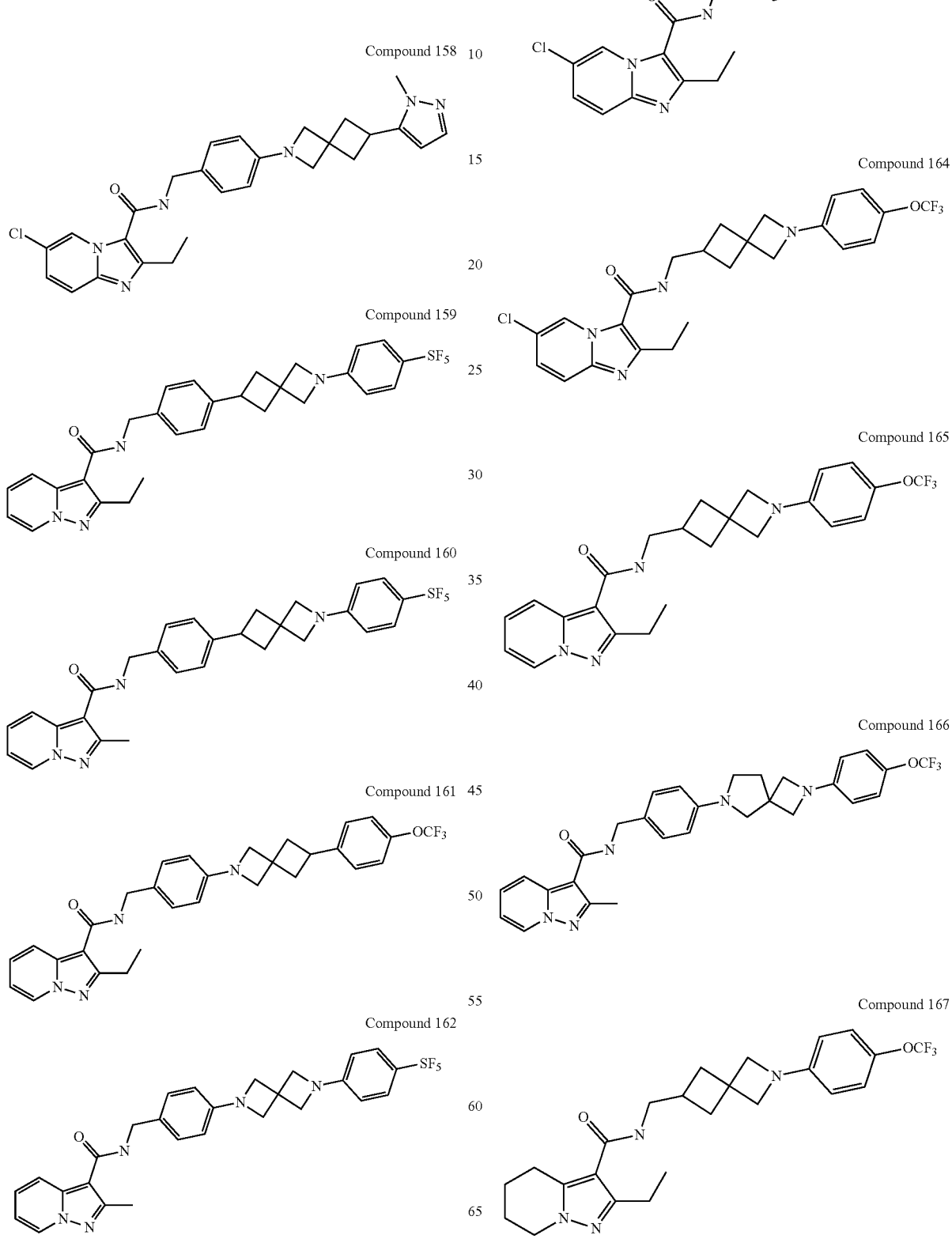

Compound 168

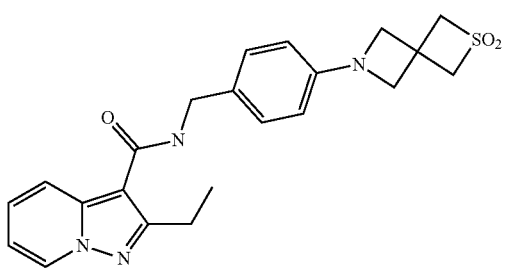

Characterising Data Table

| Compound No | Melting Point (Kofler or DSC) | LCMS Rt | UV Area % | MW exact | BPM1/ BPM2 | LCMS Method |
|---|---|---|---|---|---|---|
| 1 | | 3.21 | 97.9 | 506.2 | 507.1 | Method A |
| 17 | | 3.18 | 98.3 | 427.2 | 428.1 | Method A |
| 2 | | 4.40 | 96.9 | 568.2 | 569.1 | Method A |
| 3 | | 4.88 | 99.3 | 569.2 | 570.1 | Method A |
| 23 | | 3.39 | 94.2 | 450.2 | 451.2 | Method A |
| 22 | | 3.72 | 99.6 | 484.2 | 485.1 | Method A |
| 5 | | 4.45 | 99.3 | 570.2 | 571.1 | Method A |
| 9 | | 4.08 | 97.0 | 485.2 | 486.1 | Method A |
| 7 | | 3.96 | 100.0 | 568.2 | 569.1 | Method A |
| 15 | | 4.41 | 100.0 | 520.2 | 521.2 | Method B |
| 4 | | 4.10 | 98.1 | 569.2 | 570.1 | Method A |

Characterising Data Table

| Compound No | Melting Point (Kofler or DSC) | LCMS Rt | UV Area % | MW exact | BPM1/ BPM2 | LCMS Method |
|---|---|---|---|---|---|---|
| 12 | 25° C. to 300° C./ 10° C.min/ 40 µl Al | 3.33 | 98.7 | 394.2 | 395.4/ 393.1 | Method C |
| 25 | | 3.69 | 95.0 | 620.2 | 621.2 | Method A |
| 6 | | 3.64 | 99.4 | 539.3 | 540.2 | Method A |
| 8 | | 4.49 | 97.7 | 569.2 | 570.1 | Method A |
| 10 | | 4.16 | 92.1 | 610.2 | 611.1 | Method A |
| 18 | | 5.10 | 99.1 | 412.2 | 413.1 | Method A |
| 24 | | 3.96 | 96.3 | 526.2 | 527.1 | Method A |
| 13 | 131.37° C./ −58.88 J/g 25° C. to 350° C./ 10° C.min/ 40 µl Al | 3.43 | 98.8 | 444.1 | 445/ 442.9 | Method C |
| 16 | | 4.12 | 98.4 | 426.2 | 427.7 | Method B |
| 26 | | 3.52 | 100.0 | 619.2 | 620.2 | Method A |
| 19 | | 2.52 | 99.6 | 396.2 | 397.1 | Method A |
| 11 | | 2.52 | 97.1 | 486.2 | 487.1/ 409/ | Method A Method C |
| 21 | | 2.58 | 96.7 | 410.2 | 407 | |
| 14 | | 3.29 | 100.0 | 550.2 | 551.2 | Method A |
| 27 | 136° C. (Kofler) | 2.47 | 92.7 | 396.2 | 397.1/ 395 | Method C |
| 28 | | 2.44 | 95.5 | 485.2 | 486.1 | Method A |
| 29 | | 4.45 | 98.2 | 534.2 | 535.1 | Method B |
| 30 | 160° C. (Kofler) | 2.38 | 99.4 | 368.1 | 369/ 367 | Method C |
| 31 | | 2.39 | 97.7 | 406.2 | 407.2 | Method A |

Further Characterising Data

| Compound No. | Melting Point (Kofler or DS) | LCMS Rt | UV Area % | MW (theor) | BPM1/ BPM2 | LSMS Method |
|---|---|---|---|---|---|---|
| 28 | | 3.78 | 96.6 | 597.2 | 598.1 | METHOD D |
| 14 | | 3.29 | 100.0 | 550.2 | 551.2 | METHOD D |
| 15 | | 4.41 | 100.0 | 520.2 | 521.2 | METHOD E |
| 1 | | 3.21 | 97.9 | 506.2 | 507.1 | METHOD D |
| 7 | | 3.96 | 100.0 | 568.2 | 569.1 | METHOD D |
| 29 | | 4.45 | 98.2 | 534.2 | 535.1 | METHOD E |
| 81 | | 3.79 | 100.0 | 454.2 | 455.1 | METHOD E |
| 16 | | 3.01 | 99.7 | 426.2 | 427.1 | METHOD D |
| 4 | 184.57° C./−35.49 J/g 25° C. to 350° C./10° C.min/40 µl Al | 3.72 | 98.73 | 569.18 | 570.2/ 568.6 | METHOD F |
| 24 | | 3.96 | 96.3 | 526.2 | 527.1 | METHOD D |
| 23 | | 3.39 | 94.2 | 450.2 | 451.2 | METHOD D |
| 26 | | 3.52 | 100.0 | 619.2 | 620.2 | METHOD D |
| 22 | | 3.72 | 99.6 | 484.2 | 485.1 | METHOD D |
| 2 | | 4.40 | 96.9 | 568.2 | 569.1 | METHOD D |
| 3 | | 4.61 | 97.6 | 569.2 | 570.1 | METHOD D |
| 77 | | 2.44 | 95.47 | 485.2 | 486.1 | METHOD D |
| | | 4.49 | 97.71 | 569.2 | 570.1 | METHOD D |
| 9 | | 4.08 | 97.02 | 485.2 | 486.1 | METHOD D |
| 13 | 131.37° C./−58.88 J/g 25° C. to 350° C./10° C.min/40 µl Al | 3.43 | 98.8 | 444.1 | 445/ 442.9 | METHOD F |
| 12 | see curve 25° C. to 300° C./10° C.min/40 Al | 3.33 | 98.7 | 394.2 | 395.4/ 393.1 | METHOD F |
| 5 | 242.43° C./−52.69 J/g 25° C. to 350° C./10° C.min/40 µl Al | 3.56 | 98.2 | 570.2 | 571.3/ 569.5 | METHOD F |
| 30 | 160° C. (Kofler) 300° C./10° C.min/40 µl Al | 2.11 | 98.2 | 368.1 | 369/ 367 | METHOD F |

-continued

| Compound No. | Melting Point (Kofler or DS) | LCMS Rt | UV Area % | MW (theor) | BPM1/ BPM2 | LSMS Method |
|---|---|---|---|---|---|---|
| 20 | see curve 25° C. to 350° C./10° C.min/40 μl Al | 2.38 | 99.4 | 410.2 | 411.1/ 409.1 | METHOD F |
| 27 | 136° C. (Kofler) | 2.47 | 92.7 | 396.2 | 397.1/ 395 | METHOD F |
| 21 | | 2.77 | 99.3 | 408.2 | 409.1 | METHOD G |
| 11 | | 2.52 | 97.06 | 486.1 | 487.1 | METHOD D |
| 18 | | 5.1 | 99.14 | 412.2 | 413.1 | METHOD H |
| 10 | | 4.16, 4.22 | 92.14, 4.77 | 610.2 | 611.1, 611.1 | METHOD D |
| 17 | | 3.18 | 98.34 | 427.2 | 428.1 | METHOD D |
| 19 | | 2.52 | 99.61 | 396.2 | 397.1 | METHOD D |
| 6 | | 3.64 | 99.4 | 539.3 | 540.2 | METHOD D |
| 31 | | 2.39 | 97.7 | 406.2 | 407.2 | METHOD D |
| 66 | | 4.41 | 97.7 | 611.2 | 612.1 | METHOD D |
| 80 | | 4.93 | 100.0 | 582.2 | 583.1 | METHOD D |
| 32 | | 3.48 | 99.5 | 506.2 | 507.1 | METHOD D |
| 79 | | 4.86 | 98.7 | 583.2 | 584.1 | METHOD D |
| 34 | | 3.52 | 96.45 | 406.2 | 407.2 | METHOD E |
| 35 | | 4.59 | 98.76 | 510.2 | 511.2 | METHOD D |
| 68 | 180.57° C./−42.61 J/g 25° C/ to 350° C./10° C.min/40 μl Al | 3.62 | 99.3 | 555.2 | 556.2/ 554.5 | METHOD F |
| 64 | | 3.4 | 98.1 | 492.2 | 493.1 | METHOD D |
| 39 | | 4.27 | 98.46 | 519.2 | 520 | METHOD D |
| 40 | | 3.72 | 97.68 | 447.2 | 448.1 | METHOD D |
| 38 | | 4.03 | 97.72 | 520.2 | 521.1 | METHOD D |
| 41 | | 2.77 | 98.27 | 491.3 | 492.2 | METHOD D |
| 70 | | 3.53 | 99.43 | 554.3 | 555.2 | METHOD D |
| 43 | | 4.02 | 99.14 | 535.0 | 535.1 | METHOD D |
| 44 | | 3.91 | 97.85 | 461.2 | 462.1 | METHOD D |
| 78 | | 3.53 | 99.32 | 411.2 | 412.2 | METHOD E |
| 48 | | 3.03 | 99.74 | 476.2 | 477.2 | METHOD D |
| 49 | | 2.93 | 97.41 | 486.2 | 487.2 | METHOD D |
| 61 | | 3 | 98.65 | 490.3 | 491.2 | METHOD D |
| 46 | | 2.83 | 95.62 | 505.3 | 506.2 | METHOD D |
| 47 | | 3.71 | 95 | 549.2 | 550.2 | METHOD D |
| 51 | | 3.67 | 98.3 | 549.6 | 550.1 | METHOD D |
| 53 | | 2.92 | 100.0 | 486.2 | 487.2 | METHOD D |
| 52 | | 3.11 | 93.0 | 500.2 | 501.2 | METHOD D |
| 65 | | 3.95 | 96.8 | 538.3 | 539.2 | METHOD D |
| 69 | | 3.79 | 98.8 | 553.3 | 554.2 | METHOD D |
| 33 | | 3.43 | 98.0 | 447.2 | 448.1 | METHOD D |
| 63 | | 5.51 | 95.4 | 507.2 | 508.1 | METHOD H |
| 60 | | 3.55 | 100.0 | 521.2 | 522.1 | METHOD D |
| 71 | | 3.55 | 100.0 | 553.3 | 554.2 | METHOD D |
| 36 | | 3.62 | 99.5 | 548.2 | 549.2 | METHOD D |
| 37 | | 4.35 | 98.4 | 509.2 | 510.2 | METHOD D |
| 42 | | 4.28 | 99.9 | 510.2 | 511.2 | METHOD D |
| 45 | | 4.16 | 98.8 | 509.2 | 510.1 | METHOD D |
| 50 | | 2.87 | 98.8 | 500.2 | 501.2 | METHOD D |
| 54 | | 3.70 | 99.1 | 507.2 | 508.1 | METHOD D |
| 55 | | 2.90 | 99.2 | 486.2 | 487.1 | METHOD D |
| 97 | | 4.40 | 99.9 | 549.2 | 550.2 | METHOD D |
| 98 | | 4.47 | 99.9 | 549.2 | 550.2 | METHOD D |
| 99 | | 2.85 | 100.0 | 486.2 | 487.2 | METHOD D |
| 100 | | 5.57 | 100.0 | 461.2 | 462.2 | METHOD H |
| 101 | | 3.70 | 100.0 | 522.0 | 522.1 | METHOD D |
| 102 | | 4.90 | 100.0 | 549.2 | 550.2 | METHOD D |
| 103 | | 4.97 | 100.0 | 549.2 | 550.2 | METHOD D |
| 104 | | 3.61 | 99.4 | 548.2 | 549.2 | METHOD D |
| 105 | | 3.78 | 100.0 | 501.2 | 502.2 | METHOD D |
| 106 | | 3.77 | 98.67 | 487.2 | 488.1 | METHOD D |
| 107 | | 3.75 | 100.0 | 501.2 | 502.2 | METHOD D |
| 108 | | 3.80 | 98.6 | 487.2 | 488.1 | METHOD D |
| 109 | | 3.95 | 96.4 | 500.2 | 501.2 | METHOD E |
| 58 | | 4.47 | 98.9 | 570.2 | 571.1 | METHOD D |
| 67 | | 4.39 | 98.9 | 554.2 | 555.1 | METHOD D |
| 110 | | 5.61 | 99.0 | 506.2 | 507.1 | METHOD H |
| 72 | | 4.16 | 99.5 | 568.2 | 569.1 | METHOD G |

-continued

| Compound No. | Melting Point (Kofler or DS) | LCMS Rt | UV Area % | MW (theor) | BPM1/ BPM2 | LSMS Method |
|---|---|---|---|---|---|---|
| 111 | | 2.87 | 97.8 | 500.2 | 501.2 | METHOD G |
| 73 | | 3.61, 3.68 | 91.65, 7.33 | 569.2 | 570.1 | METHOD I |
| 74 | | 5.43 | 99.9 | 553.3 | 554.2 | METHOD H |
| 112 | | 3.74 | 98.9 | 548.2 | 549.2 | METHOD G |
| 113 | | 5.18 | 99.1 | 520.2 | 521.1 | METHOD J |
| 56 | | 4.86 | 96.5 | 550.2 | 551.2 | METHOD G |
| 57 | | 4.47 | 96.8 | 551.2 | 552.1 | METHOD G |
| 59 | | 3.67 | 95.3 | 502.2 | 503.1 | METHOD G |
| 114 | | 5.40 | 99.1 | 581.2 | 582.1 | METHOD G |
| 115 | | 5.07 | 98.0 | 509.2 | 510.2 | METHOD G |
| 76 | 136.04° C./−55.97 J/g 25° C. to 350° C./10° C.min/40 µl Al | 3.88 | 96.9 | 583.2 | 584.3/ 582.7 | METHOD F |
| 75 | 183.86° C./−50.09 J/g 25° C. to 300° C./10° C.min/40 µl Al | 3.89 | 100.0 | 583.2 | 584.3/ 582.6 | METHOD F |
| 92 | 80.75° C./−33.76 J/g 25° C. to 350° C./10° C.min/40 µl Al | 3.16 | 100 | 504.2 | 505.1/ 503.5 | METHOD F |
| 116 | | 2.86 | 99.8 | 436.2 | 437.1 | METHOD G |
| 84 | 137.48° C./−87.44 J/g 25° C. to 350° C./10° C.min/40 µl Al | 3.06 | 100.0 | 438.2 | 439.1/ 437.4 | METHOD F |
| 87 | 190.35° C./−55.85 J/g 25° C./ to 250° C./10° C.min/40 µl Al | 3.61 | 100.0 | 532.2 | 533.2/ 531.6 | METHOD F |
| 88 | 156.54° C./ −49.74 J/g 25° C. to 350° C./10° C.min/40 µl Al | 3.44 | 97.2 | 533.2 | 534.2/ 532.4 | METHOD F |
| 86 | 127.22° C./−63.46 J/g 25° C. to 350° C./10° C.min/40 µl Al | 2.85 | 96.4 | 439.2 | 440.1/ 438.3 | METHOD F |
| 83 | 108.84° C./−49.64 J/g 25° C. to 350° C./10° C.min/40 µl Al | 3.86 | 100.0 | 554.2 | 555.2 613.6 [M + CH$_3$COO]— 539.4/ | METHOD F |
| 82 | 190.78° C./−58.34 J/g 25° C. to 350° C./10° C.min/40 µl Al | 3.54 | 96.8 | 538.3 | 597.6 [M + CH$_3$COO]— | METHOD F |
| 117 | 167.85° C./−87.32 J/g 25° C. to 350° C./10° C.min/40 µl Al | 3.48 | 100.0 | 492.2 | 493.1/ 491.4 | METHOD F |
| 89 | 192.86° C./−45.19 J/g 25° C. to 220° C./10° C.min/40 µl Al | 3.02 | 100.0 | 485.2 | 486.2/ 484.4 | METHOD F |
| 85 | 147.41° C./−31.45 J/g | 2.52 | 99.5 | 408.3 | 409.2/ 467.3 [M + CH$_3$COO]— | METHOD F |
| 90 | 237.63° C./−116.22 J/g 25° C. to 300° C./10° C.min/40 µl Al | 2.30 | 100.0 | 451.2 | 452.5/ 450.2 | METHOD K |
| 91 | 204.21° C./−81.42 J/g 25° C. to 300° C./10° C.min/40 µl Al | 2.72 | 100.0 | 513.2 | 514.5/ 512.3 | METHOD K |
| 93 | 182.04° C./−67.31 J/g 25° C. to 300° C./10° C.min/40 µl Al | 3.19 | 98.32 | 486.2 | 487.5/ 485.3 | METHOD K |
| 118 | 201.34° C./−67.10 J/g^−1 25° C. to 350° C./10° C.min/40 µl Al | 2.39 | 94.45 | 398.1 | 399.4/ 397.2 | METHOD K |
| 119 | 147.85° C./−51.51 J/g 2.5° C. to 350° C./10° C.min/40 µl Al | 3 | 100 | 485.2 | 486.4/ 484.3 | METHOD K |
| 120 | 139.57° C./−113.34 J/g 25° C. to 350° C./10° C.min/40 µl Al | 3.02 | 100 | 485.2 | 486.5/ 484.2 | METHOD K |
| 94 | 168.80° C./−55.36 J/g 25° C. to 350° C./10° C.min/40 µl Al | 3.61 | 99.27 | 485.2 | 486.1/ 484.3 | METHOD F |
| 95 | 154.23° C./−78.85 J/g 25° C. to 350° C./10° C.min/40 µl Al | 2.84 | 100 | 480.2 | 481.4/ 497.2 | METHOD K |
| 121 | 241.08° C./−75.05 J/g 25° C. to 350° C./10° C.min/40 µl Al | 2.65 | 96.76 | 487.2 | 488.1/ 486.3 | METHOD F |

-continued

| Compound No. | Melting Point (Kofler or DS) | LCMS Rt | UV Area % | MW (theor) | BPM1/ BPM2 | LSMS Method |
|---|---|---|---|---|---|---|
| 122 | 161.23° C./−54.16 J/g 25° C. to 350° C./10° C.min/40 μl Al | 2.92 | 96.6 | 486.2 | 487.1/ 485.4 | METHOD F |
| 96 | 182.82° C./−91.28 J/g 25° C. to 300° C./10° C.min/40 μl Al | 2.62 | 100 | 422.2 | 423.5/ 421.2 | METHOD K |
| Cpd 123 | 166.63° C./−55.15 J/g, 25° C. to 300° C./10° C.min/40 μl Al (DSC: 25° C. to 300° C./10° C.min/40 μl Al) | 2.58 | 97.1 | 475.2 | 476.2/ 474.3 | METHOD F |
| Cpd 124 | 135.97° C./−75.64 J/g, 25° C. to 300° C./10° C.min/40 μl Al (DSC: 25° C. to 300° C./10° C.min/40 μl Al) | 3.02 | 100.0 | 491.2 | 492.4/ 490.3 | METHOD K |
| Cpd 125 | 146.77° C./−81.28 J/g^−1, 25° C. to 350° C./10° C.min/40 μl Al (DSC: 25° C. to 350° C./10° C.min/40 μl Al) | 3.35 | 100.0 | 472.2 | 473.1/ 471.3 | METHOD F |
| Cpd 126 | 187.49° C./−68.56 J/g; 289.39° C./+284.49 J/g (DSC: 25° C. to 300° C./10° C.min/40 μl Al) | 2.59 | 99.3 | 423.1 | 424/ 482.2 [M + CH$_3$COO]— | METHOD F |
| Cpd 127 | 201.15° C./−111.61 J/g (DSC: 25° C. to 300° C./10° C.min/40 μl Al) | 3.39 | 98.7 | 436.2 | 437.1/ 495.3 [M + CH$_3$COO]— | METHOD F |
| Cpd 128 | 160.59° C./−94.05 J/g (DSC: 25° C. to 300° C./10° C.min/40 μl Al) | 2.97 | 100.0 | 505.2 | 506.1/ 504.3 | METHOD F |
| Cpd 129 | 188.46° C./−42.53 J/g (DSC: 25° C. to 350° C./10° C.min/40 μl Al) | 2.68 | 90.7 | 414.1 | 414.9/ 413.1 | METHOD F |
| Cpd 158 | 101.95° C./−40.87 J/g (DSC: 25° C. to 350° C./10° C.min/40 μl Al) | 2.93 | 100.0 | 488.2 | 489.1/ 487.4 | METHOD F |
| Cpd 152 | see curve (DSC: 25° C. to 350° C./10° C.min/40 μl Al) | 3.41 | 98.5 | 519.2 | 520.1/ 518.4 | METHOD F |
| Cpd 148 | 158.14° C./−65.57 J/g (DSC: 25° C. to 350° C./10° C.min/40 μl Al) | 3 | 100.0 | 445.1 | 446/ 444.3 | METHOD F |
| Cpd 133 | 84.29° C./−42.38 J/g^−1 (DSC: 25° C. to 350° C./10° C.min/40 μl Al) | 3.18 | 100.0 | 473.2 | 474.1/ 472.3 | METHOD F |
| Cpd 159 | 177.08° C./−85.31 J/g (DSC: 25° C. to 350° C./10° C.min/40 μl Al) | 3.76 | 100.0 | 576.2 | 575.4/ 577.2 | METHOD F |
| Cpd 141 | 158.48° C./−115.36 J/g^−1 (DSC: 25° C. to 350° C./10° C.min/40 μl Al) | 3.64 | 98.9 | 520.2 | 521.2/ 579.5 [M + CH$_3$COO]— | METHOD F |
| Cpd 142 | 193.19° C./−79.28 J/g^−1 (DSC: 25° C. to 350° C./10° C.min/40 μl Al) | 3.4 | 100.0 | 521.2 | 522.2/ 580.5 [M + CH$_3$COO]— | METHOD F |
| Cpd 131 | 172.76° C./−68.86 J/g (DSC: 25° C. to 350° C./10° C.min/40 μl Al) | 3.31 | 100.0 | 493.1 | 494.1/ 492.3 | METHOD F |

-continued

| Compound No. | Melting Point (Kofler or DS) | LCMS Rt | UV Area % | MW (theor) | BPM1/ BPM2 | LSMS Method |
|---|---|---|---|---|---|---|
| Cpd 144 | 135.80° C./−64.11 J/g^−1 (DSC: 25° C. to 350° C./10° C.min/40 μl Al) | 3.51 | 97.8 | 535.2 | 536.2/ 594.5 [M + CH$_3$COO]— | METHOD F |
| Cpd 138 | 105.98° C./−50.26 J/g (DSC: 25° C. to 350° C./10° C.min/40 μl Al) | 3.75 | 98.5 | 534.2 | 535.2/ 593.5 [M + CH$_3$COO]— | METHOD F |
| Cpd 130 | 169.56° C./−68.85 J/g (DSC: 25° C. to 350° C./10° C.min/40 μl Al) | 2.91 | 100.0 | 462.2 | 463.5/ 521.3 [M + CH$_3$COO]— | METHOD K |
| Cpd 134 | 188.07° C./−99.63 J/g (DSC: 25° C. to 350° C./10° C.min/40 μl Al) | 2.89 | 100.0 | 486.2 | 487.2/ 485.5 | METHOD F |
| Cpd 160 | 166.29° C./−77.23 J/g (DSC: 25° C. to 350° C./10° C.min/40 μl Al) | 3.52 | 100.0 | 562.2 | 563.4/ 621.4 [M + CH$_3$COO]— | METHOD K |
| Cpd 143 | 130.31° C./−83.46 Jg^−1 (DSC: 25° C. to 350° C./10° C.min/40 μl Al) | 2.73 | 97.9 | 378.2 | 379/ 437.3 | METHOD F |
| Cpd 153 | 150.61° C./−64.88 J/g^−1 (DSC: 25° C. to 350° C./10° C.min/40 μl Al) | 3.5 | 98.7 | 521.2 | 522./ 520.5 | METHOD F |
| Cpd 161 | 126.57° C./−47.92 J/g (DSC: 25° C. to 350° C./10° C.min/40 μl Al) | 3.61 | 100.0 | 534.2 | 535.5/ 593.3 [M + CH$_3$COO]— | METHOD K |
| Cpd 162 | 238.06° C./−64.81 J/g (DSC: 25° C. to 350° C./10° C.min/40 μl Al) | 3.27 | 100.0 | 563.2 | 564.5/ 622.4 [M + CH$_3$COO]— | METHOD K |
| Cpd 132 | 149.46° C./−64.76 J/g (DSC: 25° C. to 350° C./10° C.min/40 μl Al) | 2.99 | 100.0 | 486.2 | 487.1/ 485.4 | METHOD F |
| Cpd 163 | 142.39° C./−61.91 J/g (DSC: 25° C. to 350° C./10° C.min/40 μl Al) | 3.37 | 100.0 | 408.2 | 409.4 407.4 | METHOD K |
| Cpd 149 | 141.92° C./−60.55 J/g (DSC: 25° C. to 350° C./10° C.min/40 μl Al) | 3.98 | 100.0 | 586.2 | 587.4/ 585.3 | METHOD K |
| Cpd 164 | 165.12° C./−58.86 J/g (DSC: 25° C. to 350° C./10° C.min/40 μl Al) | 3.52 | 100.0 | 492.15 | 493.5/ 491.2 | METHOD K |
| Cpd 157 | 144.55° C./−60.51 J/g^−1 (DSC: 25° C. to 350° C./10° C.min/40 μl Al) | 3.67 | 99.5 | 552.2 | 553.5/ 551.4 | METHOD K |
| Cpd 139 | 135.21° C./−62.94 J/g^−1 (DSC: 25° C. to 350° C./10° C.min/40 μl Al) | 3.62 | 100.0 | 538.3 | 539.5/ 597.5 [M + CH$_3$COO]— | METHOD F |
| Cpd 165 | 150.69° C./−73.99 J/g (DSC: 25° C. to 350° C./10° C.min/40 μl Al) | 3.4 | 100.0 | 458.2 | 459.2/ 457.3 | METHOD F |
| Cpd 150 | 144.49° C./−43.61 J/g (DSC: 25° C. to 350° C./10° C.min/40 μl Al) | 4.03 | 97.0 | 586.2 | 587.3/ 585.4 | METHOD F |
| Cpd 146 | 119.23° C./−38.89 J/g^−1 (DSC: 25° C. to 350° C./10° C.min/40 μl Al) | 3.88 | 100.0 | 568.2 | 569.5/ 627.4 [M + CH$_3$COO]— | METHOD K |

-continued

| Compound No. | Melting Point (Kofler or DS) | LCMS Rt | UV Area % | MW (theor) | BPM1/ BPM2 | LSMS Method |
|---|---|---|---|---|---|---|
| Cpd 147 | 151.74° C./−63.26 J/g^−1 (DSC: 25° C. to 350° C./10° C.min/40 µl Al) | 3.66 | 100.0 | 564.2 | 565.4/ 623.5 [M + $CH_3COO$]— | METHOD F |
| Cpd 140 | 121.52° C./−62.48 J/g (DSC: 25° C. to 350° C./10° C.min/40 µl Al) | 3.45 | 99.4 | 472.2 | 473.2/ 531.6 [M + $CH_3COO$]— | METHOD F |
| Cpd 154 | 132.95° C./−79.92 J/g^−1 (DSC: 25° C. to 350° C./10° C.min/40 µl Al) | 3.25 | 100.0 | 540.1 | 541.5/ 539.3 | METHOD K |
| Cpd 155 | 232.10° C./−88.86 J/g^−1 (DSC: 25° C. to 350° C./10° C.min/40 µl Al) | 2.44 | 100.0 | 458.1 | 459.5/ 457.2 | METHOD K |
| Cpd 166 | 156.21° C./−30.90 J/g (DSC: 25'C to 350° C./10° C.min/40 µl Al) | 5.22 | 100.0 | 535.2 | 536.3/ 594.4 [M + $CH_3COO$]— | METHOD F |
| Cpd 145 | 198.95° C./−102.61 J/g (DSC: 25° C. to 350° C./10° C.min/40 µl Al) | 3.42 | 100.0 | 539.3 | 540.4/ 598.7 [M + $CH_3COO$]— | METHOD F |
| Cpd 167 | 164.95° C./−78.44 J/g^−1 (DSC: 25° C. to 350° C./10° C.min/40 µl Al) | 3.66 | 98.0 | 538.3 | 539.4/ 597.6 [M + $CH_3COO$]— | METHOD F |
| Cpd 156 | 202.90° C./−47.56 J/g^−1 (DSC: 25° C. to 350° C./10° C.min/40 µl Al) | 2.13 | 100.0 | 428.2 | 429.2/ 427.4 | METHOD F |
| Cpd 136 | 163.21° C./−60.16 J/g (DSC: 25° C. to 350° C./10° C.min/40 µl Al) | 3.05 | 99.4 | 475.16 | 476.2/ 474.4 | METHOD F |
| Cpd 151 | 164.83° C./−27.18 J/g (DSC: 25° C. to 350° C./10° C.min/40 µl Al) | 4.32 | 98.9 | 584.2 | 585.3/ 583.5 | METHOD F |
| Cpd 135 | 148.28° C./−63.15 J/g (DSC: 25° C. to 350° C./10° C.min/40 µl Al) | 3.22 | 98.8 | 474.16 | 475.2/ 473.4 | METHOD F |
| Cpd 137 | 201.30° C./−41.79 J/g (DSC: 25° C. to 350° C./10° C.min/40 µl Al) | 3.65 | 98.9 | 550.2 | 551.3/ 549.5 | METHOD F |
| Cpd 168 | 183.37° C./−57.51 J/g (DSC: 25° C. to 350° C./10° C.min/40 µl Al) | 2.33 | 100.0 | 424.2 | 425.1/ 423.1 | METHOD F |

Analytical Methods

LCMS

The mass of some compounds was recorded with LCMS (liquid chromatography mass spectrometry). The methods used are described below.

General Procedure Method C

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time, etc) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

When a compound is a mixture of isomers which give different peaks in the LCMS method, only the retention time of the main component is given in the LCMS table.

TABLE

LCMS Method codes (Flow expressed in mL/min; column temperature (T) in ° C.; Run time in minutes).

| Method code | Instrument | Column | Mobile phase | gradient | Flow | Column T | Run time |
|---|---|---|---|---|---|---|---|
| Method C | Waters: Acquity UPLC ®-DAD and Quattro Micro ™ | Waters: BEH C18 (1.7 µm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 | 40 | 6.2 |

General Procedure LCMS Methods A and B

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time, etc) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^+$, etc). For molecules with multiple isotopic patterns (Br, Cl . . . ), the reported value is the one obtained for the lowest isotope mass. All results were obtained with experimental uncertainties that are commonly associated with the method used.

Hereinafter, "MSD" Mass Selective Detector, "DAD" Diode Array Detector.

General Procedure

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl . . . ), the reported value is the one obtained for the lowest isotope mass. All results were obtained with experimental uncertainties that are commonly associated with the method used.

Hereinafter, "SQD" means Single Quadrupole Detector, "RT" room temperature, "BEH" bridged ethylsiloxane/silica hybrid, "HSS" High Strength Silica, "DAD" Diode Array Detector.

TABLE

LCMS Method codes (Flow expressed in mL/min; column temperature (T) in ° C.; Run time in minutes).

| Method code | Instrument | Column | Mobile phase | gradient | Flow | Run time |
|---|---|---|---|---|---|---|
| Method B | Agilent: 1100/1200-DAD and MSD | Agilent: TC-C18 (5 µm, 2.1 × 50 mm) | A: $CF_3COOH$ 0.1% in water, B: $CF_3COOH$ 0.05% in $CH_3CN$ | 100% A for 1 min, to 40% A in 4 min, to 15% A in 2.5 min, back to 100% A in 2 min. | 0.8 50 | 10.5 |
| Method A | Agilent: 1100/1200-DAD and MSD | Agilent: TC-C18 (5 µm, 2.1 × 50 mm) | A: $CF_3COOH$ 0.1% in water, B: $CF_3COOH$ 0.05% in $CH_3CN$ | 90% A for 0.8 min, to 20% A in 3.7 min, held for 3 min, back to 90% A in 2 min. | 0.8 50 | 10.5 |

TABLE

LCMS Method codes (Flow expressed in mL/min; column temperature (T) in °C.; Run time in minutes).

| Method code | Instrument | Column | Mobile phase | gradient | Flow Column T | Run time |
|---|---|---|---|---|---|---|
| Method F | Waters: Acquity UPLC®-DAD and Quattro Micro™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 40 | 6.2 |
| Method K | Waters: Acquity® H-Class-DAD and SQD2™ | Waters: BEH C18 (1.7 μm, 2.1 × 100 mm) | A: 95% $CH_3COONH_4$ 7 mM/5% $CH_3CN$, B: $CH_3CN$ | 84.2% A for 10.5% A in 2.18 min, held for 1.96 min, back to 84.2% A in 0.73 min, held for 0.73 min. | 0.343 40 | 6.1 |

Hereinafter, "MSD" Mass Selective Detector, "DAD" Diode Array Detector.

TABLE

LCMS Method codes (Flow expressed in mL/min; column temperature (T) in °C.; Run time in minutes).

| Method code | Instrument | Column | Mobile phase | gradient | Flow Column T | Run time |
|---|---|---|---|---|---|---|
| Method E | Agilent: 1100/1200-DAD and MSD | Agilent: TC-C18 (5 μm, 2.1 × 50 mm) | A: $CF_3COOH$ 0.1% in water, B: $CF_3COOH$ 0.05% in $CH_3CN$ | 100% A for 1 min, to 40% A in 4 min, to 15% A in 2.5 min, back to 100% A in 2 min. | 0.8 50 | 10.5 |
| Method D | Agilent: 1100/1200-DAD and MSD | Agilent: (5 μm, 2.1 × 50 mm) | A: $CF_3COOH$ 0.1% in water, B: $CF_3COOH$ 0.05% in $CH_3CN$ | 90% A for 0.8 min, to 20% A in 3.7 min, for 3 min, back to 90% A in 2 min. | 0.8 50 | 10.5 |
| Method H | Agilent: 1100/1200-DAD and MSD | Waters: XBridge™ Shield RP18 (5 μm, 2.1 × 50 mm) | A: $NH_4OH$ 0.05% in water, B: $CH_3CN$ | 100% A for 1 min, to 40% A in 4 min, held for 2.5 min, back to 100% A in 2 min. | 0.8 40 | 10.5 |
| Method G | Agilent: 1200-DAD and MSD6110 | Phenomenex: Luna-C18 (5 μm, 2 × 50 mm) | A: $CF_3COOH$ 0.1% in water, B: $CF_3COOH$ 0.05% in $CH_3CN$ | 90% A for 0.8 min, to 20% A in 3.7 min, held for 3 min, back to 90% A in 2 min. | 0.8 50 | 10 |
| Method I | Agilent: 1200-DAD and MSD6110 | Phenomenex: Luna-C18 (5 μm, 2 × 50 mm) | A: $CF_3COOH$ 0.1% in water, B: $CF_3COOH$ 0.05% in $CH_3CN$ | 70% A for 0.8 min, to 10% A in 3.7 min, held for 3 min, back to 70% A in 2 min. | 0.8 50 | 10 |
| Method J | Agilent: 1200-DAD and MSD6110 | Phenomenex: Luna-C18 (5 μm, 2 × 50 mm) | A: $CF_3COOH$ 0.1% in water, B: $CF_3COOH$ 0.05% in $CH_3CN$ | 100% A for 1 min, to 40% A in 4 min, to 15% A in 2.5 min, back to 100% A in 2 min. | 0.8 | 10 |

Pharmacological Examples

MIC Determination for Testing Compounds Against *M. tuberculosis*.

Test 1

Appropriate solutions of experimental and reference compounds were made in 96 well plates with 7H9 medium. Samples of *Mycobacterium tuberculosis* strain H37Rv were taken from cultures in logarithmic growth phase. These were first diluted to obtain an optical density of 0.3 at 600 nm wavelength and then diluted 1/100, resulting in an inoculum of approximately 5×10 exp5 colony forming units per well. Plates were incubated at 37° C. in plastic bags to prevent evaporation. After 7 days, resazurin was added to all wells. Two days later, fluorescence was measured on a Gemini EM Microplate Reader with 543 excitation and 590 nm emission wavelengths and $MIC_{50}$ and/or $pIC_{50}$ values (or the like, e.g. $IC_{50}$, $IC_{90}$, $pIC_{90}$, etc) were (or may be) calculated.

Test 2

Round-bottom, sterile 96-well plastic microtiter plates are filled with 100 μl of Middlebrook (1×) 7H9 broth medium. Subsequently, an extra 100 μl medium is added to column 2. Stock solutions (200× final test concentration) of compounds are added in 2 μl volumes to a series of duplicate wells in column 2 so as to allow evaluation of their effects on bacterial growth. Serial 2-fold dilutions are made directly in the microtiter plates from column 2 to 11 using a multipipette. Pipette tips are changed after every 3 dilutions to minimize pipetting errors with high hydrophobic compounds. Untreated control samples with (column 1) and without (column 12) inoculum are included in each microtiter plate. Approximately 10000 CFU per well of *Mycobacterium tuberculosis* (strain H37RV), in a volume of 100 μl in Middlebrook (1×) 7H9 broth medium, is added to the rows A to H, except column 12. The same volume of broth medium without inoculum is added to column 12 in row A to H. The cultures are incubated at 37° C. for 7 days in a humidified atmosphere (incubator with open air valve and continuous ventilation). On day 7 the bacterial growth is checked visually.

The 90% minimal inhibitory concentration ($MIC_{90}$) is determined as the concentration with no visual bacterial growth.

Test 3: Time Kill Assays

Bactericidal or bacteriostatic activity of the compounds can be determined in a time kill assay using the broth dilution method. In a time kill assay on *Mycobacterium tuberculosis* (strain H37RV), the starting inoculum of *M. tuberculosis* is $10^6$ CFU/ml in Middlebrook (1×) 7H9 broth. The antibacterial compounds are used at the concentration of 0.1 to 10 times the $MIC_{90}$. Tubes receiving no antibacterial agent constitute the culture growth control. The tubes containing the microorganism and the test compounds are incubated at 37° C. After 0, 1, 4, 7, 14 and 21 days of incubation samples are removed for determination of viable counts by serial dilution ($10^{-1}$ to $10^{-6}$) in Middlebrook 7H9 medium and plating (100 μl) on Middlebrook 7H11 agar. The plates are incubated at 37° C. for 21 days and the number of colonies are determined. Killing curves can be constructed by plotting the $\log_{10}$CFU per ml versus time. A bactericidal effect is commonly defined as 3-$\log_{10}$ decrease in number of CFU per ml as compared to untreated inoculum. The potential carryover effect of the drugs is removed by serial dilutions and counting the colonies at highest dilution used for plating.

Test 4 (see also test 1 above; in this test a different strain of *Mycobacterium tuberculosis* strain is employed) Appropriate solutions of experimental and reference compounds were made in 96 well plates with 7H9 medium. Samples of *Mycobacterium tuberculosis* strain EH 4.0 (361.269) were taken from cultures in stationary growth phase. These were first diluted to obtain an optical density of 0.3 at 600 nm wavelength and then diluted 1/100, resulting in an inoculum of approximately 5×10 exp5 colony forming units per well. Plates were incubated at 37° C. in plastic bags to prevent evaporation. After 7 days, resazurin was added to all wells. Two days later, fluorescence was measured on a Gemini EM Microplate Reader with 543 nm excitation and 590 nm emission wavelengths and MIC50 and/or pIC50 values (or the like, e.g. IC50, IC90, pIC90, etc) were (or may be) calculated. $pIC_{50}$ values may be recorded below in μg/mL.

RESULTS

Compounds of the invention/examples, for example when tested in Test 1 or Test 2 described above, may typically have an $IC_{90}$ value from 0.01 to 10 μg/ml. Compounds of the invention/examples, for example when tested in Test 1 or Test 2 described above, may typically have a $pIC_{50}$ from 3 to 10 (e.g. from 4.0 to 9.0, such as from 5.0 to 8.0) Compounds of the examples were tested in Test 1 described above (in section "Pharmacological Examples") and the following results were obtained:

| Biological Data Table | | | |
|---|---|---|---|
| Compound No | pIC50 | pIC50 * | pIC50 ** |
| 1 | 8.03 | 7.88 | |
| 17 | 7.82 | 6.5 | 6.33 |
| 2 | 7.79 | 7.83 | 7.93 |
| 3 | 7.59 | 7.58 | 7.59 |
| 23 | 7.32 | 7.35 | 7.35 |
| 22 | 7.26 | 7.18 | 7.24 |
| 5 | 7.16 | 7.13 | 7.13 |
| 9 | 7.08 | 7.14 | 7.27 |
| 7 | 7 | 7.12 | 7.1 |
| 15 | 6.99 | 7.02 | |
| 4 | 6.92 | | |
| 12 | 6.89 | 7.15 | 6.97 |
| 25 | 6.87 | 6.88 | 6.96 |
| 6 | 6.85 | 6.99 | 6.89 |
| 8 | 6.83 | 6.73 | 6.77 |
| 10 | 6.83 | 6.85 | 6.97 |
| 18 | 6.72 | 6.91 | 6.9 |
| 24 | 6.7 | 6.56 | 6.94 |
| 13 | 6.57 | 6.59 | 6.58 |
| 16 | 6.55 | 6.61 | |
| 26 | 6.17 | 6.16 | 6.23 |
| 19 | 6.1 | 5.94 | 5.97 |
| 11 | 5.73 | 5.52 | 5.92 |
| 21 | 5.61 | 5.98 | 5.86 |
| 14 | 5.55 | 5.53 | |
| 27 | 5.39 | 5.38 | 5.54 |
| 28 | 5.22 | 5.12 | 5.13 |
| 29 | 5.1 | 5.17 | 5.15 |
| 30 | 5.05 | <4.9 | 4.96 |
| 31 | <4.9 | <4.9 | <4.9 |

* and ** denote repeated ($2^{nd}$ and $3^{rd}$) tests in the relevant assay; there may be some experimental deviation observed in the results Further Biological Data Compounds of the examples were tested in Test 4 described above (in section "Pharmacological Examples") and the following results were obtained:

| Compound No | pIC$_{50}$ |
|---|---|
| 28 | 8.5 |
| 14 | 6.4 |
| 15 | 6.8 |
| 1 | 7.0 |
| 7 | 7.8 |
| 29 | 5.1 |
| 81 | 8.3 |
| 30 | 5.1 |
| 20 | 6.5 |
| 27 | 6.4 |
| 21 | 7.0 |
| 11 | 6.1 |
| 18 | 7.5 |
| 10 | 7.5 |
| 17 | 7.4 |
| 19 | 5.9 |
| 6 | 7.6 |
| 31 | <4.9 |
| 66 | 8.1 |
| 80 | <4.9 |
| 32 | 7.4 |
| 79 | <4.9 |
| 34 | <4.9 |
| 35 | 5.1 |
| 68 | 7.2 |
| 64 | 7.0 |
| 39 | <4.9 |
| 40 | <4.9 |
| 38 | <4.9 |
| 41 | 5.1 |
| 70 | 6.5 |
| 43 | <4.9 |
| 44 | 5.1 |
| 78 | 5.6 |
| 48 | 5.2 |
| 49 | <4.9 |
| 61 | 6.2 |
| 46 | 5.1 |
| 47 | 5.2 |
| 121 | 5.6 |
| 122 | 6.1 |
| 96 | 6.9 |
| 124 | 7.1/7.2 |
| 123 | 5.8 |
| 125 | 8.7 |
| 158 | 6.4 |
| 152 | 7.8 |
| 148 | 7.8 |
| 133 | 8.7 |
| 159 | 7.4 |
| 141 | 7.5 |
| 142 | 6.9 |
| 131 | 8.3 |
| 16 | 8.0 |
| 4 | 8.3 |
| 24 | 6.6 |
| 23 | 7.5 |
| 26 | 6.4 |
| 22 | 7.9 |
| 2 | 7.3 |
| 51 | 5.2 |
| 53 | <4.9 |
| 52 | 5.1 |
| 65 | 8.0 |
| 69 | 7.5 |
| 33 | <4.9 |
| 63 | 6.5 |
| 60 | 7.0 |
| 71 | 6.5 |
| 36 | 5.1 |
| 37 | 5.4 |
| 42 | 5.0 |
| 45 | 5.1 |
| 50 | <4.9 |
| 54 | 5.1 |
| 55 | <4.9 |
| 97 | <4.9 |
| 98 | <4.9 |
| 99 | <4.9 |
| 100 | <4.9 |
| 101 | 5.8 |
| 102 | 5.4 |
| 103 | 5.1 |
| 104 | <4.9 |
| 105 | <4.9 |
| 106 | <4.9 |
| 107 | <4.9 |
| 108 | <4.9 |
| 109 | <4.9 |
| 58 | 7.0 |
| 67 | 8.0 |
| 110 | <4.9 |
| 126 | 5/4.9 |
| 127 | 6.9/7.0 |
| 128 | 7.5 |
| 129 | 6.4/6.5 |
| 144 | 7.1 |
| 138 | 7.4 |
| 130 | 7.8 |
| 134 | 8.2 |
| 160 | 7.5 |
| 143 | 6.4 |
| 153 | 8.7 |
| 161 | 5.6 |
| 162 | 5.1 |
| 132 | 5.1 |
| 3 | 8.3 |
| 77 | 6.1 |
| 8 | 7.3 |
| 9 | 7.9 |
| 13 | 7.5 |
| 12 | 7.5 |
| 5 | 7.5 |
| 72 | 8.0 |
| 111 | <4.9 |
| 73 | 6.7 |
| 74 | 7.2 |
| 112 | 5.5 |
| 113 | <4.9 |
| 56 | 8.2 |
| 57 | 8.1 |
| 59 | 6.5 |
| 114 | 4.9 |
| 115 | 5.5 |
| 76 | 7.6 |
| 75 | 7.8 |
| 92 | 6.6 |
| 116 | 6.5 |
| 84 | 7.0 |
| 87 | 6.6 |
| 88 | 6.6 |
| 86 | 6.8 |
| 83 | 7.0 |
| 82 | 7.2 |
| 117 | 7.7 |
| 89 | 5.2 |
| 85 | 6.0 |
| 90 | 4.9 |
| 91 | 5.0 |
| 93 | 6.9 |
| 118 | 4.9 |
| 119 | 6.2 |
| 120 | 5.0 |
| 94 | 7.1 |
| 95 | 6.8 |
| 163 | 5.1 |
| 149 | 8.7 |
| 164 | 5.1 |

-continued

| Compound No | pIC$_{50}$ |
|---|---|
| 157 | 5.1 |
| 139 | 5.1 |
| 165 | 5.1 |
| 150 | 8.7 |
| 146 | 6.5 |
| 147 | 5.9 |
| 140 | 5.8 |

The invention claimed is:

1. A process for preparing 6-chloro-2-ethyl-N-({4-[2-(trifluoromethanesulfonyl)-2-azaspiro[3.3]heptan-6-yl]phenyl}methyl)imidazo[1,2-a]pyridine-3-carboxamide, which comprises converting intermediate FF, intermediate FF

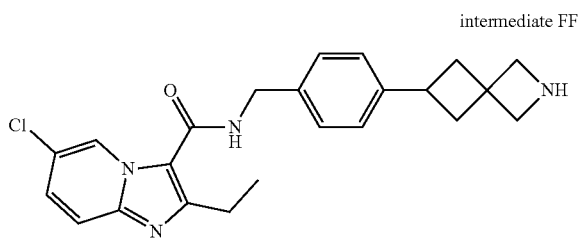 [SMILES: CCc1nc2ccc(Cl)cn2c1C(=O)NCc1ccc(C2CC3(CNC3)C2)cc1]

or a salt thereof, to 6-chloro-2-ethyl-N-({4-[2-(trifluoromethanesulfonyl)-2-azaspiro[3.3]heptan-6-yl]phenyl}methyl)imidazo[1,2-a]pyridine-3-carboxamide.

2. The process as claimed in claim 1, wherein the intermediate FF is in the form of a HCl salt.

3. The process as claimed in claim 1, wherein the converting is performed in the presence of Tf$_2$O.

4. The process as claimed in claim 3, wherein the intermediate FF is prepared by deprotection of intermediate FE, intermediate FE

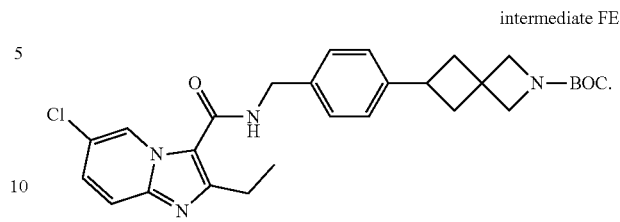

5. The process as claimed in claim 4, wherein the intermediate FE is prepared by reaction of intermediate FD, intermediate FD

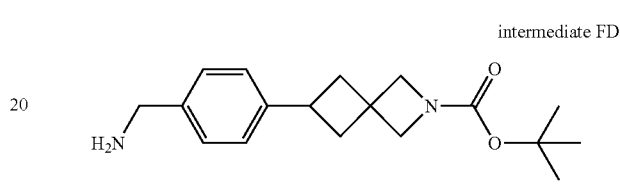

with the following compound,

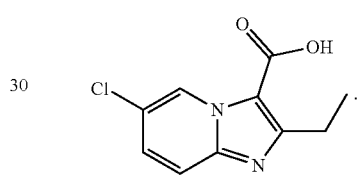

6. The process for the preparation of 6-chloro-2-ethyl-N-({4-[2-(trifluoromethanesulfonyl)-2-azaspiro[3.3]heptan-6-yl]phenyl}methyl)imidazo[1,2-a]pyridine-3-carboxamide, which comprises a process according to the following scheme:

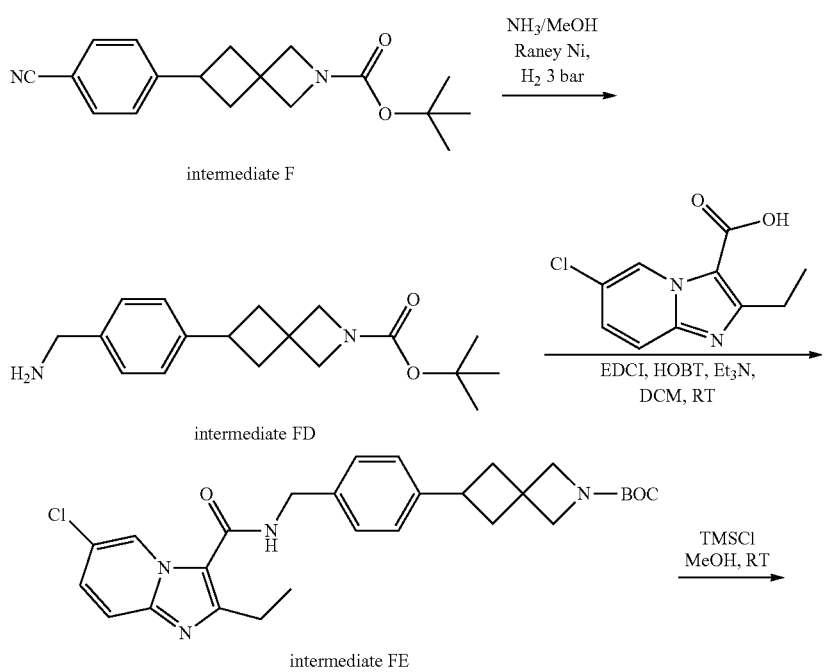

-continued

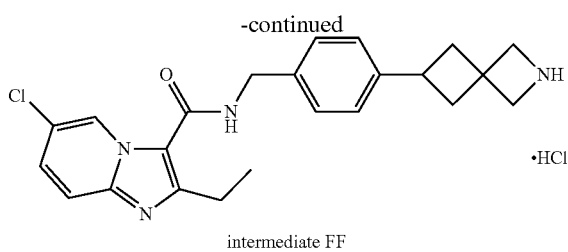

intermediate FF

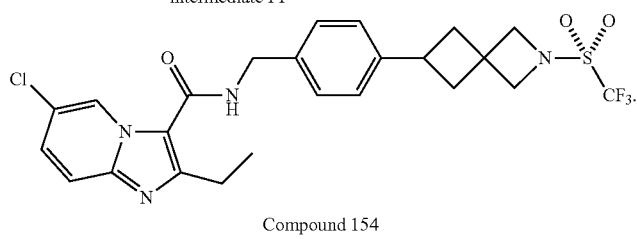

Compound 154

7. A compound intermediate FF:

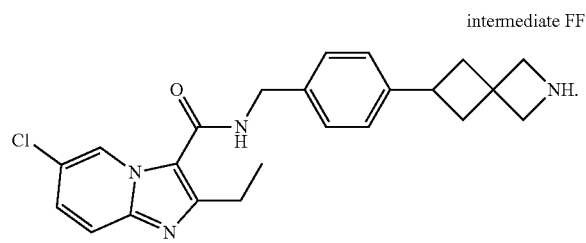

intermediate FF

8. The process as claimed in claim 2, wherein the converting is performed in the presence of Tf$_2$O.

9. The process as claimed in claim 1, wherein the intermediate FF is prepared by deprotection of intermediate FE,

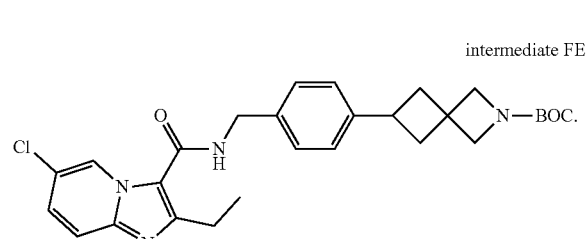

intermediate FE

10. The process as claimed in claim 2, wherein the intermediate FF is prepared by deprotection of intermediate FE,

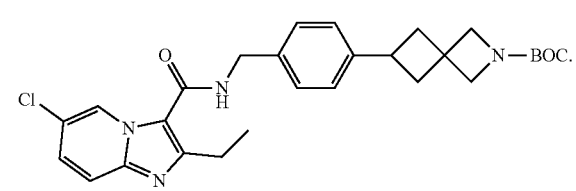

intermediate FE

11. The process as claimed in claim 8, wherein the intermediate FF is prepared by deprotection of intermediate FE,

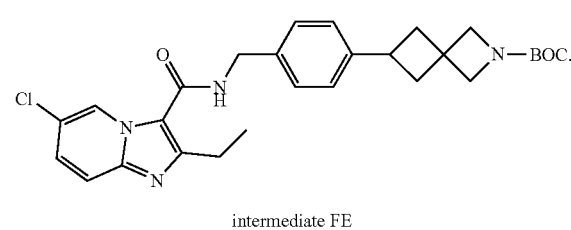

intermediate FE

12. The process as claimed in claim 9, wherein the intermediate FE is prepared by reaction of intermediate FD,

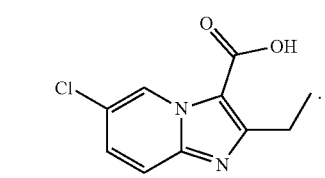

intermediate FD with the following compound,

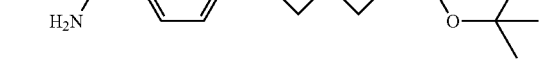

13. The process as claimed in claim 10, wherein the intermediate FE is prepared by reaction of intermediate FD,

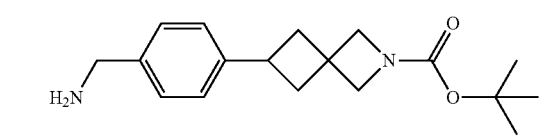

intermediate FD with the following compound,
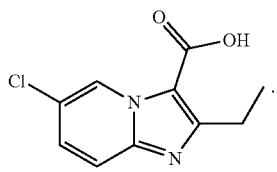
14. A process as claimed in claim 11, wherein the intermediate FE is prepared by reaction of intermediate FD,
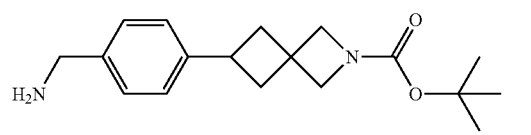
intermediate FD
with the following compound,
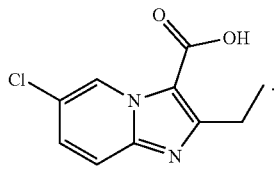
* * * * *